US012545878B2

(12) United States Patent
McFarland et al.

(10) Patent No.: US 12,545,878 B2
(45) Date of Patent: Feb. 10, 2026

(54) SYSTEMS AND APPARATUSES FOR CELLULAR THERAPEUTICS MANUFACTURE

(71) Applicant: BERKELEY LIGHTS, INC., Emeryville, CA (US)

(72) Inventors: Andrew W. McFarland, Berkeley, CA (US); Peter J. Beemiller, Emeryville, CA (US); Guido K. Stadler, San Francisco, CA (US); Alexander J. Mastroianni, Alameda, CA (US); Joshua J. Cardiel Rivera, Beaverton, OR (US); Darcy K. Kelly-Greene, Pleasanton, CA (US); Jonathan Cloud Dragon Hubbard, Oakland, CA (US); Natalie C. Marks, Albany, CA (US); Long Van Le, San Francisco, CA (US); Ke-Chih Lin, Emeryville, CA (US)

(73) Assignee: Bruker Cellular Analysis, Inc., Emeryville, CA (US)

( * ) Notice: Subject to any disclaimer, the term of this patent is extended or adjusted under 35 U.S.C. 154(b) by 644 days.

(21) Appl. No.: 18/147,356

(22) Filed: Dec. 28, 2022

(65) Prior Publication Data

US 2023/0313107 A1 Oct. 5, 2023

Related U.S. Application Data

(60) Provisional application No. 63/294,839, filed on Dec. 29, 2021.

(51) Int. Cl.
*C12M 1/00* (2006.01)
*C12M 1/34* (2006.01)
(Continued)

(52) U.S. Cl.
CPC ............ *C12M 29/10* (2013.01); *C12M 23/16* (2013.01); *C12M 23/40* (2013.01); *C12M 23/42* (2013.01);
(Continued)

(58) Field of Classification Search
CPC ...... C12M 29/10; C12M 23/16; C12M 23/40; C12M 23/42; C12M 41/12; C12M 41/36;
(Continued)

(56) References Cited

U.S. PATENT DOCUMENTS 7,367,550 B2 5/2008 Lee
8,492,140 B2 7/2013 Smith et al.
(Continued)

FOREIGN PATENT DOCUMENTS

WO WO 2009/072003 6/2009
WO WO 2020/227772 11/2020

OTHER PUBLICATIONS

Khoo, B. L. et al., "Liquid biopsy and therapeutic response: Circulating tumor cell cultures for evaluation of anticancer treatment", Science Advancement, 2, 1600274, 2016.
(Continued)

*Primary Examiner* — Liban M Hassan
(74) *Attorney, Agent, or Firm* — Vista IP Law Group, LLP

(57) ABSTRACT

Cartridge for manufacturing a population of cells suitable for formulation as a cellular therapeutic are disclosed herein, along with systems for operating the cartridges and performing methods to generate the population of cells suitable for formulation as a cellular therapeutic. The population of cells suitable for formulation as a cellular therapeutic can be T-cells, including CAR T-cells. The systems and methods can be largely automated.

37 Claims, 71 Drawing Sheets

(51) Int. Cl.
*C12M 3/00* (2006.01)
*C12M 3/06* (2006.01)
*C12N 5/0783* (2010.01)

(52) U.S. Cl.
CPC ............ *C12M 41/12* (2013.01); *C12M 41/36* (2013.01); *C12N 5/0636* (2013.01); *B01L 2300/0883* (2013.01)

(58) Field of Classification Search
CPC ................. C12M 23/02; C12N 5/0636; C12N 2501/2302; C12N 2501/2321; C12N 2501/51; C12N 2501/515; C12N 2501/53; B01L 2300/0883
See application file for complete search history.

(56) References Cited

U.S. PATENT DOCUMENTS

| | | | |
|---|---|---|---|
| 9,176,060 | B2 | 11/2015 | Lee et al. |
| 9,248,421 | B2 | 2/2016 | Lee et al. |
| 9,328,962 | B2 | 5/2016 | Lee et al. |
| 9,499,780 | B2 | 11/2016 | Smith et al. |
| 9,534,195 | B2 | 1/2017 | Smith et al. |
| 9,574,167 | B2 | 2/2017 | Lee et al. |
| 9,783,768 | B2 | 10/2017 | Larcher et al. |
| 10,723,986 | B2 | 7/2020 | Smith et al. |
| 2010/0035292 | A1 | 2/2010 | Levhenko et al. |
| 2018/0230453 | A1 | 8/2018 | Lee et al. |
| 2018/0243739 | A1 * | 8/2018 | Schenk zu Schweinsberg ........... B01L 3/5029 |
| 2020/0123491 | A1 | 4/2020 | Beemiller et al. |

OTHER PUBLICATIONS

Park, J.Y. et al., "Ice-lithographic fabrication of concave microwells and a microfluidic network", Biomedical Microdevices, 11, 129-133, 2009.

International Search Report and Written Opinion in corresponding PCT Application No. PCT/US 22/12194, mailed Jun. 7, 2022.

* cited by examiner

DC Dendritic cell stimulation
0.25 aAPC stimulation - 0.25 µg costimulation antibody / 1e7 beads
0.75 aAPC stimulation - 0.75 µg costimulation antibody / 1e7 beads
2.25 aAPC stimulation - 2.25 µg costimulation antibody / 1e7 beads Polymer = convoluted 2.8 micron polymeric bead Single Patient Cartridge – Prototype

5

Single Patient Cartridge – Functional Characteristics

- Closed
  - All reagents on board
  - All fluidics contained
- Sterile
- Disposable
- Embedded analytics for quality control:
  - Dose
  - Identity
  - Purity
  - Potency
  - Selectivity
  - Safety

SYSTEMS AND APPARATUSES FOR CELLULAR THERAPEUTICS MANUFACTURE

CROSS-REFERENCE TO RELATED APPLICATIONS

This application claims priority to and the benefit of U.S. Provisional Application No. 63/294,839, filed Dec. 29, 2021, the contents of which is incorporated into the present application by reference.

BACKGROUND OF THE INVENTION

Cellular therapeutics offer a potentially powerful approach to treating many different diseases successfully. To date, though, few cellular therapies have been approved for use in patients, in part due to the difficulties of manufacturing the therapies in a consistent and predictable manner. Moreover, the available approaches for cell therapy manufacturing have been cost-prohibitive and lack scalability. Product quality and release testing are a significant portion of both the cost and lead time for the manufacture and delivery of a cell therapy to a patient. See, e.g., https://www.sagentia.com/files/2018/07/Quality-control-testing-in-CAR-T-cell-manufacture.pdf, accessed on Jan. 11, 2021. Although robotic cell culture systems have been available for years (see, e.g., Sharma et al., 2011), to date no technological solution exists that allows for an integrated solution that automates and miniaturizes QC measurements to ensure cellular therapeutic safety by simultaneously reducing manual handling and labor steps, material costs, contamination risks, and sample and media requirements. In the case of cytotoxic T cell therapies, T lymphocyte activation by antigen presenting dendritic cells is one approach for preparing tumor-targeting cytotoxic T lymphocytes. However, use of dendritic cells is costly, labor intensive, and often produces inconsistent results, making synthetic activation surfaces critical to the cost-effective manufacture of T cell therapeutics. Accordingly, there is a need for cell therapy manufacturing systems that provide a level of automation and consistency necessary to reliably produce cellular therapeutics in a cost-effective and scalable manner. Some embodiments of the present disclosure are directed to such cell therapy manufacturing systems and method of using such systems to produce high quality therapeutics, including cytotoxic T cell therapeutics.

SUMMARY OF THE INVENTION

Aspects of the disclosure comprise a cartridge for manufacturing a population of cells in accordance with various embodiments. In various embodiments, the cartridge for manufacturing a population of cells can comprise a sealed enclosure with an inlet port and an outlet port. In various embodiments, the sealed enclosure can be hermetically sealed and/or sterile. In various embodiments, a first fluidic network can be connected to the outlet port and/or a second fluidic network can be connected to the inlet port; optionally, the first and second fluidic networks can be interconnected. In various embodiments, a first reagent reservoir can be connected to the first fluidic network. In various embodiments, a cell analysis region can be connected to the first fluidic network. In various embodiments, the cell analysis region has a sequestration pen defined therein. In various embodiments, the cartridge can comprise a chamber for culturing cells, wherein the chamber comprises a plurality of openings, including a first input opening for introduction of fluid into the chamber, a first output opening for removal of fluid from the chamber, and a second output opening for removal of fluid from the chamber. In various embodiments, the first and second output openings of the chamber are positioned at different vertical elevations within the chamber. In various embodiments, the chamber is connected to each of the outlet port, the first reagent reservoir, and the first cell analysis region via connections between the first and/or second output openings and the first fluidic network. In various embodiments, the cartridge can comprise a first reservoir for cell culture medium. In various embodiments, the first reservoir for cell culture medium can be connected to the second fluidic network. In various embodiments, the chamber is connected to each of the inlet port and the first reservoir for cell culture medium via connections between the first input opening and the second fluidic network. In various embodiments, an internal surface of a base of the chamber comprises a plurality of concave features defined thereon. In various embodiments, each concave feature of the plurality of concave features on the internal surface of the base of the chamber defines an elongated cavity; optionally, a long axis of each elongated cavity can be substantially parallel to a long access of every other elongated cavity of the plurality of concave features. In various embodiments, the long axis of each elongated cavity includes a first end and a second end, and an angle defined by the internal surface of the base of the chamber and a line segment connecting the first end of the long axis with the deepest point of the elongated cavity can be between 45° and 90°, while an angle defined by the internal surface of the base of the chamber and a line segment connecting the second end of the long axis with the deepest point of the elongated cavity can be less than 45°.

Aspects of the disclosure comprise a system for operating a cartridge in accordance with various embodiments. In various embodiments, the system comprises a receptacle capable of receiving the cartridge. The cartridge can be any of the cartridges disclosed or suggested herein. In various embodiments, the system can include a first heating and cooling element capable of regulating a temperature of a growth chamber of the cartridge. In various embodiments, the system can include a plurality of air flow regulators, each air flow regulator of the plurality capable of interfacing with the cartridge and controllably and independently providing pressurized gas to the cartridge. The pressurized gas can be filtered gas. In various embodiments, the system can include an actuator for moving (e.g., oscillating) the cartridge. In various embodiments, the movement of the cartridge can induce agitation of fluid present within the cartridge (e.g., the growth chamber of the cartridge). In various embodiments, the system can include a controller module in communication with the first heating and cooling element, the plurality of air flow regulators, and the actuator. The controller module can, for example, be capable of controlling a setting of the heating and cooling element (e.g., to regulate the temperature of the growth chamber), controlling each regulator of the plurality of air flow regulators (e.g., to control fluidics operations within the cartridge), and/or controlling the actuator (e.g., to control movements of fluids within the cartridge). In various embodiments, the receptacle can include a cartridge holder configured to interface with the cartridge and a support for receiving and supporting the cartridge holder. The cartridge holder can at least partially enclose the cartridge.

Aspects of the disclosure comprise a method for manufacturing a population of cells suitable for formulation as a cellular therapeutic in accordance with various embodiments. In various embodiments, the method can include introducing a cell sample from a subject into the inlet port of a cartridge. The cartridge can be any of the cartridges disclosed or suggested herein. In various embodiments, the method can include transporting the cell sample from an inlet port of the cartridge to the chamber (e.g., a growth chamber) of the cartridge. In various embodiments, the method can include incubating the cell sample in the chamber of the cartridge under conditions suitable for cellular proliferation. In various embodiments, the method can include agitating the cartridge so as to resuspend a proliferated cell sample present in the chamber. In various embodiments, the method can include transferring a first fraction of the proliferated cell sample from the chamber of the cartridge to a first analysis region of the cartridge. In various embodiments, the method can include analyzing the first fraction of the cell sample for cell count and/or cellular characteristics. In various embodiments, the method can include optionally repeating the steps of incubating, resuspending, transferring, and analyzing one or more times (e.g., to generate a father proliferated cell sample). In various embodiments, the method can include exporting the proliferated (or further proliferated) cell sample from the cartridge. In various embodiments, the cell sample can be a mammalian cell sample (e.g., a human cell sample). In various embodiments, the cell sample can include, consist substantially of, or consist of peripheral blood mononuclear cells (PBMCs).

Additional aspects of the disclosure comprise a cartridge for manufacturing a population of cells. In various embodiments, the cartridge comprises a sealed, sterile enclosure with an inlet port and an outlet port. In various embodiments, the cartridge comprises a first fluidic network connected to the outlet port and/or a second fluidic network connected to the inlet port; optionally, the first and second fluidic networks can be interconnected. In various embodiments, the cartridge comprises a first reagent reservoir connected to the first fluidic network. In various embodiments, the cartridge comprises a cell analysis region connected to the first fluidic network. In various embodiments, the cartridge comprises a chamber for culturing cells, wherein the chamber comprises a plurality of openings, including a first input opening for introduction of fluid into the chamber, a first output opening for removal of fluid from the chamber, and a second output opening for removal of fluid from the chamber. In various embodiments, the first and second output openings of the chamber are positioned at different vertical elevations within the chamber. In various embodiments, the chamber is connected to each of the outlet port, the first reagent reservoir, and the first cell analysis region via connections between the first and/or second output openings and the first fluidic network. In various embodiments, an internal surface of the base of the chamber comprises a plurality of concave features defined thereon. In various embodiments, each concave feature of the plurality of concave features on the internal surface of the base of the first chamber defines an elongated cavity (e.g., in the shape of a bisected tear-drop); optionally, a long axis of each elongated cavity is substantially parallel to a long access of every other elongated cavity of the plurality of concave features. In various embodiments, each elongated cavity includes a deepest point, the long axis of each elongated cavity has a first end and a second end, an angle defined by the internal surface of the base of the chamber and a line segment connecting the first end of the long axis with the deepest point of the elongated cavity is between 45° and 90°, and an angle defined by the internal surface of the base of the chamber and a line segment connecting the second end of the long axis with the deepest point of the elongated cavity is less than 45°.

BRIEF DESCRIPTION OF THE DRAWINGS

FIGS. 20A-201 are graphical representations of the characterization of activation using an antigen-presenting surface according to some embodiments of the disclosure.

FIG. 37E illustrates an activation assay process overlaid on a cell therapy manufacturing system 3700 according to various embodiments.

FIG. 371 illustrates a process flow diagram for a bioreactor monitoring process using a cell therapy manufacturing system according to various embodiments.

DETAILED DESCRIPTION OF THE INVENTION

Figure 1A:
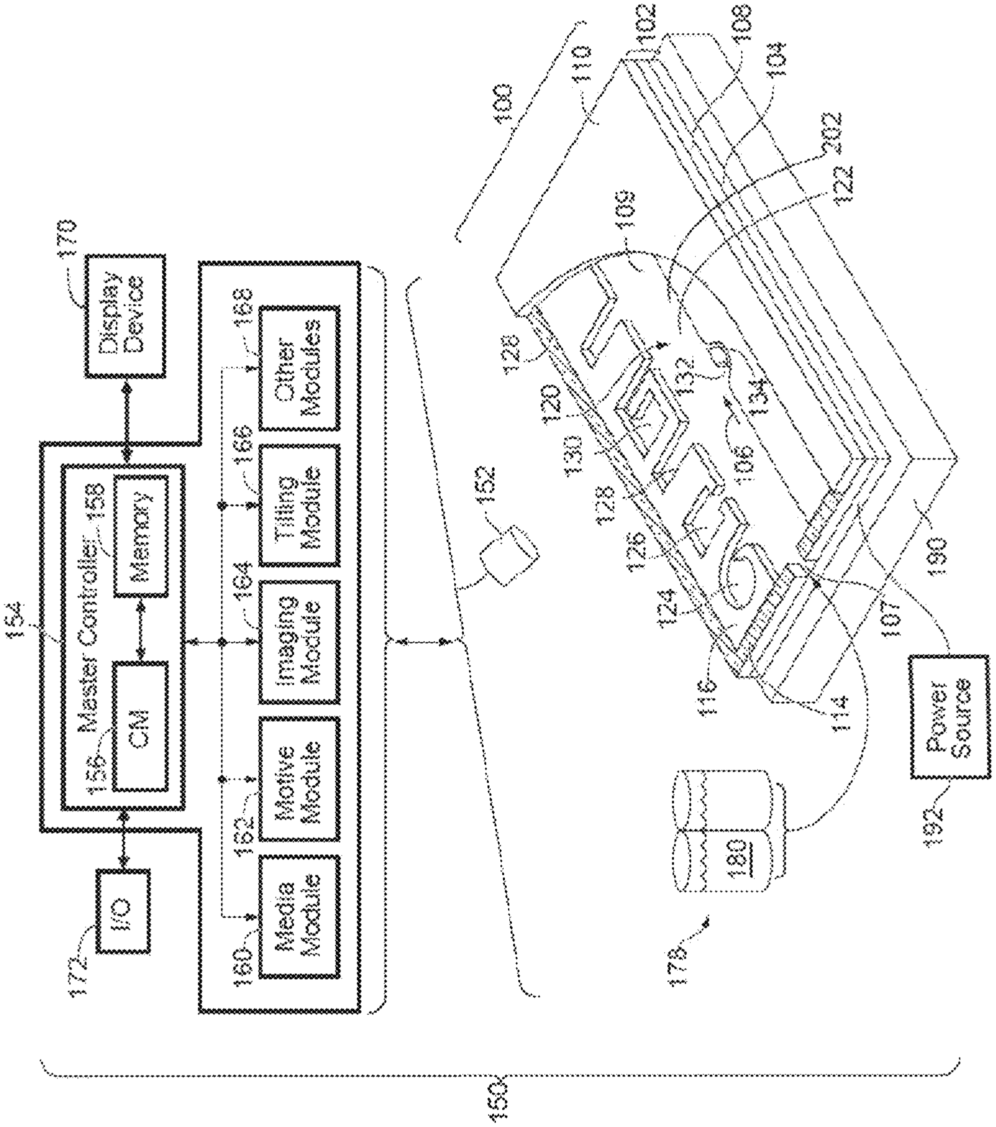
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. The term "or" is used in an inclusive sense, i.e., equivalent to "and/or," unless the context dictates otherwise. It is noted that, as used in this specification and the appended claims, the singular forms "a," "an," and "the," and any singular use of any word, include plural referents unless expressly and unequivocally limited to one referent. As used herein, the terms "comprise," "include," and grammatical variants thereof are intended to be non-limiting, such that recitation of items in a list is not to the exclusion of other like items that can be substituted or added to the listed items. Section divisions in the specification are for ease of review only and do not limit any combination of elements discussed. In case of any contradiction or conflict between material incorporated by reference and the expressly described content provided herein, the expressly described content controls.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

I. EXEMPLARY DESCRIPTION OF TERMS

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein, "alkyl" refers to a straight or branched hydrocarbon chain radical consisting solely of carbon and hydrogen atoms, containing no unsaturation, having from one to six carbon atoms (e.g., $C_1$-$C_6$ alkyl). Whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated. In some embodiments, it is a $C_1$-$C_3$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), hexyl, and the like.

Unless stated otherwise specifically in the specification, an alkyl group may be optionally substituted by one or more substituents which independently are: aryl, arylalkyl, heteroaryl, heteroaryl alkyl, hydroxy, halo, cyano, trifluoromethyl, trifluoromethoxy, nitro, trimethylsilanyl, —OR', —SR', —OC(O)—R', $—N(R')_2$, —C(O)R', —C(O)OR', $—OC(O)N(R')_2$, $—C (O)N(R)_2$, —N(R)C(O)OR', —N(R')C(O)R', $—N(R')C(O)N(R')_2$, $N(R')C(NR) N(R')_2$, —N(R')S(O) [R'(where is 1 or 2), —S (O)OR' (where t is 1 or 2), $—S(O)N(R')_2$ (where t is 1 or 2), or $PO_3 (R')_2$ where each R' is independently hydrogen, alkyl, fluoroalkyl, aryl, aralkyl, heterocycloalkyl, or heteroaryl.

As referred to herein, a fluorinated alkyl moiety is an alkyl moiety having one or more hydrogens of the alkyl moiety replaced by a fluoro substituent. A perfluorinated alkyl moiety has all hydrogens attached to the alkyl moiety replaced by fluoro substituents.

As referred to herein, a "halo" moiety is a bromo, chloro, or fluoro moiety.

As referred to herein, an "olefinic" compound is an organic molecule which contains an "alkene" moiety. An alkene moiety refers to a group consisting of at least two carbon atoms and at least one carbon-carbon double bond. The non-alkene portion of the molecule may be any class of organic molecule, and in some embodiments, may include alkyl or fluorinated (including but not limited to perfluorinated) alkyl moieties, any of which may be further substituted.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments (in which case it may be supplemented with carbon dioxide, e.g., up to about 5%) and/or for creating pressure to drive fluid flow within the cartridge. The air may be provided as a filtered, controlled composition and may be conditioned as described herein.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 UL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term “clonal cells” refers to cells of the same clonal colony.

As used herein, a “colony” of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term “maintaining (a) cell(s)” refers to providing an environment comprising both fluidic and gaseous components and, optionally a surface, that provides the conditions necessary to keep the cells viable and/or expanding.

As used herein, the term “expanding” when referring to cells, refers to increasing in cell number.

As referred to herein, “gas permeable” means that the material or structure is permeable to at least one of oxygen, carbon dioxide, or nitrogen. In some embodiments, the gas permeable material or structure is permeable to more than one of oxygen, carbon dioxide and nitrogen and may further be permeable to all three of these gases.

A “component” of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, “diffuse” and “diffusion” refer to thermodynamic movement of a component of the fluidic medium down a concentration gradient.

The phrase “flow of a medium” means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase “substantially no flow” refers to a rate of flow of a fluidic medium that, when averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase “fluidically connected” means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

As used herein, a “flow path” refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, “isolating a micro-object” confines a micro-object to a defined area within the microfluidic device.

A microfluidic (or nanofluidic) device can comprise “swept” regions and “unswept” regions. As used herein, a “swept” region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an “unswept” region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a “non-sweeping” rate of fluidic medium flow means a rate of flow in a flow region, such as a microfluidic channel, which is sufficient to permit components of a second fluidic medium in an isolation region of the sequestration pen to diffuse into the first fluidic medium in the flow region and/or components of the first fluidic medium to diffuse into the second fluidic medium in the isolation region; and further wherein the first medium does not substantially flow into the isolation region.

As used herein, “synthetic surface” refers to an interface between a support structure and a gaseous/liquid medium, where the synthetic surface is prepared by non-biological processes. In various embodiments, a synthetic surface can comprise an antigen-presenting surface. The synthetic surface may have biologically derived materials connected to it, e.g., primary and co-activating molecules as described herein, to provide an antigen-presenting synthetic surface, provided that the synthetic surface is not expressed by a biological organism. In various embodiments, the support structure is solid, such as the non-surface exposed portions of a bead, a wafer, or a substrate, cover or circuit material of a microfluidic device and does not enclose a biological nucleus or organelle.

As used herein, “co-activating” refers to a binding interaction between a biological macromolecule, fragment thereof, or synthetic or modified version thereof and a T-cell, other than the primary T-cell receptor/antigen: MHC binding interaction, that enhances a productive immune response to produce activation of the T cell. Co-activating interactions are antigen-nonspecific interactions, e.g., between a T-cell surface protein able to engage in intracellular signaling such as CD28, CD2, ICOS, etc., and an agonist thereof. "Co-activation" and "co-activating" as used herein is equivalent to the terms co-stimulation and co-stimulating, respectively.

As used herein, a "TCR co-activating molecule" is a biological macromolecule, fragment thereof, or synthetic or modified version thereof that binds to one or more co-receptors on a T-Cell that activate distal signaling molecules which amplify and/or complete the response instigated by antigen specific binding of the TCR. In one example, signaling molecules such as transcription factors Nuclear Factor kappa B (NFkB) and Nuclear factor of activated T cells (NFAT) are activated by the TCR co-activating molecule. The TCR co-activating molecule can be, for example, an agonist of the CD28 receptor, which signals through the phosphoinositide 3 kinase (PI3K)/Akt pathway. See FIG. 4.

As used herein, "CD28high" refers to a phenotype of high CD28 surface expression in a T cell. Those skilled in the art are familiar with the CD28high phenotype and appropriate ways of identifying CD28high T cells. Unless otherwise indicated, CD28high T cells include T cells that meet any of the following criteria. In some embodiments, a CD28high T cell is a T cell that expresses higher levels of CD28 than a resting CD8+ T cell. A CD28high T cell may also express higher levels of CD28 than an irrelevant non-antigen specific T cell. In some embodiments, CD28high T cells are a population in which the level of surface CD28 which can be measured by FACS is equal to or greater than the level of surface CD28 present on circulating memory T cells which can be measured by FACS. In some embodiments, a CD28high T cell has a level of surface CD28 equal to or greater than the level of surface CD28 present on circulating memory T cells from the same sample or individual. Expression of surface CD28 can be determined by FACS and the mean (e.g., geometric mean) or median level of surface CD28 present on circulating memory T cells can be used for determining whether a given T cell is CD28high. In some embodiments, a CD28high T cell is a T cell that expresses CD28 at a significantly higher level than expression typical of naïve CD8 T cells from the same sample or individual, e.g., higher than 75%, 80%, 85%, 87.5%, 90%, 92.5%, or 95% of the naïve T cells. Naïve CD8 T cells can be identified and characterized by known methods, e.g., flow cytometrically, as CD8+ cells expressing detectable CD28 and minimal or no CD45RO.

As used herein, a "TCR adjunct activating molecule" stimulates classes of signaling molecules which amplify the antigen-specific TCR interaction and are distinct from the TCR co-activating molecules. For example, TCR proximal signaling by phosphorylation of the TCR proximal signaling complex is one route by which TCR adjunct activating molecules can act. The TCR adjunct activating molecule may be, for example, an agonist of the CD2 receptor. See FIG. 4.

As used herein, an "activated T cell" is a T cell that has experienced antigen (or a descendant thereof) and is capable of mounting an antigen-specific response to that antigen. Activated T cells are generally positive for at least one of CD28, CD45RO, CD127, and CD197.

The term "antigen-presenting surface," as used herein, generally means a surface having the ability to activate T-cells. The antigen-presenting surface may have biologically derived materials connected to it, e.g., primary and co-activating molecules as described herein. In various embodiments, antigen-presenting surfaces may comprise anti-CD3. In various embodiments, antigen-presenting surfaces may comprise anti-CD28. In some embodiments, antigen-presenting surfaces may comprise anti-CD3 and anti-CD28. Surfaces described herein can undergo treatment to become antigen-antigen presenting surfaces. Non-limiting examples support structures having surfaces can include beads, magnetic beads, well-plates, capillaries, surfaces within a bioreactor (e.g. dimples).

The term "cell therapy product vessel," as used herein, generally refers to a sterile compartment or container that can be suitable for receiving a cell therapeutic during a fill process. In various embodiments, cell therapy product vessel can comprise a flexible container that is malleable and can deform to fit in various spaces (e.g. within a box). In some embodiments, the flexible container can comprise an intravenous bag. In alternative embodiments, cell therapy product vessels can comprise rigid structures that are resistant to puncture or tear.

The term "denaturation," as used herein, generally refers to any molecule that loses quaternary structure, tertiary structure, and secondary structure which is present in their native state. Non-limiting examples include proteins or nucleic acids being exposed to an external compound or environmental condition such as acid, base, temperature, pressure, radiation, etc.

The term "cartridge," as used herein can be used interchangeably with the term "cassette" and generally refers to an apparatus suitable for carrying out one or more steps (e.g. sorting, activating, transfection, and/or fill and formulation) in a cell therapy manufacturing process. For example, a cell therapy manufacturing system can receive cells (e.g. T-cells) from a subject and process them using the cartridge. In some embodiments, the cell therapy manufacturing system can produce a cell therapy product (e.g. a treatment for a subject) using the cartridge.

In various embodiments a cell manufacturing system can comprise a cartridge. In various embodiments, cartridges can be modular devices that can be inserted into the instrument and processed. In various embodiments, cartridges can be customized to carry out one or more steps of a cell therapy manufacturing process for a specific set of conditions. Conditions can comprise, for example, the manufacture of a specific cell type, such as engineered T-cells, CAR T-cells, endogenous T cells, or the like, for a disease condition, such as a cancer (e.g. blood cancer, liver cancer, lung cancer, etc.). In various embodiments, cartridges can be adapted to process a specific subject sample type (e.g. whole blood sample). In various embodiments, cartridges can be replaced after each subject sample has been processed. In various embodiments, cartridges can be re-used. In some embodiments, cartridges can an integrated component on the instrument.

In various embodiments, a cartridge can comprise one or more fluidic networks and at least one chamber. In various embodiments, the chamber can comprise a bioreactor for culturing a cell therapy product (e.g. a cell therapy treatment comprising T-cells). In various embodiments, cartridges can be a modular component of a cell therapy manufacturing system. In various embodiments, cartridges can include reservoirs, valves, chambers, and analytical components for a variety of cell therapy manufacturing processes. Non-limiting examples of processes that can be carried out on the cartridge include cell sample introduction, sorting/selection, activation, transduction, culture, cell counting and/or characterization, clean-up steps, formulation and fill, or any combination thereof.

The term "detectable label," as used herein, generally means anything that can be detected. More specifically, detectable labels can comprise fluorescent molecules such as fluorophores or barcodes. Detectable labels can be coupled to carbohydrate, protein, nucleotide sequences (e.g., oligos), sugars, amino acids, nucleotides, or other biological molecules. In various embodiments, detectable labels can be coupled to a target molecule, either directly or indirectly via an intermediary, thereby allowing for detection of the target molecule. Detectable labels can be exogenous or endogenous. In various applications, detectable labels can comprise quenching agents for reducing a signal intensity being emitted by another molecule (e.g. a fluorophore).

In various embodiments, detectable labels can be analyzed by laboratory equipment (e.g. flow cytometers, microscopes, etc.). In various embodiments, detectable labels can be quantitatively analyzed.

The term "nucleic acid construct," as used herein, generally refers to a molecule that can modify a cell for use in cell therapy or cell therapy manufacturing. In various embodiments, a nucleic acid construct can comprise one or more nucleotide sequences encoding a molecule for use in cell therapy or cell therapy manufacturing. Nucleic acid constructs can be inserted into a host genome (e.g. a T-cell) and be expressed. In various embodiments, insertion can occur using gene editing machinery (e.g. lentiviral vectors). In various embodiments, a nucleic acid construct can comprise one or more genes encoding a chimeric antigen receptor (CAR) molecule.

The term "sample," as used herein, generally refers to a sample from a subject of interest (e.g. human subject) and may include a cell sample. Thus, the sample can include one or more cells, such as immunological cells or blood cells (e.g., T cells, NK cells, macrophages, or the like). The sample may be derived from another sample. For example, the sample may include only a subset of the cells (and other material) from the sample taken directly from the subject. The sample may include a tissue sample, such as a biopsy, core biopsy, needle aspirate, or fine needle aspirate. The sample may include a fluid sample, such as a blood sample, urine sample, or saliva sample. The sample may include a skin sample. The sample may include a cheek swab. The sample may originate from blood, plasma, serum, urine, saliva, mucosal excretions, sputum, stool, or tears. The sample may originate from red blood cells or white blood cells. The sample may originate from spinal fluid, CNS fluid, gastric fluid, amniotic fluid, cyst fluid, peritoneal fluid, marrow, bile, other body fluids.

The term "sortavation," as used herein, generally refers to a step in a cell therapy manufacturing process. In various embodiments, sortavation can comprise one or more sorting steps combined with one or more activation steps (e.g., T cell activation steps).

The term "subject," as used herein, generally refers to an animal, such as a mammal (e.g., human subject) or other animal (e.g., bird). For example, the subject can include a vertebrate, a mammal, a rodent (e.g., a mouse), a primate, a simian or a human. Animals may include, but are not limited to, farm animals, sport animals, and pets. A subject can include a healthy or asymptomatic individual, an individual that has or is suspected of having a disease (e.g., cancer) or a pre-disposition to the disease, and/or an individual that is in need of therapy or suspected of needing therapy. A subject can be a patient.

The term "treatment," as used herein, generally refers to a cellular product that can be produced using the cell therapy manufacturing methods and systems described herein. The product can comprise live cells. In various embodiments, the live cells can include T-cells. In various embodiments, the T-cells can be CAR T-cells. In various embodiments, the T-cells can be engineered T-cells. In various embodiments, the T-cells can be endogenous T-cells (i.e., T-cells from a subject that have not been genetically engineered).

II. OVERVIEW OF CELL THERAPY MANUFACTURING SYSTEMS AND CARTRIDGE

A. Cell Therapy Manufacturing System (CTMS) and Cartridge

Although cell-based immunotherapy for cancer treatment is a promising development, current systems for producing cell therapy products can require enormous resources in terms of space, operator knowledge, and cost. Additional challenges include reproducibility. Existing systems can comprise suites of equipment where each piece of equipment can carry out only one process or sub-process of a cell therapy manufacturing method. With this comes material handling and contamination issues that require even more resources to limit.

What is needed is an integrated, automated system and cartridge capable of receiving a sample (e.g., blood sample) from a patient and processing the sample through the various steps of the cell therapy manufacturing method to produce a product that can be used by the patient. Such a system can be completely enclosed from the beginning of the workflow until the end in order to ensure the produce is free from contamination. Such a system can also allow for any accompanying quality control procedures to be handled in-line or within the system. The novel cartridges, instruments, systems and methods described herein solve these issues and more.

B. Synthetic T-Cell Activation Surfaces

In biological organisms, dendritic cells function to capture, process, and present exogenous antigens to adaptive immune cells (e.g. T-cells). However, the current use of antigen presenting dendritic cells to activate T lymphocytes (T-cells) presents several disadvantageous aspects. Currently, dendritic cells must be obtained from donor sources, increasing cost and limiting throughput. Additionally, dendritic cells, in most cases, must be matured for each sequence of T lymphocyte activation, which can require a lead time of about 7 days. Irradiation of dendritic cells is also required, which limits where such processing can be performed.

In various embodiments, replacing the use of autologous antigen presenting dendritic cells with synthetic surfaces for activating T lymphocytes may afford greater reproducibility when stimulating and expanding T lymphocytes for a subject or a therapeutically relevant population. The synthetic surfaces may be engineered for antigen-specific activation of T lymphocytes, providing more controllable, characterizable, reproducible and/or more rapid development of populations of activated T lymphocytes having desirable phenotypes for treatment of cancer in accordance with various embodiments. Alternatively, the synthetic surfaces may be engineered for non-antigen-specific activation of T lymphocytes (e.g., genetically engineered T lymphocytes), which can also provide more controllable, characterizable, reproducible and/or more rapid development of populations of activated T lymphocytes having desirable phenotypes for treatment of cancer in accordance with various embodiments. Activating synthetic surfaces, whether antigen-specific or not, can also allow for more control and selectivity over T cell activation, including more precise targeting of desired T cell phenotypes following activation, e.g., enrichment of particular forms of memory T cells. Furthermore, activating synthetic surfaces can also take advantage of economies of scale and/or provide reproducibility to a greater degree than using autologous antigen presenting dendritic cells. As such, this technology can make cellular therapies available to patients in need thereof in greater numbers. Additionally, the systems and methods described herein can reduce the time necessary to produce a cell therapy product due to the nature of the integrated system for carrying out cell therapy manufacturing processes. Providing T cells useful for cellular therapies more rapidly can be especially important for patients with advanced disease. The structure of such activating synthetic surfaces and their methods of preparation and use are described herein. In some embodiments, the activating synthetic surfaces comprise primary activating ligands (e.g. an MHC class I molecule bound to an antigenic peptide or a CD3 agonist, such as an anti-CD3 antibody) in combination with TCR co-activating molecules (e.g. a CD28 molecule) and/or adjunct TCR activating molecules, which together serve to activate T cells. Surface density can range for these components and ratios of one to another that can further improve efficacy are also disclosed herein. In some embodiments, the activating synthetic surfaces and their methods of preparation and use provide one or more of the foregoing advantages (e.g. cost savings, time savings, a controlled and well characterized process).

III. OVERVIEW OF EXEMPLARY CELL THERAPY MANUFACTURING WORKFLOW

Figure 28:
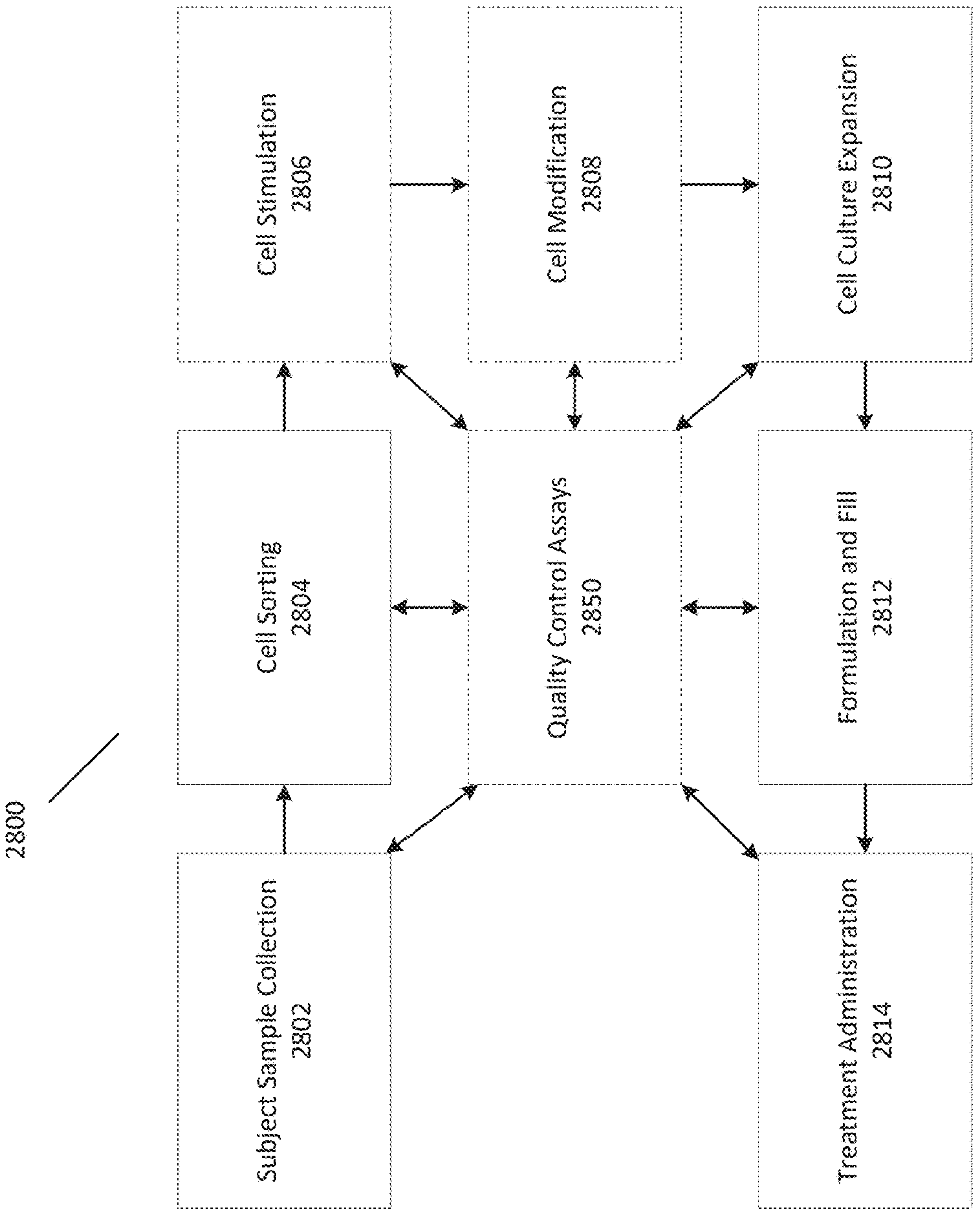
FIG. 28 is a schematic block diagram of an exemplary cell therapy workflow for producing a product for cell therapy according to various embodiments of the disclosure.

Cell therapy manufacturing workflows described herein can comprise producing a cell therapy product. In various cases, workflows can be directed toward producing a product comprising live cells (e.g., immunological cells, such as CAR T-cells, engineered T-cells, or endogenous T-cells, or stem cells) that can be transferred into a subject for a specific application. Some applications can include treatment of a disease or an illness. Some applications can include treatment of cancer. FIG. 28 is a schematic diagram of an exemplary cell therapy workflow 2800 for producing a product for cell therapy. Cell therapy workflow 2800 may include various operations, non-limiting examples can include subject sample collection 2802, cell sorting 2804, cell stimulation 2806, cell modification 2808, cell culture expansion 2810, finalize product (e.g., formulation and fill) 2812, treatment administration 2814, and one or more quality control assays 2850.

A. Subject Sample Collection

Subject sample collection 2802 may include, for example, obtaining a cell sample of one or more subjects, such as mammalian subjects (e.g., human subjects). The cell sample may take the form of a specimen obtained via one or more sampling methods. The cell sample may comprise a whole blood sample or cells from a specific tissue, such as lymph nodes, spleen, or a source of stem cells, such as bone marrow, liver, adipose tissue, muscle, skin, gingival tissue, blood vessels, brain, embryonic tissue, or the like. The cell sample may be obtained in any of several different ways. In various embodiments, the cell sample includes a whole blood sample obtained via a blood draw. In other embodiments, the cell sample can be derived from whole blood, for example, a serum sample, a plasma sample, a fractionated blood sample (e.g., enriched for white blood cells (WBCs), lymphocytes, T-cells, NK cells, macrophages, other types of blood cells, or a combination thereof). In other embodiments, the cell sample can be obtained by dissociation of a tissue biopsy (e.g., dissociated bone marrow cells, liver cells, adipose cells, muscle cells, skin cells, gingival cells, endothelial cells, neurological cells, embryonic cells, etc.). In some embodiments, a dissociated cell sample can be partially purified or purified to select for cells of interest. Cell samples may include nucleotides (e.g., ssDNA, dsDNA, RNA), organelles, amino acids, peptides, proteins, carbohydrates, or any combination thereof.

In various embodiments, a cell sample obtained from subject sample collection 2802 can comprise white blood cells (e.g., T-cells) harvested from a whole blood sample. The harvesting can include using centrifugation methods. In some embodiments, the centrifugation methods can comprise apheresis (e.g., leukapheresis). Leukapheresis can be an effective procedure for separating white blood cells from other whole blood constituents. In various embodiments, leukapheresis can produce a leukopak from a cell sample. Other whole blood constituents can be returned to the subject (e.g., human subject). In some embodiments, the harvesting can include using a microfluidic post array for deterministic lateral displacement (DLD). For example, the microfluidic post array can be used to remove red blood cells and/or other cells from a whole blood sample, and/or to alter the medium in which the white blood cells (e.g., T-cells) are suspended.

In various embodiments, a cell sample obtained from subjection sample collection 2802 can undergo a tissue dissociation process (e.g., an enzymatic digestion process). In various embodiments, the system described herein can comprise one or more reservoirs for storing enzymes and other reagents for carrying out a tissue dissociation process. The contents of the reservoirs can be delivered, via a fluidic network, to a location in the system where the tissue dissociation process can be carried out. In many embodiments, a tissue dissociation process can be carried out in chamber (e.g., a bioreactor chamber of a cartridge).

B. Cell Sorting and Cell Stimulation

Various cell types (e.g., immunological cells, such as T-cells, NK cells, stem cells, pluripotent cells, ipscs, progenitor cells, or the like) may benefit by including cell sorting 2804 in a cell therapy workflow 2800. Many cell types may also benefit from cell stimulation 2806 [(e.g., activation for T-cells and NK cells) and/or (e.g., differentiation for stem cells, pluripotent cells, ipscs, progenitor cells, or the like)] as performed on a cell therapy manufacturing system described herein.

In various embodiments, a cell therapy manufacturing system can include necessary elements (e.g., reagents and hardware) for carrying out a variety of different cell therapy workflows 2800. For example, in many embodiments, a cell therapy manufacturing workflow 2800 may include a cell sorting 2804 step and exclude a stimulation step 2806. In other embodiments, a cell therapy workflow 2800 may include a discrete cell sorting 2804 step and a discrete cell stimulation 2806 step. In alternate embodiments, a cell therapy workflow 2800 may include integrated cell sorting 2804 and cell stimulation steps 2806 (e.g., a cell sorting and cell stimulation step overlapping in time).

Whether to include cell stimulation 2806 may, at least in part, be determined by a cell type or characteristic of a cell being processed. In many embodiments described herein, cell stimulation can initiate an immune response.

In various cell therapy workflows 2800, cell sorting 2804 and/or cell stimulation 2806 can be followed by cell proliferation. In other cell therapy workflows 2800, cell sorting 2804 and/or cell stimulation 2806 can be followed by cell modification 2808.

a. Cell Sorting

For cell-based cell therapies, effective cell sorting 2804 may generate purer cell therapy products which may result in more effective patient outcomes (e.g., increased five-year survival and/or fewer and less severe side effects).

In various embodiments, cell sorting 2804 can be used in isolating desired cells by selection based on one or more of the following: size, live, CD8 positive, and tetramer positive. In various embodiments, sorting can comprise isolating activated T-cells from non-activated T-cells. Various methods of cell sorting 2804 are described below and throughout.

b. Cell Stimulation

In various cell therapy workflows 2800, cell sorting 2804 and T-cell activation 2806 may comprise a combined step ("sortavation"). In various embodiments, the cell sample from subject sample collection 2802 can undergo cell sorting 2804 and T-cell activation 2806. In various embodiments, the cell undergoing activation may originate from a cell sample, such as, a T-cell enriched sample (e.g., a leukopak or a sample produced using a microfluidic post array).

In various embodiments, the systems described herein may be suited for executing a variety of different cell stimulation 2806 processes of a cell therapy workflow 2800. Non-limiting examples of cell stimulation 2806 processes include stimulation of T-cells or NK via an activation process carried out on a cell therapy manufacturing system. Additional non-limiting examples of cell stimulation 2806 processes include stimulation of various cell types such as stem cells, pluripotent cells, ipscs, progenitor cells, or the like during differentiation.

A variety of cell types may also benefit from cell stimulation 2806 (e.g., activation for T-cells and NK cells) and/or differentiation (e.g., for stem cells, pluripotent cells, ipscs, progenitor cells, or the like) using the systems and methods described herein.

In various embodiments, cells (e.g., T-cells) can be contacted with growth stimulatory molecules, such as growth factors or cytokines, and/or molecules that induce phenotypic change, such as activation. In cell therapy manufacturing systems for processing cells (e.g., T-cells) undergoing an activation step, a common characteristic of both dendritic cells and synthetic activation surfaces may be antigen presentation for the cell engagement. For example, in various embodiments, cells may be activated using activating molecules such as molecular ligands. Activating ligands may comprise primary molecules (e.g., MHC bound to an antigen of interest, or an antigen recognized by a CAR) and co-activating molecules (e.g., CD28, CD2, or the like). Additional examples of stimulatory molecules and their methods of use are provided below and throughout.

For cell therapy workflows 2800 used in processing T-cells, activation, in general, may include a primary signal and a co-stimulatory signal. In various embodiments, the primary signal can propagate via a T-cell receptor (e.g., by targeting the T-cell receptor directly or via CD3). In various embodiments, the co-stimulatory signal can propagate via CD28, CD2, and/or other molecules. In the case of CAR T-cells or other types of engineered T-cells, T-cell activation may occur prior to transduction or transfection.

Some cell therapy workflows 2800 used for processing T-cells may use dendritic cells to carry out cell stimulation 2806 processes. In various embodiments, cell-based T-cell activation can be carried out using the systems described herein. Some cell therapy manufacturing systems can include synthetic surfaces capable of mimicking of the function of dendritic cells.

Synthetic surface-based T-cell activation can be carried out on one or more of the synthetic activation surfaces described herein. In some embodiments, the synthetic surface may comprise beads. In some embodiments, the beads can be magnetically manipulatable. In alternative embodiments, the synthetic surface can comprise non-bead structures such as planar surfaces.

Alternatively or in addition to activation, a cell therapy manufacturing system may carry out cellular differentiation processes and steps. In various embodiments, a cell type (e.g., pluripotent stem cells) may undergo differentiation in a cell therapy manufacturing process.

In various embodiments, magnetic beads can be used for sorting and activation of T-cells without needing to remove the beads/cells until harvest. In such embodiments, cell sorting 2804 and T-cell activation 2806 can occur simultaneously. An advantage to this approach includes the ability to include washing and enrichment steps without loss of stimulatory molecules (e.g., use of CD3/CD28 antibody-coated magnetic beads). Commercially available systems for carrying out cell sorting can comprise a fluorescence activated cell sorter (FACS). In some embodiments, cell sorting methods can be carried using the systems described herein. In some embodiments, similar beads can be used for cell sorting and a cell stimulation step can be omitted.

C. Cell Modification

Aspects of cell therapy manufacturing methods and systems can comprise cell modification 2808 to a cell using gene transfer systems and methods (e.g., transfection or transduction) to encode a host cell (e.g., T-cell, NK cell, stem cell, and/or stem cell) with a nucleic acid construct. In various embodiments, cell modification 2808 can be carried out using viral methods (e.g., transduction). In alternative embodiments, cell modification 2808 can be carried out using non-viral methods (e.g., transfection).

Non-limiting examples of viral approaches to cell modification 2808 include retroviral, lentiviral, adenovirus, and adeno-associated viruses. In various viral approaches, cell stimulation 2806 (e.g., differentiation, in the case of stem cells or activation, in the case of T-cells) may be concurrent with cell modification 2808. Non-limiting examples of non-viral approaches to genetic delivery include liposome mediated or plasmid mediated methods. Other non-limiting approaches may include use of CRISPR/Cas machinery.

In some aspects, retroviral cell modification 2808 can comprise copying a nucleotide genome of the virus into a double stranded DNA nucleotide sequence. As such, an integrated form of the viral genome can be transcribed as a normal cellular gene. In various embodiments, lentiviral cell modification 2808 can occur while the cells are non-cycling.

An exemplary non-viral cell modification 2808 method can comprise use a plasmid-based expression system. In some embodiments, the plasmid-based method can comprise transposon/transposase systems. In various embodiments, the transposon/transposase systems may be introduced to cells by electroporation, cell compression, or chemical treatment.

Another exemplary non-viral cell modification 2808 can comprise use of messenger (mRNA) transfer systems. In some embodiments, mRNA transfer systems can comprise transient expression of a transgene. In other embodiments, mRNA transfer systems can result in permanent expression of the transgene.

In various embodiments, T-cell modification can engineer T-cells to comprise receptors (e.g., chimeric antigen receptors (CARs) capable of antigen-binding and causing T-cell activation. In various embodiments, T-cell modification 2808 can generate CAR T-cells. In various embodiments, the nucleic acid construct can comprise a chimeric antigen receptor (CAR) molecule. In other embodiments, the nucleic acid construct can comprise a T-cell receptor (TCR) having a desired antigen specificity.

In various embodiments, cell modification 2808 may occur using non-viral methods such as through a cell differentiation process. A non-limiting example of a non-viral vector includes mesenchymal stem/stromal cells (MSCs). In various embodiments, non-viral vectors may undergo cell modification 2808 via cell differentiation in various cell therapy workflows 2800.

In various embodiments, vectors that do not integrate with a host genome (e.g., adenoviral vectors) can transduce dividing cells. In alternative embodiments, vectors that do not integrate with a host genome (e.g., adenoviral vectors) can transduce quiescent cells.

D. Cell Culture Expansion

Aspects of cell therapy effectiveness depend on having enough cells for administering to the subject. As such, the cells can be cultured through one or more expansion phases to produce an expanded population of cells. In various embodiments, a cell culture expansion 2810 method for quickly generating large numbers of cells can be used in conjunction with the other methods described herein.

For methods of manufacturing T-cell therapeutics, expansion can include an increase in the number of cytolytic T-cells. In various embodiments, expansion can include an increase in the number of helper T-cells.

In various aspects, a method of cell culture expansion 2810 can comprise contacting the cells with an in vitro cell culture medium. In various embodiments, the cell culture medium can comprise factors that support T-cell activation and/or the generation of cytolytic T-cells. For example, the cell culture medium can include a CD3 agonist (e.g., an anti-CD3 antibody), a CD28 agonist (e.g., an anti-CD28 antibody), a CD2 agonist (e.g., an anti-CD2 antibody), a cytokine (e.g., one or more of IL2, IL7, IL15, and IL21), or any combination thereof. Still further embodiments can comprise incubating the culture, thereby producing an expanded population of antigen specific, MHC-restricted T lymphocytes. In various embodiments, a cell culture medium can comprise growth factors growth factors, cytokines, chemokines, transcription factors, enzymes and/or microRNAs and, optionally, other molecules that control cell stimulation (e.g., activation and differentiation).

Aspects of cell culture expansion 2810 can comprise use of feeder cells in accordance with various embodiments. In some expansion protocols, cells can be cultured in association with a disproportionately large concentration of nondividing feeder cells (e.g., y-irradiated peripheral blood mononuclear cells ("PBMC") in accordance with various embodiments. In various embodiments, non-dividing peripheral blood mononuclear cells (PBMC) can be added to the in vitro cell culture medium.

Aspects of cell culture expansion 2810 can comprise adding non-dividing EBV-transformed lymphoblastoid cells (LCL) as feeder cells in accordance with some embodiments. Some embodiments can further comprise adding a CD3 agonist (e.g., anti-CD3 antibody) and a cytokine (e.g., IL-2) to the culture medium. Still further embodiments can comprise incubating the culture, thereby producing an expanded population of antigen specific, MHC-restricted T lymphocytes.

E. Formulation and Fill

In various aspects, formulation and fill 2810 comprises one or more steps that bring the expanded cell population to a therapeutic form suitable for administering to a subject. In various embodiments, formulation and fill 2810 comprises one or more steps that bring the expanded cell population to a form suitable as a precursor to administering to a subject. Formulation and fill 2810 steps can comprise generation of conditions suitable for maintaining a living cell population.

In various embodiments, formulation and fill 2810 can be important for stabilizing the expanded cell population to achieve reasonable shelf life and storage and handling conditions. Stabilization can include protection from aggregation, denaturation, or other degradative pathways. In various embodiments, a formulation can comprise therapeutic and additional molecules.

In various embodiments, additional molecules can comprise salt molecules in a solution (e.g., saline solution). Saline solution can be optimized for cell longevity during storage conditions. In various embodiments, the solution can comprise an organosulfur compound. In various embodiments, the solution can comprise dimethyl sulfoxide DMSO ($(CH_3)_2SO$).

In various embodiments, additional molecules can comprise molecules for stabilizing cells under conditions such as sugars and polyols. In some embodiments, harsh conditions can comprise dehydration. In various embodiments, harsh conditions can comprise elevated or decreased temperatures.

In various embodiments, additional molecules can comprise amino acids, surfactants, buffer agents (e.g., phosphate, acetate, citrate, succinate, or tris), tonicifying agents, preservatives, antioxidants, and chelators.

An exemplary formulation may comprise resuspension of a washed cell pellet in a 1:1 volume equivalent of two preformulated excipient solutions: 5% w/v human serum albumin (HSA) in saline, and CryoStor® CS10 (10% w/v DMSO).

In various aspects, formulation and fill 2810 comprises a process for filling one or more vessels with the therapeutic (e.g., a processed sample).

In various aspects of the methods described herein, can comprise a sterile transfer of the therapeutic (e.g., a treatment) from a cell expansion process to a cell therapy product vessel (e.g., an intravenous bag).

F. Treatment Administration

In various embodiments, treatment administration 2814 can be a final step in the exemplary cell therapy workflow 2800 where a treatment can be administered to a subject. In various embodiments, the treatment can be administered to the same subject providing the sample. In various embodiments, the treatment can be administered to a different subject than provided the sample. In some embodiments, the different subject receiving the treatment can be genetically matched with the subject providing the sample (e.g., they can be from the same family, such as siblings, or parent-offspring pairs, etc.).

In various embodiments, treatment administration 2814 can comprise administration of the treatment to the subject from the cell therapy product vessel. In various embodiments, intermediary steps can be required to prepare the treatment from the cell therapy product vessel.

G. Quality Control Assays

Various quality control assays 2850 can be used in the exemplary cell therapy workflow 2800. For example, a subject can be pre-screened, and a sample can be tested prior to entering the workflow, during the workflow, and the final product (e.g., the treatment) can be assayed for quality control purposes.

In various embodiments, quality control assays 2850 may relate to a health history of the subject, prescreening the subject for infectious disease or other illness, blood characterization tests, etc.

In various embodiments, quality control assays 2850 may be performed on the sample provided by the subject prior to being processed through a cell therapy manufacturing workflow 2800. In various embodiments, the sample can be assayed for volume and concentration (e.g., cell count and/or concentration of cells of interest). Observations may also be made during this time relating to cell morphology (e.g., cell shape, size, and physical characteristics).

In various embodiments, analytical devices such as flow cytometers and microscopes can be used to evaluate cell surface markers and cell purity. In various embodiments, dye exclusion assays may be performed for cell viability.

In various embodiments, quality control assays 2850 may be performed to ensure a subject is suitable to receive a treatment. In various embodiments, a human leukocyte antigen (HLA) assay may be performed. HLA assays can be performed when the subject providing a sample is not the same as a subject receiving the treatment. In various embodiments, an ABO blood test may be performed on the subject donor and the subject donee.

In various embodiments, quality control assays 2850 may be performed at any point during the cell therapy manufacturing workflow 2800, including for example, while in process. For example, the sample may be assayed for volume, cell concentration, cell number, and purity (e.g., steps 2804-2812).

In various embodiments, an in-process assay can comprise a confluence assessment. In various embodiments, the in-process assay for confluence assessment may comprise optical components for generating a quantitative measurement. In various embodiments, the in-process assay can comprise a gene expression assay.

In various embodiments, quality control assays 2850 (e.g., produce release quality control assays) may be performed after cell culture expansion 2810 has occurred. The assay may be direct to measuring volume, cell concentration, cell number, purity, and potency.

Aspects of evaluating cell therapy products often include the use of potency assays. In various embodiments, potency assays can quantitatively measure a biological activity of a product. In some embodiments, potency assays can describe the similarity between a desired clinical response and the biological activity.

In various embodiments, potency assays can be used for comparative purposes across and performed at the same time across more than one production sample.

In vitro potency assays can include measurement of a biochemical or physiological response. For example, cell surface markers and activation markers responding to potency can be assessed. Non-limiting examples of in vitro systems used for potency assays can include bead-based ELISA, and microfluidic cytometry (e.g., to determine cell size, cell shape, marker-based cell identity, cell viability, and the like.

An example of an in vitro cell function assay can include a cytotoxicity assay in accordance with various embodiments. In various embodiments, the cytotoxicity assay can comprise contacting one or more product T-cells with one or more targets. In various embodiments, cytotoxicity assays can include measuring a biomarker for apoptosis.

Non-limiting examples of biomarkers for apoptosis can include activated caspase 2, 3, 7, 8 and 9. In various embodiments, activated caspase 2, 3, 7, 8 and 9 may be detected by immunoreaction or substrate/active site interactions. An additional non-limiting example of a biomarker for apoptosis can comprise cytochrome c. In various embodiments, cytochrome c can be measured using an enzyme-linked immunosorbent assay. Another non-limiting example of biomarkers for apoptosis can comprise externalized phosphatidylserine. In various embodiments, externalized phosphatidylserine can indicate an early apoptosis event. In various embodiments, annexin binding to an externalized ligand can be measured. Nucleosomal DNA can be another non-limiting example of a biomarker for apoptosis. In various embodiments, polymerase chain reaction can be performed in nucleosomal DNA analysis. In various embodiments, polymerase chain reaction can be measured quantitatively.

IV. EXEMPLARY CELL THERAPY MANUFACTURING SYSTEM

A. Cell Therapy Manufacturing System Architecture

Figure 29A:
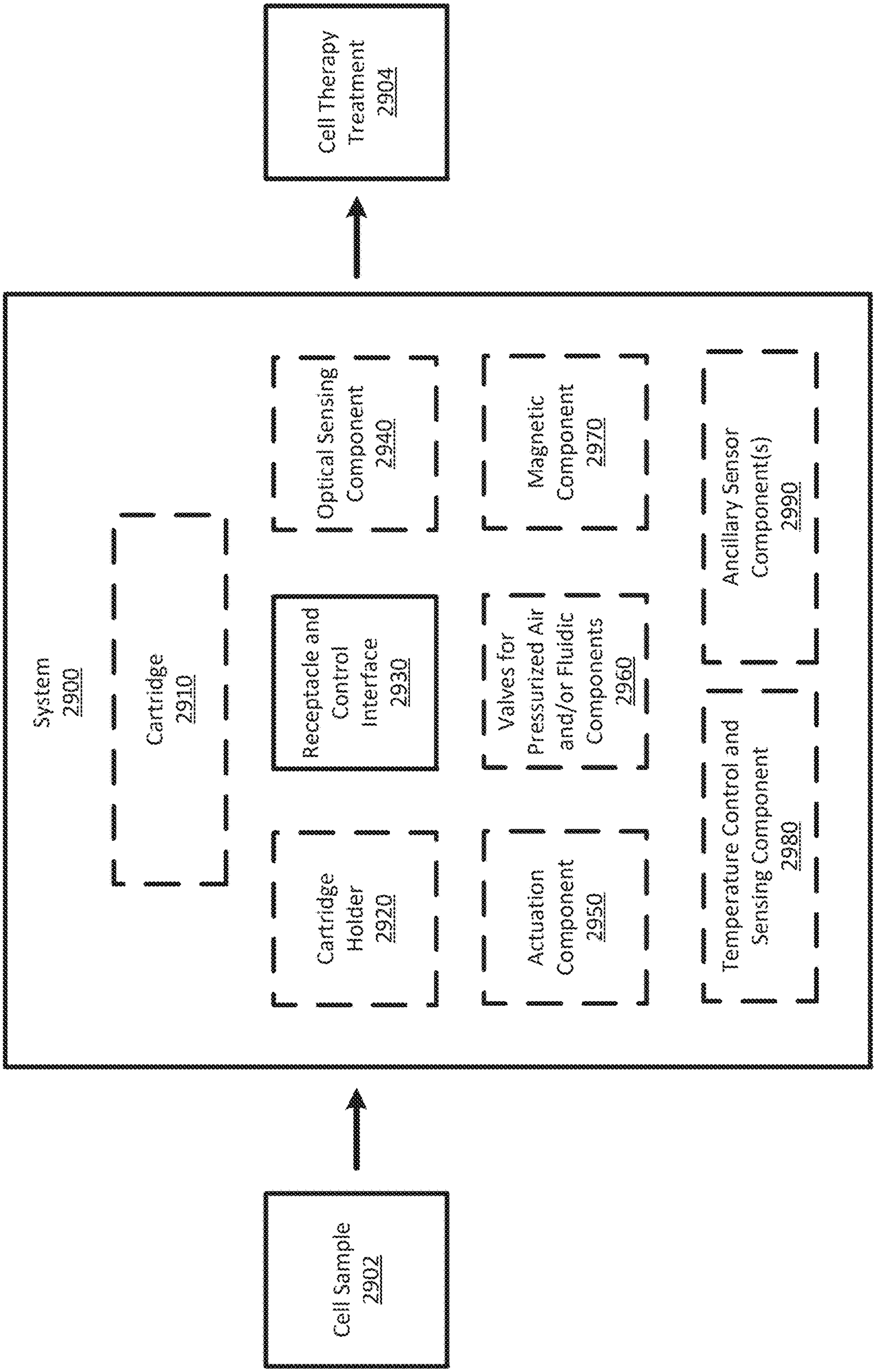
FIG. 29A illustrates a schematic block diagram of a cell therapy manufacturing system, in accordance with various embodiments.

FIG. 29A illustrates a schematic block diagram of a cell therapy manufacturing system (CTMS) 2900, in accordance with various embodiments. As illustrated in FIG. 29A, CTMS 2900, or the system 2900, is an apparatus for manufacturing therapeutic quantities of desired cells. For example, CTMS 2900 is designed to produce a cell therapy treatment 2904 based on input cell sample 2902. In accordance with various embodiments, the cell therapy treatment type or the cell type may include, for example, CAR cells, NK, T lymphocytes and other immune cells, hematopoietic progenitors and stem cells, including MSCs, and embryonic and induced pluripotent stem cells (iPSCs).

As illustrated in FIG. 29A, the CTMS 2900 is an integrated system configured to receive a self-contained cartridge (or cassette) 2910, which is designed for manufacturing a population of cells suitable for formulation as a cellular therapeutic. In accordance with various embodiments, the cartridge 2910 can include one or more components within the cartridge 2910 that is a sealed enclosure (e.g., hermetically sealed and/or sterile) with one or more inlet and/or outlet ports. In various embodiments, the cartridge 2910 can include a first fluidic network connected to an outlet port, a first reagent reservoir connected to the first fluidic network, a first cell analysis region connected to the first fluidic network, and a chamber for culturing cells. In various embodiments, the chamber can include a first input opening for introduction of fluid into the chamber, a first output opening for removal of fluid from the chamber, and a second output opening for removal of fluid from the chamber. In various embodiments, the chamber can be connected to each of the outlet port, the first reagent reservoir, and the first cell analysis region via the first fluidic network. In various embodiments, the first and second output openings can be positioned at different vertical elevations within the chamber. In various embodiments, an internal surface of a base of the chamber can include a plurality of concave features defined thereon. An example embodiment of the cartridge 2910 is further described in detail with respect to FIGS. 30A, 30B, and 31.

In accordance with various embodiments and implementations, the cartridge 2910 can be received optionally via a holder, such as, a cartridge holder 2920 (also referred to herein as "cassette holder 2920") of the CTMS 2900 and can be programed to interface via a receptacle and control interface 2930 (also referred to herein as receptacle 2930) of the CTMS 2900. In addition, the CTMS 2900 can include one or more components used in facilitating or enabling the manufacturing of cells within the CTMS 2900 and/or the cartridge 2910. As illustrated in FIG. 29A, the CTMS 2900 can optionally include an optical sensing component 2940, an actuation component 2950, one or more valves for pressurized air and/or fluidic components 2960, a magnetic component 2970, a temperature control and sensing component 2980, and/or one or more ancillary sensor component(s) 2990, as described further below.

Figures 29B, 29C:
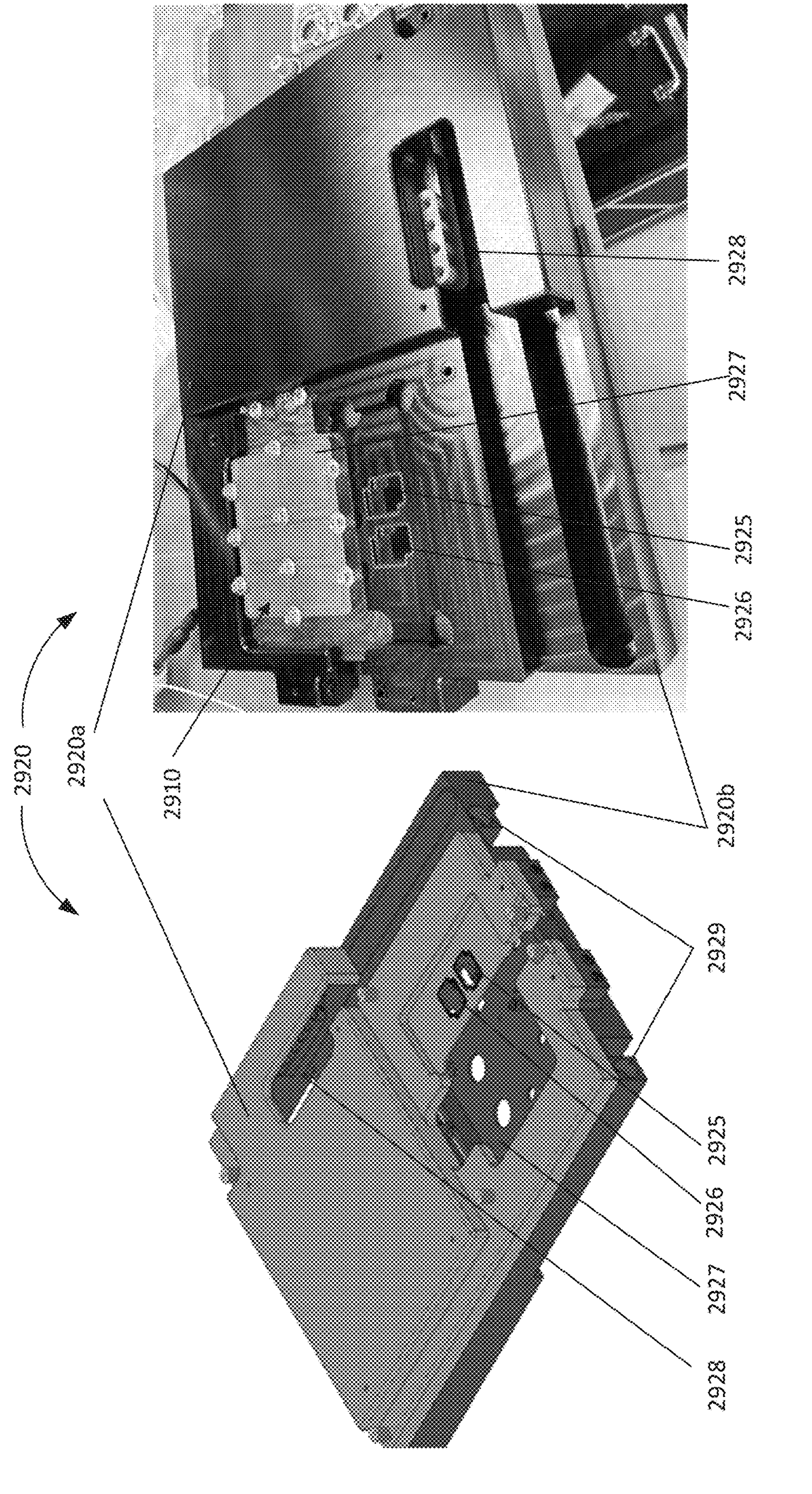
FIGS. 29B and 29C illustrate an example configuration of the CTMS system of FIG. 29A, in accordance with various embodiments.
Figure 29D:
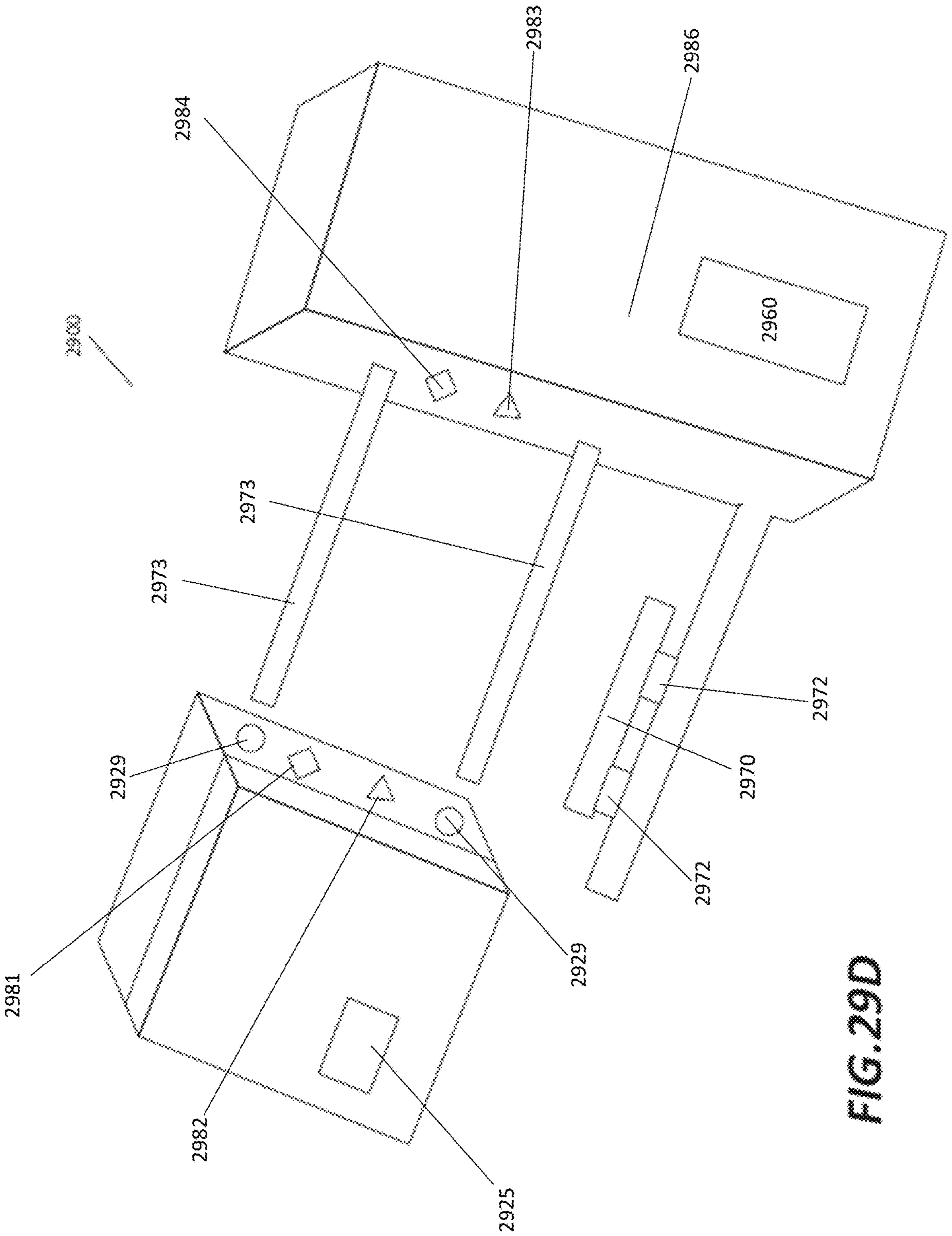
FIG. 29D and 29E illustrate an example configuration of various components of the cell therapy manufacturing system, in accordance with various embodiments.
Figure 29E:
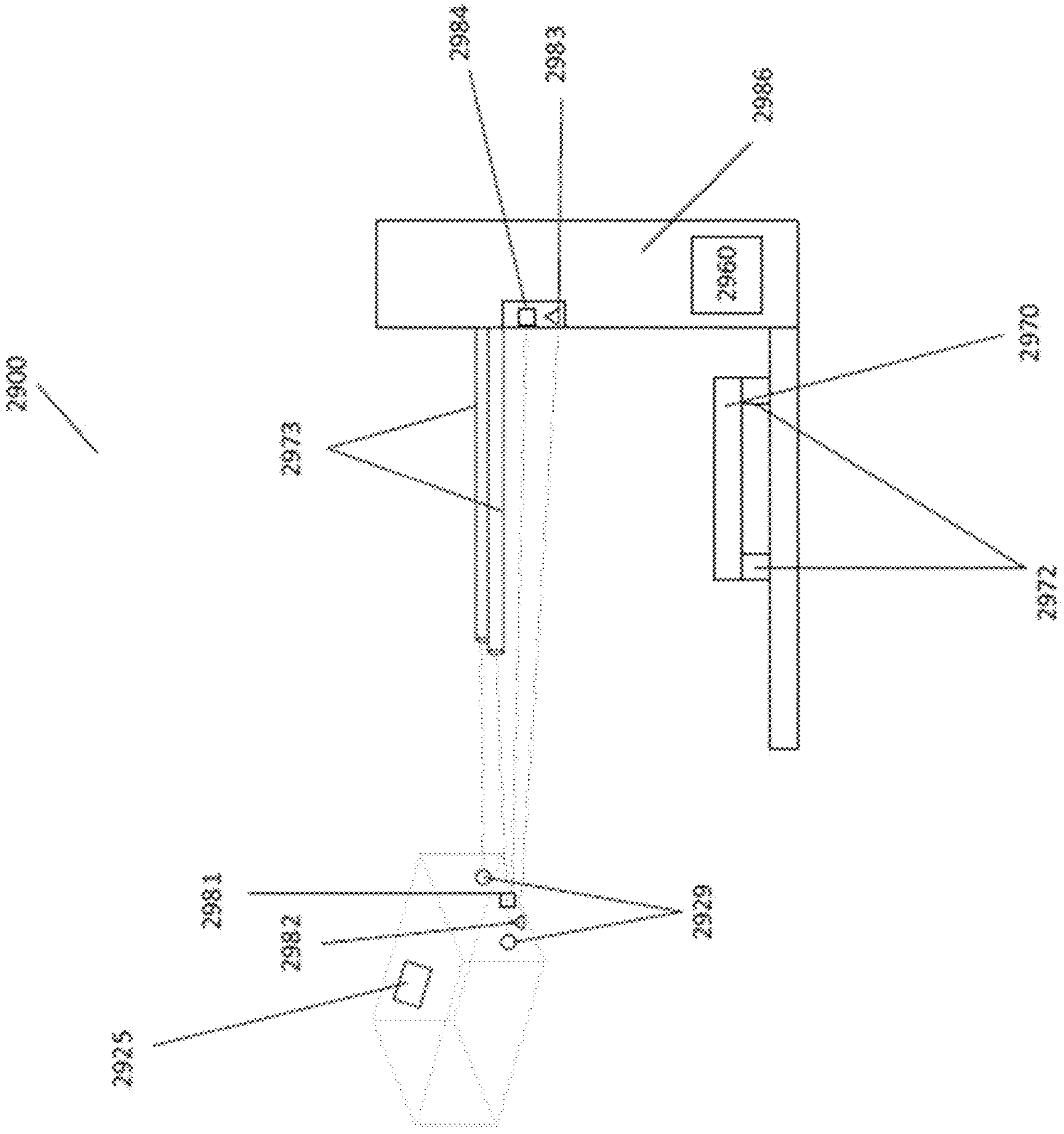

FIGS. 29B and 29C illustrate an example configuration of the CTMS system 2900 of FIG. 29A, in accordance with various embodiments. As illustrated in the example configuration of FIGS. 29B and 29C, the cartridge 2910 is encased within the cartridge holder 2920, which includes a first portion 2920*a* (e.g., a lid) and a second portion 2920*b* (e.g., a base) for enclosing, or partially enclosing, a cartridge 2910. As illustrated, the first portion of the cartridge holder 2920*a* includes, for example, four "windows", including windows 2925 and 2926 for each of the two microfluidic chips integrated into the cartridge 2910, a larger window 2927 adjacent to the two microfluidic chip windows, and a fourth window 2928 in the elevated first portion of the cartridge holder 2920*a*. This specific configuration with specific number of components or arrangements is illustrated merely as an example, and thus, non-limiting by any means. Further, the two latter windows 2927 and 2928 are configured to provide access to pneumatically actuated valves (not shown in FIGS. 29B and 29C) in the cartridge 2910, where each window include an open side to allow the cartridge 2910 to be removed from the cartridge holder 2920 easily, for example, without necessitating the disconnection of air supply lines (not shown) that control the valves, such as the one or more valves for pressurized air and/or fluidic components 2960. Also as illustrated in FIGS. 29D and 29H, the second portion of the cartridge holder 2920*b* may include a receiver 2929 for mounting the cartridge 2910 onto a receptacle 2973 the system 2900. In various embodiments, the mounted cartridge 2910 is positioned of the magnetic component 2970.

In various embodiments, a receiver 2929 may comprise one or more holes and a receptacle 2973 may comprise one or more rods for inserting into the one or more holes for mounting a cartridge 2910 to a cartridge holder 2920. In some embodiments, a receiver 2929 may comprise one or more grooves or protrusions and a receptacle 2973 may comprise one or more opposing protrusions or grooves for mounting a cartridge 2910 to a cartridge holder 2920. In some embodiments, a receiver 2929 may comprise one or more interlocking features and a receptacle 2973 may comprise one or more opposing interlocking features for mounting a cartridge 2910 to a cartridge holder 2920. In various embodiments, a receiver 2929 may comprise one or more tracks and a receptacle 2973 may comprise one or more rails for interacting with the one or more tracks for mounting a cartridge 2910 to a cartridge holder 2920.

As further illustrated in FIG. 29A, the receptacle and control interface 2930 (i.e., "receptacle 2930") of the CTMS 2900 is designed as a stage or nest for the cartridge 2910 and for interfacing with the cartridge 2910 with one or more components of the CTMS 2900. In various embodiments, the receptacle and control interface 2930 may include a pair of rods used as receptacle that can be inserted into holes of the second portion 2920*b* (e.g., a base) of the cartridge 2920. The illustrated use of rods to mount and position the cartridge holder 2920, which in turns mounts and positions the cartridge 2910, with respect to one or more other components within the CTMS 2900. One of the functions of the receptacle 2930 includes, for example, allowing the cartridge 2910 to be positioned with respect to an optical train within the CTMS 2900. The optical train is similar to the optical train described with respect to FIGS. 3A and 3B, and thus more detail can be found in the description of the optical train described with respect to FIGS. 3A and 3B. In various embodiments, the optical train is used as part of the optional optical sensing component 2940 in the CTMS 2900, which can enable OEP-enabled processes (also referred to herein as "OEP sensor 2940").

In various implementations, a configuration of the CTMS 2900 can include the cartridge holder 2920 that surrounds the cartridge 2910 partially or completely and can interface with the receptacle 2930 at a receiving position within the CTMS 2900. In various embodiments, the CTMS 2900 may include some means for manipulating the cartridge 2910 and/or the cartridge holder 2920, for example, via an actuation mechanism, as illustrated in FIG. 29A. In various embodiments, the actuation mechanism may be operated via an actuation component 2950 (also referred to herein as "actuation mechanism 2950"), which can be configured to traverse, tilt, actuate, oscillate, or otherwise manipulate one or more components in the cartridge 2910 or the cartridge 2910 itself with respect to the CTMS 2900. In various embodiments, the actuation component 2950 can also be designed to actuate or oscillate the cartridge 2910, and thereby facilitating mixing a medium and cells within a bioreactor of the cartridge 2910.

In various embodiments, one or more valves for pressurized air and/or fluidic components 2960 may include valve control, for example, a mechanical or rotary valve, or via pneumatic actuation, e.g., pneumatically actuated valves supported by one or more pumps (not shown). FIGS. 29D, 29E, and 29I illustrate an example configuration of various components of the CTMS 2900, in accordance with various embodiments. In various embodiments, the cell therapy manufacturing system 2900 can comprise an instrument 2986 (e.g., a housing) for organizing various components of the system 2900. In some embodiments, an instrument 2986 can be any device (e.g., a bread board or an industrial design) to hold, organize, mount, and/or power any of the components or sub-components described herein. In various embodiments, the instrument 2986 comprises one or more receptacles 2973 for mounting a cartridge holder 2920 to the CTMS 2900. In various embodiments, the cartridge holder can comprise a first portion 2920*a* and a second portion 2920*b* of the cartridge holder. In various embodiments, the first portion 2920*a* and the second portion 2920*b* can encase a cartridge 2910. In various embodiments a window 2927 of the first portion 2920*a* of the cartridge holder 2910 can provide optical access to the encased cartridge 2910. In various embodiments, one or more windows can provide one or more analytical devices access to contents of the cartridge (e.g., cells).

As illustrated in FIGS. 29D, 29E and 29I, the cartridge 2910/cartridge holder 2920 can slide along the pair of rods that are used as receptacle to move to and from the one or more valves for pressurized air and/or fluidic components 2960, thereby enabling physical connections of one or more inlets and/or outlets of the cartridge 2910 with the one or more valves for pressurized air and/or fluidic components 2960. In various embodiments, a physical connection may comprise coupling a fluidic connector 2981 of the cartridge holder 2920 to an opposing fluidic connector 2983 of the instrument 2986, thereby, joining one or more fluidic networks of the CTMS system 2900. In some embodiments, the fluidic connectors 2981, 2983 include connections for one or more individual lines. In some embodiments, the fluidic connectors 2981, 2983 include connections for one or more manifolds for ease of connecting multiple individual lines at once. In various embodiments, the fluidic connectors 2981, 2983 may include one or more single-use aseptic connection manifolds. In various embodiments, the fluidic connectors 2981, 2983 may include one or more single-use aseptic connection input ports and/or one or more single-use aspect connection outlet ports.

In various embodiments, the control systems described herein benefit from electronic communication occurring between the various components (e.g., the components of the instrument 2986, the cartridge holder 2920, and the cartridge 2910 of the CTMS system 2900. In various embodiments, a cartridge holder 2920 can comprise an electronic connector 2982. In various embodiments, a second portion 2920*b* of the cartridge holder can comprise the electronic connector 2982. In various embodiments, an instrument 2986 can comprise an opposing electronic connector 2984. In various embodiments, the electronic connectors 2982, 2984 can provided electronic communication between the described components of the CTMS system 2900.

Figure 29F:
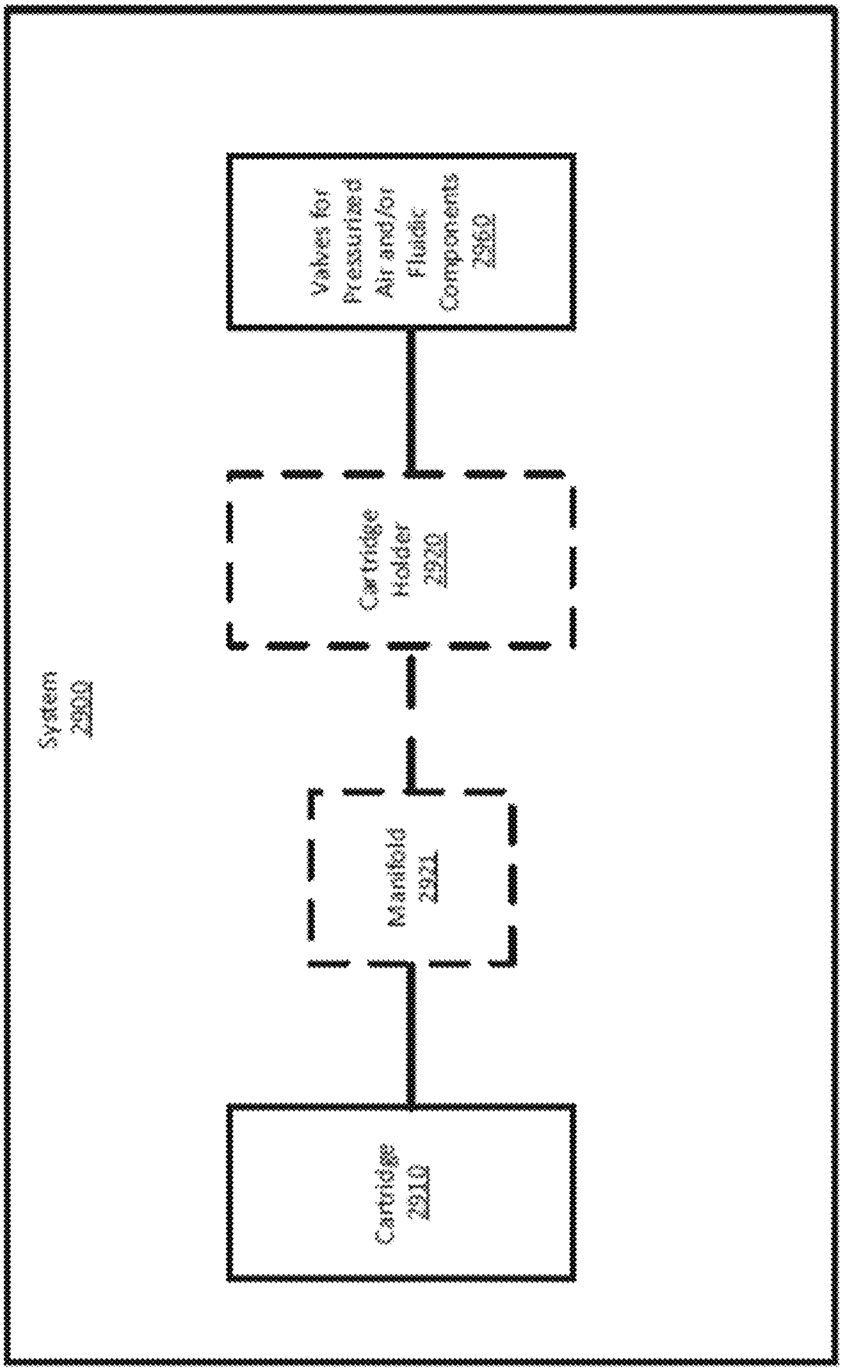
FIG. 29F illustrates another example configuration of various components of the cell therapy manufacturing system, in accordance with various embodiments.

FIG. 29F illustrates another example configuration of various components of the cell therapy manufacturing system, in accordance with various embodiments. In various embodiments, the connection lines for pressurized air or fluidic connections can go directly to the cartridge 2910 to the one or more valves for pressurized air and/or fluidic components 2960. As illustrated in FIG. 29F, the connection lines between the cartridge 2910 and one or more valves for pressurized air and/or fluidic components 2960 can be connected through the cartridge holder 2920, in accordance with one or more embodiments. In accordance with various embodiments, the cartridge holder 2920 can include a manifold 2921 for interfacing with one or more connectors on the cartridge 2910. In accordance with various embodiments, the manifold 2921 can provide sterility in the connection between an external source and the cartridge 2910 and/or cartridge holder 2920. In various embodiments, the manifold 2921 can be a one-time use disposable manifold. In some embodiments, the connection lines between the cartridge 2910 and one or more valves for pressurized air and/or fluidic components 2960 can be connected through the manifold 2921. In more than one embodiments, the connection lines between the cartridge 2910 and one or more valves for pressurized air and/or fluidic components 2960 can be connected through the manifold 2921 and the cartridge holder 2920.

In various embodiments, the CTMS 2900 may include magnet component 2970, as illustrated in FIGS. 29D, 29E, and 29I. In various embodiments, the magnet component 2970 can offer non-contact manipulation of the cells and medium within the cartridge 2910 (e.g., within a bioreactor of the cartridge 2910). In various embodiments, the magnet component 2970 can be moved closer to, or farther away from, one or more components (e.g., bioreactor) of the cartridge 2910, as illustrated in FIGS. 29D, 29E, and 29I. In various embodiments, the magnet component 2970 can be moved up and/or down with respect to the bottom surface of the cartridge 2910/cartridge holder 2920. In various embodiments, the movement of the magnetic component 2970 can be facilitated by a mechanical drive 2972. In various embodiments, the mechanical drive 2972 can comprise a screw assembly and the movement of the magnet component 2970 can be facilitated by the use of a screw movement (e.g., a screw of the screw assembly) or any other suitable mechanism with fine and/or precision control. In various embodiments, the magnet component 2970 can include permanent magnet, rare-earth metal based permanent magnet, or electromagnets, which can be used to manipulate magnetic beads within the bioreactor, for example, to selectively pull-down magnetic beads towards the bottom of the bioreactor. In various embodiments, Cells can bind to magnetic beads according to the methods described herein.

As further illustrated in FIG. 29A, the CTMS 2900 can optionally include a temperature control and sensing component 2980 (also referred to herein as "thermal system 2980") can be configured to enable temperature regulation of one or more temperature zones or areas within the cartridge 2910. In various embodiments, the temperature control and sensing component 2980 can be configured to regulate the temperature via one or more included/embedded heating elements in the cartridge 2910 or one or more heating elements placed proximal to one or more areas/zones of the cartridge 2910 for heating, controlling, and/or maintaining a pre-set temperature or range of temperatures for the one or more designated areas/zones. In various embodiments, the heating element may include a resistive heating or thermoelectric heating, such as Peltier heating. In various embodiments, the temperature may be regulated via a cooling mechanism that can include liquid or air cooling.

In various embodiments, the CTMS 2900 may also optionally include ancillary sensor component(s) 2990, such as, an oxygen sensing component or oxygen sensor (now shown) or pH sensing component or pH sensor (also not shown). The oxygen sensor, for example, can be configured to sense an amount of oxygen present in any of the one or more components in the cartridge 2910 or the CTMS system 2900. The pH sensing component or pH sensor, for example, can be configured to sense pH of one or more fluids that contain within the cartridge 2910 or the CTMS 2900. In various embodiments, the CTMS 2900 can also include a non-optical sensing component, which can be configured for manipulation of various materials within the cartridge 2910.

In various embodiments, the CTMS 2900 further includes ancillary components (not shown) to provide support to one or more functions of the cartridge 2910. Example ancillary components may include, but not limited to, fluid pump, vacuum or suction pumps, etc. In various embodiments, the ancillary components of the CTMS 2900 may include inlet and/or outlet ports for connecting to a media bag containing reagents and cells for culturing.

Figure 29G:
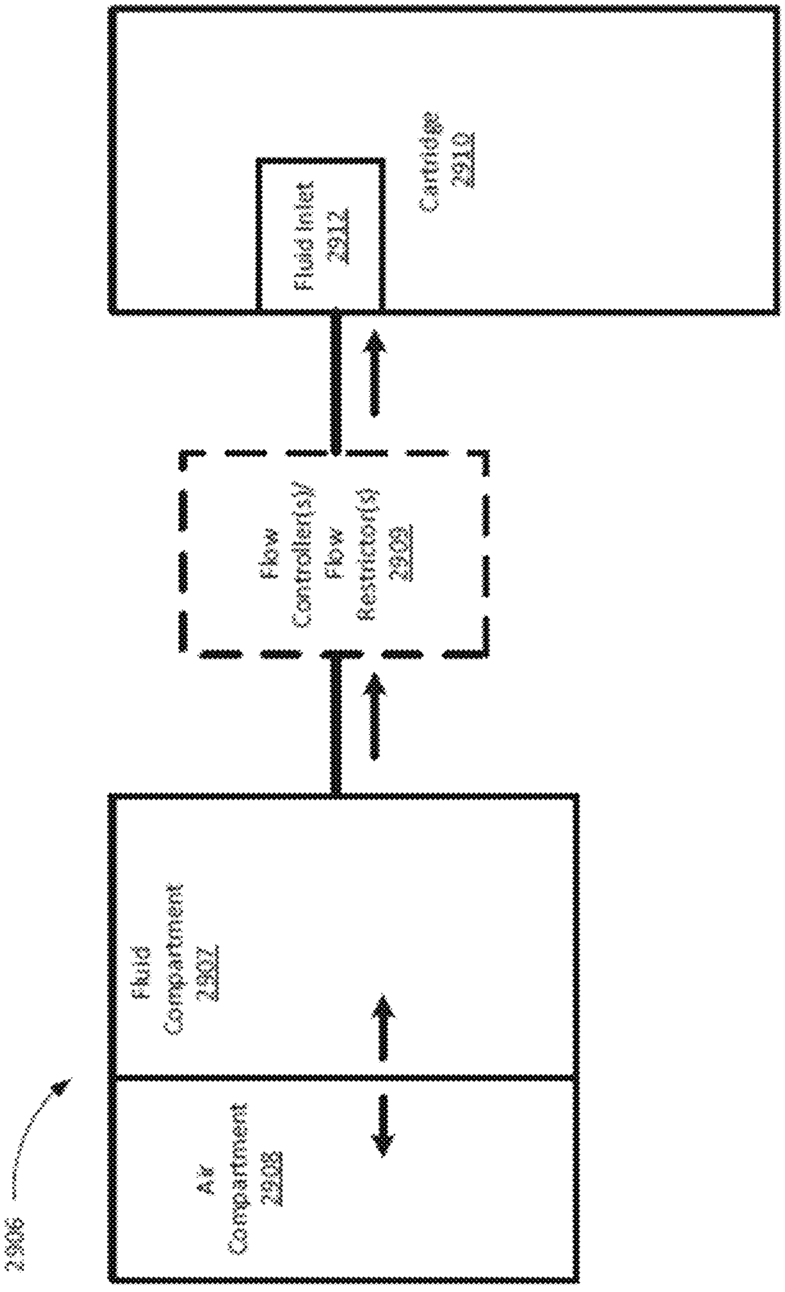
FIG. 29G illustrates an example configuration of an external (media) bag in connection with various components of the cell therapy manufacturing system, in accordance with various embodiments.
Figure 29H:
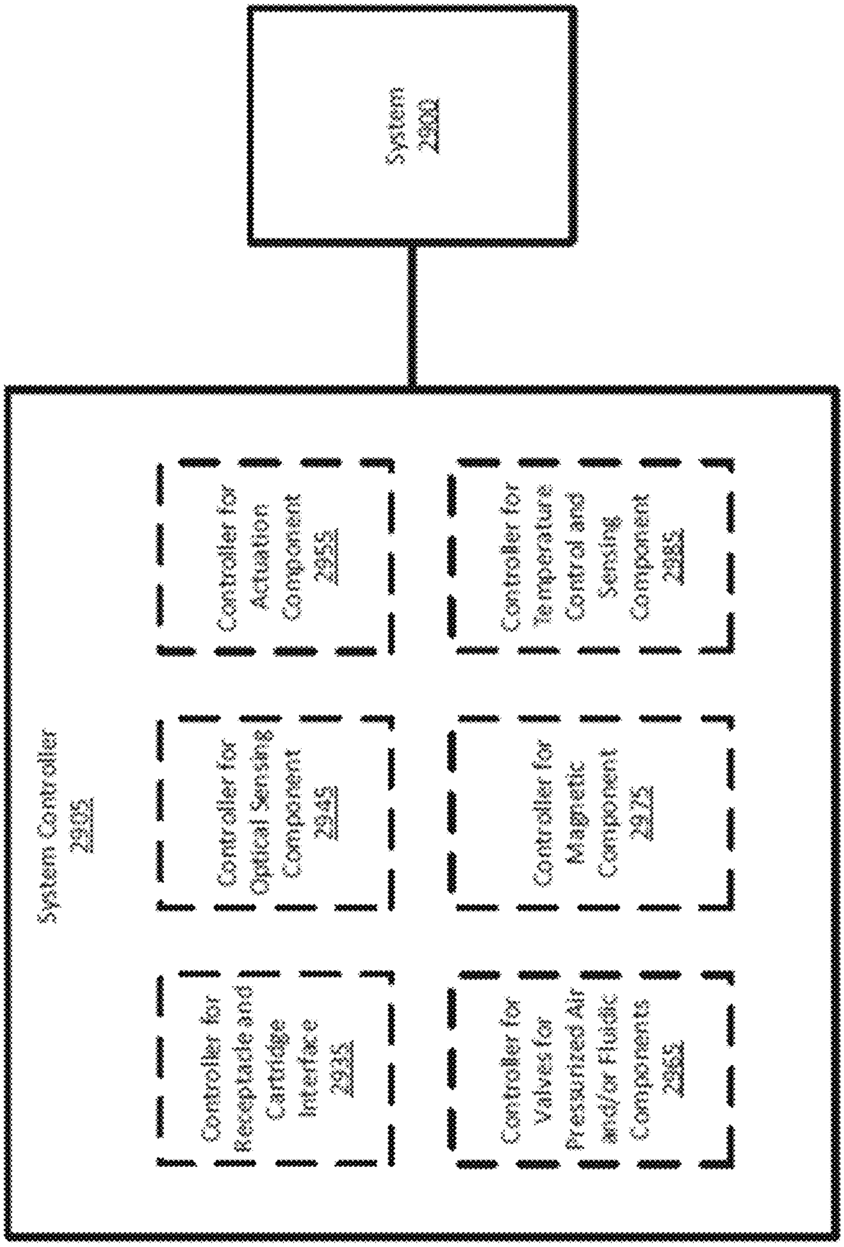
FIG. 29H illustrates additional components of the cell therapy manufacturing system, in accordance with various embodiments.
Figure 29I:
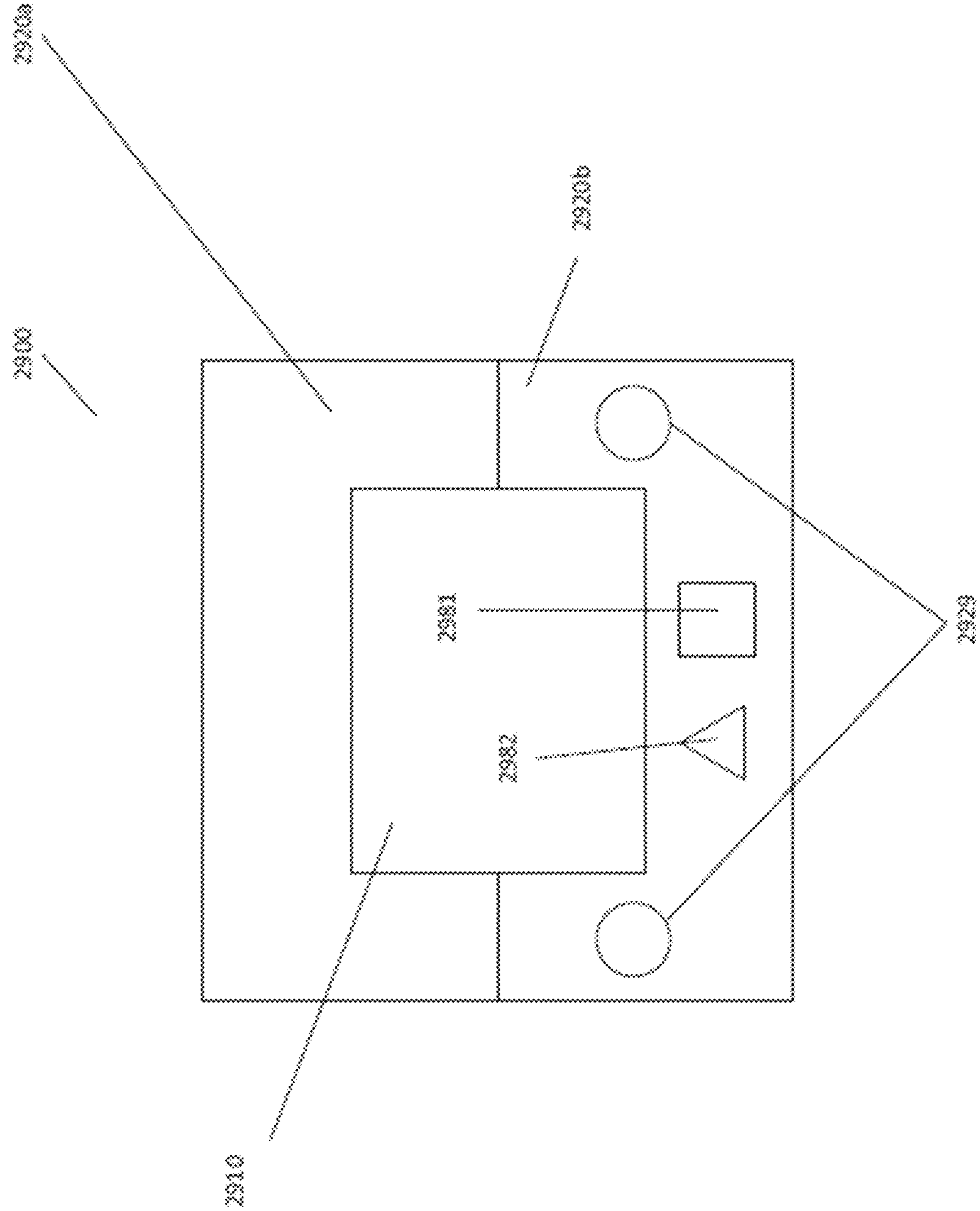
FIG. 29I illustrates an example configuration of various components of the cell therapy manufacturing system, in accordance with various embodiments.

FIG. 29G illustrates an example configuration of an external (media) bag in connection with various components of the cell therapy manufacturing system, in accordance with various embodiments. As illustrated in FIG. 29G, a media bag 2906 can include a fluid compartment 2907 and an air compartment 2908. By filling or pressurizing the air compartment 2908 with a fluid (i.e., air or gas), the fluid compartment 2907 can be squeezed to pump out a fluid, such as reagent, growth or culture media. As further illustrated in FIG. 29G, the outflow of the fluid from the fluid compartment 2907 can be regulated or controlled to flow at a desired flow rate by using an optional flow controller(s) or flow restrictor(s) 2909 along the connection line between the media bag 2906 and an inlet of the cartridge 2910 (and/or via the cartridge 2920 and/or the manifold 2921).

In various embodiments, for each or subset of components of the CTMS 2900, one or more controllers can be interfaced to control or facilitate various aspects and functions of each individual component of the CTMS 2900. Further detail of the one or more controllers of the components of the CTMS 2900 is described below with respect to FIG. 29G.

As illustrated in FIG. 29G, the CTMS 2900 can be controlled via a system controller implemented to be used with the system 2900, in accordance with various embodiments. In accordance with various implementations, the CTMS 2900 includes a system controller 2905 for controlling various components of the system and for interfacing with an operator or a user. In various embodiments, the CTMS 2900 may include a user interface (not shown) for operation of the CTMS 2900.

As illustrated in FIG. 29H, the system controller 2905 can be configured to control the CTMS 2900 (or the system 2900), where the system controller 2905 can include a controller for each of the components, multiple components, or a subset of components of the CTMS 2900. In various embodiments, the system controller 2905 can include a controller for receptacle and control interface 2935, a controller for optical sensing component 2945, a controller for actuation component 2955, a controller for one or more valves for pressurized air and/or fluidic components 2965, a controller for magnetic component 2975, a controller for temperature control and sensing component 2985, in accordance with various embodiments disclosed herein.

In various embodiments, the controller for receptacle and control interface 2935 used for in operating or controlling the receptacle and control interface 2930 as a stage or nest for the cartridge 2910 and for interfacing with the cartridge 2910 with one or more components of the CTMS 2900 and the system controller 2905. In various embodiments, the controller for receptacle and control interface 2935 can be used to move the cartridge holder 2920 to move along on the pair of rods that are inserted into holes of the base of the cartridge 2920. The operator or the user of the CTMS 2900 may be able to use the controller for receptacle and control interface 2935 to control movements and positioning of the cartridge holder 2920, which in turns controls the movements and positioning of the cartridge 2910, with respect to one or more other components within the CTMS 2900. This includes positioning the cartridge 2910 and/or the cartridge holder 2920 with respect to an optical train within the CTMS 2900 to enable OEP-enabled processes.

In various embodiments, the controller for optical sensing component 2945 is a control system or module for interacting with the optical sensing component 2940 and to facilitate OEP-enabled processes and to manipulate various materials within the cartridge 2910. In various embodiments, the optical sensing component 2940 of the CTMS 2900 is configured to work with microfluidic devices or chips that are integrated within the cartridge 2910. In various embodiments, the microfluidic devices or chips can include optically-actuated electrokinetic devices, devices having an optoelectronic tweezer (OET) configuration, and devices having an opto-electrowetting (OEW) configuration. Examples of microfluidic devices or chips that are integrated within the cartridge 2910 include pens in which biological micro-objects can be placed, cultured, and/or monitored, in accordance with various embodiments. As disclosed herein, the cartridge 2910 may include one or more microfluidic devices or chips that are capable of working with the optical sensing component 2940 of the CTMS 2900. Additionally or alternatively, the cartridge 2910 may include one or more microfluidic devices or chips that are capable of working with non-optical sensing component for manipulation of various materials within the cartridge 2910. Further detail with respect to controller for optical sensing component 2945 and optical sensing component 2940 or OEP-based techniques are described with respect to FIGS. 1B and 1C, and an example optical setup is illustrated and described with respect to FIG. 3B.

In various implementations, positioning or manipulating of the cartridge 2910 and/or the cartridge holder 2920, for example, can be controlled via the controller for actuation component 2955. This controller 2955 allows the operator or the user to move, tilt, actuate, oscillate, or otherwise manipulate one or more components in the cartridge 2910 or the cartridge 2910 itself with respect to the CTMS 2900. In various embodiments, the controller for actuation component 2955 can also be used to actuate or oscillate the cartridge 2910, and thereby facilitating mixing a medium and cells within a bioreactor of the cartridge 2910. In various embodiments, an input for the controller for actuation component 2955 can be from the user or the operator, or the input can be based on pre-programmed set of actions based on feedback from the CTMS 2900, for example.

In various embodiments, the controller for one or more valves for pressurized air and/or fluidic components 2965 enables the operator or the user to configure a control of one or more valves, including a mechanical or rotary valve, or via pneumatic actuation, e.g., pneumatically actuated valves supported by one or more pumps (not shown). In various embodiments and implementations, the controller for one or more valves for pressurized air and/or fluidic components 2965 can be used for controlling fluid flow (e.g., air or liquid, including reagent, culture or growth media) between a media bag and one or more inlets and/or outlets of the cartridge 2910. In various embodiments, the controller for one or more valves for pressurized air and/or fluidic components 2965 can be used to control fluid flow in the connection lines at one or more portions between the media bag and one or more inlets and/or outlets (e.g., fluid inlet 2912) of the cartridge 2910, including along the connection lines connected through the manifold 2921 and/or the cartridge holder 2920, with or without one or more flow controller(s) or flow restrictor(s) 2909, as illustrated in FIGS. 29F and 29G.

In various embodiments, the controller for magnet component 2975 enables the operator or the user to configure non-contact manipulation of the cells and medium within the cartridge 2910 (e.g., within a bioreactor of the cartridge 2910). In various embodiments, the controller for magnet component 2975 can be configured to move closer to, or farther away from, one or more components (e.g., bioreactor) of the cartridge 2910, as illustrated in FIGS. 29D and 29H. In various embodiments, the magnet component 2970 can be controlled via the controller 2975 to move up and/or down with respect to the bottom surface of the cartridge 2910/cartridge holder 2920. In various embodiments, the movement of the magnet component 2970 can be facilitated by controlling the rotation of the screw or any other suitable mechanism with fine and/or precision control. In various embodiments, by controlling the movement of the magnet component 2970, the operator or the user can manipulate magnetic beads within the bioreactor, for example, to selectively pull-down magnetic beads towards the bottom of the bioreactor in the cartridge 2910.

In various embodiments, the CTMS 2900 includes a controller for temperature control and sensing component 2985 for interacting with temperature control and sensing component 2980. In various embodiments, the controller for temperature control and sensing component 2985 can be configured to enable temperature regulation of one or more temperature zones or areas within the cartridge 2910. In various embodiments, the controller for temperature control and sensing component 2985 can be configured to maintain one or more zones, areas, or components with a pre-set temperature. For example, the cartridge 2910 can be configured by the operator or the user to maintain a warm zone that includes a bioreactor, another warm zone (perhaps with a different temperature setting) that includes the OEP chips, one or more cold zones that include one or more reservoirs for storing reagents or the like, and one or more zones that are kept at room or ambient temperature for some of the reservoirs. In various embodiments, the controller for temperature control and sensing component 2985 allows configuring an experimental condition such that the temperature or range of temperature in each of the zones/areas/components in the cartridge 2910 can be pre-set or maintained for each zone, each area, or each component individually, independently of others, in groups of two, three, or four, or altogether. With the disclosed capabilities of the temperature control and sensing component 2980 and its controller 2985, maintaining certain temperatures in certain zones while keeping a different temperature in a different zone can help the CTMS 2900 to maintain reagents or cells or enabling cell growth, etc., at their respective optimal environment.

In various embodiments, the system controller 2095 may include a controller (e.g., control system or module) for interacting with various ancillary sensor component(s) 2990, including for example, oxygen sensing component or oxygen sensor or pH sensing component or pH sensor. In various embodiments, the pH sensing component or pH sensor may be located in the CTMS system 2900 or in the cartridge 2910. In various embodiments, the pH sensor 2980 may be located in the bioreactor section or other portions of the cartridge 2910, and fluidically coupled to the bioreactor or any other portions that a pH measurement is needed. In various embodiments, the pH sensor can be configured for constant, intermittent, or scheduled monitoring of the pH in the bioreactor wherein a portion of the fluid of the bioreactor is sampled periodically.

In various embodiments, the system controller 2095 may include a controller (e.g., control system or module) for interacting with non-optical sensing component 2990 for manipulation of various materials within the cartridge 2910.

B. CELL THERAPY MANUFACTURING CARTRIDGE

Figure 30A:
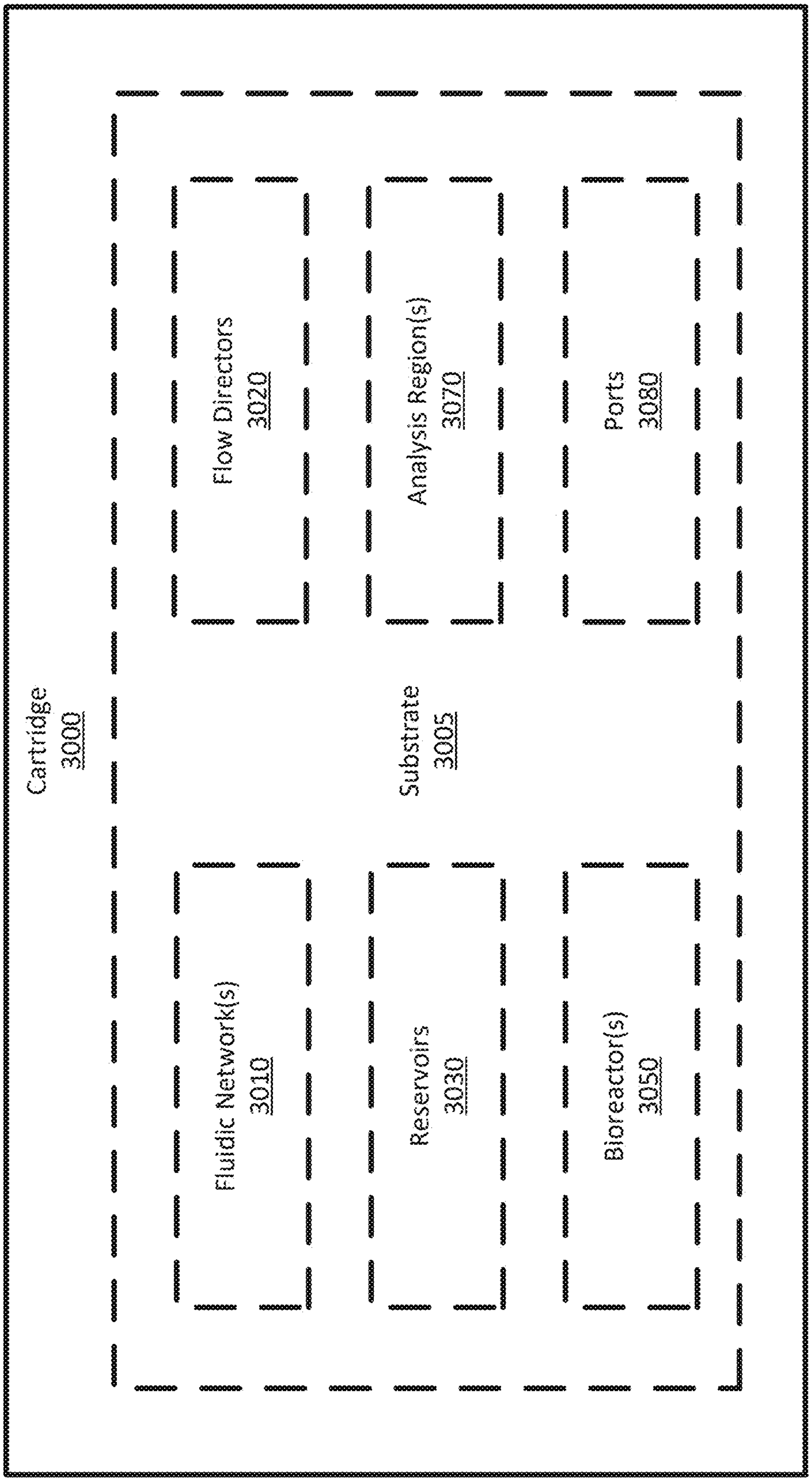
FIG. 30A illustrates a schematic block diagram of a cell therapy manufacturing system cartridge, in accordance with various embodiments.

Now referring to FIG. 30A, which illustrates a schematic block diagram of a cell therapy manufacturing system cartridge 3000 (also referred to herein as "CTMS cartridge 3000" or "cartridge 3000"), in accordance with various embodiments. The cartridge 3000 is designed for manufacturing a population of cells suitable for formulation as a cellular therapeutic. The cartridge 3000 is designed to work with a system, such as, the CTMS system 2900 of FIG. 29A. The term cartridge and cassette are used interchangeably throughout this disclosure, thus, cartridge 3000 can be referred to as cassette 3000. In various embodiments, a single cartridge 3000 can be used for various biochemistry applications, including for example, but not limited to, TCR, CAR-T, stem, TIL, etc.). Biochemistry may be different for each specific configuration of the cartridge 3000. In various embodiments, a single cartridge 3000 is used for a single biochemistry application.

As illustrated in FIG. 30A, the cartridge 3000 includes a substrate 3005 that houses a plurality of components, which include, but not limited to, one or more fluidic network(s) 3010 (also referred to as "fluidic networks 3010"), one of more flow director(s) 3020 (also referred to as "flow directors 3020"), one or more reservoir(s) 3030 (also referred to as "reservoirs 3030"), one or more bioreactor(s) 3050 (also referred to as "bioreactor 3050"), one or more analysis region(s) 3070 (also referred to as "analysis regions 3070"), and/or a plurality of ports 3080 (also referred to as "ports 3080"). Depending on the configuration, the cartridge 3000 can include any or all of the components illustrated in FIG. 30A.

In various embodiments, the substrate 3005 (also referred to herein as "frame 3005") can be made of Ultem or polypropylene, or any suitable material.

In various embodiments, the fluidic networks 3010 include a plurality of interconnected channels to and from various components of the cartridge 3000. In various embodiments, the fluidic networks 3010 include a plurality of valves and/or flow directors that are used to manipulate a flow of fluids, which may contain, for example but not limited to, reagents, cells, etc. within the channels to and from various components of the cartridge 3000. In various embodiments, the fluidic networks 3010 can be coupled to one or more inlets or outlets for introduction of a cell sample from a subject or removal of materials (e.g., waste fluid, resuspended cells, etc.) from the cartridge 3000.

In various embodiments, the flow directors 3020 can include a plurality of valves, including but not limited to rotary valves, 2-way or 4-way valves, etc. In various embodiments, the flow directors 3020, in conjunction with the fluidic networks 3010, can manipulate the flow of fluids within the cartridge 3000. For example, the flow directors 3020 in combination with the fluidic networks 3010 can be used to mix fluids, isolate certain channels, declog/clear the channels, sterilize the channels, and in some instances, can help with reducing dead volumes within the channels (e.g., by using gas to push fluids in one or more of the channels) of the fluidic networks 3010.

In various embodiments, the reservoirs 3030 can include reservoirs for storing reagents or cells. In various embodiments, one or more of the reservoirs 3030 are in fluid communication with the flow directors 3020 and/or one or more of channels of the fluidic networks 3010.

In various embodiments, reagents can be stored in one or more reservoirs 3030 for use during operation of the cartridge 3000. In various embodiments, reagents can be replenished or added to the cartridge 3000 via one or more ports 3080, which are connected directly to one or more bags of reagents or indirectly via one or more fluidics connections, for example, of the CTMS 2900 illustrated and described with respect to FIGS. 29A and 29B.

In various embodiments, the bioreactor 3050 can be designed for culturing cells. The bioreactor 3050 can include a plurality of openings (e.g., inlet ports), a base, side walls, and/or a moveable lid.

In various embodiments, the bioreactor 3050 can include functionalized surfaces within any or all surfaces of the bioreactor 3050. In various embodiments, the functionalized surfaces include chemically functionalized surfaces, biochemically functionalized surfaces, biologically functionalized surfaces, structurally engineered surfaces, among many other approaches.

In various embodiments, the functionalized surfaces include concave features, such as, dimples, various shapes and aspect ratio of features, including for example, hemi-spherical, oval, etc. The cartridge of any one of claims 1 to 17, wherein each concave feature of the plurality of concave features on the internal surface of the base of the first chamber defines a hemi-spherical cavity. In various embodiments, each concave feature of the plurality of concave features on an internal surface of the base (e.g., a floor or lowest center of gravity) of the chamber (e.g., a bioreactor)

defines an elongated cavity (e.g., in the shape of a bisected tear-drop) and, optionally, wherein a long axis of each elongated cavity is substantially parallel to a long access of every other elongated cavity of the plurality of concave features.

In various embodiments, each elongated cavity includes a deepest point, wherein the long axis of each elongated cavity includes a first end and a second end, wherein an angle defined by the internal surface of the base of the chamber and a line segment connecting the first end of the long axis with the deepest point of the elongated cavity is between 45° and 90°. In various embodiments, an angle defined by the internal surface of the base of the chamber and a line segment connecting the second end of the long axis with the deepest point of the elongated cavity is less than 45°.

In various embodiments, a line segment connecting the first end of the long axis with the deepest point of the elongated cavity is shorter than a line segment connecting the second end of the long axis with the deepest point of the elongated cavity.

In various embodiments, one or more functionalized surfaces of the bioreactor 3050 can be used for activating T cells. In various embodiments, one or more functionalized surfaces of the bioreactor 3050 can be used for surface blocking ligands.

In various embodiments, the bioreactor 3050 is fluidically coupled to the fluidic networks 3010 via one or more of the plurality of openings.

In various embodiments, the bioreactor 3050 includes an inlet to the bioreactor 3050 for introduction of fluid (e.g., cell sample, culture medium, reagents, etc.) into the bioreactor 3050.

In various embodiments, the bioreactor 3050 can include a moveable lid, which can be actuated via, for example, a pneumatic actuator, to facilitate the flow of medium, e.g., reagents and cells, in and/or out of the bioreactor 3050. In various embodiments, the bioreactor 3050 can include a mechanism for using pressurized air or gas to facilitate the flow of medium, e.g., reagents and cells, in and/or out of the bioreactor 3050.

In various embodiments, the analysis regions 3070 may include a hemocytometer or one or more microfluidic chips or devices that can be used with an optical-based sensing component, such as, the optical sensing component 2940 of the CTMS 2900, or any suitable optical based analysis technique. In various embodiments, the microfluidic chips or devices (also referred to herein as "OptoElectroPositioning chip" or simply "OEP-chip") can include electrode activation substrate for use with a method based on dielectrophoresis. In various embodiments, the microfluidic chips or devices that are OEP-chips and are capable of performing optical-based cell manipulation, can enable Poisson loading of cells, although not required during the loading of the cells. For example, a microfluidic chip or device has a dielectrophoresis (DEP) configuration, DEP force can be used to load the cells in or out of a channel or a chamber, such as a bioreactor 3050. As described in various embodiments herein, the DEP force can be generated optically, such as by an optoelectronic tweezers (OET) configuration and/or electrically, such as by activation of electrodes/electrode regions in a temporal/spatial pattern. Similarly, electrowetting force may be provided optically, such as by an opto-electro wetting (OEW) configuration and/or electrically, such as by activation of electrodes/electrode regions in a temporal spatial pattern. Thus, in accordance with various embodiments, the DEP force can be activated by structured light, such as a light included as part of the optical-based sensing component 2940. Additional details of optical-based sensing approach are described further below with respect to FIGS. 1B and 1C.

In various embodiments, the analysis regions 3070 may include a hemocytometer or one or more microfluidic chips or devices that can be used with the non-optical sensing component 2990 of the CTMS 2900 (also referred to herein as "Non-OEP Chip"). In various embodiments, the microfluidic chips or devices that are non-OEP do not include electrode activation surface, and accordingly, the substrate can have any substrate surface. Accordingly, the non-OEP microfluidic chips or devices may need Poisson loading of cells.

i. Bioreactor Modules

Figure 35:
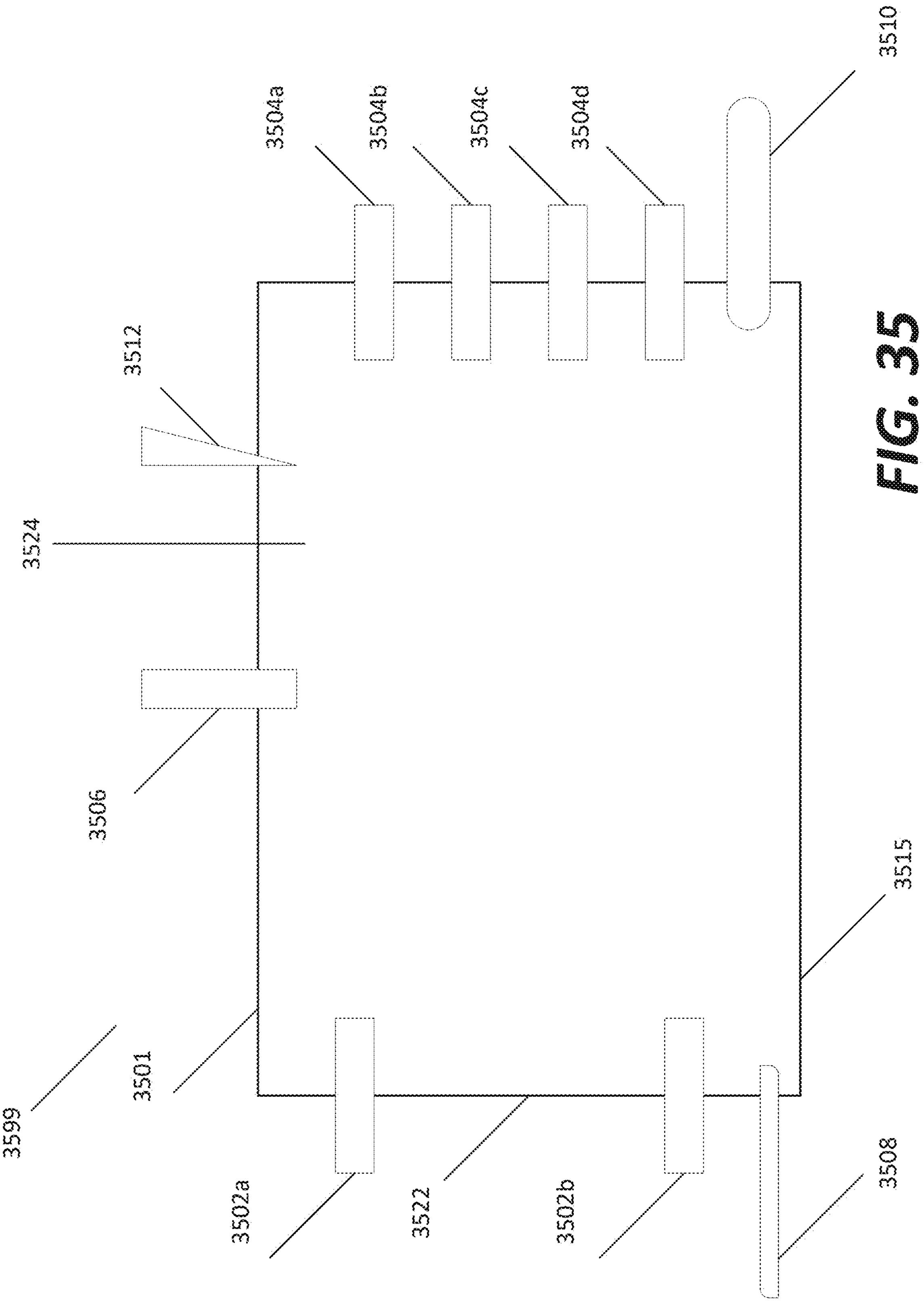
FIG. 35 is an illustration of a bioreactor of a cell therapy manufacturing system according to various embodiments.

As illustrated in FIG. 35, a bioreactor 3599 is provided in accordance with various embodiments. In various embodiments, the bioreactor 3599 can be fluidically connected to a fluidic network of the CTMS. In various embodiments, the bioreactor 3599 comprises a sterile bioreactor compartment 3524 connected to the fluidic network through one for more inlet ports 3502*a*, 3502*b*.

In various embodiments, inlet ports 3502*a*, 3502*b* can be positioned at pre-selected elevations. In various embodiments, inlet ports 3502*a*, 3502*b* can allow reagents, media, cells, etc. to enter the bioreactor 3599 and facilitate the various processes and methods (e.g., sorting, T-cell activation, expansion) described herein. In various embodiments, inlet ports 3502*a*, 3502*b* can comprise valves.

In various embodiments, one or more sensors 3508, 3510, 3512 may be fluidically or optically connected to the bioreactor 3599. In various embodiments, aliquots of a fluid from within the bioreactor 3599 can be removed and directed to the one more sensors 3508, 3510, 3512 for analysis. In alternative embodiments, the one or more sensors 3508, 3510, 3512 can be in direct fluidic or optical contact with the contents (e.g., a fluid) within the bioreactor compartment 3524 of the bioreactor 3599.

In various embodiments, the one or more sensors comprise a dissolved oxygen sensor 3508. In various embodiments, the one or more sensors comprise a pH sensor 3510. In various embodiments, the one or more sensors comprise a pressure sensor 3512. In various embodiments, the one or more sensors comprise a temperature sensor.

In various embodiments, the one or more sensors 3508, 3510, 3512 can electronically communicate with the control system. In response to an environmental condition or a step in a pre-defined process, the control system can activate a temperature control and sensing component, a tilt mechanism and actuation component, one or more valves, a gas source, or any other component of the system.

In various embodiments, fluid may exit the bioreactor 3599 through one or more outlet ports 3504*a*, 3504*b*, 3504*c*, 3504*d*. In various embodiments, outlet ports 3504*a*, 3504*b*, 3504*c*, 3504*d* may comprise valves.

In various embodiments, the bioreactor 3599 can comprise an access port 3506.

In various embodiments, the bioreactor 3599 comprises a bioreactor wall 3522. The bioreactor wall 3522 can take any shape capable for forming a bioreactor compartment 3524. In various embodiments, the bioreactor wall 3522 comprises a surface 3515 (e.g., an interior surface). In some embodiments, all or a part of the surface 3515 can be functionalized to create an antigen-presenting surface.

ii. In-Line QC Assay Modules

Returning to FIG. 30A, in various embodiments, the analysis regions 3070 can be used for various assay types. In various embodiments, the analysis regions 3070 of the cartridge 3000 provides unique capabilities for facilitating in-line quality control assays (e.g., cell count and viability), as described in further details here and below.

One advantage aspect of performing an in-line QC assay is the ability for the CTMS system and cartridge 3000 to perform the assay without having to take samples out of the cartridge and/or system to provide a constant, intermittent, and/or scheduled quality control check as needed.

In various embodiments, the ports 3080 include one or more input and output ports for fluid intake and/or outflow. In various embodiments, the ports 3080 of the cartridge 3000 are fluidically connected to one or more tubes, reservoirs, pumps, etc. of a system, such as the CTMS 2900 illustrated and described with respect to FIGS. 29A and 29B.

Figure 30B:
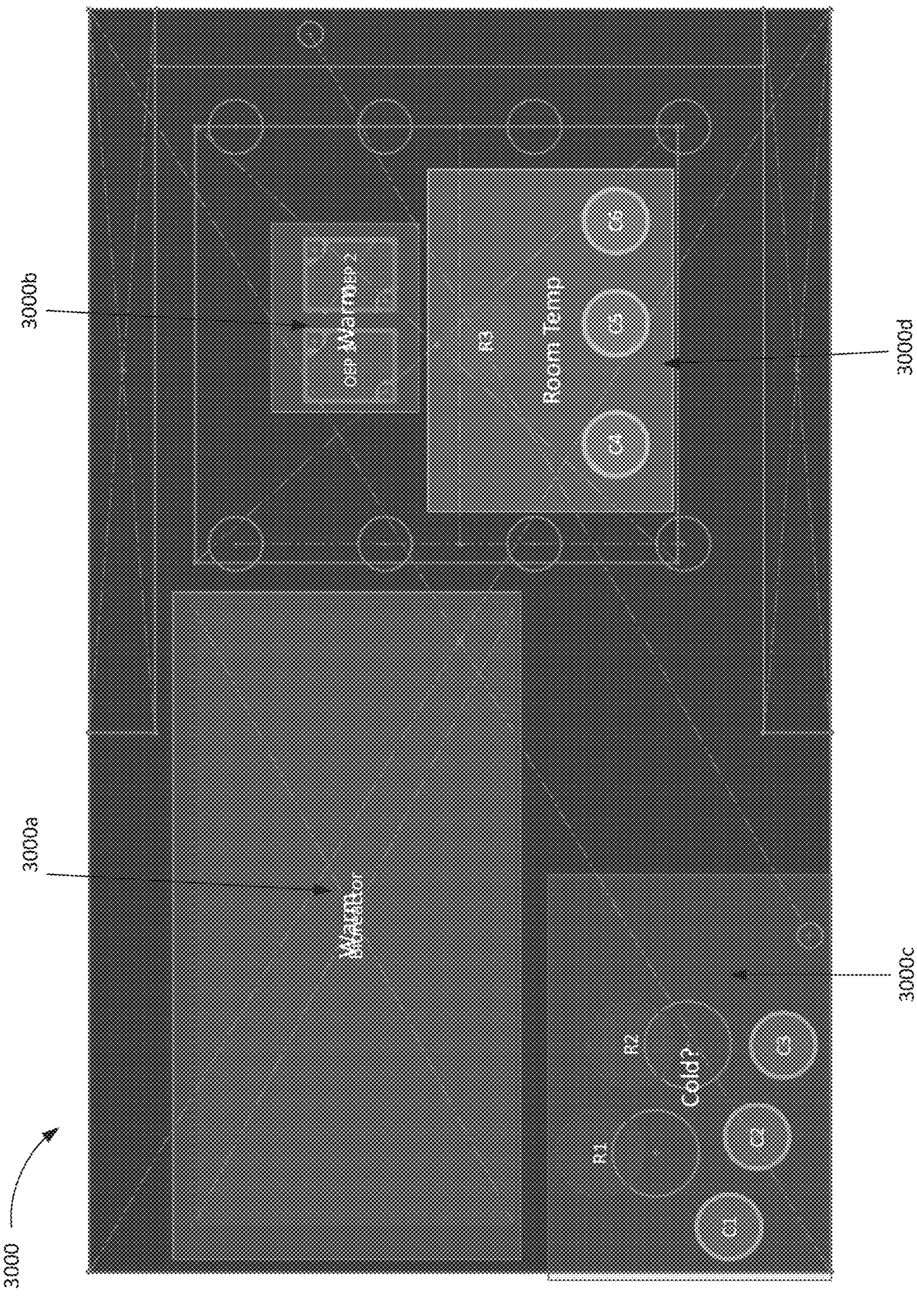
FIG. 30B illustrates a cartridge including one or more zones, areas, or components with a pre-set temperature, in accordance with various embodiments.

As illustrated in FIG. 30B, cartridge 3000 can include one or more zones, areas, or components with a pre-set temperature, in accordance with various embodiments. As shown in the figure, the cartridge 3000 includes a warm zone 3000*a* that includes a bioreactor, another warm zone 3000*b* (perhaps with a different temperature setting) that includes the OEP chips, one or more cold zones 3000*c* that include one or more reservoirs for storing reagents or the like, and one or more zones 3000*d* that are kept at room or ambient temperature for some of the reservoirs. In various embodiments, the temperature or range of temperature in each of the zones/areas/components in the cartridge 3000 can be pre-set or maintained for each zone, each area, or each component individually, independently of others, in groups of two, three, or four, or altogether. Maintaining certain temperatures in certain zones while keeping a different temperature in a different zone may help with maintaining reagents or cells or enabling cell growth, etc., at their respective optimal environment.

Figure 31:
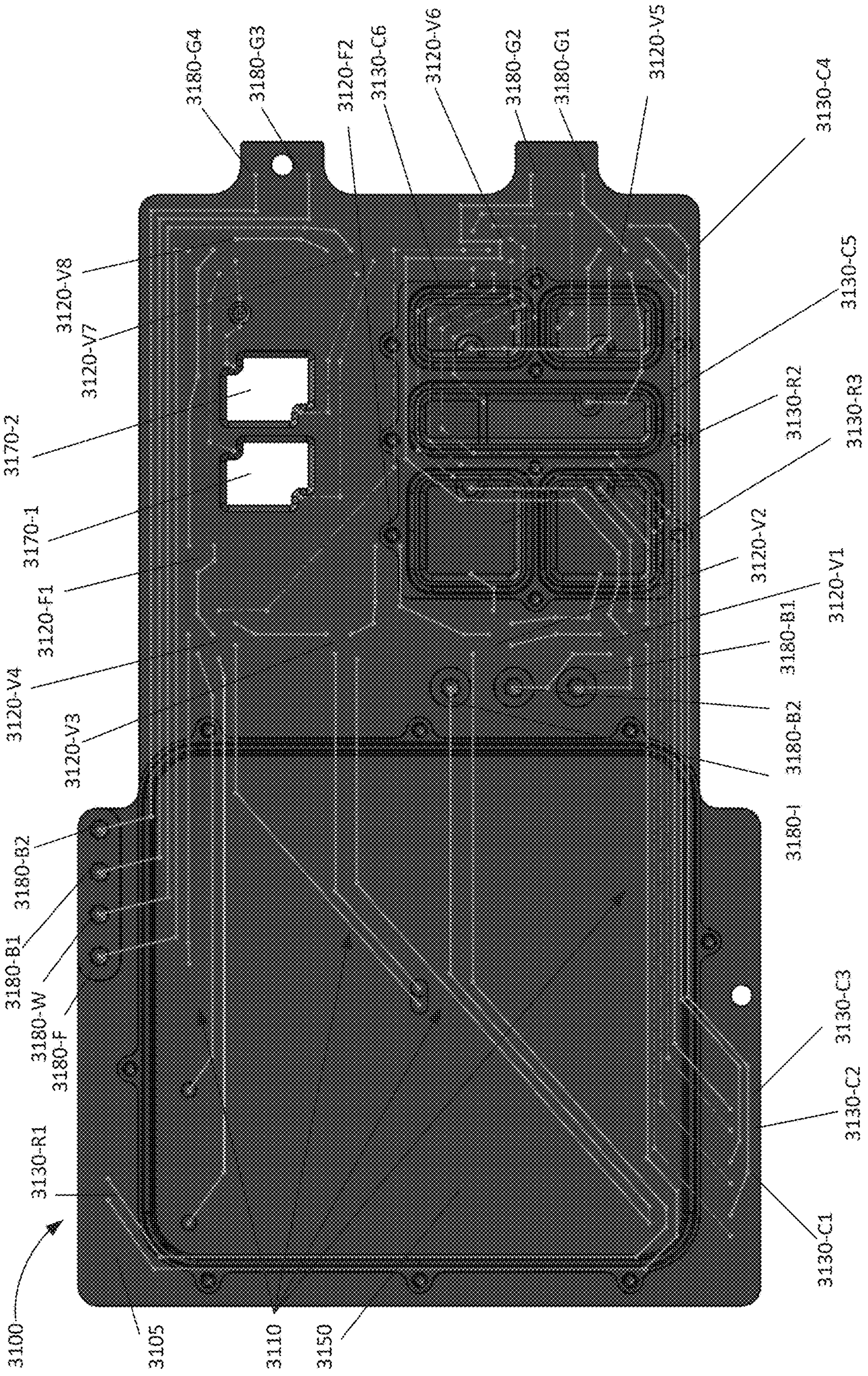
FIG. 31 illustrates an example configuration of a cartridge, in accordance with various embodiments.

FIG. 31 illustrates an example configuration of a cartridge 3100, in accordance with various embodiments. Although shown in a specific layout in the illustration of FIG. 31, the placement of any or all of the components illustrated in the cartridge 3100 can be designed based on the specificities and configuration of the cell therapy manufacturing system (CTMS) used in manufacturing of cells.

As illustrated, the cartridge 3100 includes a substrate 3105 that houses a plurality of components, which include, but not limited to, one or more fluidic networks 3110 (also referred to as "fluidic networks 3110"), one of more flow directors 3120 (also referred to as "flow directors 3120"), one or more reservoirs 3130 (also referred to as "reservoirs 3130"), one or more bioreactors 3150 (also referred to as "bioreactor 3150"), one or more analysis regions 3170 (also referred to as "analysis regions 3170"), and/or a plurality of ports 3180 (also referred to as "ports 3180").

In various embodiments, the fluidic networks 3110 include a plurality of interconnected channels to and from various components, such as, for example, one or more flow directors 3120, one or more reservoirs 3130, the bioreactor 3150, one or more analysis regions 3170, or one or more ports 3180.

As illustrated in FIG. 31, the flow directors 3120 include flow directors 3120-F1 and 3120-F2 (collectively referred to herein as "3120-F") and a plurality of valves 3120-V1, 3120-V2, 3120-V3, 3120-V4, 3120-V5, 3120-V6, 3120-V7, and 3120-V8 (collectively referred to herein as "valves 3120-V").

In various embodiments, the flow directors 3120-F may be flow meters or thermal flow sensors.

In various embodiments, the plurality of valves 3120-V are rotary valves configured for flow control of one or more channels within the fluidic networks 3110. In various embodiments, the plurality of valves 3120-V are controlled via a motor to rotate to open and close certain channels that the specific value is fluidically connected to.

In various embodiments, the plurality of valves 3120-V are made of PEEK, PTFE, Ultem, or any suitable material.

In various embodiments, the reservoirs 3130 include a plurality of reservoirs 3130 for storing reagent. In various embodiments, the plurality of reservoirs 3130 include QC reagent reservoirs 3130-C1, 3130-C2, 3130-C3, 3130-C4, 3130-C5, and 3130-C6 (collectively referred to herein as "QC reagent reservoirs 3130-C") and bioreactor reagent reservoirs 3130-R1, 3130-R2, 3130-R3 (collectively referred to herein as "bioreactor reagent reservoirs 3130-R").

In various embodiments, the QC reagent reservoirs 3130-C are configured to store reagent for use in QC. In various embodiments, the QC reagent reservoirs 3130-C have a storage volume from about 0.01 mL to about 50 mL, from about 0.1 mL to about 25 mL, or from about 1 mL to about 5 mL, inclusive of any storge volume range therebetween. In various embodiments, the QC reagent reservoirs 3130-C are configured to store reagent at room temperature or at ranges of temperature between about 0° C. and about 45° C., about 2° C. and about 35° C., or about 4° C. and about 25° C., inclusive of any temperature ranges therebetween.

In various embodiments, the bioreactor reagent reservoirs 3130-R are configured to store reagent for use in the bioreactor 3150. In various embodiments, the bioreactor reagent reservoirs 3130-R have a storage volume from about 0.01 mL to about 80 mL, from about 0.1 mL to about 30 mL, or from about 1 mL to about 8 mL, inclusive of any storge volume range therebetween. In various embodiments, the bioreactor reagent reservoirs 3130-R are configured to store reagent at ranges of temperature between about 0° C. and about 45° C., about 2° C. and about 35° C., or about 4° C. and about 25° C., inclusive of any temperature ranges therebetween.

In various embodiments, the plurality of reservoirs 3130 are made of Ultem; COC, COP, Polycarbonate, or any suitable material.

In various embodiments, the bioreactor 3150 is configured to culture cells (e.g., T-cell expansion). In various embodiments, the bioreactor 3150 is configured to perform sorting processes (e.g., T-cell sorting). In various embodiments, the bioreactor 3150 is configured to perform activation processes (e.g., T-cell activation). In various embodiments, the bioreactor 3150 is configured to perform sortavation processes (e.g., T-cell sorting and activation as parallel processes). In various embodiments, the bioreactor 3150 can perform the steps of the processes using an automated control system for introducing and removing fluids or heat, increasing or decreasing dissolved gas concentrations within the fluid, altering pH of the fluid, as non-limiting examples of controllable environmental conditions of a bioreactor 3150.

In various embodiments, the bioreactor 3150 is configured to perform biochemical reactions at ranges of temperature between about 18° C. and about 45° C., about 21° C. and about 40° C., or about 25° C. and about 36° C., inclusive of any temperature ranges therebetween.

In various embodiments, the analysis regions 3170 are used for conducting QC assays. In various embodiments, the analysis regions 3170 include one or more microfluidic chips or devices, such as analysis regions 3170-1 and 3170-2 that can be used with an optical-based sensing component, such as, the optical sensing component 2940 of the CTMS 2900, or any suitable optical based analysis technique, or used with the non-optical sensing component 2990 of the CTMS 2900. Regardless of the technique being used, the analysis regions 3170 are configured to perform assays pertinent for cell manufacturing. In various embodiments, the microfluidic chips or devices that are integrated in the analysis regions 3170 of the cartridge 3100 may or may not include substrates with electrode activation surfaces. In various embodiments, the analysis regions 3170 are configured to perform the analysis at ranges of temperature between about 0° C. and about 70° C., about 10° C. and about 60° C., or about 18° C. and about 50° C., inclusive of any temperature ranges therebetween.

In various embodiments, the plurality of ports 3180 include a plurality of ports for fluid intake and/or outflow. As illustrated in FIG. 31, the plurality of ports 3180 include ports 3180-G1, 3180-G2, 3180-G3, and 3180-G4 (collectively referred to herein as "ports 3180-G") for connecting to gas sources, for example, for intake of gas to use in moving fluids and/or media within the fluidic networks 3110 or any of the other components within the cartridge 3100. In various embodiments, the plurality of ports 3180 include an injection port 3180-1 for injecting materials, including cells and/or fluids into the cartridge 3100, final port 3180-F for outputting final products, waste port 3180-W for storing waste from the reactions within the cartridge 3100, and ports 3180-B1 and 3180-B2 for attaching bags of media, fluids, and/or any pertinent materials to be input or output from the cartridge 3100.

V. EXEMPLARY CELL THERAPY MANUFACTURING PROCESSES

In various embodiments, the methods for cell therapy manufacturing described in this section can be carried out using a cell therapy manufacturing system 3700 (see FIG. 37A) and subsystems described in the various sections herein. Various processes of the cell therapy manufacturing system 3700 can be directed toward receiving a cell sample and then processing the sample or a portion of the sample (e.g., culturing) to produce a product (e.g., a cell therapy product).

Figure 37A:
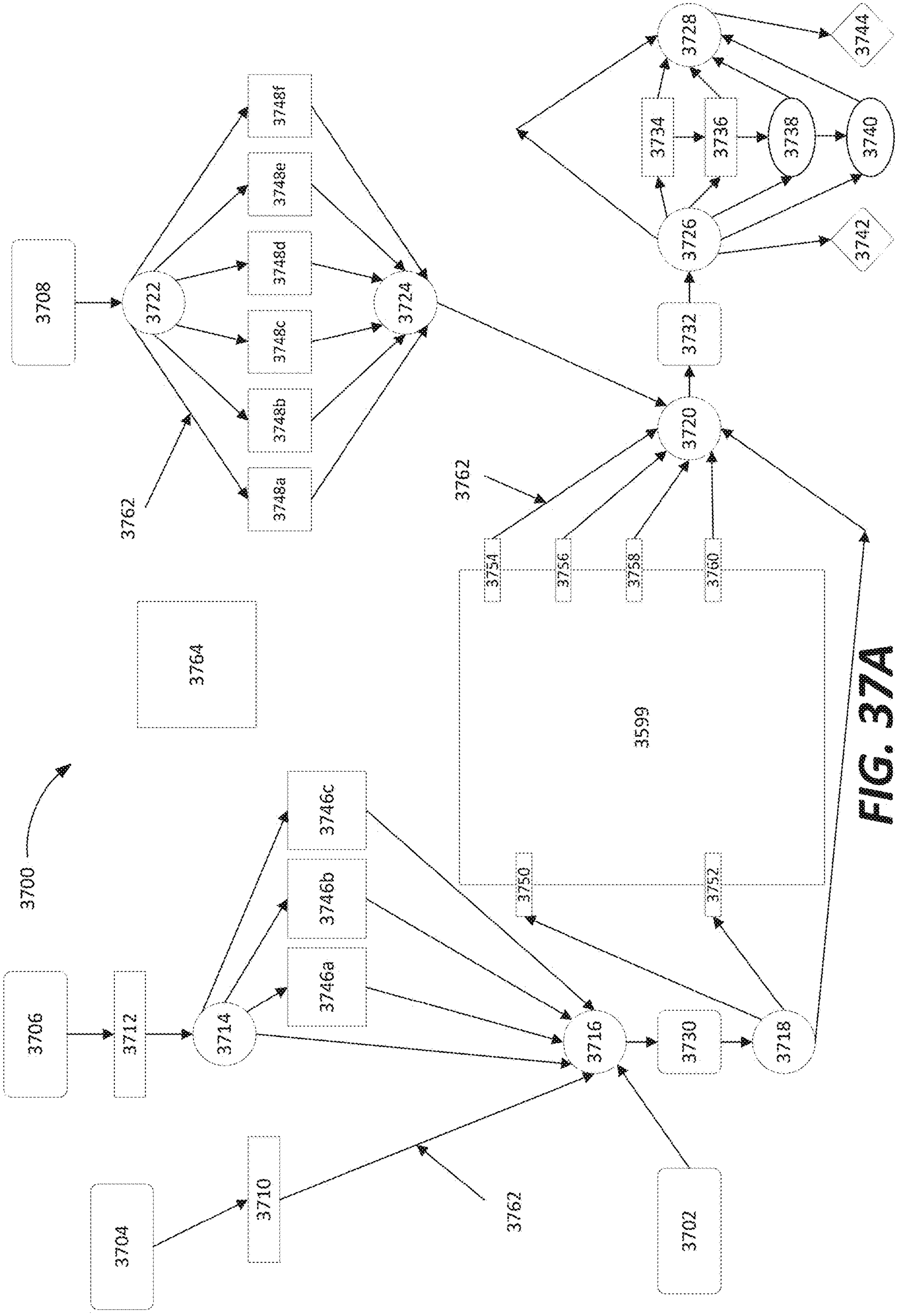
FIG. 37A illustrates a process flow diagram for a cell therapy manufacturing system according to various embodiments.
Figure 37B:
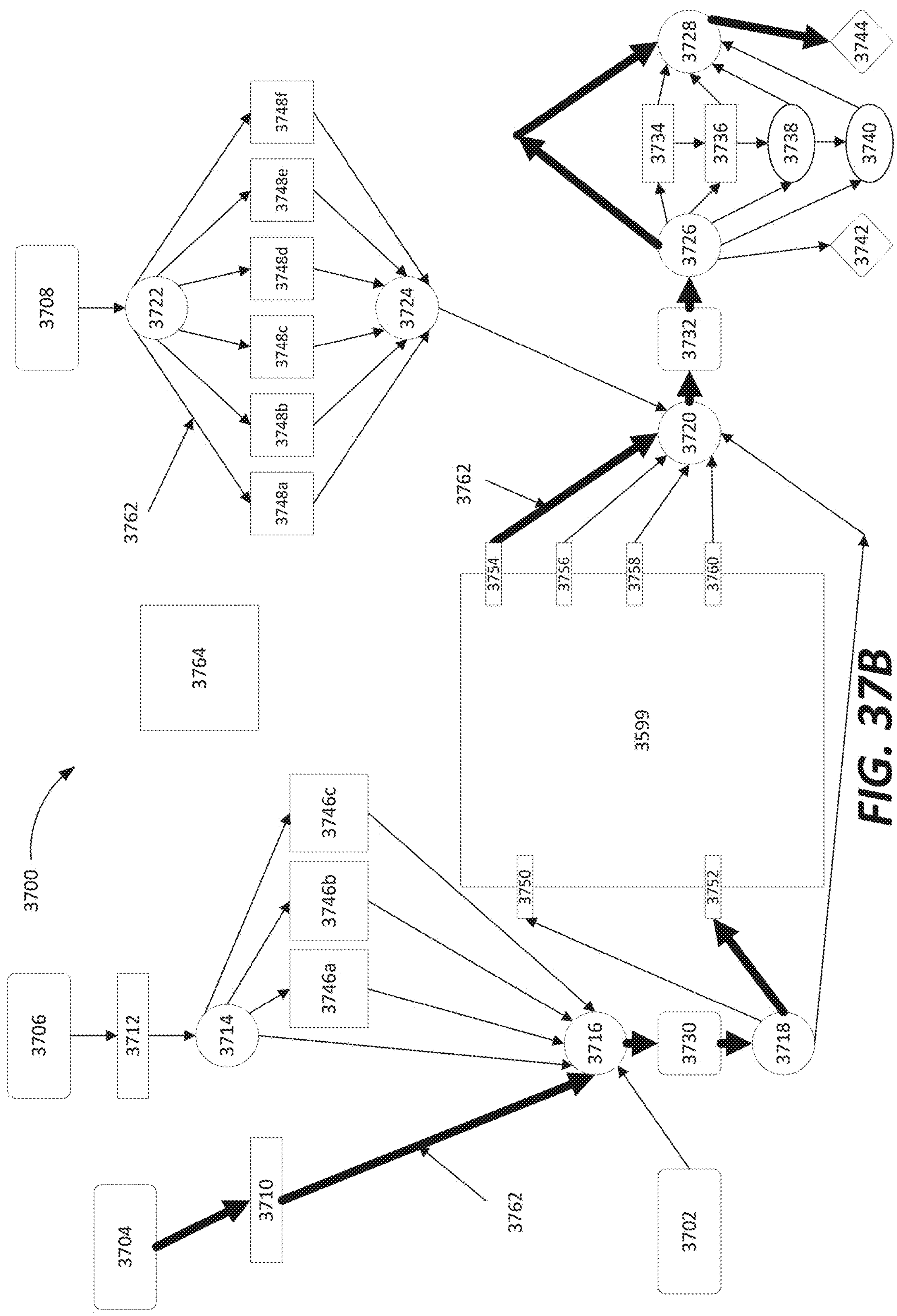
FIG. 37B illustrates a process flow diagram for introducing cells into a cell therapy manufacturing system according to various embodiments.

Referring to FIG. 37B, a flow path through a cell therapy manufacturing system 3700 of a process for introducing cells (e.g., T-cells) into the cell therapy manufacturing system 3700 is disclosed, in accordance with various embodiments. In various embodiments, cell sample can be introduced through a primary inlet aseptically and fluidically coupled to a fluidic network 3762 the system. In various embodiments, for example, the fluidic network 3762 of the system can direct the contents of a container 3710 to a bioreactor 3599 (see also FIG. 35). In various embodiments, the cell therapy manufacturing system 3700 comprises an enclosed, sterile system of various chambers (e.g., a bioreactor 3599 comprising a chamber) can compartments connected by a fluidic network 3762.

In various embodiments, the contents can comprise a cell sample from a subject. A non-limiting example of the cell sample can include whole blood. Whole blood can be obtained from a blood draw from the subject. Another non-limiting example of a cell sample can include a tissue sample.

A non-limiting example of a method to import T-cells into the cell therapy manufacturing system can comprise aseptically and fluidically connecting a container 3710 to a cell therapy manufacturing system 3700. In various embodiments, a sterile compartment of the container can store a cell sample from a subject that includes starting material (e.g., a medium including T-cells) to undergo one of more processes of the cell therapy manufacturing system 3700.

In various embodiments, the flexible container can be fluidically and aseptically connected to a system for processing and then enter a cartridge. In various embodiments, the flexible container can be fluidically and aseptically connected to a cartridge directly.

As described herein, various embodiments of the cell therapy manufacturing system 3700 can comprise a pressurized fluid source (e.g., a source for liquid or a gas source 3702, 3704, 3706, 3708. In various embodiments, the gas source 3704 can pressurize a fluidic network 3762 using the gas source 3704 to move to contents of the container through the cell therapy manufacturing system 3700. In various embodiments, the fluidic network 3762 comprises valves 3714 and flow sensors 3730 that can be controlled by other systems (e.g., a control system for receiving sensor data and actuating system components such as, for example, flow directors or valves). In various embodiments, cell sample can move through the fluidic network 3762 using additional or alternative means. For example, pumps can be used in some embodiments to move the cell sample through the fluidic network 3762. Pumps can be peristaltic pumps in accordance with various embodiments. In various embodiments, gravity can be drive cell sample through the fluidic network 3762.

Various environmental factors can impact a cell sample. For example, temperature, medium composition, and physical trauma can be considered when designing and/or operating a cell therapy manufacturing system 3700. As a non-limiting example, the possibility of physical trauma impacting the cell sample can be mitigated by maintaining optimal pressure conditions for the cell sample. In various embodiments, a gas source 3702, 3704, 3706, 3708 can be operated to pressurize a fluidic network 3762, or a portion thereof, within a range of pressures that can allow cells within cell sample to survive, and in various embodiments, proliferate. Pressures can be adjusted to mitigate cell damage. Pressures can be adjusted to eliminate cell damage. In various embodiments, low pressures can be selected.

In various embodiments, the cell sample can be directed through a one or more valves (e.g., 3716) to an inlet port 3750, 3752 of a bioreactor 3599. In various embodiments, the cell sample can be directed to a second inlet port 3752. In various embodiments, the cell sample can be directed to a first inlet port 3750. In various embodiments, inlet ports 3750, 3752 can be affixed to a bioreactor wall 3512 allow sterile entry of the cell sample into the bioreactor 3599. In various embodiments, introducing the cell sample to a lower position, through a lower port (e.g., the second inlet port 3752) within the bioreactor 3599 can prevent cell damage in some embodiments. In various embodiments, introduction of the cell sample at a lower position in the bioreactor 3599 can reduce bioreactor foaming.

In various embodiments, a cell sample can enter the bioreactor 3599 using a second inlet port 3752 until a fluid reaches a specified level. In various embodiments, a control system 3764 can actuate a valve 3718 to redirect fluid flow from the second inlet port 3752 of the bioreactor 3599 to the first inlet port 3750 of the bioreactor 3599 upon reaching the specified level. In various embodiments, a fluid level sensor can be used to determine the fluid level of the bioreactor 3599. The fluid level sensor can relay fluid level information to a control system 3764 in accordance with various embodiments. The control system 3764 can then compare the fluid level of the bioreactor 3599 to the specified fluid level and determine whether to actuate the valve 3718. In various embodiments, a control system can comprise a receptacle and control interface 2930.

In various embodiments, the bioreactor 3599 comprises a finite volume (previously discussed). As such, as the gas source 3704 introduces pressurized gas to enable introduction of the cell sample into the bioreactor 3599 excess fluid or gas needs to be discharged. In various embodiments, fluid can be discharged through outlet ports 3754, 3756, 3758, 3760. In various embodiments, as a cell sample can be introduced into the bioreactor 3599 through the second inlet port 3752 as fluid is being released through one or more outlet ports 3754, 3756, 3758, 3760. In accordance with various embodiments, fluid release can occur using an outlet port that is not submerged by the liquid (e.g., the cell sample) being introduced into the bioreactor 3599. In various embodiments, outlet ports 3754, 3756, 3758, 3760 can be closed as they become submerged. In various embodiments, a level measured by the level sensor can determine a sequence for outlet port 3754, 3756, 3758, 3760 closure. In various embodiments, fluids introduced into the bioreactor 3599 can be quantified prior to introduction into the cell therapy manufacturing system 3700 and those quantities can be used by a control system 3764 to determine when to actuate port valves or covers.

In various embodiments, inlet ports 2750, 3752 and outlet ports 3754, 3756, 3758, 3760 can be closed or opened for a variety of reasons. In various embodiments, a process step (e.g., cell sample introduction, T-cell activation, expansion, etc.) can determine the occurrence and rate of inflow and/or outflow of fluids comprising media and reagents using the ports. In various embodiments, an environments condition (e.g., pressure, fluid level, pH, or dissolved oxygen) within the bioreactor 3599 can determine inflow and/or outflow of media and reagents.

When the fluid (e.g., pressurized gas) exits an outlet port 3754, 3756, 3758, 3760 it can be directed through a valve 3720 in accordance with various embodiments. In various embodiments, a fluid flow sensor 3732 can determine a flow rate of the fluid as the fluid leaves the bioreactor 3599. In various embodiments, one or more additional valves 3734, 3728 can direct the fluid to a waste receptacle 3744.

In various embodiments, the flow rate of the fluid information can be received by the system controller 3764 from the fluid flow sensor 3720. In various embodiments, the system controller 3764 can actuate a valve at the gas source 3704 to increase or decrease the fluid flow rate.

In various embodiments, the fluid in waste receptacle 3744 can undergo further testing. In various embodiments, further testing can comprise one or more biological assays.

In various embodiments, a waste receptacle 3744 can comprise a sterile compartment surrounded by a waste receptacle wall.

a. T-Cell Sorting, Activation, and Surfaces

Various embodiments can comprise a cell sorting process using the cell therapy manufacturing system as a discrete process from a T-cell activation process. In various embodiments, a cell sorting process and a T-cell activation process can be combined into a single step. Combining processes can shorten the cell therapy manufacturing process. In various embodiments, a cell sorting process, a T-cell activation process, and an expansion process can be combined.

In various embodiments, the surfaces (e.g. antigen-presenting surfaces) described herein can be suitable for sorting and activating T-cells concurrently.

i. T-Cell Sorting Techniques

Various embodiments can include rapid and automated systems and methods for cell sorting. In various embodiments, the cell sorting techniques disclosed herein can serve to selectively deplete or enrich cells of a specific phenotype. In various embodiments, cell sorting techniques disclosed herein can sort using immunomagnetic selection.

Traditional cell sorting technologies have been adapted from existing instrumentation relating to research (e.g., flow cytometry). A disadvantage to using these technologies as a stand-alone device in a cell therapy manufacturing workflow may be that they include open systems where cell sample contamination can result in workflow disruptions causing a cell therapy product to be unusable. Additional contributing problems relate to current sorting systems jeopardizing cell viability. The contributing problems specifically relate to cells being subjected to harsh physical forces (e.g., flowing through the flow cell of flow cytometer).

Therefore, the closed cell therapy manufacturing systems for executing sorting processes described herein solve the current contamination challenge within the cell therapy field. In various embodiments, the sorting methods carried out on the cell therapy manufacturing system can purify cells based multiple parameters.

Figure 32:
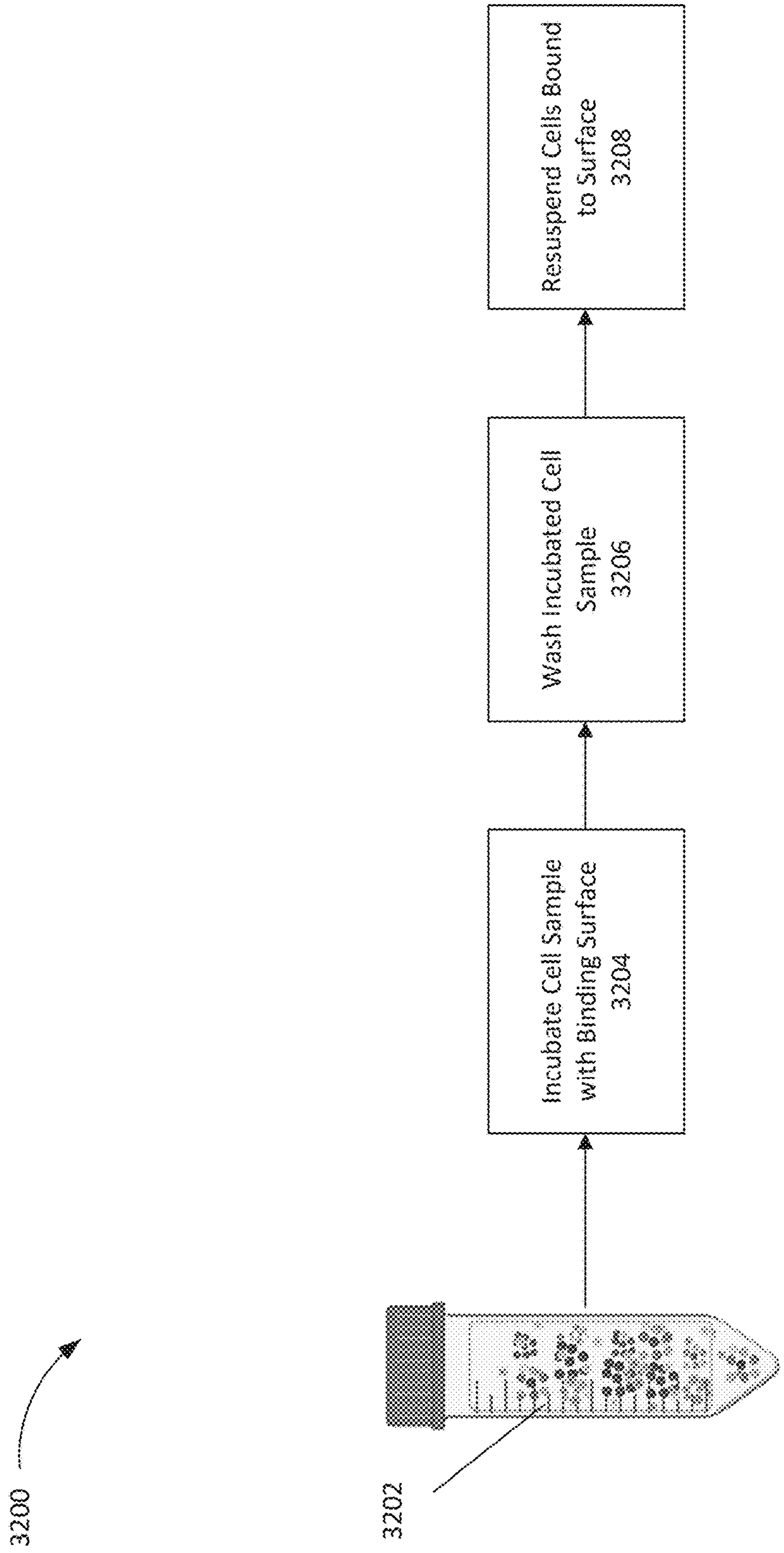
FIG. 32 illustrates a schematic flow diagram for a cell sample sorting process 3200 according to various embodiments.

FIG. 32 illustrates a schematic flow diagram for a cell sample sorting process 3200 according to various embodiments.

Step 3202 provides a cell sample according to various embodiments. In various embodiments, the cell sample can undergo an assortment of pre-processing steps. For example, when the cell sample comprises whole blood, methods employing one or more columns combined with centrifugation steps may be used prior to Step 3204. In some embodiments, a cell sample can be diluted with a buffer. In some embodiments, the buffer can comprise PBS/EDTA.

Step 3204 incubates the cell sample with a binding surface according to various embodiments. In various embodiments, T-cells of the cell sample can bind to the binding surface. In various embodiments, molecules other than T-cells cannot bind to the surface. In various embodiments, the T-cells are specifically bound. In various embodiments, a molecule bound (e.g., covalently) to the surface can bind the T-cells. In various embodiments, a T-cell receptor embedded in a phospholipid bilayer of the T-cell can bind the molecule bound to the surface.

In various embodiments, the molecule bound to the cell can comprise an antigen-presenting surface. In various embodiments, the antigen-presenting surface can comprise MHC class I molecule. Non-limiting examples of incubation times can comprise 1, 2, 3, 4, 5, 6, 7, 8, 9, 10, 24, 48, or 72 hours and any range of these.

In various embodiments, an antigen-presenting surface can provide primary and co-stimulatory signals. In various embodiments, an antigen-presenting surface can comprise anti-CD3 antibodies. In various embodiments, an antigen-presenting surface can comprise anti-CD28 antibodies. In various embodiments, an antigen-presenting surface can comprise anti-CD3 antibodies and anti-CD28 antibodies. Aspects of the embodiments include T-cell specifically binding to anti-CD3 antibodies. Aspects of the embodiments include T-cell specifically binding to anti-CD28 antibodies. Aspects of the embodiments include T-cell specifically binding to anti-CD28 antibodies and anti-CD3 antibodies.

In some embodiments, the antigen-presenting surface can comprise MHC class I molecule. In some embodiments, the MHC class I molecule can comprise an antigenic peptide. Aspects of the embodiments include T-cells binding to MHC class I molecules.

Incubating cell sample with binding surface at step 3204 can occur in a variety of locations within the cell therapy manufacturing system in accordance with various embodiments. In various embodiments, the surface can be located anywhere in the instrument where fluid can flow (e.g., a fluidic network or a chamber). In various embodiments, the surface can be located in the cartridge (e.g., a fluidic network or bioreactor chamber) of the cell therapy manufacturing system.

In various embodiments, the surface can be located in the cartridge.

Aspects of the disclosure include combining beads with the cell sample. In various embodiments, the beads can comprise an antigen-presenting surface. The surface can be coated with activating molecules (e.g., the antigen-presenting molecules, such as, for example, anti-CD3 antibody and anti-CD28 antibody, as described herein). In various embodiments, T-cells from the cell sample can comprise T-cell receptors that can bind to the antigen-presenting surface of the beads. In various embodiments, beads can be manipulated for cell sorting purposes.

In various embodiments, beads complexed with T-cells can be sorted from other cells and non-soluble molecules. For example, in some embodiments, bead-T-cell complexes can be isolated and purified using filtration. In various embodiments, bead-T-cell complexes can be isolated and purified using optical manipulation. In some embodiments, bead-T-cell complexes can be centrifuged into a pellet and the supernatant can be removed.

In various embodiments, beads can be magnetized. Embodiments using magnetized beads can enable bead-T-cell complexes to be magnetically secured to a surface during incubation and washing.

Step 3206 can include the washing of the incubated cell sample according to various embodiments. Aspects of the disclosure comprise methods and systems for washing T-cells bound to a surface. In various embodiments, one or more washing steps can purify the cell sample by isolating T-cells. Washing removes unbound molecules while preserving T-cells in accordance with various embodiments. In various embodiments, washing can remove debris, dead cells, or other unwanted molecules in the cell sample. For example, in various embodiments unbound molecules can comprise cells other than T-cells, protein, carbohydrate, nucleic acids, ions, cell waste, etc.

A method of washing can comprise removing a portion of media (e.g., a liquid suspension) from the cell sample. In various embodiments, new media can be added during or after removing the portion of media. In various embodiments, the removed media comprises the unbound molecules. In various embodiments, T-cells stay bound during the removal and addition steps. In various embodiments, removal and addition of media can be completed any number of times. For example, a cell sample including T-cells bound to a surface can undergo 1, 2, 3, 4, 5, 6, 7, 8, 9, or 10 rounds of washing (e.g., removal of a portion of media from the cell sample and addition of media to the cell sample).

The number of wash steps/rounds can be determined by a purity metric. The purity metric can comprise a percentage a T-cells in proportion to other cells. The purity metric can comprise a percentage of T-cells in proportion to other non-solubilized molecules.

At step 3208, T-cells bound to the surface can be resuspended. Once T-cells have been isolated and purified they can be resuspended in a buffer appropriate for introduction to a next step of a cell therapy manufacturing process. In various embodiments, the buffer can comprise a PBS/EDTA buffer.

ii. On-System Approaches (Instrument)

Various embodiments can of the cell therapy manufacturing system can comprise completing a cell sample sorting process 3200 on an instrument in accordance with the various cell sorting methods disclosed herein. In various embodiments, the cell therapy manufacturing system can comprise an instrument and a cartridge. In various embodiments, the cartridge can comprise a modular apparatus that can be fluidically coupled to the fluidic network of the instrument. In various embodiments, a cell sample sorting process 3200 can be carried out on the instrument of the system. In various embodiments, cell a sample sorting process 3200 can occur prior to the cell sample or a portion thereof entering the cartridge. In various embodiments, T-cells of the cell sample can undergo a pre-sorting process within the instrument (e.g., washing and/or purifying).

Aspects of the cell sample sorting process 3200 can be carried out using one or more surfaces. In various embodiments, a cell sample sorting process 3200 can use one or more surfaces within the instrument. For example, a surface can be located within the fluidic network of the instrument in various embodiments. In various embodiments, a surface may be located within one or more channels of the fluidic network of the instrument. In additional and alternate embodiments, a surface can be located within a chamber or compartment of the instrument, wherein the chamber or compartment can be fluidically and aseptically coupled to the fluidic network of the instrument.

In various embodiments, step 3202 provides a cell sample (e.g., a leukopak) according to various embodiments. In various embodiments, the cell sample can be aseptically stored in a container. In various embodiments, the container can be aseptically connected to a port (e.g., a primary port of the cell therapy manufacturing system for receiving a sample) using one or more aseptic connectors.

In various embodiments, the container storing the cells sample can be positioned within an instrument housing. In various embodiments, the container can be positioned outside of the instrument housing and the primary port can connect the container to a fluidic network of the of the instrument.

In various embodiments, one or more gas sources can pressurize a fluidic network of the instrument to move the cell sample from the container to the surface (e.g. antigen-presenting surface). In various embodiments, cell sample movement can be controlled using a controller to actuate one or more valves of the instrument. In various embodiments, the controller can determine a flow path to the one or more surfaces and actuate the appropriate valves. In various embodiments, the controller can receive flow rate information from one or more flow sensors. The flow rate information can then be used to adjust the valves to achieve a desired flow rate.

In various embodiments, step 3204 can be carried out using the one or more surfaces within the instrument. In various embodiments, T-cells of the cell sample can adhere to the one or more surfaces.

As previously discussed, the one or more surfaces can comprise an antigen-presenting surface and T-cells of the cell sample can bind to the one or more antigen-presenting surfaces of the instrument. In some embodiments, as described herein, T-cells can bind to magnetizable beads and the magnetizable beads can be magnetically bound to the one or more surfaces of the instrument. In various embodiments, cells can be incubated for a specified amount of time for T-cells to bind to the surface.

Once the specified amount of time has elapsed, the cells sample (e.g. bound T-cells) can be washed on the instrument using a wash incubated cell sample process 3206. As previously discussed, wash steps (e.g. addition and removal of fluid such as a wash buffer) can occur one or more times.

In various embodiments, after step 3206 has been completed, a process to resuspend cells bound to surface 3208 can commence within the instrument. In various embodiments, resuspension can comprise actuating one or more valves using the controller to create a flow path for introducing a resuspending buffer (e.g. PBS/EDTA).

iii. On-System Approaches (Cartridge)

Various embodiments of the cell therapy manufacturing system can comprise completing a cell sample sorting process 3200 on a cartridge in accordance with the various cell sorting methods disclosed herein. In various embodiments, the cell therapy manufacturing system can comprise an instrument and a cartridge. In various embodiments, the cartridge can comprise a modular apparatus that can be fluidically coupled to the fluidic network of the instrument. In some embodiments, a cell sample sorting process 3200 can be carried out on the cartridge of the system. In various embodiments, cell a sample sorting process 3200 can occur after the cell sample or a portion thereof enters the cartridge. In various embodiments, T-cells of the cell sample can undergo a pre-sorting process one the cartridge (e.g., washing and/or purifying).

In various embodiments, step 3202 can provide a cell sample to the cell therapy manufacturing system through a primary inlet port. In various embodiments, the primary inlet port can fluidically couple to a fluidic network of a cartridge directly. In various embodiments, the primary inlet port can fluidically couple to the fluidic network of a cartridge via a fluidic network of an instrument of the system.

In various embodiments, a purpose of a cell sample sorting process 3200 can include positioning sorted T-cells in a bioreactor. In various embodiments, the bioreactor can be positioned on the cartridge. Positioning T-cells within the bioreactor can comprise directing the cell sample through the fluidic network to the bioreactor using one or more valves in accordance with various embodiments.

In various aspects, T-cells can be immobilized on a surface of the cartridge in accordance with step 3204 by incubating the cell sample with the surface (e.g. a binding surface). In various embodiments, the surface can be located within a fluidic network. In various embodiments, the surface can be located within the bioreactor.

One or more wash steps 3206 can be used to remove cell debris and other unwanted molecules from the cell sample. A wash process can comprise actuating one or more valves of the cartridge to provide a motive force for moving wash fluid through the system using a pressurized gas source. In various embodiments, wash fluid can enter the bioreactor through one or more inlet ports and fluid (e.g. fluid from the cell sample, wash fluid, and pressurized gas) can exit the bioreactor through one or more outlet ports. A wash process can involve one or more fluid addition steps to the bioreactor and one or more fluid removal steps from the bioreactor.

Once the T-cells have reached a desired level of purity step 3208 can resuspend T-cells bound to the surface. In various embodiments, the T-cells can remain bound to the surface as a new media is added. In various embodiments, the T-cells can be released from the surface as new media is added.

iv. Off-System Approaches

In various embodiments, a cell sample can be pre-sorted prior to being introduced to the cell therapy and manufacturing system. In various embodiments, antigen-presenting beads can be combined with the cells sample. In various embodiments, a centrifuge can exert force on the T-cells to create a pellet within a test tube. In various embodiments, a supernatant of the cell sample can be removed, and the pellet can be resuspended in a liquid (e.g., buffer). In various embodiments, cells can be pelleted and resuspended one or more times until a desired purity is reached.

In various embodiments, a cells sample can be pre-sorted using a fluorescently activated cell sorting (FACS) process. In various embodiments, T-cells can be labeled and for FACS sorting. In various embodiments, T-cells can be bound to beads for sorting.

In various embodiments, T-cells can be bound to magnetizable beads. In various embodiments, a surface can be activated for restraining the T-cells for washing and resuspension.

v. Exemplary Method of Cell Sorting

An exemplary cell sample sorting process can be carried out using the system shown in FIG. 37A. In various embodiments, a container 3710 comprising a cell sample can be introduced into the cell therapy manufacturing system 3700. In various embodiments, the cell sample can enter a fluidic network through a primary inlet port through an aseptic connector. In various embodiments, one or more a valves 3716, 3718 can be actuated to an open position allowing fluid flow through the cell therapy manufacturing system. In various embodiments, gas source 3704 can pressurize the fluidic network and drive the cell sample to a chamber. In various embodiments, the chamber can be a bioreactor 3599.

In various embodiments, a flow rate of the cell sample traveling from the container 3710 to the chamber can be measured by flow sensor 3730. The flow sensor 3730 can be position anywhere in the fluidic network between, for example, the container 3710 and the chamber. In various embodiments, flow sensor 3730 can electronically communicate the flow rate to a control system 3764. The control system 3764 can actuate one or more valves 3716, 3718 to increase the flow rate or reduce the flow rate in accordance with various embodiments. In various embodiments, a specified flow rate for introduction of the cell sample into the cell therapy manufacturing system can be stored in the control system 3764. In various embodiments, the control system 3764 can adjust the flow rate based on the specified flow rate by comparing the two In various embodiments, T-cells can be incubated in proximity to a surface until a portion of the T-cells bind to the surface. In various embodiments, the T-cells can bind directly to the surface. In various embodiments, the T-cells can bind through an intermediary (e.g., a bead).

In various embodiments, a container 3712 can be aseptically connected to the cell therapy and manufacturing system. In various embodiments, the container 3712 may store the wash fluid (e.g., buffer or media). In various embodiments, the wash fluid may be stored in one or more reagent reservoirs 3746*a*, 3746*b*, 3746*c*.

One or more valves 3714, 3716, 3718 can be actuated to allow gas source 3706 pressurized the fluidic network, thereby, transporting the wash fluid to the chamber through an inlet port 3750, 3752 in accordance with various embodiments.

In various embodiments, fluid (e.g., wash fluid or a liquid/suspended portion of the cell sample) can leave the bioreactor through one or more outlet ports 3754, 3756, 3758, 3760. In various embodiments, the fluid can comprise gas. In various embodiments, the fluid can comprise wash fluid. In various embodiments, the fluid can comprise any unbound molecules from the cell sample. In various embodiments, after leaving the one or more outlet ports 3754, 3756, 3758, 3760, the fluid can travel through one or more valves 3720, 3726, 3728 to a waste receptacle 3744. In various embodiments, a flow rate of the fluid existing the chamber can be monitored using a flow sensor 3732. The flow rate sensor 3732 can be positioned anywhere between the chamber and waste receptacle 3744 in accordance with various embodiments. In various embodiments, the flow sensor can electronically communicate the flow rate to the control system 3764. In various embodiments, the control system 3764 can actuate one of more of the valves 3720, 3726, 3728 to adjust the flow rate.

In various embodiments, wash fluid can be added to the chamber in one or more steps. In various embodiments, wash fluid can be removed from the chamber in one or more steps. Addition and removal of fluid from the chamber while the T-cells are bound can occur any number of times until a desired T-cell purity is reached.

In various embodiments, the control system 3764 can comprise instructions for one or more cell sorting protocols. In various embodiments, sensors can electronically communicate sensor data (e.g., flow rates, pH, pressure, dissolved oxygen, etc.) to the control system 3764. In various embodiments the control system 3764 can use the electronic data to adjust flow rates and/or environmental conditions within the chamber.

In various embodiments, the washed cell sample can be resuspended. For example, T-cells of cell sample can be resuspended in a buffer. In various embodiments, the buffer can comprise PBS and EDTA.

vi. T-Cell Activation Structures and Surfaces

In various natural systems, antigens from diseased cells (e.g., cancer cells) can be taken up and presented on a cell surface of antigen-presenting cells (APCs) and the APCs can then activate T-cells allowing them to recognize the diseased cells. For a cell therapy manufacturing system to be effective, a cell sample containing T-cells can undergo a similar process occurring in biological organisms. In various embodiments, a cell therapy manufacturing system can comprise use of APCs for T-cell activation. In alternate embodiments, synthetic surfaces can be used for presenting antigens.

As described herein, the surfaces described herein (e.g., surfaces used in a cell sample sorting process and elsewhere) can include activating molecules for T-cell activation. In various embodiments, activation can be carried out after a cell sample sorting process is complete. In various embodiments, a T-cell activation process or a portion thereof can occur in conjunction with a cell sorting process.

Figure 33A:
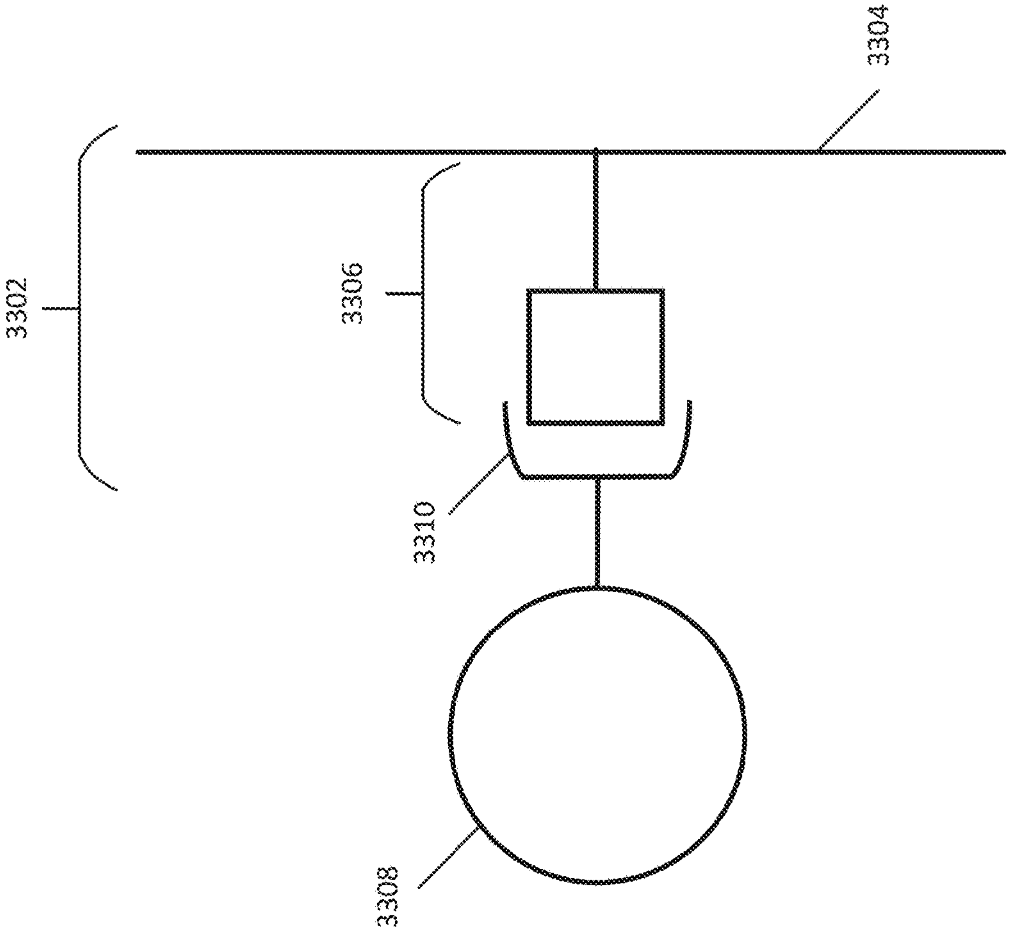
FIG. 33A illustrates a T-cell receptor of a T-cell bound to a synthetic antigen-presenting surface in accordance with various embodiments.

FIG. 33A illustrates a T-cell receptor 3310 of a T-cell 3308 bound to a synthetic antigen-presenting surface 3302 in accordance with various embodiments. In various embodiments, a synthetic antigen-presenting surface 3302 can comprise an antigen 3306 bound to a surface 3304. In various embodiments, the surface 3304 can be located within a cell therapy manufacturing system. In some embodiments, the surface 3304 can be located within a sterile fluidic network of an instrument of the system. In various embodiments, the surface 3304 can be located within a sterile portion of a cartridge of the cell therapy manufacturing system. In various embodiments, the surface 3304 can be located within a chamber of the cartridge. In various embodiments, the chamber may comprise a bioreactor.

Figure 33B:
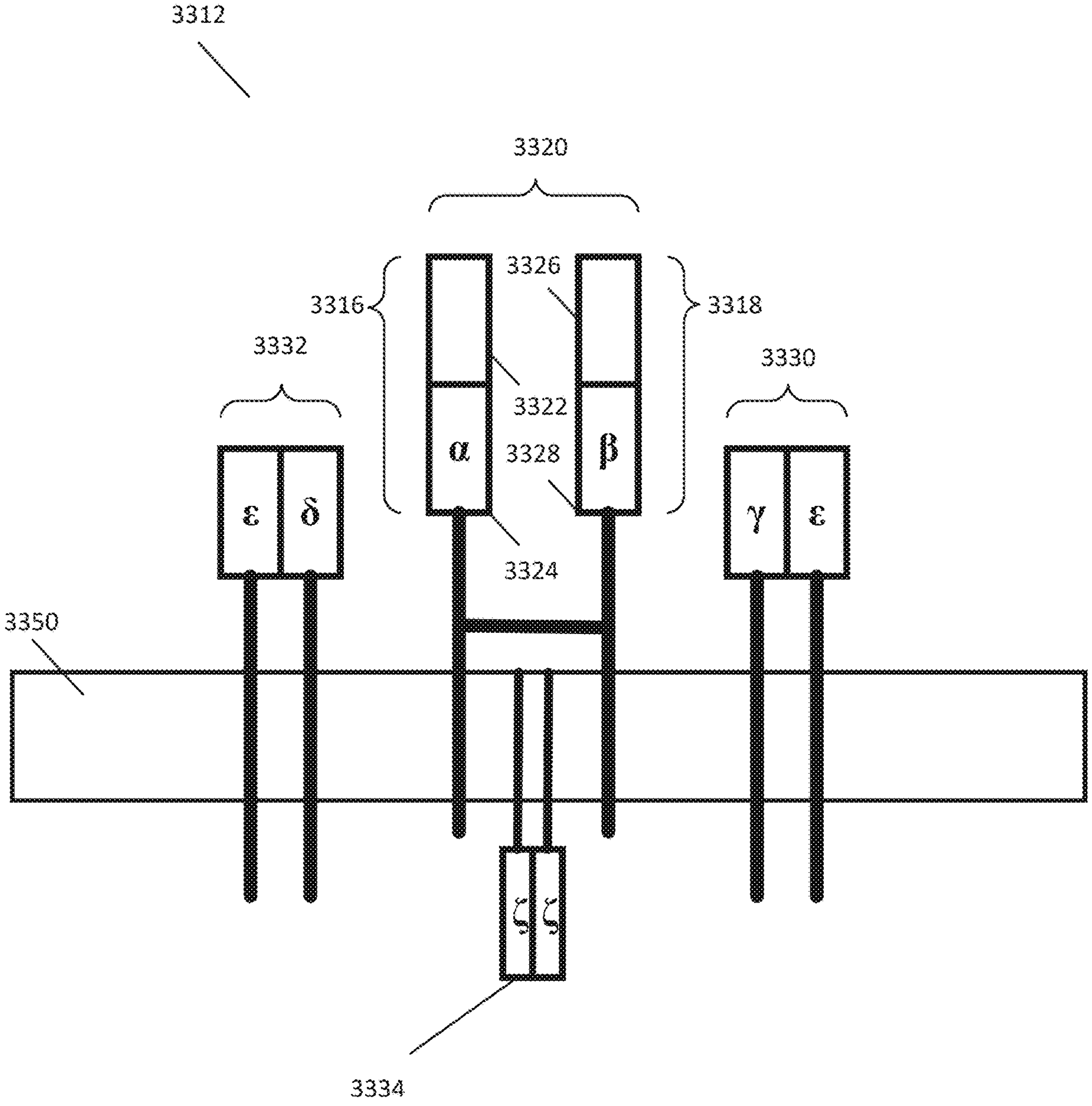
FIG. 33B illustrates a T cell Receptor (TCR) complex embedded in a T-cell membrane in accordance with various embodiments.

Various embodiments of an adaptive immune response system comprise T-cells including membrane associated TCR. In various embodiments, adaptive immune responses comprise CD28 for providing a co-stimulatory signal. Referring to FIG. 33B, a T cell Receptor (TCR) complex 3312 is illustrated embedded in a T-cell membrane 3314 in accordance with various embodiments. In various embodiments, a TCR complex 3312 can comprise a disulfide-linked membrane-anchored heterodimeric protein. In many embodiments, the disulfide-linked membrane-anchored heterodimeric protein can comprise an alpha (a) chain 3316 and a beta (B) chain 3318. In various embodiments, TCR complex 3312 can comprise an alternate receptor, formed by gamma (γ) and delta (0) chains. In various embodiments, a TCR complex 3312 a chain 3316 and β chain 3318 form the structure of an antigen-binding site (e.g. pMHC binding site 3320).

In various T-cell conformations, an a chain 3316 can comprise two extracellular domains, including a variable region 3322 and a constant region 3324. In various embodiments, a β chain 3318 can comprise two extracellular domains, including a variable region 3326 and a constant region 3328. In some conformations, the constant regions 3324, 3328 can be adjacent to a cell membrane 3314. In various conformations, the variable regions 3322, 3326 can form a pMHC binding site 3320 and can bind a pMHC (See FIG. 33C).

Each of the TCR chains 3316, 3318 can comprise a variable region 3322, 3326 and each variable region 3322, 3326 can comprise three hypervariable or complementarity-determining regions (CDRs). In various embodiments, CDR1, CDR2, and CDR3 can be arranged non-consecutively on the amino acid sequence of the variable region 3322, 3326 of the TCR complex 3312. In various embodiments, CDR3 can be the primary region for recognizing a processed antigenic peptide of a pMHC.

Figure 4:
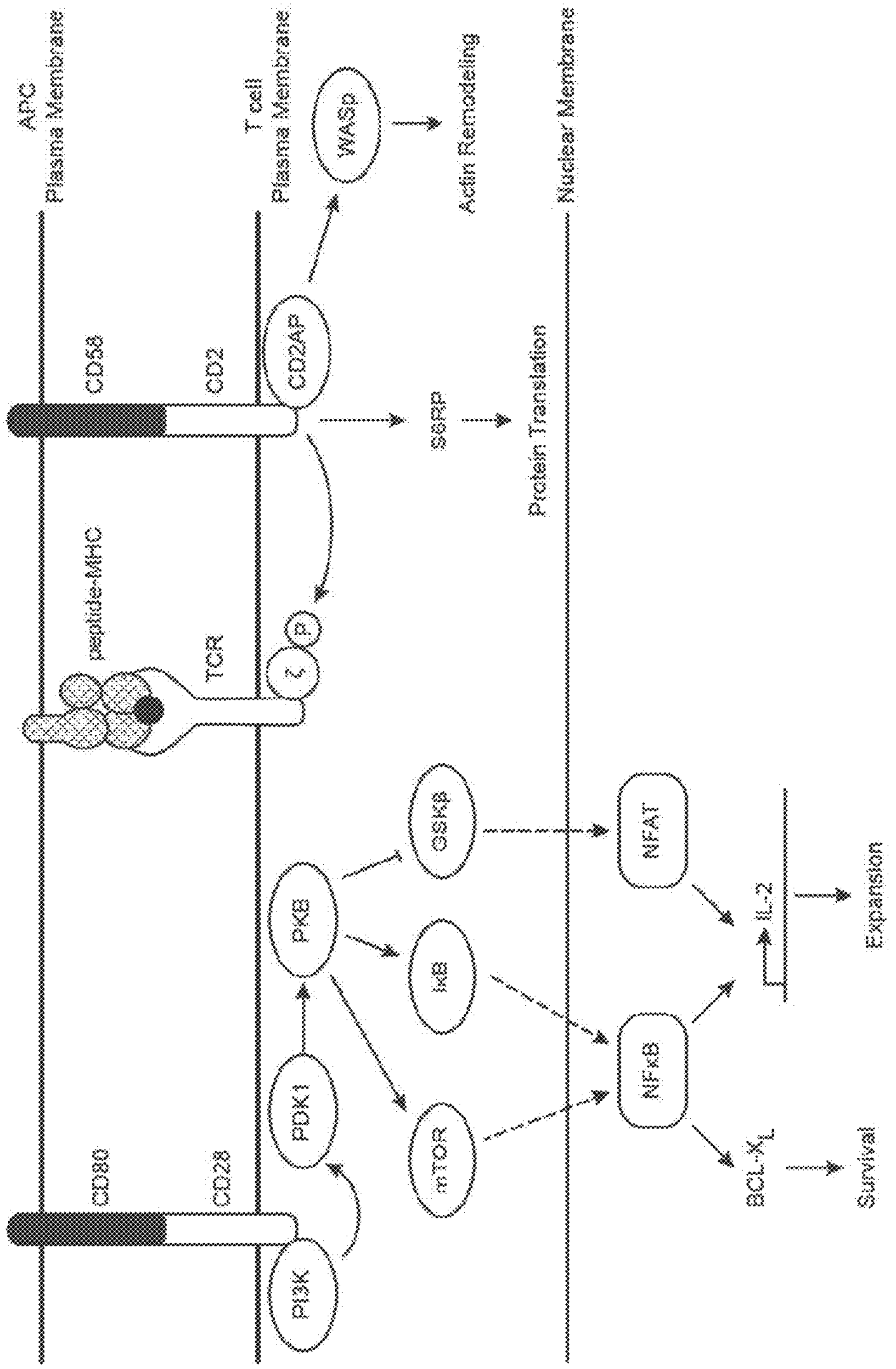
FIG. 4 is a graphical representation of T cell activation pathways according to an embodiment of the disclosure.

Aspects of immune response can require TCR complex 3312 to propagate a signal to cause T-cell activation (See FIG. 4). In various embodiments, CD3 molecules 3330, 3332 has a longer cytoplastic tail than a chain 3316 and β chain 3318 for allowing signal transduction to occur. In various embodiments, TCR complex 3312 comprises a first CD3 molecule 3330 comprising a γ chain associated with an ε chain. In various embodiments, TCR complex 3312 comprises a second CD3 molecule 3332 comprising a δ chain associated with an & chain.

In various embodiments, ζ chains 3334 of a TCR complex 3312 can couple peptide recognition to several intracellular signal-transduction pathways, including, T-cell activation.

Aspects of an adaptive T-cell immune response comprise recognition of peptides (e.g. antigens) by T-cells. In various embodiments, antigens can be presented on a synthetic surface of the cell therapy manufacturing system (e.g., a support structure, an interior wall within the cell therapy manufacturing system, a bead, etc.). In various embodiments of the cell therapy manufacturing system, a major histocompatibility complex (MHC) can be bound to one or more of the surfaces described herein.

Figure 33C:
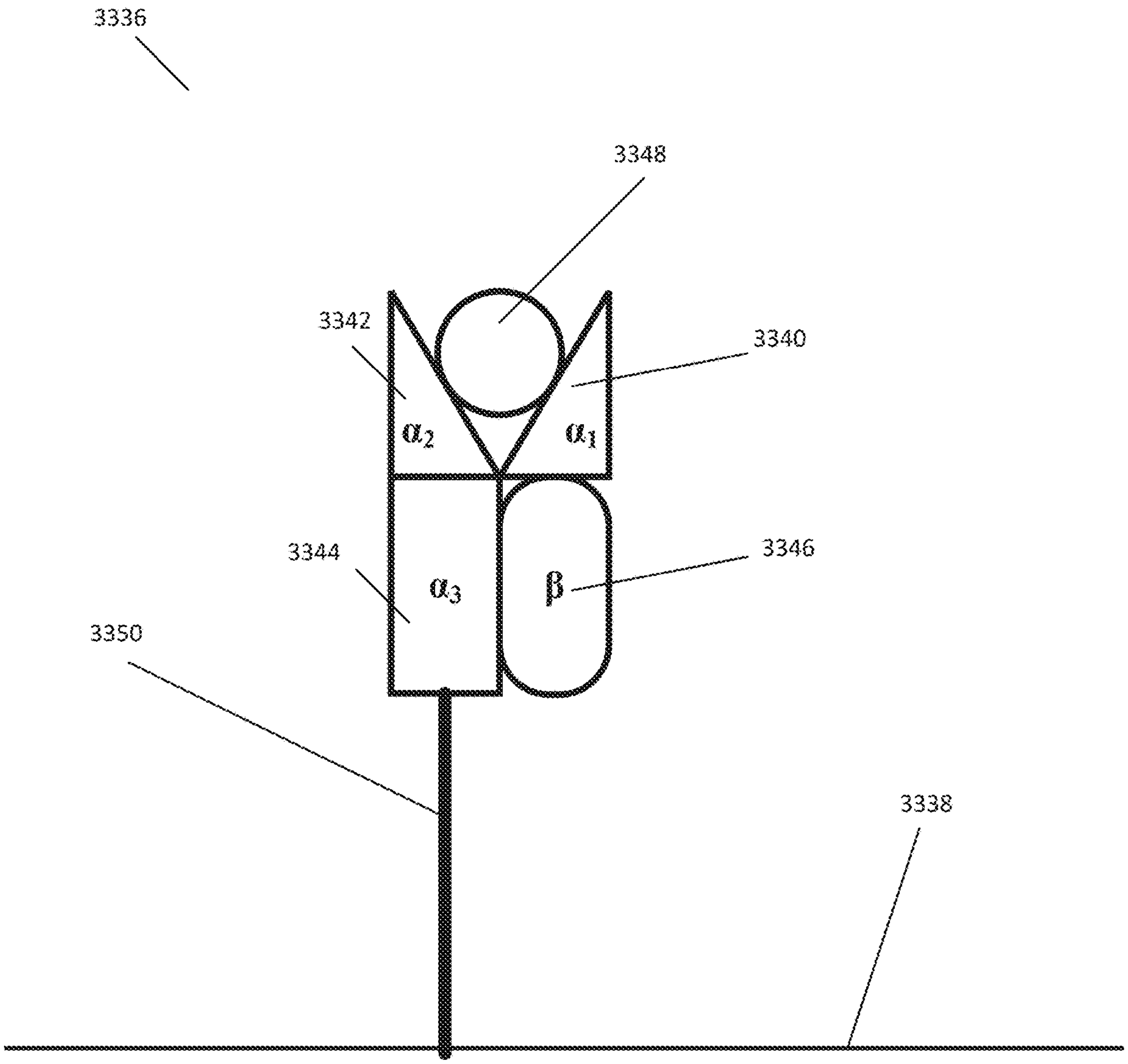
FIG. 33C illustrates a pMHC molecule as part of an antigen-presenting surface of a cell therapy manufacturing system according to various embodiments.

Referring to FIG. 33C, pMHC 3336 is shown bound to a surface 3338, thereby forming an antigen-presenting surface of a cell therapy manufacturing system according to various embodiments. In various embodiments, a pMHC 3336 can comprise an alpha chain 3340, 3342, 3344 and a beta chain 3346. In some embodiments, pMHC 3326 can comprise a peptide 3348 that can serve as an antigen. In various embodiments, the alpha chain 3340, 3342, 3344 and the beta chain 3346 can be associated to one another with non-covalent bonds.

In various embodiments, an alpha chain can comprise approximately 350 amino acids and include three globular domains 3340, 3342, 3344. In various embodiments, the three globular domains can be designated $a_1$ 3340, $a_2$ 3342, and $a_3$ 3344.

In various embodiments, the N terminal of an alpha chain can be located in the $a_1$ 3340 globular domain. In various embodiments, $a_1$ 3340 and $a_2$ 3342 can extend away from a surface for TCR binding. In various embodiments, $a_1$ 3340 and $a_2$ 3342 can each comprise roughly 90 amino acids. In various embodiments, $a_2$ 3342 can comprise a loop of 63 amino acids and formation can be cause by disulfide bonds. In various embodiments, $a_1$ and $a_2$ can interact to form a peptide binding region of pMHC 3326.

In various embodiments, a linker region 3350 can anchor pMHC 3326 to a surface 3338. In various embodiments, the linker region 3350 can comprise a covalent bond. In various embodiments, the covalent bond can form between the surface and $a_3$ 3344 of pMHC 3336. In some embodiments, $a_3$ 3344 can comprise a disulfide bond enclosing 86 amino acids to form a loop structure. In various embodiments, the linker region 3350 can comprise additional compounds (e.g., PEG, biotin, streptavidin, avid, etc.) to facilitate pMHC surface binding.

In various embodiments, an $a_3$ 3344 globular domain can interact with a CD8 co-receptor of T-cells. In some embodiments, an $a_3$-CD8 interaction can hold pMHC 3326 in place and a TCR on a cell membrane surface of the T-cell can bind $a_1$-$a_2$ heterodimer ligand. In some embodiments, the $a_3$-CD8 interaction can allow the $a_1$-$a_2$ heterodimer ligand to interrogate the MHC associated peptide for antigenicity. In various embodiments, the C terminal of an alpha chain can be located in the $a_3$ 3344 globular domain. In various embodiments, the covalent bond connecting pMHC 3326 and surface 3338 can connect the C terminal of the alpha chain and a moiety on the surface.

The cytoplastic tails of CD8 can interact with Lck (lymphocyte-specific protein tyrosine kinase) and Lck can phosphorylate the cytoplasmic portion of CD3 and ζ-chains of the TCR complex. Phosphorylation of CD3 and the ζ-chains can lead to activation of a variety of transcription factors (e.g. NFAT, NF-κB, and AP-1) that can ultimately affect expression of certain genes downstream of a signaling cascade.

In various embodiments, a beta chain 3346 of pMHC can comprise a disulfide loop. In various embodiments, beta chain 3346 can noncovalently interact with a $a_3$ 3344 globular domain.

a. Synthetic T-Cell Activation Surfaces

In various embodiments, an antigen-presenting synthetic surface is provided for activating a T lymphocyte (T-cell) comprising: a plurality of primary activating molecular ligands, and a plurality of co-activating molecular ligands each comprising a T-cell receptor (TCR) co-activating molecule or an adjunct TCR activating molecule, wherein each of the plurality of primary activating molecular ligands and the plurality of co-activating molecular ligands are specifically bound to the antigen-presenting synthetic surface in accordance with various embodiments. Each primary activating molecular ligand can comprise a major histocompatibility complex (MHC) molecule configured to bind to a TCR of the T-cell. In various embodiments, the MHC molecule can comprise a MHC Class 1 molecule. In some other embodiments, the MHC molecule can comprise a MHC Class II molecule. In various embodiments, the primary activating molecular ligand comprises an antigenic peptide (e.g., covalently, or non-covalently bound to an MHC molecule). In various embodiments, the plurality of co-activating molecular ligands comprises a plurality of TCR co-activating molecules and a plurality of adjunct TCR activating molecules. In various embodiments, the TCR co-activating molecules and the adjunct TCR activating molecules can be present in a ratio of about 1:100 to about 100:1, e.g., about 20:1 to about 1:20, or about 10:1 to about 1:20. In various embodiments, one or more of the plurality of co-activating molecular ligands is a TCR co-activating molecule which can activate signaling molecules such as transcription factors Nuclear Factor kappa B (NF KB) and Nuclear factor of activated T-cells (NFAT). In various embodiments, the TCR co-activating molecule can be an agonist of the CD28 receptor, which signals through the phosphoinositide 3 kinase (PI3K)/Akt pathway. In various embodiments, one or more of the plurality of co-activating molecular ligands can be a TCR adjunct activating molecule which can activate a TCR proximal signaling, e.g., by phosphorylation of the TCR proximal signaling complex. The TCR adjunct activating molecule may be, for example, an agonist of the CD2 receptor. Exemplary pathways that can be activated through the CD28 and CD2 receptors (and additional details) are shown in FIG. 4. The T-cell activated by the antigen-presenting synthetic surface may be a naïve T-cell in accordance with various embodiments. The antigen-presenting synthetic surface may be an antigen-presenting bead, an antigen-presenting wafer, an antigen-presenting inner surface of a tube (e.g., glass or polymer tube), or an antigen-presenting inner surface of a microfluidic device (e.g., surface within a cell therapy manufacturing system). In various embodiments, any of the surfaces described herein can comprise an antigen-presenting surface and may comprise any combination of features described herein. In various embodiments, a cartridge may comprise one or more antigen-presenting surfaces. In various embodiments, an instrument may comprise one or more antigen-presenting surfaces.

In various embodiments, the antigen-presenting synthetic surface can be configured to activate a T-cell in vitro (e.g., activation using the cell therapy manufacturing system). The primary activating molecular ligand may comprise a MHC molecule having an amino acid sequence and may be connected covalently to the surface of the antigen-presenting synthetic surface via a C-terminal connection. The MHC molecule may present a N-terminal portion of the MHC molecule oriented away from the surface, thereby facilitating specific binding of the MHC molecule with the TCR of a T-cell disposed upon the surface. The MHC molecule may include a MHC peptide. Clusters of at least four of the MHC molecules may be disposed at locations upon the antigen-presenting synthetic surface such that when the surface is exposed to an aqueous environment, a MHC tetramer may be formed.

In various embodiments of the cell therapy manufacturing system, each of the plurality of primary activating molecular ligands may be covalently connected to the antigen-presenting synthetic surface via a linker. In some embodiments, an MHC molecule of a primary activating molecular ligand may be connected to the antigen-presenting synthetic surface through a covalent linkage. Covalent linkages can be formed, for example, using Click chemistry and an appropriate Click reagent pair. Likewise, other ligands described herein, such as co-activating molecular ligands (comprising TCR co-activating molecules and/or adjunct TCR activating molecules), growth stimulatory molecular ligands, and additional stimulatory molecular ligands may be covalently connected to the surface of the antigen presenting synthetic surface via a linker, and the linkage can be formed using Click chemistry and an appropriate Click reagent pair.

In various embodiments, the MHC molecule may be connected to the antigen presenting synthetic surface non-covalently through a coupling group (CG), such as a biotin/streptavidin binding pair interaction. In some embodiments, one member of the coupling group is covalently associated with the surface (e.g., streptavidin). Further examples of coupling groups include, but are not limited to biotin/avidin, biotin/NeutrAvidin, and digoxygenin/anti-digoxygenin. Streptavidin, avidin, and NeutrAvidin represent examples of biotin-binding agents. Likewise, other ligands described herein, such as co-activating molecular ligands (comprising TCR co-activating molecules and/or adjunct TCR activating molecules), growth stimulatory molecular ligands, and additional stimulatory molecular ligands may be noncovalently coupled to the antigen presenting synthetic surface, and the coupling group may include biotin or digoxygenin.

In various embodiments, one member of the CG binding pair may itself be covalently bound to the surface, e.g., through one or more linkers. The covalent linkage to the surface can be through a series of about 15, 20, 25, 30, 35, 40, 45, 50, 55, 60, 65, 70, 75, 80, 85, 95, 100, 200 bond lengths, or any number of bond lengths therebetween. In various embodiments, the member of the CG binding pair covalently bound to the surface is bound through a Click reagent pair. This may also be true for CG binding pair members involved in associating other ligands described herein (such as co-activating molecular ligands, TCR co-activating molecules, adjunct TCR activating molecules, growth stimulatory molecules, and additional stimulatory molecules) with the surface. Further, since some binding pair members such as streptavidin have multiple binding sites (e.g., four in streptavidin), a primary activating molecular ligand may be coupled to the antigen presenting synthetic surface by a biotin/streptavidin/biotin linkage. Again, this may also be true for CG binding pair members involved in associating other ligands described herein (such as co-activating molecular ligands, TCR co-activating molecules, adjunct TCR activating molecules, growth stimulatory molecules, and additional stimulatory molecules) with the surface.

In various embodiments, a first member of the CG binding pair is covalently associated with the primary activating molecular ligand and a second member of the CG binding pair is non-covalently associated with the surface. For example, the first member of the CG binding pair can be a biotin covalently associated with the primary activating molecular ligand; and the second member of the CG binding pair can be a streptavidin non-covalently associated with the surface (e.g., through an additional biotin, wherein the additional biotin is covalently associated with the surface). In various embodiments, the biotin covalently associated with the surface is linked to the surface through a series of about 15, 20, 25, 30, 35, 40, 45, 50, 55, 60, 65, 70, 75, 80, 85, 95, 100, 200 bond lengths, or any number of bond lengths therebetween. For example, the biotin covalently associated with the surface may be linked to the surface through a series of one or more linkers having a total length as described. Again, this may also be true for CG binding pair members involved in associating other ligands described herein (such as co-activating molecular ligands, TCR co-activating molecules, adjunct TCR activating molecules, growth stimulatory molecules, and additional stimulatory molecules) with the surface. Noncovalently associating the second member of the CG binding pair, such as streptavidin, with the surface may facilitate loading ligands such as primary activating molecular ligands, co-activating molecular ligands, TCR co-activating molecules, and adjunct TCR activating molecules at greater densities than if the second member of the CG binding pair is covalently associated with the surface.

The primary activating molecular ligand (e.g., comprising a MHC molecule) may further include an antigenic peptide that comprises a tumor associated antigen. The tumor associated antigen may be noncovalently associated with the primary activating molecular ligand (e.g., MHC molecule). The tumor associated antigen may be presented by the primary activating molecular ligand (e.g., MHC molecule) in an orientation which can initiate activation of a T lymphocyte. The tumor associated antigen may be a peptide. Some non-limiting examples of tumor associated antigens include MART1 (peptide sequence ELAGIGILTV), for melanoma, NYESO1 (peptide sequence SLLMWITQV), involved in melanoma and some carcinomas, SLC45A2, TCL1, and VCX3A, but the disclosure is not so limited. Additional examples of tumor antigens include peptides comprising a segment of amino acid sequence from a protein expressed on the surface of a tumor cell such as CD19, CD20, CLL-1, TRP-2, LAGE-1, HER2, EphA2, FOLR1, MAGE-A1, mesothelin, SOX2, PSM, CA125, T antigen, etc. The peptide can be from an extracellular domain of the tumor associated antigen. An antigen is considered tumor associated if it is expressed at a higher level on a tumor cell than on a healthy cell of the type from which the tumor cell was derived. The T cell which recognizes this tumor associated antigen is an antigen specific T-cell. Any tumor associated antigen may be utilized in the antigen presenting surface described herein. In various embodiments, the tumor associated antigen is a neoantigenic peptide, e.g., encoded by a mutant gene in a tumor cell. For detailed discussion of neoantigenic peptides, see, e.g., US 2011/0293637, which is entirely incorporated herein by reference for all purposes.

The antigen presenting synthetic surface can include a plurality of co-activating molecular ligands each comprising a TCR co-activating molecule or an adjunct TCR activating molecule. In various embodiments, the plurality of co-activating molecular ligands include a plurality of TCR co-activating molecules. In various embodiments, the plurality of co-activating molecular ligands include a plurality of adjunct TCE activating molecules. In various embodiments, the plurality of co-activating molecular ligands may include TCR co-activating molecules and adjunct TCR activating molecules. The TCR co-activating molecules and the adjunct TCR activating molecules can be present in a ratio of one to the other such as about 100:1 to 1:100, 10:1 to 1:20, 5:1 to 1:5, 3:1 to 1:3, 2:1 to 1:2, or the like. In various embodiments, the plurality of co-activating molecular ligands may include TCR co-activating molecules and adjunct TCR activating molecules in a ratio ranging from about 3:1 to about 1:3.

The TCR co-activating molecule or adjunct TCR activating molecule may include a protein, e.g., an antibody or a fragment thereof. In various embodiments, the TCR co-activating molecule may be a CD28 binding molecule (e.g., including a CD80 molecule) or a fragment thereof which retains binding ability to CD28. In various embodiments, the TCR co-activating molecule may be a CD28 binding molecule (e.g., including a CD80 molecule) or a fragment thereof which specifically binds to CD28. In some embodiments, the TCR co-activating molecule may be a CD28 binding molecule (e.g., including a CD80 molecule) or a CD28-binding fragment thereof. In various embodiments, the TCR co-activating molecule may include an anti-CD28 antibody or a fragment thereof (e.g., a CD28-binding fragment).

In various embodiments, each of the plurality of co-activating molecular ligands may be covalently connected to the antigen-presenting synthetic surface via a linker. In other embodiments, each of the plurality of co-activating molecular ligands may be noncovalently bound to a linker covalently bound to the antigen-presenting synthetic surface. The TCR co-activating molecule or adjunct TCR activating molecule may be connected to the covalently modified surface noncovalently through a CG, such as a biotin/streptavidin binding pair interaction. For example, the TCR co-activating molecule or adjunct TCR activating molecule may further comprise a site-specific C-terminal biotin moiety that interacts with a streptavidin, which may be associated covalently or noncovalently with the surface as described herein. A site-specific C-terminal biotin moiety can be added to a TCR co-activating molecule or adjunct TCR activating molecule using known methods, e.g., using a biotin ligase such as the BirA enzyme. See, e.g., Fairhead et al., Methods Mol Biol 1266:171-184, 2015 which is entirely incorporated herein by reference for all purposes. Further examples of coupling groups include biotin/avidin, biotin/NeutrAvidin, and digoxygenin/anti-digoxygenin. In various embodiments, one of the CG binding pair may itself be covalently bound to the surface, e.g., through a linker, as described above. See the examples herein for exemplary TCR co-activating molecules or adjunct TCR activating molecules.

In various embodiments, the co-activating molecular ligands of the antigen-presenting synthetic surface may include a plurality of adjunct TCR activating molecules, e.g., in addition to or instead of a TCR co-activating molecule as described herein. In various embodiments, there may be additional co-activating molecular ligands. In some embodiments, the adjunct TCR activating molecules or additional co-activating molecular ligands comprise one or more of a CD2 agonist, a CD27 agonist, or a CD137 agonist. For example, the adjunct TCR activating molecule may be a CD2 binding protein or a fragment thereof, where the fragment retains binding ability with CD2. In some embodiments, the adjunct TCR activating molecule may be CD58 or a fragment thereof which retains binding ability with CD2. The adjunct TCR activating molecule may be a CD2 binding protein (e.g., CD58) or a fragment thereof, where the fragment specifically binds CD2. The adjunct TCR activating molecule may be a CD2 binding protein (e.g., CD58) or a CD2-binding fragment thereof. The adjunct TCR activating molecules or additional co-activating molecular ligands may each be an antibody to CD2, CD27, or CD137, or there may be any combination of such antibodies. The adjunct TCR activating molecules or additional co-activating molecular ligands may alternatively each comprise a fragment of an antibody to CD2, CD27, or CD137, or any combination thereof. Varlilumab (CDX-1127) is an exemplary anti-CD27 antibody. Utomilumab (PF-05082566) is an exemplary anti-CD137 antibody. CD70 or an extracellular portion thereof may also be used as a CD27 agonist. TNFSF9, also known as CD137L, or an extracellular portion thereof may also be used as a CD137 agonist. In various embodiments, the adjunct TCR activating molecules comprise an agonist of CD2, such as an anti-CD2 antibody. In various embodiments, each of the adjunct TCR activating molecules may be covalently connected to the surface via a linker. In various embodiments, each of the adjunct TCR activating molecules may be noncovalently bound to a linker covalently bound to the surface, e.g., through a CG, such as a biotin/streptavidin binding pair interaction. For example, the adjunct TCR activating molecules may comprise a site-specific C-terminal biotin moiety as discussed above that interacts with a streptavidin, which may be associated covalently or noncovalently with the surface as described herein. Further examples of coupling groups include biotin/avidin, biotin/NeutrAvidin, and digoxygenin/anti-digoxygenin. In some embodiments, one of the CG binding pair may itself be covalently bound to the surface, e.g., through a linker.

The antigen-presenting synthetic surface may further include at least one growth stimulatory molecular ligand, in accordance with various embodiments. The growth stimulatory molecular ligand may be a protein or peptide. The growth stimulatory protein or peptide may be a cytokine or fragment thereof. The growth stimulatory protein or peptide may be a growth factor receptor ligand. The growth stimulatory molecular ligand may comprise IL-21 or a fragment thereof. In various embodiments, the growth stimulatory molecular ligand may be connected to the antigen-presenting synthetic surface via a covalent linker. In various embodiments, the growth stimulatory molecular ligand may be connected to the antigen-presenting synthetic surface through a CG, such as a biotin/streptavidin binding pair interaction. Further examples of coupling groups include biotin/avidin, biotin/NeutrAvidin, and digoxygenin/anti-digoxygenin. In various embodiments, one of the CG binding pair may itself be covalently bound to the surface, e.g., through a linker. In other embodiments, the growth stimulatory molecular ligand may be attached to a surface either covalently or via a biotin/streptavidin binding interaction, where the surface is not the same surface as the antigen-presenting synthetic surface having MHC molecules connected thereto. For example, the surface to which the growth stimulatory molecular ligand is attached can be a second surface of a microfluidic device (e.g., a surface within the cell therapy manufacturing system [e.g., instrument or cartridge]) also comprising a first, antigen-presenting synthetic surface.

In various embodiments, there may be additional growth stimulatory molecular ligands, which may be one or more cytokines, or fragments thereof. In various embodiments, additional stimulatory molecular ligands including, but not limited to IL-2 or IL-7 may be connected to the antigen-presenting synthetic surface or to another surface that is not the antigen-presenting synthetic surface, as discussed above with respect to growth stimulatory molecular ligands.

In various embodiments, the antigen-presenting synthetic surface comprises an adhesion stimulatory molecular ligand, which is a ligand for a cell adhesion receptor including an ICAM protein sequence.

The additional stimulatory molecular ligands and/or adhesion stimulatory molecular ligands may be covalently connected to a surface or may be noncovalently connected to a surface through a CG, such as a biotin/streptavidin binding pair interaction. Further examples of coupling groups include biotin/avidin, biotin/NeutrAvidin, and digoxygenin/anti-digoxygenin. In various embodiments, one of the CG binding pair may itself be covalently bound to the surface, e.g., through a linker via a biotin/streptavidin binding interaction.

In various embodiments, the antigen-presenting synthetic surface comprises a plurality of surface-blocking molecular ligands, which may include a linker and a terminal surface-blocking group. The linker can include a linear chain of 6 or more atoms (e.g., 7, 8, 9, 10, 11, 12, 13, 14, 15, 20, 25, 30, 35, 40, 45, 50, 75, 100, or more atoms) covalently linked together. Optionally, the linker has a linear structure. The terminal surface-blocking group may be a hydrophilic moiety, an amphiphilic moiety, a zwitterionic moiety, or a negatively charged moiety. In various embodiments, the terminal blocking group comprises a terminal hydroxyl group. In some embodiments, the terminal blocking group comprises a terminal carboxyl group. In various embodiments, the terminal blocking group comprises a terminal zwitterionic group. The plurality of surface-blocking molecular ligands may have all the same terminal surface-blocking group or may have a mixture of terminal surface-blocking groups. Without being bound by theory, the terminal surface-blocking group as well as a hydrophilic linker of the surface-blocking molecular ligand may interact with water molecules in the aqueous media surrounding the antigen-presenting synthetic surface to create a more hydrophilic surface overall. This enhanced hydrophilic nature may render the contact between the antigen-presenting synthetic surface and a cell more compatible and more similar to natural intercellular interactions and/or cell-extracellular fluidic environment in-vivo. The linker can comprise, for example, a polymer. The polymer may include a polymer including alkylene ether moieties. A wide variety of alkylene ether containing polymers may be suitable for use on the surfaces described herein. One class of alkylene ether containing polymers is polyethylene glycol (PEG Mw<100,000 Da), which are known in the art to be biocompatible. In various embodiments, a PEG may have an Mw of about 88 Da, 100 Da, 132 Da, 176 Da, 200 Da, 220 Da, 264 Da, 308 Da, 352 Da, 396 Da, 440 Da, 500 Da, 600 Da, 700 Da, 800 Da, 900 Da, 1000 Da, 1500 Da, 2000 Da, 5000 Da, 10,000 Da or 20,000 Da, or may have a Mw that falls within a range defined by any two of the foregoing values. In various embodiments, the PEG polymer has a polyethylene moiety repeat of about 3, 4, 5, 10, 15, 25 units, or any value therebetween. In various embodiments, the PEG is a carboxyl substituted PEG moiety. In various embodiments, the PEG is a hydroxyl substituted PEG moiety. In some embodiments, each of the plurality of surface-blocking molecular ligands may have a linker having the same length as the linkers of the other ligands of the plurality. In various embodiments, the linkers of the plurality of surface-blocking molecular ligands may have varied lengths. In various embodiments, the surface-blocking group and the length of the linker may be same for each of the plurality of surface-blocking molecular ligands. Alternatively, the surface blocking group and the length of the linker may vary within the plurality of the surface-blocking molecular ligands and may include 2, 3, or 4 different surface-blocking groups and/or 2, 3, 4, or more different lengths, chosen in any combination. In general, the surface-blocking molecular ligands have a length and/or structure that is sufficiently short so as not to sterically hinder the binding and/or function of the primary activating molecular ligands and the co-activating molecular ligands. For example, in various embodiments, the length of the surface-blocking molecular ligands is equal to or less than the length of the other linkers bound to the surface (e.g., linkers that connect coupling groups, primary activating molecular ligands, co-stimulating molecular ligands, or other ligands). In some embodiments, the length of the surface-blocking molecular ligands is about 1 or more angstroms (e.g., about 2, 3, 4, 5, 10, 15, 20, 25, 30, 35, 40, 45, 50, 75, 100, or more angstroms) less than the length of the other linkers bound to the surface (e.g., linkers that connect coupling groups, primary activating molecular ligands, co-stimulating molecular ligands, or other ligands). In various embodiments, the length of the surface-blocking molecular ligands is about 1 to about 100 angstroms (e.g., about 2 to about 75, about 3 to about 50, about 4 to about 40, or about 5 to about 30 angstroms) less than the length of the other linkers bound to the surface. When the surface-blocking molecular ligands have a length that is the same or somewhat less than the length of the other linkers bound to the surface, the resulting surface effectively presents the ligands attached to the other linkers in a manner that is readily available for coupling and/or interacting with cells. With respect to antigen-presenting beads, it has been found that including a surface-blocking molecular ligand such as a hydrophilic polymer, e.g., a PEG or PEO polymer and/or ligands comprising terminal hydroxyl or carboxyl groups, can beneficially reduce aggregation of the beads through hydrophobic interactions. The surface-blocking molecular ligands can be attached to the surface after the primary and other (e.g., coactivating, adjunct, etc.) ligands discussed above or may be introduced before any of the activating or co-activating species are attached to the surface, as set forth in any embodiments disclosed herein.

The antigen-presenting synthetic surface may comprise glass, metal, a polymer, or a metal oxide, in accordance with various embodiments. In various embodiments, the antigen-presenting synthetic surface is a surface of a wafer having any kind of configuration, a surface of a bead, at least one inner surface of a fluidic circuit containing device (e.g., microfluidic device) configured to contain a plurality of cells, or an inner surface of a tube (e.g., glass or polymer tube). In various embodiments, the wafer having an antigen-presenting synthetic surface configured to activate T lymphocytes may be sized to fit within a well of a standard 48, 96 or 384 wellplate. In various embodiments, beads having an antigen-presenting synthetic surface configured to activate T lymphocytes may be disposed for use within a wellplate or within a fluidic circuit containing device. In various embodiments, the density of the plurality of primary activating molecular ligands on the antigen-presenting synthetic surface (or in each portion or sub-region where it is attached) may be from about 50 to about 500 molecules per square micron; about $4\times10^2$ to about $2\times10^3$ molecules per square micron; about $1\times10^3$ to about $2\times10^4$ molecules per square micron; about $5\times10^3$ to about $3\times10^4$ molecules per square micron; about $4\times10^2$ to about $3\times10^4$ molecules per square micron; about $4\times10^2$ to about $2\times10^3$ molecules per square micron; about $2\times10^3$ to about $5\times10^3$ molecules per square micron; about $5\times10^3$ to about $2\times10^4$ molecules per square micron; about $1\times10^4$ to about $2\times10^4$ molecules per square micron; or about $1.25\times10^4$ to about $1.75\times10^4$ molecules per square micron.

In various embodiments, the density of the plurality of co-activating molecular ligands on the antigen-presenting synthetic surface (or in each portion or sub-region where it is attached) is from about 20 to about 250 molecules per square micron; about $2\times10^2$ to about $1\times10^3$ molecules per square micron; about 500 to about $5\times10^3$ molecules per square micron; about $1\times10^3$ to about $1\times10^4$ molecules per square micron; about $5\times10^2$ to about $2\times10^4$ molecules per square micron; about $5\times10^2$ to about $1.5\times10^4$ molecules per square micron; about $5\times10^3$ to about $2\times10^4$ molecules per square micron, about $5\times10^3$ to about $1.5\times10^4$ molecules per square micron, about $1\times10^4$ to about $2\times10^4$ per square micron, about $1\times10^4$ to about $1.5\times10^4$ per square micron, about $1.25\times10^4$ to about $1.75\times10^4$, or about $1.25\times10^4$ to about $1.5\times10^4$ per square micron.

b. Exemplary Unpatterned Planar Surfaces

In various embodiments, an antigen-presenting synthetic surface may comprise an unpatterned surface having a plurality of primary activating molecular ligands distributed evenly thereon. The primary activating molecular ligands can comprise MHC molecules, each of which may include a tumor associated antigen in accordance with various embodiments. In various embodiments, the unpatterned surface may further include a plurality of co-activating molecular ligands (e.g., TCR co-activating molecules and/or adjunct TCR activating molecules) distributed evenly thereon. The co-activating molecular ligands may be as described above for antigen-presenting surfaces, in any combination. In various embodiments, the density of the primary activating molecular ligands and the co-activating molecular ligands may the same ranges as described herein for antigen-presenting surfaces. The unpatterned antigen-presenting synthetic surface may further include additional growth stimulatory, adhesive, and/or surface-blocking molecular ligands, as described above for antigen-presenting surfaces, each of which (if present) can be evenly distributed on the unpatterned surface in accordance with various embodiments. For example, the unpatterned surface can include an adjunct stimulatory molecule such as IL-21 connected to the surface. In various embodiments, the primary activating molecular ligands, co-activating molecular ligands, and/or additional ligands may be linked to the surface as described above for the antigen-presenting surfaces. As used herein, a surface having a ligand "distributed evenly" thereon is characterized in that no portion of the surface having a size of 10% the total surface area, or greater, has a statistically significant higher concentration of ligand as compared to the average ligand concentration of the total surface area of the surface in accordance with various embodiments.

c. Exemplary Patterned Planar Surfaces

Figure 7B:
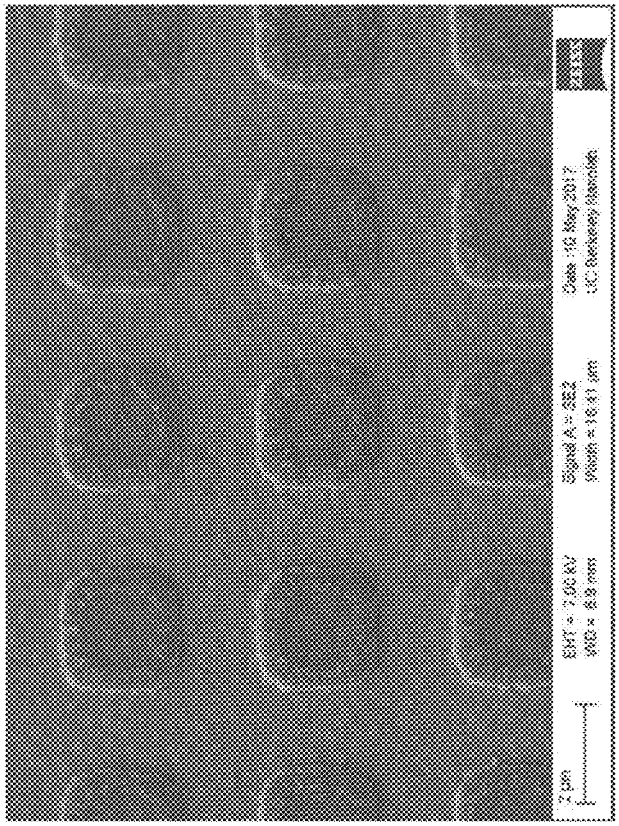
FIGS. 7A and 7B are scanning electron micrograph representations of patterned antigen presenting surfaces according to some embodiments of the disclosure.
Figure 7A:
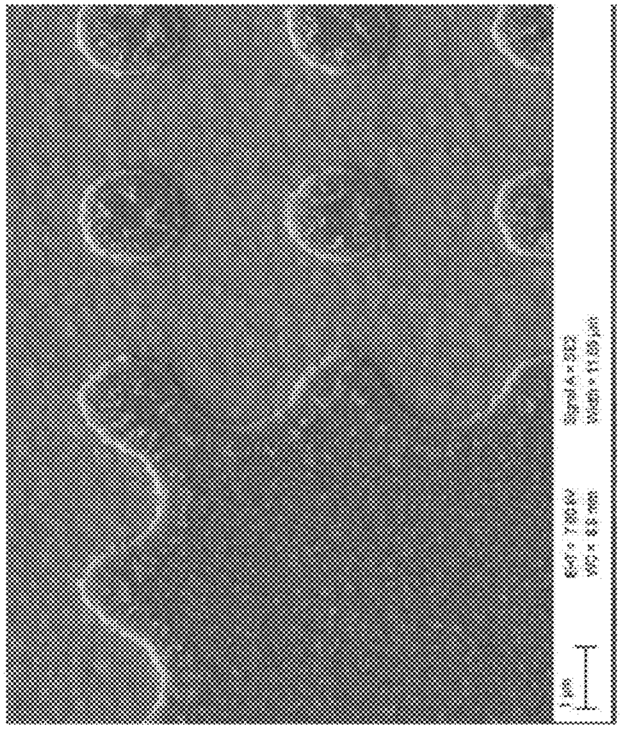

In various embodiments, the antigen-presenting synthetic surface may be patterned and may have a plurality of regions, each region including a plurality of the primary activating molecular ligands comprising MHC molecules, where the plurality of regions can be separated by a region configured to substantially exclude the primary activating molecular ligands. The antigen-presenting synthetic surface may be a planar surface. In various embodiments, each of the plurality of regions including the at least a plurality of the primary activating molecular ligands may further include a plurality of the co-activating molecular ligands, e.g., a TCR co-activating molecule and/or an adjunct TCR activating molecule. In various embodiments, the co-activating molecular ligands may be any of the co-activating molecular ligands as described herein and in any combination. In various embodiments, the primary activating molecular ligands and/or co-activating molecular ligands may be linked to the surface as described herein for the antigen-presenting surfaces. The density of the primary activating molecular ligands and/or the co-activating molecular ligands in each of the regions containing the primary activating molecular ligands and/or the co-activating molecular ligands may be in the same range as the densities described herein for antigen-presenting surfaces. In some embodiments, each of the plurality of regions comprising at least the plurality of the primary activating molecular ligands has an area of about 0.10 square microns to about 4.0 square microns. In other embodiments, the area of each of the plurality of regions may be about 0.20 square microns to about 0.8 square microns. The plurality of regions may be separated from each other by about 2 microns, about 3 microns, about 4 microns, or about 5 microns. The pitch between each region of the plurality and its neighbor may be about 2 microns, about 3 microns, about 4 microns, about 5 microns, or about 6 microns. See FIGS. 7A and 7B showing two embodiments of a patterned surface.

In various embodiments, the region configured to substantially exclude the primary activating molecular ligands comprising MHC molecules may also be configured to substantially exclude TCR co-activating molecules and/or adjunct TCR activating molecules.

In various embodiments, the region configured to substantially exclude the primary activating molecular ligands and optionally the TCR co-activating molecules and/or adjunct TCR activating molecules may also be configured to include one or more of surface-blocking molecular ligands, growth stimulatory molecules, additional stimulatory molecules, and adhesion stimulatory molecular ligands. In various embodiments, the growth stimulatory molecules and/or additional stimulatory molecules include a cytokine or fragment thereof, and may further include IL-21 or fragment thereof. In various embodiments, the region configured to substantially exclude the primary activating molecular ligands and optionally the TCR co-activating molecules and/or adjunct TCR activating molecules may further be configured to include one or more supportive moieties. The supportive moieties may provide adhesive motifs to support T lymphocyte growth or may provide hydrophilic moieties providing a generally supportive environment for cell growth. The moiety providing adhesive support may include a peptide sequence including a RGD motif. In various embodiments, the moiety providing adhesive support may be an ICAM sequence. A moiety providing hydrophilicity may be a moiety such as a PEG moiety or carboxylic acid substituted PEG moiety.

d. Beads

Figure 33D:
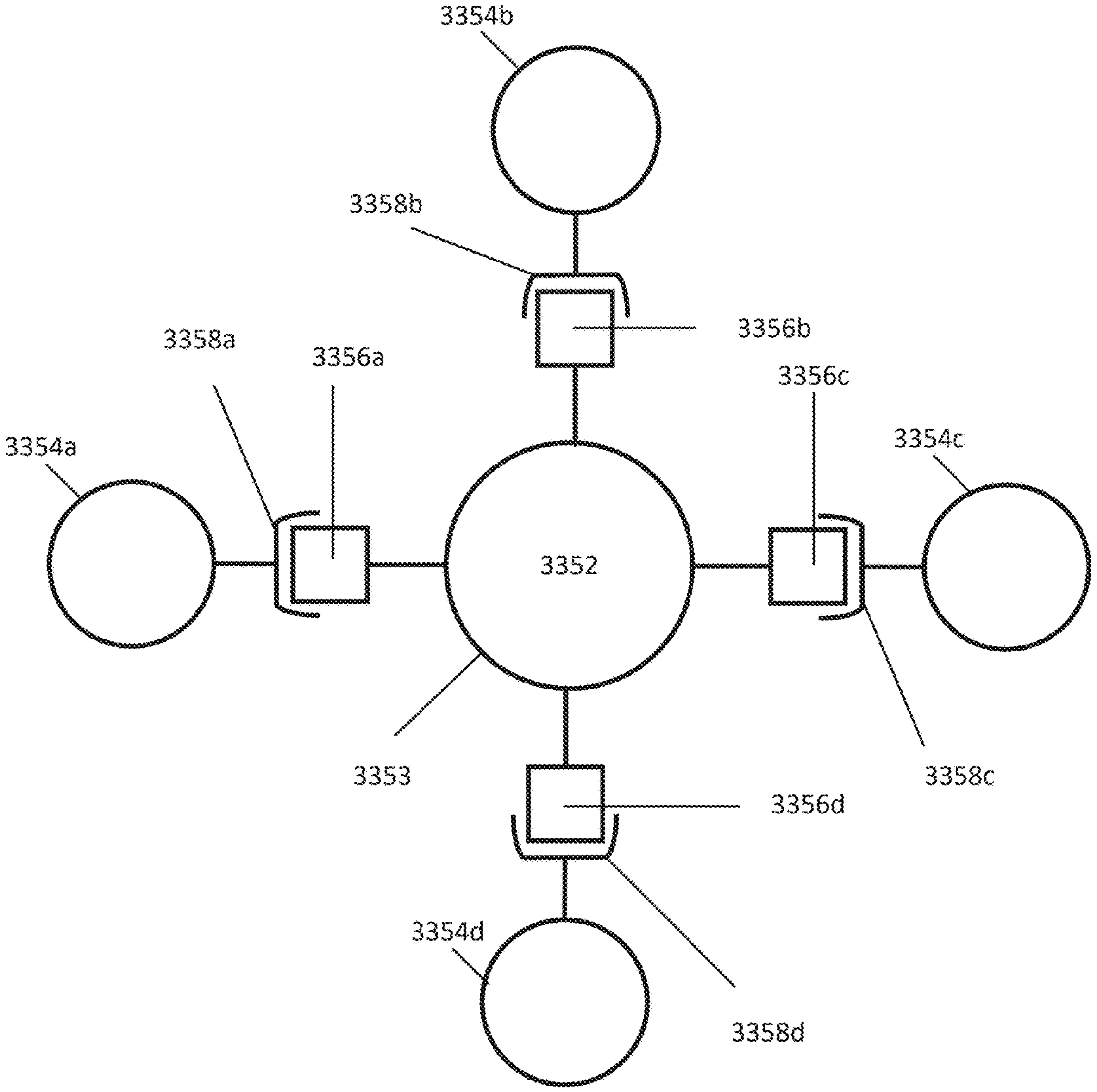

FIG. 33D illustrates a bead 3352 comprising a surface 3353 according to various embodiments. In various embodiments, the surface 3353 can comprise an antigen-presenting surface. In various embodiments, the surface 3353 may comprise one or more antigen-presenting molecules 3356*a*, 3356*b*, 3356*c*, 3356*d*. In various embodiments, beads 3352 can be introduced to T-cells 3354*a*, 3354*b*, 3354*c*, 3354*d* during a cell sorting process. In various embodiments, beads 3352 can be introduced to T-cells 3354*a*, 3354*b*, 3354*c*, 3354*d* during a T-cell activation process. In various embodiments, beads 3352 can be introduced to T-cells 3354*a*, 3354*b*, 3354*c*, 3354*d* during a sortavation process (e.g. combined cell sorting and T-cell activation processes).

Not being bound by any particular theory, certain experiments have indicated that it may be advantageous to provide and use beads for T-cell activation that have relatively defined surface-area to volume ratios. Such beads may present the relevant ligands (e.g. antigens) in a more accessible way so that they interact more efficiently with T-cells during activation. Such beads may provide a desired degree of T-cell activation with fewer ligands needed than beads with higher surface-area to volume ratios and/or may provide a higher degree of T-cell activation or more T-cells with desired features (e.g., antigen specificity and/or marker phenotypes described herein) than beads with higher surface-area to volume ratios in accordance with various embodiments. An ideally spherical solid has the lowest possible surface-area to volume ratio. Accordingly, in various embodiments, the bead surface-area can be within 10% of the surface-area of a sphere of an equal size (volume or diameter), and is referred to herein as "substantially spherical." For example, for a bead with a 2.8 μm diameter (1.4 μm radius), the corresponding ideal sphere would have a surface area of 4TTr2=24.63 um2. A substantially spherical 2.8 μm diameter bead with a surface-area within 10% of the surface-area of an ideal sphere of an equal volume or diameter would therefore have a surface-area less than or equal to 27.093 $\mu m^2$. It is noted that certain commercially available beads are reported as having higher surface areas; for example, Dynabeads M-270 Epoxy are described in their product literature as having a specific surface area of 2-5 $m^2/g$ and a 2.8 μm diameter, and the literature also indicates that 1 mg of beads is 6-7×107 beads. Multiplying the specific surface area by 1 mg/6-7×107 beads gives a surface area per bead of 28 to 83 $\mu m^2$ per bead, which is more than 10% greater than the surface-area of an ideal sphere with a 2.8 μm diameter. Polymer beads having a surface area more than 10% greater than the surface-area of an ideal sphere are referred to herein as a "convoluted bead." In various embodiments, a polymer bead may be either substantially spherical or convoluted. In some embodiments, the polymer bead is not convoluted, but is substantially spherical.

Referring to FIG. 37A, beads can be stored in one or more reagent reservoirs 3746*a*, 3746*b*, 3746*c* prior to use. In various embodiments, one or more valves 3714, 3716, 3718 may be actuated by a control system 3764 for releasing the beads 3352 from the one or more reagent reservoirs 3746*a*, 3746*b*, 3746*c*. In various embodiments, the beads may be introduced to T-cells by flowing them through a fluidic network of the cell therapy manufacturing system. In various embodiments, a pressurized gas from a gas source 3706 can provide the motive force for the beads. In alternate embodiments, one or more pumps (e.g., peristaltic jump) can provide the motive force. In various embodiments, beads may cause activation of the T-cells.

In various embodiments, activation may occur within bioreactor 3599 of the cell therapy manufacturing system. In various embodiments, the beads can flow into the bioreactor 3599 through one or more inlet ports 3750, 3752.

vii. T-Cell Activation Methods

In various embodiments, a T-cell activation process or method can be carried out on a cell therapy manufacturing system.

Exemplary methods of activating T lymphocytes comprise contacting a plurality of T lymphocytes with an antigen-presenting synthetic surface including a plurality of primary activating molecular ligands, each including a major histocompatibility (MHC) molecule configured to bind to a T-cell receptor of the T cell, and a plurality of co-activating molecular ligands each including a T cell receptor (TCR) co-activating molecule or an adjunct TCR activating molecule, and, culturing the plurality of T lymphocytes in contact with the antigen-presenting synthetic surface, thereby converting at least a portion of the plurality of T Lymphocytes to activated T lymphocytes. The antigen-presenting surface may be any antigen-presenting surface as described herein. In some embodiments, the MHC molecule is an MHC Class 1 molecule. Any of the antigen-presenting synthetic surfaces described herein can be used. In various embodiments, the plurality of MHC molecules may each include an amino acid sequence, and further may be connected to the antigen-presenting synthetic surface via a C-terminal connection of the amino acid sequence. Alternatively, the MHC molecule can be connected to the antigen-presenting synthetic surface through a noncovalent association. Any noncovalent association can be used, e.g., biotinylation of the MHC and binding thereof to streptavidin on the surface. In various embodiments, the MHC molecule may further include an antigen molecule, such as a tumor associated antigen, e.g., any of the tumor associated antigens described herein. In various embodiments, the antigen molecule may be MART1, NYESO1, SLC45A2, TCL1, or VCX3A.

In various embodiments, the co-activating molecules may be connected to the antigen-presenting synthetic surface, as described herein. The T cell receptor (TCR) co-activating molecule or an adjunct TCR activating molecule of the plurality of co-activating molecules may be any TCR co-activating molecule or any adjunct TCR activating molecule as described herein and may be provided in any ratio described herein.

In various embodiments, the method may further include contacting the plurality of T lymphocytes with a plurality of growth stimulatory molecular ligands. In various embodiments, each of the growth stimulatory molecular ligands may include a growth factor receptor ligand. In various embodiments, contacting the plurality of T lymphocytes with the plurality of growth stimulatory molecular ligands may be performed after a first period of culturing of at least one day. In various embodiments, the plurality of growth stimulatory molecular ligands may include IL-21 or a fragment thereof. In various embodiments, the plurality of growth stimulatory molecular ligands may be connected to the antigen-presenting synthetic surface. In various embodiments, the plurality of growth stimulatory molecular ligands may be connected to a surface (e.g., of a bead) that is a different surface than the antigen-presenting synthetic surface including the biomolecules including MHC molecules. In various embodiments, the plurality of growth stimulatory molecular ligands may be connected to the antigen-presenting synthetic surface including MHC molecules.

In various embodiments, the method may include using antigen presenting surfaces on beads. When beads having antigen presenting surfaces are used, the ratio of beads to T lymphocytes may be about 1:1; about 3:1; about 5:1; about 7:1 or about 10:1. The beads may have antigen presenting MHC molecules and anti-CD28 antibodies attached thereto in any method as described herein. In various embodiments, IL-21 may also be attached to the antigen presenting surface of the bead. In various embodiments, IL-21 may be attached to a second bead that has IL-21 as the only biomolecule contributing to activation.

In various embodiments, the method may be performed using a planar surface which may be patterned or unpatterned.

In various embodiments, a first period of culturing may be performed for 4, 5, 6, 7, or 8 days. During the first period of culturing, growth stimulatory molecules such as IL-21, IL-2, and/or IL-7 may be added in solution or may be added on bead to feed the T lymphocytes.

At the end of a first period of culture, the population of cells may include a mixture of unactivated and activated T lymphocytes. Flow cytometry using multiple cell surface markers can be performed to determine the extent of activation and the phenotype of the cells analyzed.

In various embodiments, a second period of culture can be performed. If the antigen presenting surfaces are beads, a second aliquot of beads containing the primary activating molecular ligand including the MHC molecule, which includes the tumor associated antigen and co-activating molecules (e.g., TCR co-activating molecules and/or adjunct TCR activating molecules, such as anti-CD28 antibodies and/to anti-CD2 antibodies, respectively) may be provided to the T lymphocytes, e.g., by addition to the wellplate, chamber of the fluidic circuit containing device, or microfluidic device having sequestration pens as described herein.

The antigen presenting beads may further include additional growth stimulatory molecules, e.g., IL-21, connected thereto. The antigen presenting beads may be added to the cells being cultured in about a 1:1; about 3:1, about 5:1; or about 10:1 ratio to the cells. In various embodiments, a second aliquot of IL-21 may be added as a second set of beads having IL-21 connected thereto, or further, may be added as a solution. IL-2 and IL-7 may also be added during the second period of culturing to activate additional numbers of T lymphocytes.

When a patterned or unpatterned wafer, inner surface of a fluidic circuit containing device, inner surface of a tube, or inner surface of a microfluidic device having sequestration pens is used, a second period of culturing may be accomplished by continuing to culture in contact with the same antigen presenting surface. Alternatively, a new antigen presenting surface may be brought into contact with the T lymphocytes resultant from the first period of culturing. In various embodiments, antigen presenting beads, like any described above or set forth in any embodiments disclosed herein, may be added to the wells or interior chamber of a fluidic circuit containing device or the sequestration pens of a microfluidic device. Growth stimulatory molecules such as IL-21, IL-2, IL-7, or a combination thereof may be added in solution or on beads. In some embodiments, IL-2 and IL-7 are added.

At the conclusion of the second culturing period, flow cytometry analysis can be performed to determine the extent of activation and to determine the phenotype of the further activated T lymphocytes present at that time.

In various embodiments, a third period of culturing may be included. The third period may have any of the features described herein with respect to the second period. In various embodiments, the third period can be performed in the same way as the second period. For example, all of the actions employed in the second period of culturing may be repeated to further activate T lymphocytes in the wells of the wellplate, in a tube, or in the chamber of a fluidic circuit containing device or a microfluidic device having sequestration pens.

In various embodiments, the T lymphocytes being activated comprise CD8+T lymphocytes, such as naïve CD8+T lymphocytes. In various embodiments, the T lymphocytes being activated are enriched for CD8+T lymphocytes, such as naïve CD8+T lymphocytes. Alternatively, in various embodiments, the T lymphocytes being activated comprise CD4+T lymphocytes, such as naïve CD4+T lymphocytes. In various embodiments, the T lymphocytes being activated are enriched for CD4+T lymphocytes, such as naïve CD4+T lymphocytes. CD4+T lymphocytes can be used, e.g., if T cells specific for a Class II-restricted antigen are desired.

In various embodiments, the method produces activated T lymphocytes that are CD45RO+. In various embodiments, the method produces activated T lymphocytes that are CD28+. In various embodiments, the method produces activated T lymphocytes that are CD28+CD45RO+. In various embodiments, the method produces activated T lymphocytes that are CD197+. In various embodiments, the method produces activated T lymphocytes that are CD127+. In various embodiments, the method produces activated T lymphocytes that are positive for CD28, CD45RO, CD127 and CD197, or at least any combination of three of the foregoing markers, or at least any combination of two of the foregoing markers. The activated T lymphocytes with any of the foregoing phenotypes can further be CD8+. In various embodiments, any of the foregoing phenotypes that is CD28+comprises a CD28 high phenotype.

In various embodiments, the method produces a population of T cells comprising antigen-specific T cells, wherein at least 65%, 70%, 75%, 80%, 85%, 86%, 87%, 88%, 89%, 90%, 91%, 92%, 93%, 94%, 95%, 96%, 97%, or 98% of the antigen-specific T cells are CD45RO+/CD28High cells, wherein each of the foregoing values can be modified by "about." Alternatively or in addition, in various embodiments, the method produces a population of T cells wherein at least 1%, 1.5%, 2%, 3,%, 4%, 5%, 6%, 7%, 8%, 9%, or 10% of the T cells are antigen-specific T cells; or wherein 1%-2%, 2%-3%, 3%-4%, 4%-5%, 5%-6%, 6%-7%, 7%-8%, 8%-9%, 9%-10%, 10%-11%, or 11%-12% of the T cells are antigen-specific T cells, wherein each of the foregoing values can be modified by "about." The content of the population of T cells can be determined on the "crude" product of the method following contact with the antigen-presenting surface and optionally further expansion steps, i.e., before/without enriching or separating product T cells having a particular phenotype. The determination of antigen-specificity and/or T cell marker phenotype can exclude dead cells.

In various embodiments, the method provides a population of T cells in which the fraction of T cells that are antigen-specific is increased relative to the starting population.

B. T-CELL MODIFICATION TECHNIQUES

In accordance with various embodiments, cell (e.g., T-cell) modification processes can be carried out using a cell therapy manufacturing system. In various embodiments, gene transfer systems and methods (e.g., transfection or transduction) can be used to encode a T-cell with a nucleic acid construct. In various embodiments, T-cell modification can be carried out using viral methods (e.g., transduction). In various embodiments, T-cell modification can be carried out using non-viral methods (e.g., transfection).

T-cell modification can occur prior to cells entering the cell therapy manufacturing system in accordance with various embodiments, whereby the T-cells can be prepared for an expansion process before being loaded into the cell therapy manufacturing system. In various embodiments, T-cell modification can occur on the cell therapy manufacturing system. In various embodiments, T-cell modification can occur on a cartridge of the cell therapy manufacturing system. In various embodiments, T-cell modification can occur on an instrument of the cell therapy manufacturing system prior to T-cell entry into the cartridge.

T-cell modification can occur via a variety of methods carried out on the cell therapy manufacturing system. Non-limiting examples of T-cell modification can include viral transfection, electroporation, mechanical squeeze, and chemical transfection.

Figure 34:
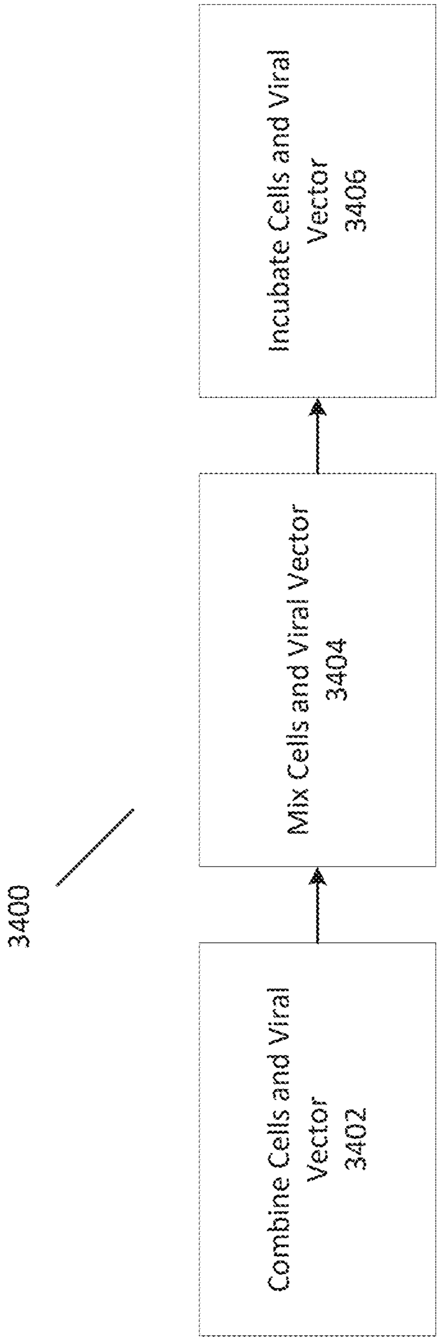
FIG. 34 is a schematic block diagram of an exemplary transduction workflow for cell therapy manufacturing system according to various embodiments of the disclosure.

FIG. 34 illustrates an example flow process diagram for an "on-system" (e.g., on-instrument) approach to T-cell modification 3400 using transduction, in accordance with various embodiments.

In various embodiments, a step 3402 of the process can comprise combining cells and viral vectors.

In various embodiments, a step 3404 of the process can comprise mixing the cells and viral vectors.

In various embodiments, a step 3406 of the process can comprise incubating cells and viral vectors.

i. "On-Instrument" Approaches ii. "On-Cartridge" Approaches

Figure 37C:
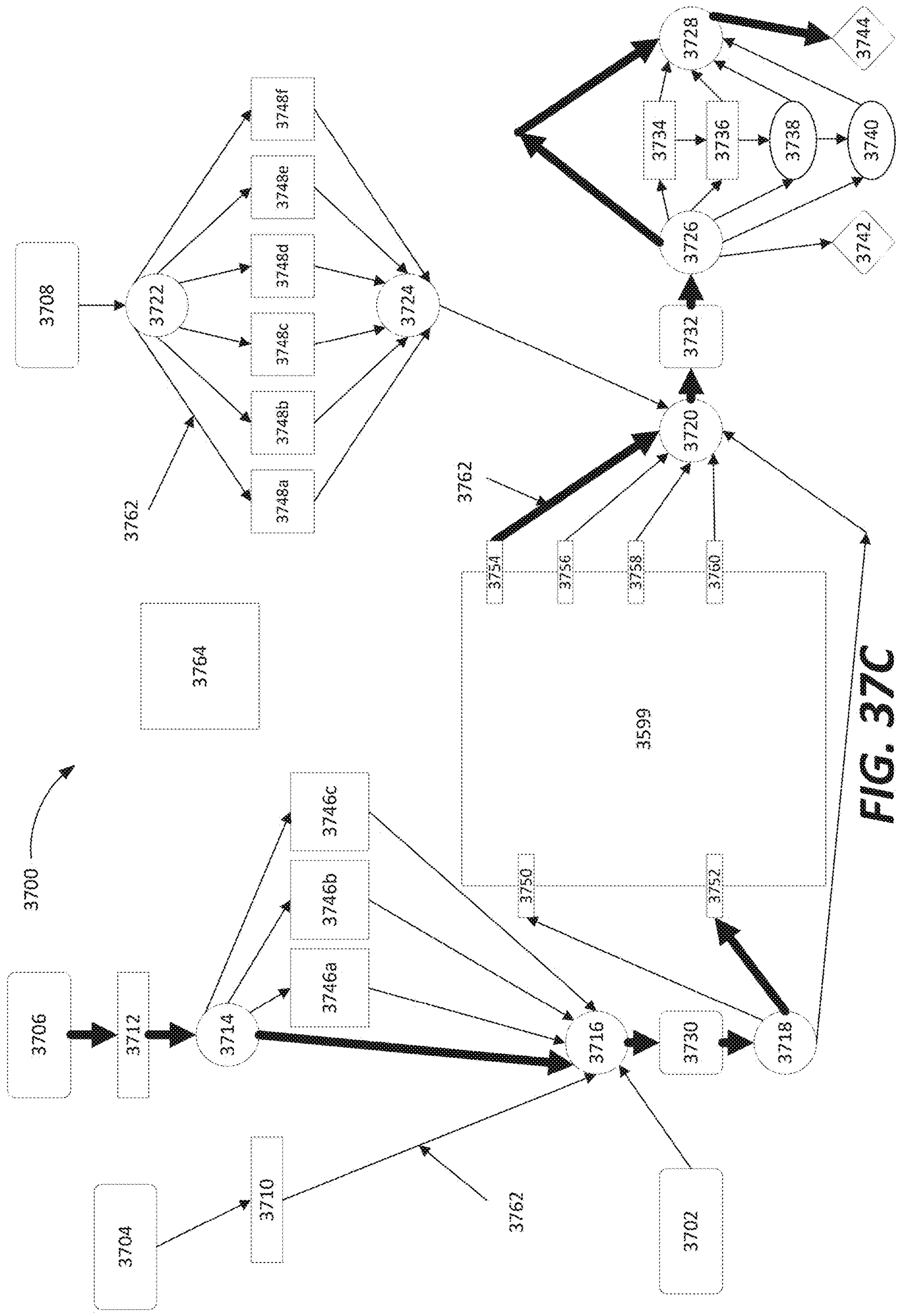
FIG. 37C illustrates a process flow diagram for cell culture (e.g. T-cell expansion) using a cell therapy manufacturing system according to various embodiments.
Figure 37D:
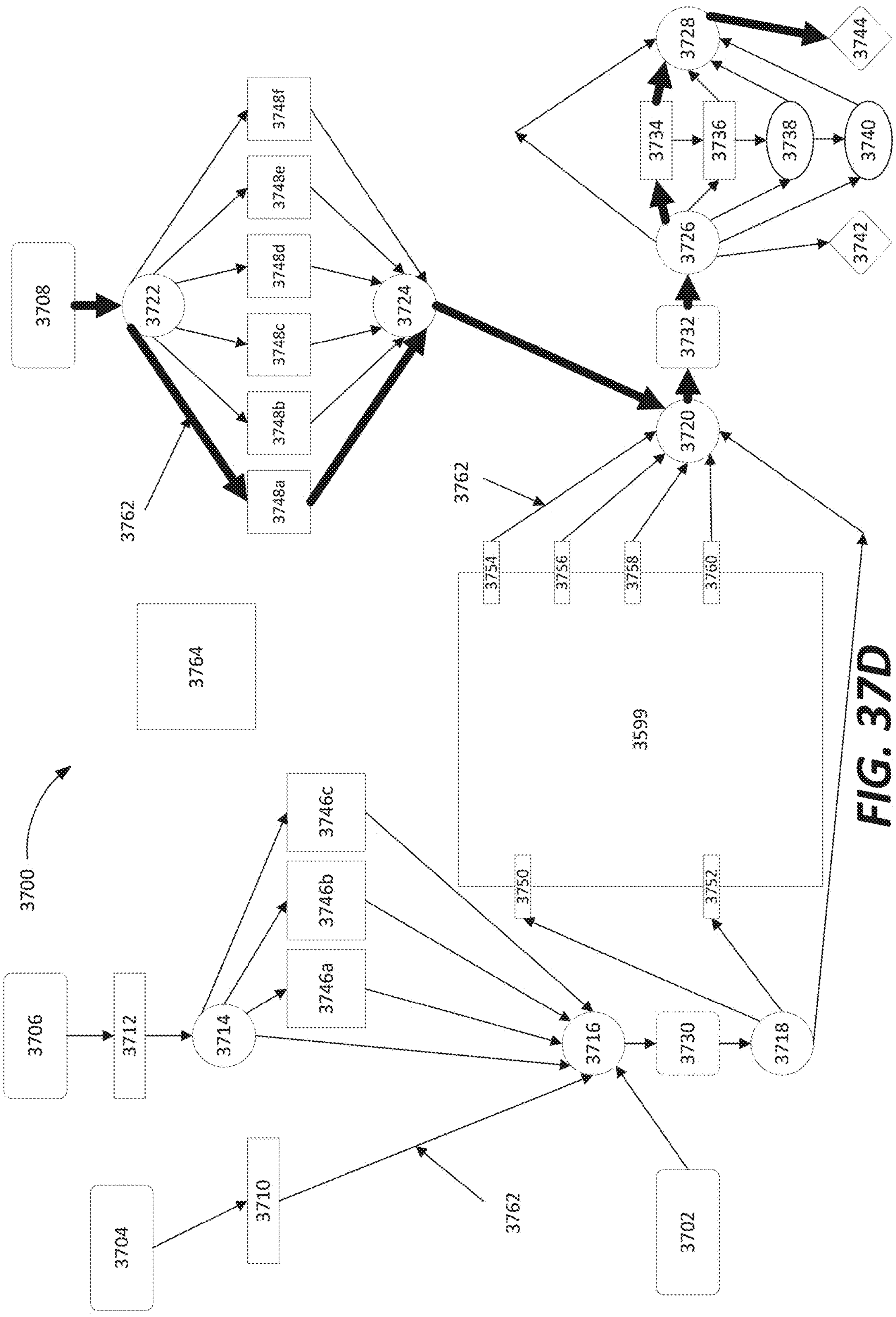
FIG. 37D illustrates a process flow diagram for a post sorting assay using a cell therapy manufacturing system according to various embodiments.
Figure 37E:
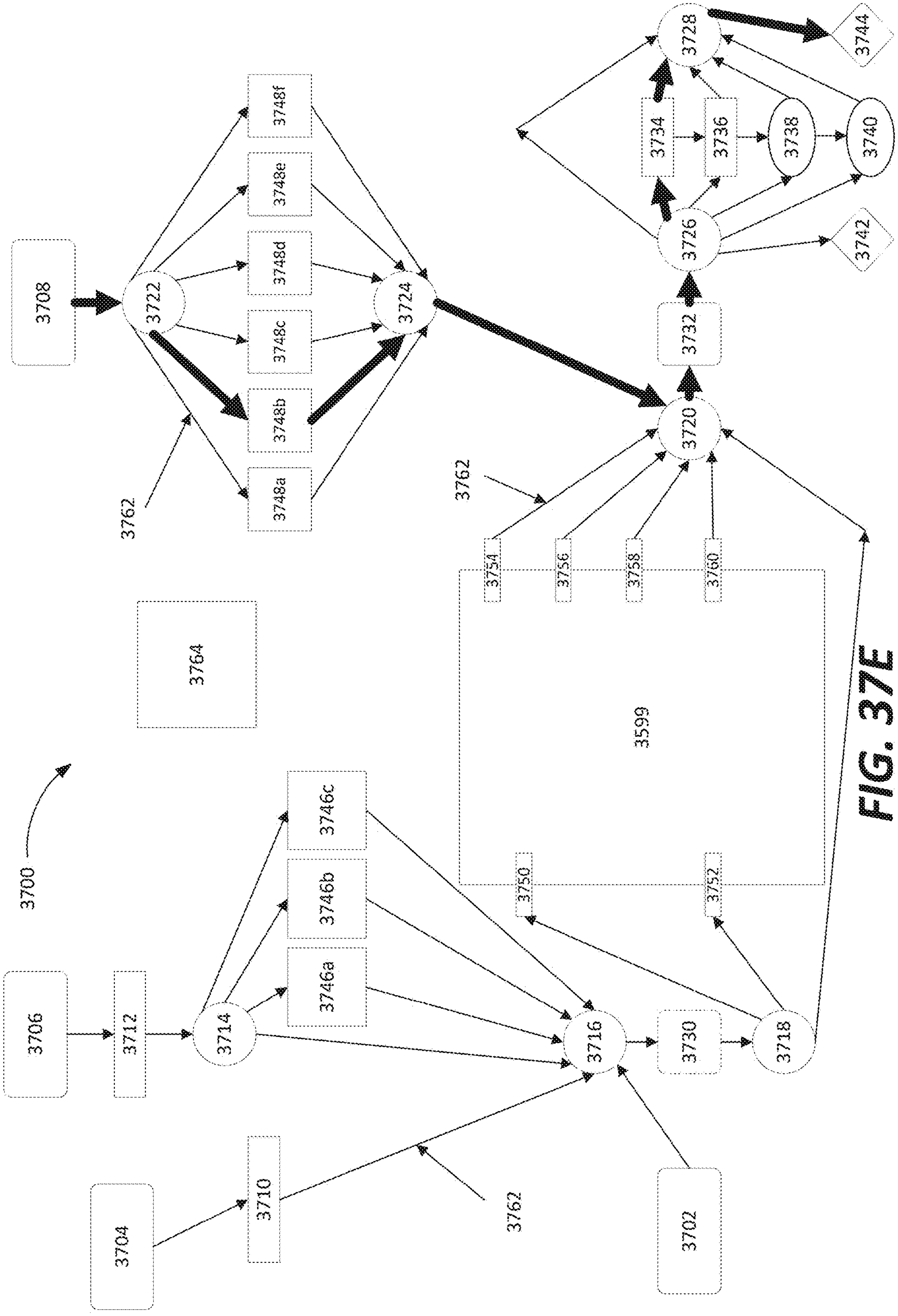
FIG. 37E illustrates a process flow diagram for an activation assay using a cell therapy manufacturing system according to various embodiments.
Figure 37F:
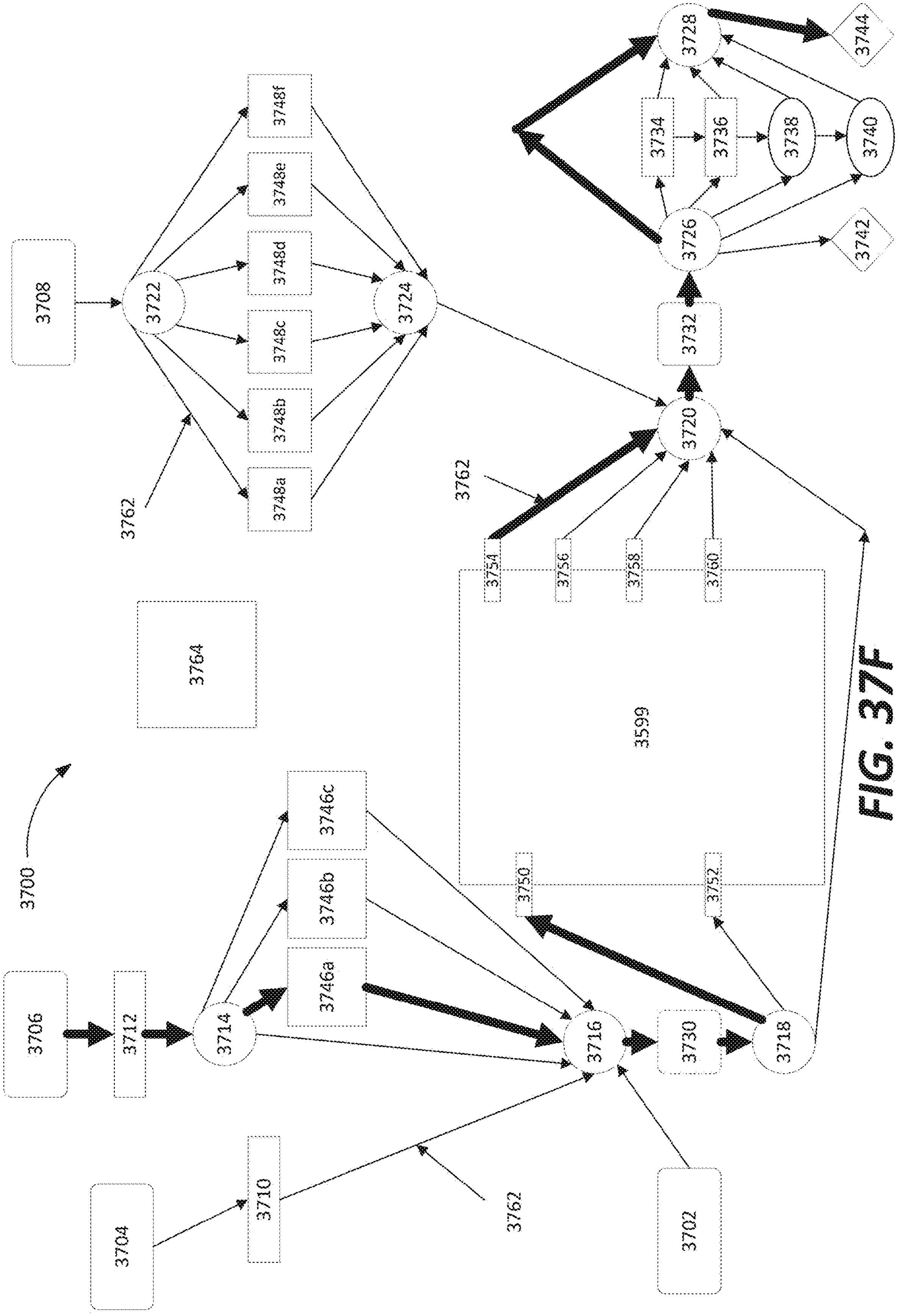
FIG. 37F illustrates a process flow diagram for a transduction process using a cell therapy manufacturing system according to various embodiments.

FIG. 37F illustrates a system for carrying out a transduction process in accordance with various embodiments. In various embodiments, a cartridge can be provided for a cell therapy manufacturing process. In various embodiments, the cartridge can be pre-configured for a defined cell therapy manufacturing process. In accordance with a defined cell therapy manufacturing process, one or more reagents can be pre-loaded onto a cartridge. In various embodiments, reagents (e.g. viral vectors, beads, etc.) can be pre-loaded into one or more reagent reservoirs 3746*a*, 3746*b*, 3746*c*.

In various embodiments, a cartridge can be fluidically coupled to an instrument of a cell therapy manufacturing system 3700. In various embodiments, a cartridge can be electronically coupled to an instrument of a cell therapy manufacturing system 3700. In various embodiments, a control system 3764 can direct one or more processes occurring on a cell therapy manufacturing system.

In various embodiments, a motive force may be provided for moving fluidic through a fluidic network of the cell therapy manufacturing system 3700. In some embodiments, the motive force can be provided by a gas source 3706. In alternative embodiments, the motive force can be provided by one or more pumps.

In various embodiments, one or more valves 3714, 3716, 3718 may be actuated allowing a pressurized gas to enter one or more reagent reservoirs 3746*a*, 3746*b*, 3746*c* and motivate one or more reagents contained therein to move to bioreactor 3599. In various embodiments, the one or more reagents comprise a viral vector. In various embodiments, T-cells can be transduced in the bioreactor 3599.

C. T-CELL EXPANSION (BIOREACTOR)

In various embodiments, one or more T-cell expansion processes can be carried out on a cell therapy manufacturing system. T-cell expansion can occur within a bioreactor of a cartridge (e.g., bioreactor 3599) in accordance with various embodiments.

i. Basic Description of Bioreactor Module

FIG. 37C illustrates a process flow diagram for cell culture (e.g. T-cell expansion) using a cell therapy manufacturing system 3700 according to various embodiments. In various embodiments, a container 3712 comprising ingredients (e.g., media) for cell culture can be aseptically connected to a fluidic network 3762 of the cell therapy manufacturing system 3700. In various embodiments, a control system can actuate one or more valves 3714, 3716, 3718 to direct the ingredients to a bioreactor 3599.

In various embodiments, flow rate of media into the bioreactor 3599 can be monitored using a flow sensor 3730. In various embodiments, a control system 3764 can receive the flow rate measurement. In various embodiments, the valves 3714, 3716, 3718 can be actuated to adjust the flow rate based on the flow rate measurement as compared to a setpoint.

In various embodiments, media can enter a second inlet port 3752. In various embodiments, the second inlet port 3752 can comprise a lower elevation to a first inlet port 3750.

In various embodiments, a gas source 3706 can provide the motive force for moving the ingredients through the fluidic network 3762. In various embodiments, one or more pumps can provide the motive force for moving the ingredients through the fluidic network 3762.

In various embodiments, fluid (e.g., gas or media) can exit one or more outlet ports 3754, 3756, 3758, 3760. In various embodiments, a gas can exit an outlet port 3754 having a higher elevation relative to other outlet ports 3756, 3758, 3760. In various embodiments, a flow path through the fluidic network 3762 can be opened via actuation of one of more valves 3720, 3726, 3728, thereby, directing the fluid to a waste receptacle 3744.

ii. Bioreactor Surfaces

Figure 36A:
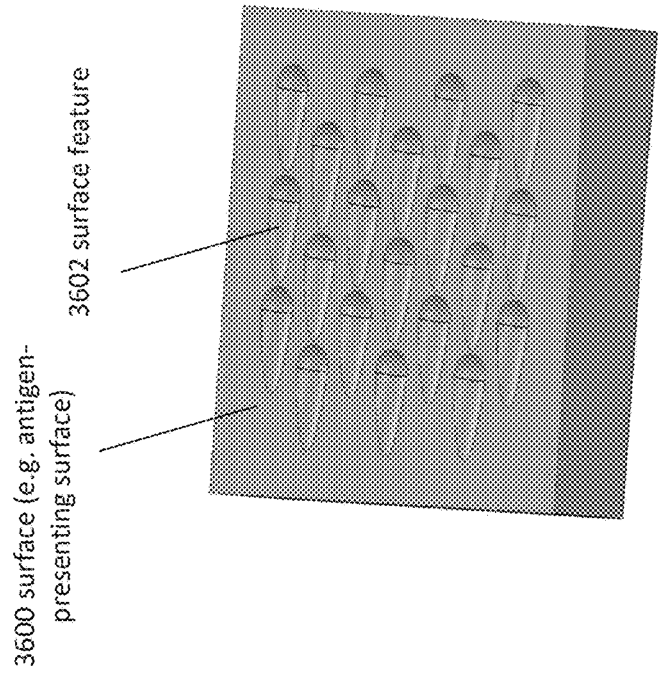
FIG. 36A-C are illustrations of a bioreactor surface according to various embodiments.
Figure 36B:
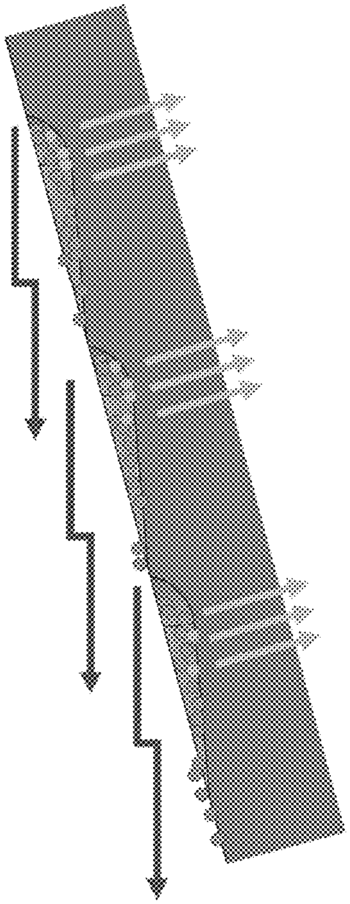
Figure 36C:
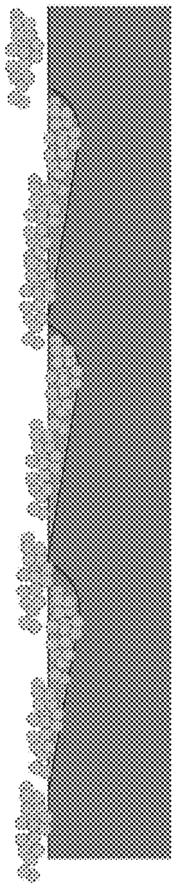

FIGS. 36A, 36B, and 36C illustrates a surface 3600 of a bioreactor according to various embodiments. In various embodiments, the surface 3600 can comprise one or more surface features 3602.

In various embodiments, surface features 3602 can comprise a recess in the surface 3600. In various embodiments, the surface feature 3602 can help the bioreactor retain health T-cells during the washing processes described herein.

In various embodiments, the surface 3600 of the bioreactor can be tilted (See FIG. 36B) for releasing waste (e.g., dead cells, debris, and/or unbound cells).

In various embodiments, target T-cells can be bound to magnetic beads and magnetic force can be applied during the washing steps described herein such that the target T-cells remain after washing.

iii. Cell Expansion Monitoring and Control

As shown in FIG. 35, bioreactor 3599 can comprise sensors capable of directly interrogating fluid within a compartment of a bioreactor. FIG. 371 illustrates an additional and/or alternate system and method of interrogating fluid of bioreactor 3599.

In various embodiments, one or more valves 3720, 3726, 3728 can be actuated to direct an aliquot of fluid from the bioreactor 3599 to one or more sensors 3738, 3740.

a. Sensors and Probes

In various embodiments, the one or more sensors 3738, 3740 can comprise a pH sensor. In various embodiments, the one or more sensors 3738, 3740 can comprise a dissolved oxygen sensor. In various embodiments, the one or more sensors 3738, 3740 can comprise a pressure sensor.

b. Modulating Bioreactor Conditions Based on Sensor Feedback

In various embodiments, an interior of a bioreactor (e.g., bioreactor 3599) comprises a set of environmental conditions.

In various embodiments, T-cells of a given cell culture optimally complete a process described herein under an optimal set of environmental conditions.

In various embodiments, one or more sensors detect the environmental conditions of the bioreactor (e.g., bioreactor 3599). In various embodiments, a control system can receive the detected environmental conditions of the bioreactor and compare them to the optimal set of environmental conditions. In various embodiments, the control system can operate hardware (e.g., valves) to introduce reagents, media, etc. into the bioreactor to adjust the environmental conditions toward the optimal set of environmental conditions.

D. In-Line Quality Control Assays

In various embodiments, assays may be performed at any step during a cell therapy manufacturing process. Non-limiting examples of assays can comprise post sorting assays, T-cell activation assays, transduction assays, cell count assays, and cytotoxicity assays.

i. In-Line Quality Control Assays

It is widely known in the industry that maintaining sterility is important, yet difficult to provide, in cell therapy manufacturing processes. Maintaining a sterile environment can ensure contaminants are avoiding which can cause run failure. As such, various embodiments of the cell therapy manufacturing system allow for assays to be carried out without leaving the sterile interior of the system or cartridge.

FIG. 37D illustrates a post sorting assay process overlaid on a cell therapy manufacturing system 3700 according to various embodiments.

FIG. 37E illustrates an activation assay process overlaid on a cell therapy manufacturing system 3700 according to various embodiments.

Figure 37G:
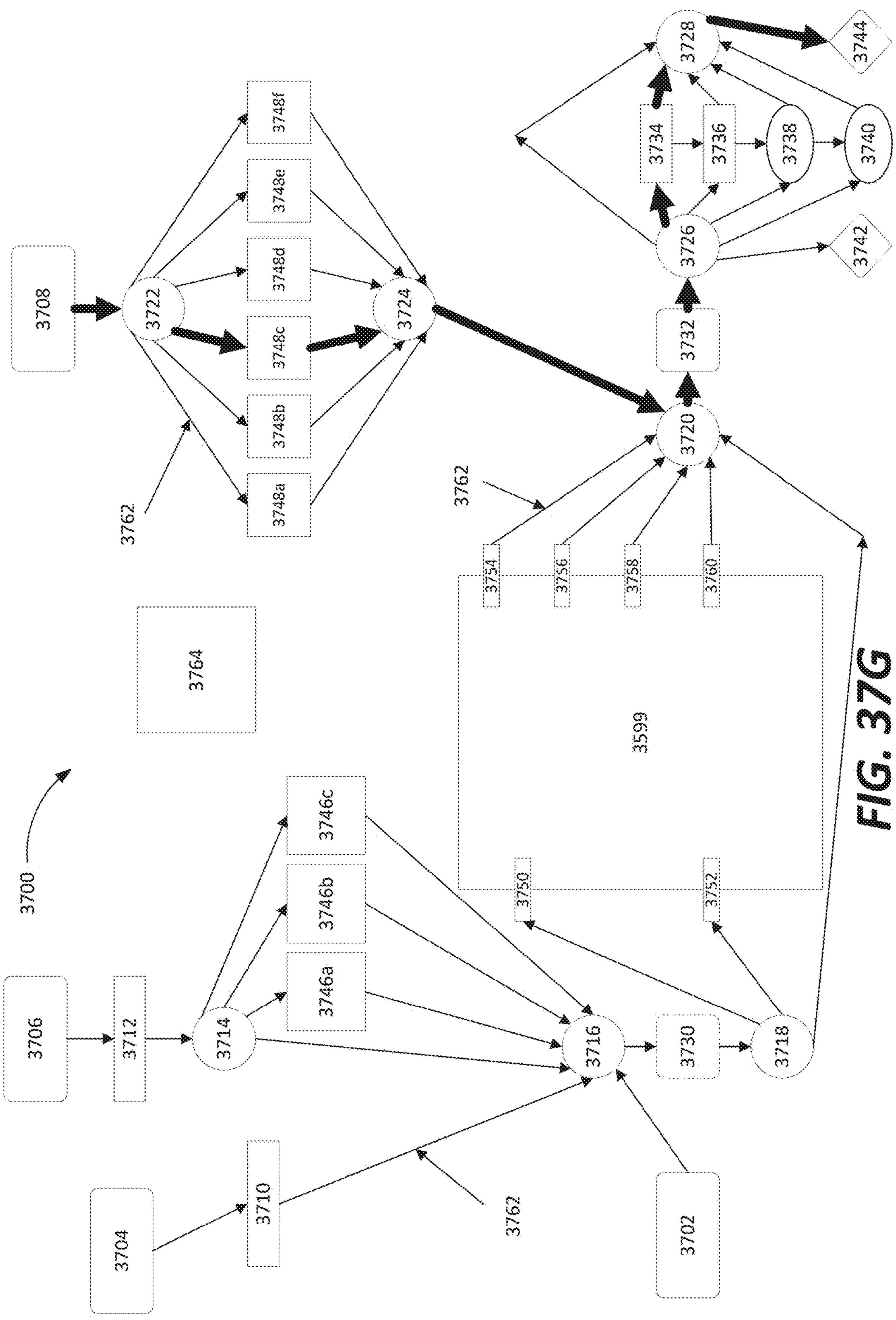
FIG. 37G illustrates a process flow diagram for a transduction assay using a cell therapy manufacturing system according to various embodiments.

FIG. 37G illustrates a transduction assay process overlaid on a cell therapy manufacturing system 3700 according to various embodiments.

Figure 37H:
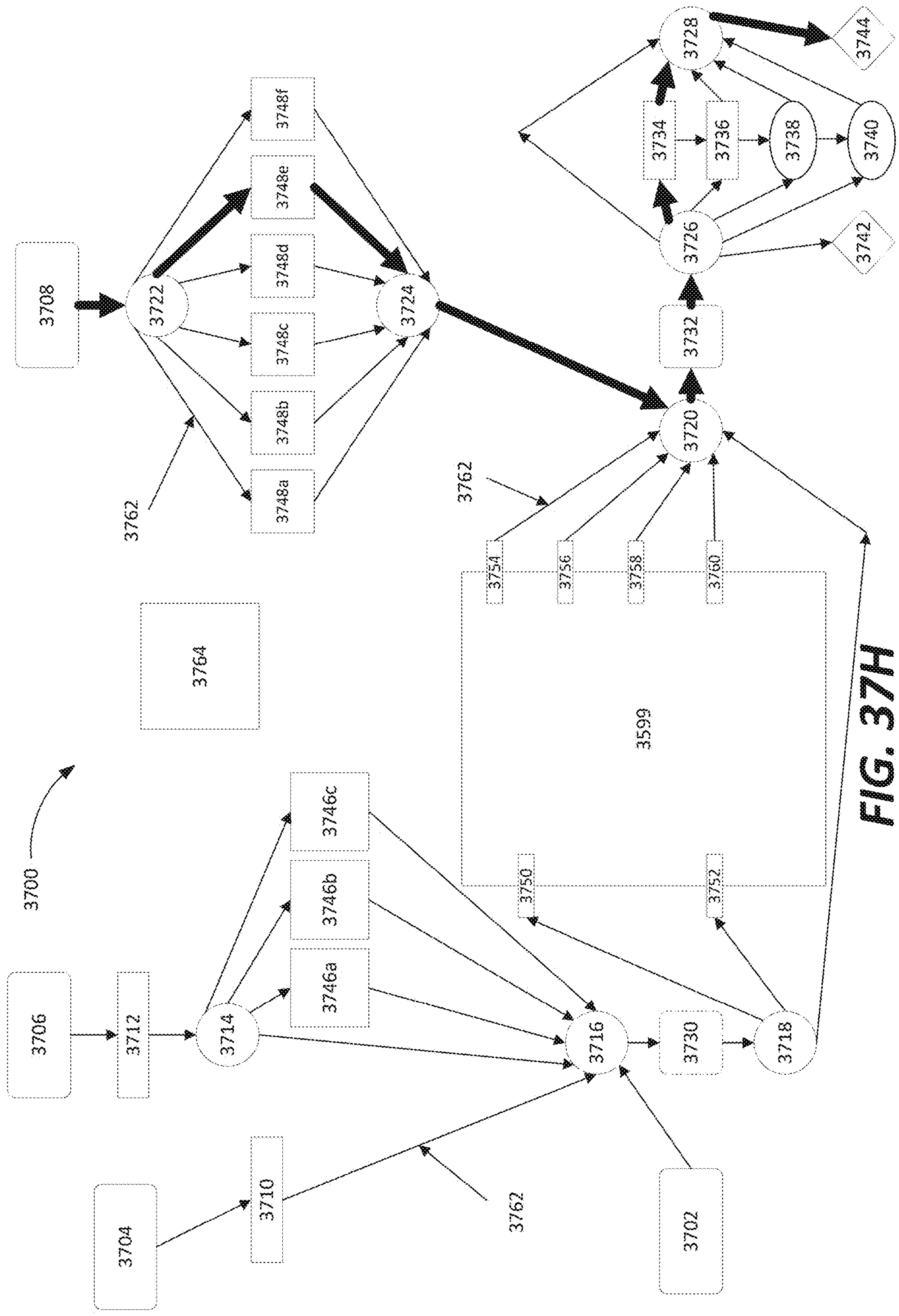
FIG. 37H illustrates a process flow diagram for a cell count assay using a cell therapy manufacturing system according to various embodiments.
Figure 37I:
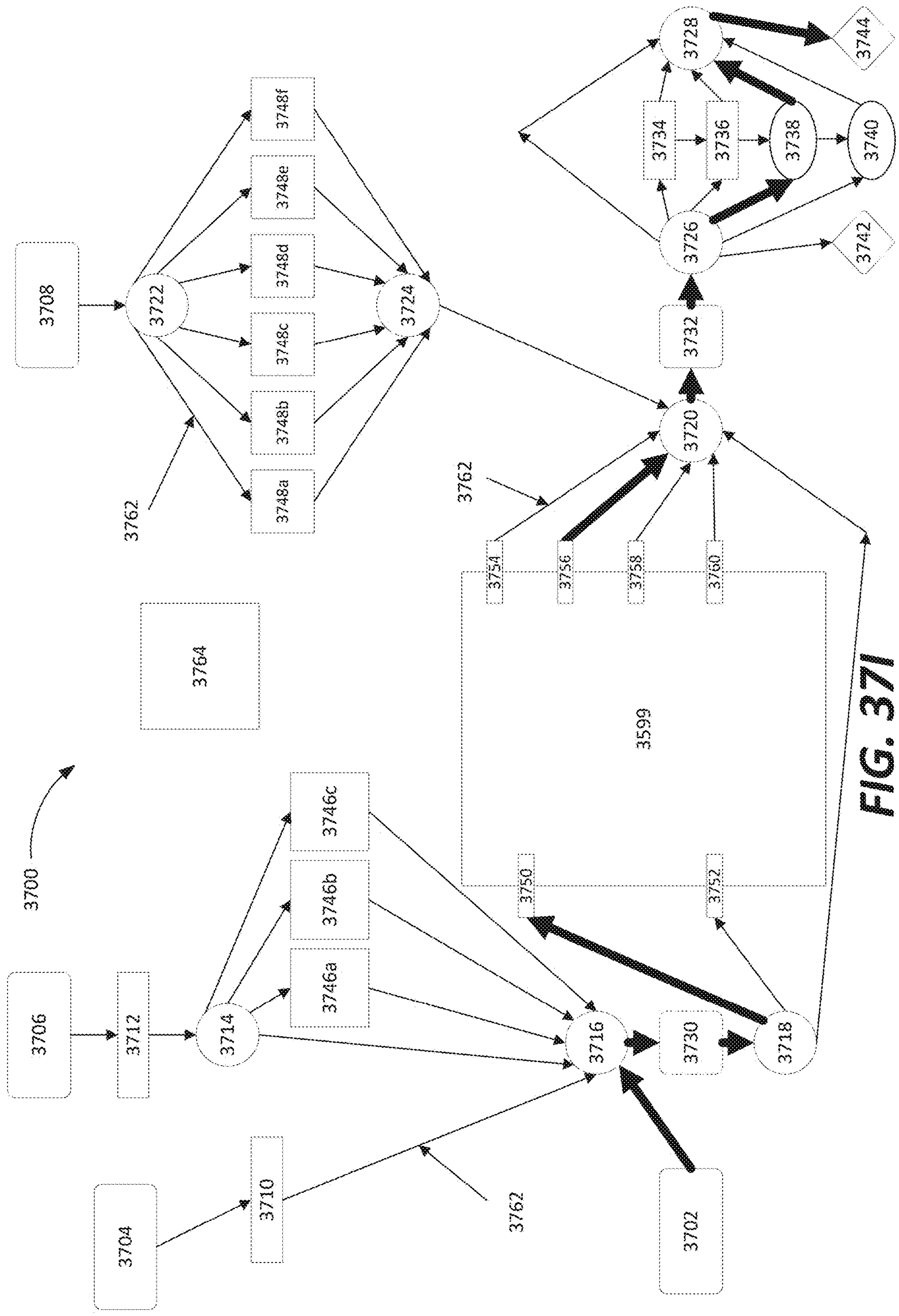

FIG. 37H illustrates a cell count assay process overlaid on a cell therapy manufacturing system 3700 according to various embodiments.

In various embodiments, the post sorting assay can comprise drawing an aliquot or a sample In various embodiments, the assays can take place within analysis region(s) on the cartridge (see, e.g., 3070 of FIG. 30A, 3734/3736 of FIG. 37A.), discussed in more detail below. As discussed herein, the region(s) can include OEP or non-OEP functionality, depending upon the assays (e.g., cytokine secretion and cell killing assays may require OEP, whereas cell counts, and cell viability measurements may not).

ii. Exemplary Assay Method

In various embodiments, reagents for the various assays can be stored in one or more assay reagent reservoirs 3748*a*, 3748*b*, 3748*c*, 3748*d*, 3748*e*, 3748*f*.

In various embodiments, an aliquot or micro-aliquot of fluid comprising T-cells can be removed from bioreactor 3599 and transferred to an analysis region 3734, 3736 for interrogation. In various embodiments, one or more valves 3720, 3726, 3728 may be actuated for creating a flow path.

In various embodiments, one or more reagents can enter the analysis region 3734, 3736 and combine with the fluid comprising T-cells. In various embodiments, T-cells can be removed from the cell therapy manufacturing system post-interrogation to a waste receptacle 3744. In various embodiments, T-cells can be preserved and reintroduced into the process.

In various embodiments, a cell therapy product can be assessed for potency using one of more of the cytotoxicity assays described herein.

VI. CELL THERAPY APPLICATIONS

Provided herein are methods of treating a subject in need of treating a cancer including obtaining a sample comprising T lymphocytes from the subject according to various embodiments. In various embodiments, a step of a method can comprise separating the T lymphocytes from other cells in the sample. In various embodiments, a step of a method can comprise contacting the T lymphocytes with an antigen-presenting synthetic surface including MHC molecules according to any method described herein, where the MHC molecules include an antigen specific for the cancer of the subject. In various embodiments, a step of a method can comprise producing a plurality of T lymphocytes activated to be specific against the cancer of the subject. In various embodiments, a step of a method can comprise separating the plurality of specific activated T lymphocytes from non-activated T lymphocytes. In various embodiments, a step of a method can comprise introducing the plurality of specific activated T lymphocytes into the subject. Also provided herein is a plurality of specific activated T lymphocytes for use in treating a cancer, wherein the plurality is prepared by a method including: obtaining a sample comprising T lymphocytes from the subject; separating the T lymphocytes from other cells in the sample; contacting the T lymphocytes with an antigen-presenting synthetic surface including MHC molecules according to any method described herein, where the MHC molecules include an antigen specific for the cancer of the subject; producing a plurality of T lymphocytes activated to be specific against the cancer of the subject; and separating the plurality of specific activated T lymphocytes from non-activated T lymphocytes. Also provided herein is the use of a plurality of specific activated T lymphocytes for the manufacture of a medicament for treating a cancer, wherein the plurality is prepared by a method including: obtaining a sample comprising T lymphocytes from the subject; separating the T lymphocytes from other cells in the sample; contacting the T lymphocytes with an antigen-presenting synthetic surface including MHC molecules according to any method described herein, where the MHC molecules include an antigen specific for the cancer of the subject; producing a plurality of T lymphocytes activated to be specific against the cancer of the subject; and separating the plurality of specific activated T lymphocytes from non-activated T lymphocytes.

Also provided is a method of treating a subject in need of treating a cancer; including introducing a plurality of specific activated T lymphocytes into the subject, wherein the plurality of specific activated T lymphocytes were produced by a method described herein. Also provided is a method of treating a subject in need of treating a cancer, including introducing a population of specific activated T lymphocytes described herein into the subject. Such methods can further comprise separating activated T lymphocytes from non-activated T lymphocytes. Also provided is a plurality of specific activated T lymphocytes for use in treating a subject in need of treating a cancer, wherein the plurality of specific activated T lymphocytes were produced by a method described herein. Also provided is a population of specific activated T lymphocytes described herein for use in treating a subject in need of treating a cancer. Also provided is a use of a plurality of specific activated T lymphocytes for the manufacture of a medicament for treating a subject in need of treating a cancer, wherein the plurality of specific activated T lymphocytes were produced by a method described herein. Also provided is a use of a population of specific activated T lymphocytes described herein for the manufacture of a medicament for treating a subject in need of treating a cancer. Such a plurality or population of specific activated T lymphocytes can be further prepared by separating activated T lymphocytes from non-activated T lymphocytes.

In various embodiments, separating the plurality of specific activated T lymphocytes may further include detecting surface biomarkers of the specific activated T lymphocytes.

In various embodiments, the specific activated T lymphocytes are autologous (i.e., derived from the subject to which they are to be administered).

In various embodiments, the methods or the preparation of the plurality or population of specific activated T lymphocytes may further include rapidly expanding the activated T lymphocytes to provide an expanded population of activated T lymphocytes. In some embodiments, the rapid expansion may be performed after separating the specific activated T lymphocytes from the non-activated T lymphocytes. The generation of sufficient levels of T lymphocytes may be achieved using rapid expansion methods described herein or known in the art. See, e.g., the Examples below; Riddell, U.S. Pat. No. 5,827,642; Riddell et al., U.S. Pat. No. 6,040,177, and Yee and Li, PCT Patent App. Pub. No. WO2009/045308 A2.

Uses of T cells in treatment of human subjects (e.g., for adoptive cell therapy) are known in the art. T cells prepared according to the methods described herein can be used in such methods. For example, adoptive cell therapy using tumor-infiltrating lymphocytes including MART-1 antigen specific T cells have been tested in the clinic (Powell et al., Blood 105:241-250, 2005). Also, administration of T cells coactivated with anti-CD3 monoclonal antibody and IL-2 was described in Chang et al., J. Clinical Oncology 21:884-890, 2003. Additional examples and/or discussion of T cell administration for the treatment of cancer are provided in Dudley et al., Science 298:850-854, 2002; Roszkowski et al., *Cancer Res* 65(4): 1570-76, 2005; Cooper et al., *Blood* 101:1637-44, 2003; Yee, US Patent App. Pub. No. 2006/0269973; Yee and Li, PCT Patent App. Pub. No. WO2009/045308 A2; Gruenberg et al., US Patent App. Pub. No. 2003/0170238; Rosenberg, U.S. Pat. No. 4,690,915; and Alajez et al., *Blood* 105:4583-89, 2005.

In various embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

In various embodiments, the number of cells in the composition is at least 109, or at least $10^{10}$ cells. In some embodiments, a single dose can comprise at least 10 million, 100 million, 1 billion, or 10 billion cells. The number of cells administered is indication specific, patient specific (e.g., size of patient), and will also vary with the purity and phenotype of the administered cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells may be greater than $10^6$ cells/ml, greater than $10^7$ cells/ml, or $10^8$ cells/ml or greater. The clinically relevant number of immune cells can be apportioned into multiple infusions that cumulatively equal or exceed 109, 1010 or $10^{11}$ cells.

various some embodiments, T lymphocytes described herein or prepared according to a method described herein of the invention may be used to confer immunity to individuals against a tumor or cancer cells. By "immunity" is meant a lessening of one or more physical symptoms associated with cancer cells or a tumor against an antigen of which the lymphocytes have been activated. The cells may be administered by infusion, with each infusion in a range of at least $10^6$ to $10^{10}$ cells/m$^2$, e.g., in the range of at least $10^7$ to $10^9$ cells/m$^2$. The clones may be administered by a single infusion, or by multiple infusions over a range of time. However, since different individuals are expected to vary in responsiveness, the type and number of cells infused, as well as the number of infusions and the time range over which multiple infusions are given are determined by the attending physician, and can be determined by examination.

Following the transfer of cells back into patients, methods may be employed to maintain their viability by treating patients with cytokines that could include IL-21 and IL-2 (Bear et al., *Cancer Immunol. Immunother.* 50:269-74, 2001; and Schultze et al., *Br. J. Haematol.* 113:455-60, 2001). In another embodiment, cells are cultured in the presence of IL-21 before administration to the patient. See, e.g., Yee, US Patent App. Pub. No. 2006/0269973. IL-21 can increase T cell frequency in a population comprising activated T cells to levels that are high enough for expansion and adoptive transfer without further antigen-specific T cell enrichment. Accordingly, such a step can further decrease the time to therapy and/or obviate a need for further selection and/or cloning.

VII. EXEMPLARY SYNTHETIC ANTIGEN-PRESENTING SURFACES OF MICROFLUIDIC DEVICES

A. Microfluidic Device

In various embodiments, a microfluidic device comprises a patterned antigen-presenting synthetic surface having a plurality of regions according to any of the foregoing embodiments. While the antigen-presenting surface of microfluidic device may be any microfluidic (or nanofluidic) device as described herein, the disclosure is not so limited. Other classes of microfluidic devices, including but not limited to microfluidic devices including microwells or microchambers such as described in WO2014/153651, WO2016/115337, or WO2017/124101, may be modified to either incorporate an antigen presenting surface as described in this section, or may be used in combination with the antigen-presenting beads or antigen-presenting wafers as described herein in the methods described in this disclosure.

In various embodiments, the antigen-presenting synthetic surface is an inner surface of a microfluidic device comprising one or more sequestration pens and a channel. At least part of a surface within one or more such sequestration pens may comprise a plurality of primary activating molecular ligands and a plurality of co-activating molecular ligands, e.g., comprising TCR co-activating molecules and/or adjunct TCR activating molecules. The primary activating molecular ligands and the co-activating molecular ligands may be any described above for antigen-presenting surfaces, and may be present in any concentration or combination as described above. The nature of the ligands attachment to the surface of the microfluidic device may be any described above as for antigen-presenting surfaces. In various embodiments, this surface within the one or more such sequestration pens can further comprise one or more of surface-blocking molecular ligands, growth stimulatory molecular ligands, additional stimulatory molecular ligands, and adhesion stimulatory molecular ligands. At least part of a surface of the channel may comprise surface-blocking molecular ligands, e.g., any of the regions configured to substantially exclude the primary activating molecular ligands described herein. In various embodiments, the surface of the channel comprises surface-blocking molecular ligands and optionally other non-stimulatory ligands, but is substantially free of other ligands present on the surface of the sequestration pen, e.g., primary activating molecular ligands and co-activating molecular ligands.

B. Modulation of Cell-to-Surface Adhesion

In various embodiments, it can be useful to modulate the capacity for cells to adhere to surfaces within the microfluidic device. A surface that has substantially hydrophilic character may not provide anchoring points for cells requiring mechanical stress of adherence to grow and expand appropriately. A surface that presents an excess of such anchoring moieties may prevent successfully growing adherent cells from being exported from within a sequestration pen and out of the microfluidic device. In various embodiments, a covalently bound surface modification comprises surface contact moieties to help anchor adherent cells. The structures of the surfaces described herein and the methods of preparing them provide the ability to select the quantity of anchoring moieties that may be desirable for a particular use. A very small percentage of adherent type motifs may be needed to provide a sufficiently adhesion enhancing environment. In various embodiments, the adhesion enhancing moieties are prepared before cells are introduced to the microfluidic device. Alternatively, an adhesion enhancing modified surface may be provided before introducing cells, and a further addition of another adhesion enhancing moiety may be made, which is designed to attach to the first modified surface either covalently or non-covalently (e.g., as in the base of biotin/streptavidin binding).

In various embodiments, adhesion enhancing surface modifications may modify the surface in a random pattern of individual molecules of a surface modifying ligand. In various embodiments, a more concentrated pattern of adhesion enhancing surface modifications may be introduced by using polymers containing multiple adhesion enhancing motifs such as positively charged lysine side chains, which can create small regions of surface modification surrounded by the remainder of the surface, which may have hydrophilic surface modifications to modulate the adhesion enhancement. This may be further elaborated by use of dendritic polymers, having multiple adhesion enhancing ligands. A dendritic polymer type surface modifying compound or reagent may be present in a very small proportion relative to a second surface modification having only hydrophilic surface contact moieties, while still providing adhesion enhancement. Further a dendritic polymer type surface modifying compound or reagent may itself have a mixed set of end functionalities which can additionally modulate the behavior of the overall surface.

In various embodiments, it may be desirable to provide regioselective introduction of surfaces. For example, in the context of a microfluidic device comprising a microfluidic channel and sequestration pens, it may be desirable to provide a first type of surface within the microfluidic channel while providing a surface within the sequestration pens opening off of the channel that provides the ability to both culture adherent-type cells successfully as well as easily export them (e.g., using dielectrophoretic or other forces) when desired. In some embodiments, the adhesion enhancing modifications may include cleavable moieties. The cleavable moieties may be cleavable under conditions compatible with the cells being cultured within, such that at any desired timepoint, the cleavable moiety may be cleaved and the nature of the surface may alter to be less enhancing for adhesion. The underlying cleaved surface may be usefully non-fouling such that export is enhanced at that time. While the examples discussed herein focus on modulating adhesion and motility, the use of these region selectively modified surfaces are not so limited. Different surface modifications for any kind of benefit for cells being cultured therein may be incorporated into the surface having a first and a second surface modification according to the disclosure.

Exemplary adherent motifs that may be used include poly-L-lysine, amine and the like, and the tripeptide sequence RGD, which is available as a biotinylated reagent and is easily adaptable to the methods described herein. Other larger biomolecules that may be used include fibronectin, laminin or collagen, amongst others. A surface modification having a structure of Formula XXVI as defined in WO2017/205830, including a polyglutamic acid surface contact moiety, can induce adherent cells to attach and grow viably. Another motif that may assist in providing an adherent site is an Elastin Like Peptide (ELP), which includes a repeat sequence of VPGXG, where X is a variable amino acid which can modulate the effects of the motif.

In various embodiments, in the context of a microfluidic device comprising a microfluidic channel and sequestration pens, a surface of the flow region (e.g., microfluidic channel) may be modified with a first covalently bound surface modification and a surface of the at least one sequestration pen may be modified with a second covalently bound surface modification, wherein the first and the second covalently bound surface modification have different surface contact moieties, different reactive moieties, or a combination thereof. The first and the second covalently bound surface modifications may be selected from any of Formula XXX, Formula V, Formula VII, Formula XXXI, Formula VIII, and/or Formula IX, all of which are as defined in WO2017/205830. When the first and the second covalently bound surface modifications both include functionalized surface of Formula XXX, Formula V, or Formula VII as defined in WO2017/205830, then orthogonal reaction chemistries are selected for the choice of the first reactive moiety and the second reactive moiety. In various embodiments, all the surfaces of the flow region may be modified with the first covalent surface modification and all the surfaces of the at least one sequestration pen may be modified with the second covalent modification.

VIII. EXEMPLARY METHODS OF PREPARING SYNTHETIC ANTIGEN-PRESENTING SURFACES

Figure 5A:
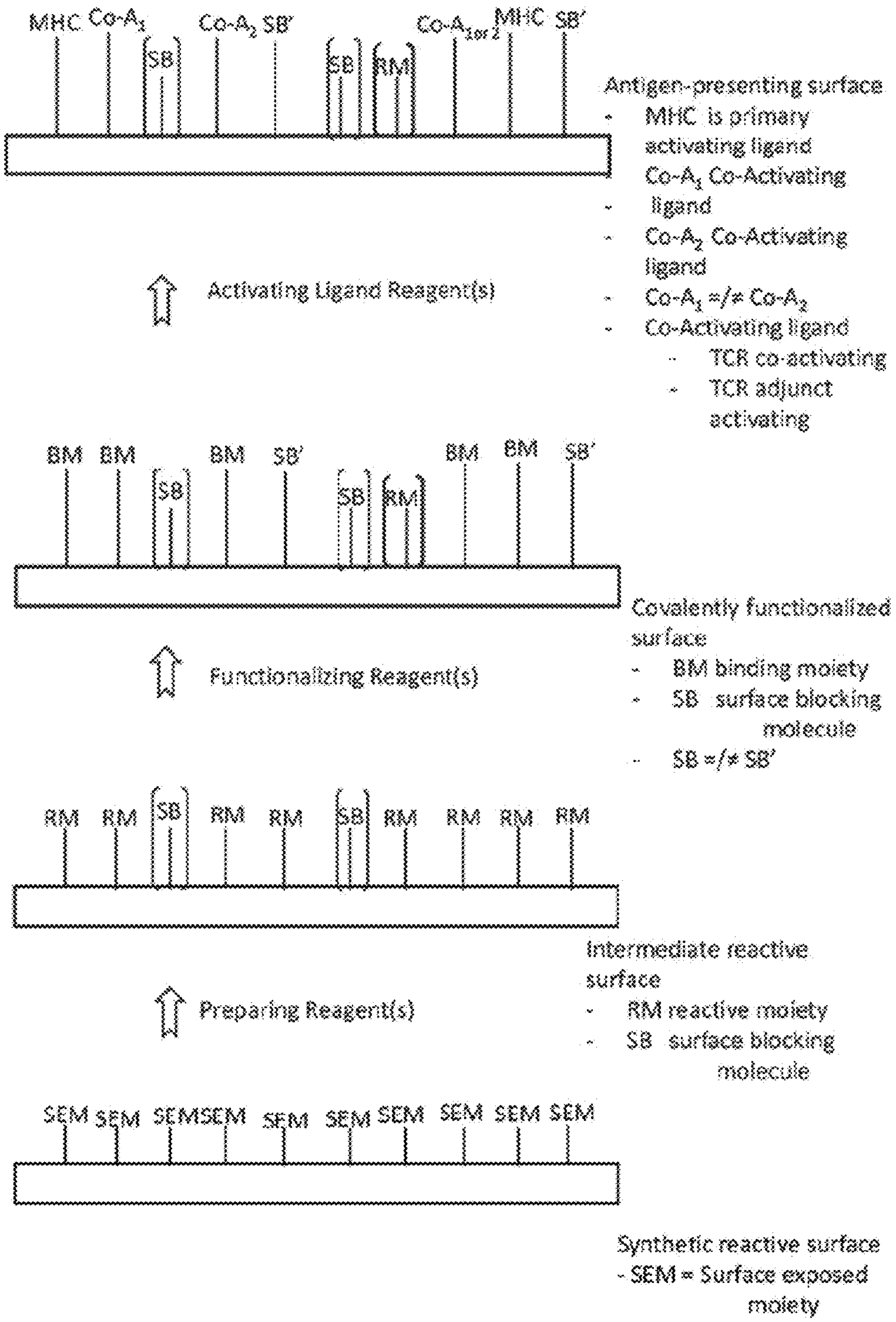
FIGS. 5A and 5B are schematic representations of preparation of antigen-presenting surfaces according to various embodiments of the disclosure.
Figure 5B:
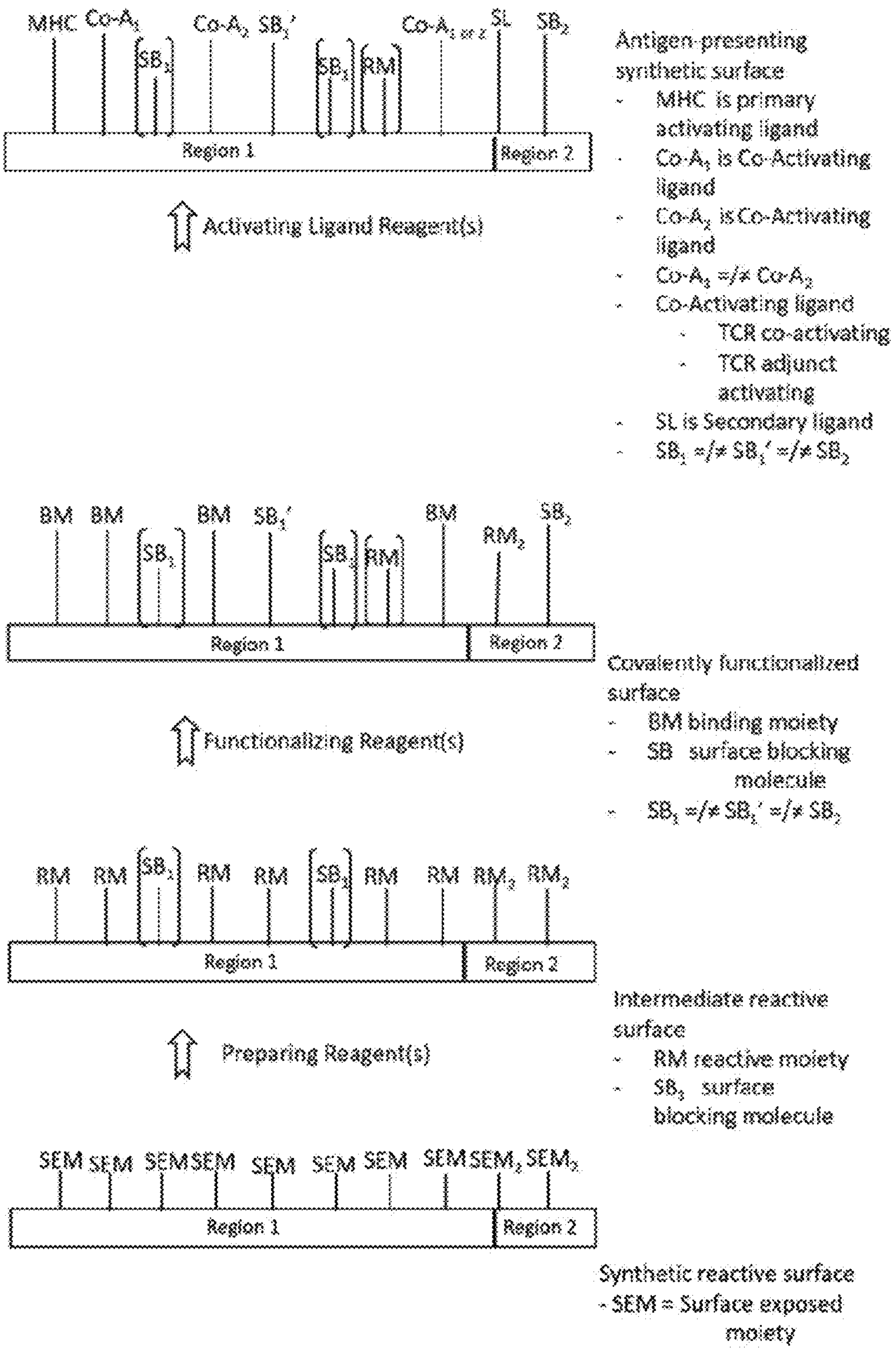

A. Methods of Preparing an Antigen-Presenting Synthetic Surface; Covalently Functionalized Surface FIGS. 5A and 5B show the structure of an antigen-presenting synthetic surface as it is constructed from an unmodified surface, adding the activating, co-activating and surface-blocking molecular ligands in one or more steps. FIG. 5A shows the process and structure for an antigen-presenting synthetic surface having a single region, while FIG. 5B shows the process and structure of each intermediate and final product for an antigen-presenting synthetic surface having two regions.

Turning to FIG. 5A, the schematic representation illustrates an exemplary procedure for preparing an antigen-presenting surface starting with a synthetic reactive surface comprising a plurality of surface-exposed moieties (SEM). Reactive moieties RM and surface-blocking molecular ligands SB, if added at this point in the preparation, are introduced by reacting the SEMs with appropriate preparing reagent(s), providing an intermediate reactive surface. The reactive moieties RM introduced to the intermediate reactive surface may be any reactive moiety described herein and may be linked to the intermediate reactive surface by any linker described herein. The intermediate reactive surface includes at least reactive moieties RM, and, in some embodiments, may include surface-blocking molecular ligands SB, which may be any surface-blocking molecular ligand as described herein.

The intermediate reactive surface is then treated with functionalizing reagents including binding moieties BM, where the functionalizing reagents react with the reactive moieties RM to introduce binding moiety BM ligands. The binding moieties so introduced may be any binding moiety BM described herein. The binding moiety BM may be streptavidin or biotin. In various embodiments, the binding moiety BM is streptavidin which is covalently attached via a linker to the covalently functionalized surface, through a reaction with a reactive moiety RM. In various embodiments, the covalently functionalized surface may introduce a streptavidin binding moiety non-covalently, in a two-part structure. This two-part structure is introduced by contacting the intermediate reactive surface with a first functionalizing reagent to introduce a biotin moiety covalently attached via a linker through reaction with the reactive moieties RM. Subsequent introduction of streptavidin, as a second functionalizing reagent, provides the covalently functionalized surface wherein the binding moiety BM, streptavidin, is non-covalently attached to a biotin moiety which itself is covalently attached to the surface. Surface-blocking molecular ligands SB' may be introduced at the same time as the introduction of the binding moieties or may be introduced to the covalently functionalized surface subsequent to the introduction of the binding moieties. The surface-blocking molecular ligands SB' may be any surface-blocking molecular ligand as described herein and may be the same as or different from surface-blocking molecular ligands SB, if surface-blocking molecular ligands SB are present. In some embodiments, surface-blocking molecular ligands SB may be present and there may be no surface-blocking molecular ligands SB'. Alternatively, there may be surface-blocking molecular ligands SB' but no surface-blocking molecular ligands SB. In some embodiments, both surface-blocking molecular ligands SB and SB' are present. Without being bound by theory, there may be some reactive moieties RM left unreacted upon the covalently functionalized surface but there are insufficient numbers of reactive moieties RM present to prevent the product antigen presenting synthetic surface from functioning. Primary activating ligands MHC and Co-Activating Ligands Co-A1 and Co-A2 are introduced by reacting the binding moieties BM,of the covalently functionalized surface, with appropriate activating ligand reagents, providing the antigen-presenting synthetic surface. Co-$A_1$ and Co-$A_2$ may be the same or different co-activating ligands. For example, Co-$A_1$ and Co-$A_2$ can comprise one, the other, or collectively both of a TCR co-activating molecule and a TCR adjunct activating molecule. Co-$A_1$ and/or Co-$A_2$, may be any combination of TCR co-activating molecule and a TCR adjunct activating molecule as described herein. In various embodiments, the primary activating ligand MHC may be introduced to the covalently functionalized surface, before the covalently functionalized surface is contacted with the co-activating ligands Co-$A_1$ and/or Co-$A_2$. In various embodiments, the primary activating ligand MHC may be introduced to the covalently functionalized surface concurrently with or subsequently to the introduction of the Co-Activating ligands Co-$A_1$ and Co-$A_2$. In some embodiments, not shown in FIG. 5A, after introduction of the primary activating ligand MHC and co-activating ligands Co-$A_1$ and/or Co-$A_2$, surface-blocking molecular ligands SB may be introduced to the antigen presenting synthetic surface by reacting surface-blocking molecules with remaining reactive moieties RM still present on the antigen-presenting synthetic surface. Also included but not illustrated in FIG. 5A, is the introduction of Secondary Ligands SL, which may be one or more growth stimulatory molecular ligands and/or adhesion stimulatory molecular ligands. Secondary Ligands SL may be any of these classes of ligands.

Figure 6:
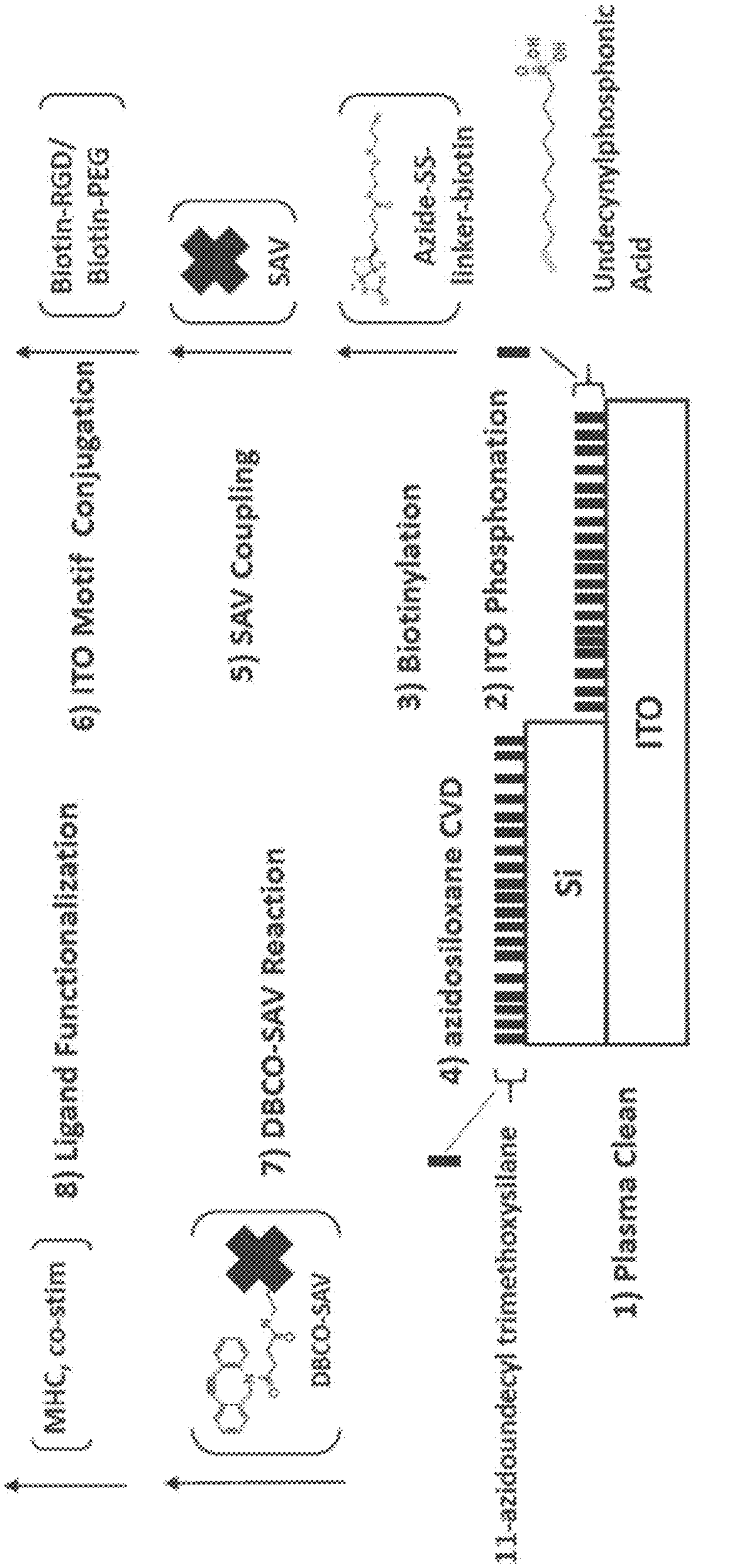
FIG. 6 is a schematic representation of the process of preparing an antigen presenting surface according to an embodiment of the disclosure

FIG. 5B provides a schematic illustration of an exemplary procedure for preparing an antigen-presenting surface comprising first and second regions starting with a synthetic reactive surface comprising a plurality of surface-exposed moieties (SEM). The surface exposed moieties SEM in Region 1 may be different from the surface exposed moieties SEM2 in Region 2, as shown in FIG. 6, where different materials may be present at the surface of the synthetic reactive surface. Reactive moieties RM are introduced in region 1 and substantially not in region 2, while reactive moieties RM2 are introduced in region 2, and substantially not in region 1, due to the use of orthogonal chemistries for each of SEM and SEM2. For example, as shown in FIG. 6, the SEM of region 1 may be reacted with an alkoxysiloxane reagent comprising an azide RM, while the SEM2 of region 2 may be reacted with a phosphonic acid reagent comprising an alkynyl RM. Surface-blocking molecular ligands SB1 are introduced in region 1, and substantially not in region 2, by reacting the SEMs with appropriate preparing reagent (s (e.g., for a surface like region 1 of FIG. 6, the reagent would be an alkoxysiloxane reagent including a surface-blocking group SB).An intermediate reactive surface having differentiated reactive moieties result from this process. Based on the differentiated reactive moieties RM and $RM_2$, further orthogonal chemistries can introduce binding moieties BM and surface-blocking molecular ligands $SB_1$' in region 1 and not substantially in region 2, and surface-blocking molecular ligands$SB_2$ are introduced in region 2, and not substantially in region 1. Thus, a covalently functionalized surface having two different regions is provided. The $SB_1$' may be the same as or different from $SB_1$; $SB_1$' may be the same as or different from SB2; and SB2 may be the same as or different from $SB_1$. Primary activating ligands MHC and Co-Activating Ligands Co-$A_1$ and Co-$A_2$ are introduced in region 1 by reacting binding moieties BM with appropriate activating ligand reagents, and secondary ligands SL are formed in region 2 by reacting RMs with appropriate reagent(s), providing the antigen-presenting synthetic surface. Secondary Ligands SL may be any of the classes of molecular ligands as described for FIG. 5A. The primary activating ligand MHC may be introduced before introducing the Co-Activating Ligands, similarly to the process described for FIG. 5A. Co-$A_1$ and Co-$A_2$ may be the same or different co-activating ligands. For example, Co-$A_1$ and Co-$A_2$ can comprise one, the other, or collectively both of a TCR co-activating molecule and a TCR adjunct activating molecule. Each of SEM, RM, SB, primary activating ligand MHC, Co-Activating Ligands Co-$A_1$ and Co-$A_2$, and secondary ligands SL may be any SEM, RM, SB, primary activating ligand MHC, Co-Activating Ligands Co-$A_1$ and Co-$A_2$, and secondary ligands SL described herein.

B. Methods of Preparing an Antigen-Presenting Synthetic Surface

A method of preparing an antigen-presenting synthetic surface for activating a T lymphocyte (T cell), is provided, comprising: reacting a plurality of primary activating molecules, with a first plurality of binding moieties of a covalently functionalized synthetic surface comprising binding moieties (e.g., a biotin-binding agent such as streptavidin, or biotin moieties that are noncovalently associated with a biotin-binding agent such as streptavidin), wherein each of the first plurality of binding moieties is configured for binding the primary activating molecule; and reacting a plurality of co-activating molecules, each comprising: a T cell receptor (TCR) co-activating molecule; or an adjunct TCR activating molecule, with a second plurality of binding moieties of the covalently functionalized synthetic surface, wherein each of the second plurality of binding moieties is configured for binding the co-activating molecule, thereby providing a plurality of specifically bound primary activating molecular ligands and a plurality of specifically bound co-activating molecular ligands on the antigen-presenting synthetic surface.

Also provided is a covalently functionalized synthetic surface comprising binding moieties (e.g., a biotin-binding agent such as streptavidin, or biotin moieties that are non-covalently associated with a biotin-binding agent such as streptavidin) and at least a first plurality of surface-blocking molecular ligands. To the extent that the following discussion describes features of a covalently functionalized synthetic surface, it applies both to embodiments of the covalently functionalized synthetic surface and to embodiments of methods of preparing an antigen-presenting surface in which a covalently functionalized synthetic surface is used.

The covalently functionalized synthetic surface may be any of the surface types described herein, e.g., a bead, wafer, inner surface of a microfluidic device, or tube (e.g., glass or polymer tube). The surface material may comprise, e.g., metal, glass, ceramic, polymer, or a metal oxide. The microfluidic device may be any microfluidic device as described herein, and may have any combination of features. The bead can be a bead with a surface-area that is within 10% of the surface-area of a sphere of an equal volume or diameter, as discussed herein in the section regarding antigen-presenting synthetic surfaces. In some embodiments, the bead may be a bead having a surface area that exceeds 10% of the surface area of a sphere of an equal volume or diameter, as discussed herein for antigen presenting surfaces. In various embodiments, the bead is not a bead that has a surface area that exceeds 10% of the surface area of a sphere of an equal volume or diameter, as discussed herein for antigen presenting surfaces.

The primary activating molecules and co-activating molecules may each be any such molecule described herein, and any combination thereof may be used. Thus, a primary activating molecule can comprise an MHC molecule and, optionally, an antigenic peptide; and a co-activating molecule can comprise any of the TCR co-activating molecules described herein or any of the adjunct TCR activating molecules described herein.

In various embodiments, reacting a plurality of primary activating molecules with a first plurality of binding moieties of a covalently functionalized synthetic surface comprising binding moieties comprises forming a noncovalent association between the primary activating molecules and the binding moieties. For example, the primary activating molecules can comprise biotin and the binding moieties can comprise a biotin-binding agent such as streptavidin (e.g., which may be covalently bound to the surface or which may be non-covalently bound to a second biotin which itself is covalently bound to the surface). In some embodiments, the biotin-binding agent such as streptavidin is linked to the surface through a series of about 15, 20, 25, 30, 35, 40, 45, 50, 55, 60, 65, 70, 75, 80, 85, 95, 100, 200 bond lengths, or any number of bond lengths therebetween. For example, the biotin-binding agent may be linked to the surface through a series of one or more linkers having a selected length as described. In another example, both the binding moieties and the primary activating molecules can comprise biotin and a free, multivalent biotin-binding agent, such as streptavidin, can be used as a noncovalent linking agent. Any other suitable noncovalent binding pair, such as those described elsewhere herein, can also be used.

Alternatively, reacting a plurality of primary activating molecules with a first plurality of binding moieties of a covalently functionalized synthetic surface comprising binding moieties can comprise forming a covalent bond. For example, an azide-alkyne reaction (such as any of those described elsewhere herein) can be used to form the covalent bond, where the primary activating molecules and the binding moieties comprise, respectively, an azide and an alkyne, or an alkyne and an azide. Other reaction pairs may be used, as is known in the art, including but not limited to maleimide and sulfides. More generally, exemplary functionalities useful for forming covalent bonds include azide, carboxylic acid and active esters thereof, succinimide ester, maleimide, keto, sulfonyl halides, sulfonic acid, dibenzocyclooctyne, alkene, alkyne, and the like. Skilled artisans are familiar with appropriate combinations and reaction conditions for forming covalent bonds using such moieties.

Where the covalently functionalized synthetic surface comprises a covalently associated biotin, the surface can further comprise noncovalently associated biotin-binding agent (e.g., streptavidin), such that the surface can be reacted with primary activating molecules and co-activating molecules that comprise biotin moieties. In some embodiments, the method of preparing an antigen-presenting synthetic surface comprises reacting a covalently functionalized synthetic surface comprising a covalently associated biotin with a biotin-binding agent (e.g., streptavidin), and then with primary activating molecules and co-activating molecules comprising biotin moieties. In some embodiments, the biotin of the covalently functionalized surface is linked to the surface through a series of about 15, 20, 25, 30, 35, 40, 45, 50, 55, 60, 65, 70, 75, 80, 85, 95, 100, 200 bond lengths, or any number of bond lengths therebetween.

In various embodiments, the reaction provides any of the densities described herein of primary activating molecular ligands on the surface, such as about $4\times10^2$ to about $3\times10^4$, $4\times10^2$ to about $2\times10^3$, about $5\times10^3$ to about $3\times10^4$, about $5\times10^3$ to about $2\times10^4$, or about $1\times10^4$ to about $2\times10^4$ molecules per square micron.

In various embodiments, reacting a plurality of co-activating molecules, each comprising: a T cell receptor (TCR) co-activating molecule; or an adjunct TCR activating molecule, with a second plurality of binding moieties of the covalently functionalized synthetic surface comprises forming a noncovalent association between the co-activating molecules and the binding moieties. Any of the embodiments described above or set forth in any embodiments disclosed herein with respect to primary activating molecules involving noncovalent binding pairs such as biotin and a biotin-binding agent such as streptavidin may be used.

Alternatively, reacting a plurality of co-activating molecules with a second plurality of binding moieties of the covalently functionalized synthetic surface can comprise forming a covalent bond. For example, an azide-alkyne reaction (such as any of those described elsewhere herein) can be used to form the covalent bond, where the primary activating molecules and the binding moieties comprise, respectively, an azide and an alkyne, or an alkyne and an azide.

In various embodiments, the reaction provides any of the densities described herein of co-activating molecular ligands on the surface, such as from about $4\times10^2$ to about $3\times10^4$, $4\times10^2$ to about $2\times10^3$, about $5\times10^3$ to about $3\times10^4$, about $5\times10^3$ to about $2\times10^4$, or about $1\times10^4$ to about $2\times10^4$ molecules per square micron.

In various embodiments, the reaction provides TCR co-activating molecules and adjunct TCR activating molecules on the surface in any of the ratios described herein, such as 100:1 to 1:100, 10:1 to 1:20, 5:1 to 1:5, or 3:1 to 1:3, wherein each of the foregoing values can be modified by "about."

In various embodiments, the reactions described above or set forth in any embodiments disclosed herein provide primary activating molecular ligands and co-activating molecular ligands on the surface in any of the ratios described herein, such as about 1:1 to about 2:1; about 1:1; or about 3:1 to about 1:3.

In various embodiments, a method of preparing an antigen-presenting surface further comprises reacting a plurality of surface-blocking molecules with a third plurality of binding moieties of the covalently functionalized surface, wherein each of the binding moieties of the third plurality is configured for binding the surface-blocking molecule. Any surface-blocking molecule described elsewhere herein may be used. Any of the reaction approaches described herein for forming noncovalent associations or a covalent bond may be used.

In various embodiments, a method of preparing an antigen-presenting surface further comprises reacting a plurality of adhesion stimulatory molecular ligands, wherein each adhesion stimulatory molecular ligand includes a ligand for a cell adhesion receptor including an ICAM protein sequence, with a fourth plurality of binding moieties of the covalently functionalized bead, wherein each of the binding moieties of the fourth plurality is configured for binding with the cell adhesion receptor ligand molecule. Any of the reaction approaches described herein for forming noncovalent associations or a covalent bond may be used.

In various embodiments, a method of preparing an antigen-presenting surface further comprises producing the intermediate reactive surface. This can include, e.g., reacting at least a first portion of surface-exposed moieties disposed at a surface of a synthetic reactive surface with a plurality of intermediate preparation molecules including reactive moieties, thereby producing the intermediate reactive surface. Methods of preparing a covalently functionalized surface, which can be used as the intermediate reactive surface, are described in detail elsewhere herein. Producing the intermediate reactive surface can comprise any of the features described herein with respect to methods of preparing a covalently functionalized surface.

In various embodiments, the methods further comprise modulating the capacity for cells to adhere to surfaces within the microfluidic device, e.g., by providing anchoring points for cells requiring mechanical stress of adherence to grow and expand appropriately. This can be accomplished by introducing a covalently bound surface modification comprising surface contact moieties to help anchor adherent cells. Any of the surface contact moieties described elsewhere herein can be used.

The covalently functionalized synthetic surface can comprise moieties suitable for use in any of the reactions described herein.

C. Methods of Preparing a Covalently Functionalized Surface

Also provided is a method of preparing a covalently functionalized surface including a plurality of streptavidin or biotin functionalities and at least a first plurality of surface-blocking molecular ligands, wherein the method includes: reacting at least a first subset of reactive moieties of an intermediate reactive synthetic surface with a plurality of linking reagents, each linking reagent including streptavidin or biotin; and reacting at least a second subset of reactive moieties of the intermediate reactive synthetic surface with a plurality of surface-blocking molecules, thereby providing the covalently functionalized synthetic surface including at the least one plurality of streptavidin or biotin functionalities and at the least first plurality of surface-blocking molecular ligands. Generally only one or the other of a linking reagent including streptavidin or a linking reagent including biotin is used. The intermediate reactive synthetic surface may be any of the surface types described herein, e.g., a bead, wafer, inner surface of a microfluidic device, or tube (e.g., glass or polymer tube). The surface material may comprise, e.g., metal, glass, ceramic, polymer, or a metal oxide. The antigen-presenting microfluidic device may be any microfluidic device as described herein, and may have any combination of features. The bead can be a bead with a surface-area is within 10% of the surface-area of a sphere of an equal volume or diameter, as discussed herein in the section regarding antigen-presenting synthetic surfaces.

In embodiments in which the linking reagents include biotin, the method can further comprise noncovalently associating streptavidin with the biotin. In such embodiments, with reference to FIG. 5A, the conversion of a reactive moiety RM to a binding moiety BM can comprise covalently attaching a biotin (corresponding to the additional biotin in the above description) through reaction with the RM and then associating a streptavidin noncovalently with the covalently attached biotin.

In some embodiments, the reactive moieties of an intermediate reactive synthetic surface are linked to the surface through a series of 5, 10, 11, 12, 13, 14, 15, 16, 17, 18, 19, 20, or, in some embodiments, greater numbers of bonds. For example, the reactive moieties can be linked through a series of 15 bonds, e.g., using (11-(X) undecyl)trimethoxy silane, where X is the reactive moiety (e.g., X can be azido). With respect to linking reagents including biotin, biotin can then be covalently associated using a linking reagent such as one having the general structure DBCO-PEG4-biotin (commercially available from BroadPharm). In some embodiments, the biotin is linked to the surface through a series of about 15, 20, 25, 30, 35, 40, 45, 50, 55, 60, 65, 70, 75, 80, 85, 95, 100, 200 bond lengths, or any number of bond lengths therebetween. . . . With respect to linking reagents including streptavidin, streptavidin can then be covalently associated using a linking reagent such as one having the general structure DBCO-PEG13-succinimide, followed by reaction of streptavidin with the succinimide. In some embodiments, the streptavidin is linked to the surface through a series of about 15, 20, 25, 30, 35, 40, 45, 50, 55, 60, 65, 70, 75, 80, 85, 95, 100, 200 bond lengths, or any number of bond lengths therebetween. The number of bonds through which a moiety is linked to a surface can be varied, e.g., by using reagents similar to those mentioned above but with alkylene and/or PEG chains of different lengths.

In various embodiments, the reactive moieties of at least first region of the intermediate reactive synthetic surface include azide moieties. In some embodiments, covalent bonds are formed through an azide-alkyne reaction, such as any azide-alkyne reaction described elsewhere herein.

In various embodiments, the covalently functionalized synthetic surface includes a second region wherein the plurality of streptavidin functionalities is excluded. In some embodiments, the at least first plurality of surface-blocking molecular ligands are disposed in the second region of the covalently functionalized synthetic surface.

In various embodiments, a method further includes reacting a second plurality of surface-blocking molecules with a second subset of reactive moieties in the at least first region of the intermediate reactive synthetic surface.

In various embodiments, the reacting of the plurality of streptavidin functionalities and the reacting of the at least first plurality of surface-blocking molecules is performed at a plurality of sub-regions of the at least first region of the covalently prepared synthetic surface including reactive moieties.

In various embodiments, the second portion of the reactive synthetic surface includes surface exposed moieties configured to substantially not react with the pluralities of the primary activating and co-activating molecules.

In various embodiments, a method further includes preparing the intermediate reactive synthetic surface, including reacting at least a first surface preparing reagent including azide reactive moieties with surface-exposed moieties disposed at least a first region of a reactive synthetic surface.

In various embodiments, the surface-exposed moieties are nucleophilic moieties. In some embodiments, the nucleophilic moiety of the surface is a hydroxide, amino or thiol. In some other embodiments, the nucleophilic moiety of the surface may be a hydroxide.

In various embodiments, the surface-exposed moieties are displaceable moieties.

In various embodiments, where two modifying reagents are used, the reaction of the first modifying reagent and the reaction of the second modifying reagent with the surface may occur at random locations upon the surface. In other embodiments, the reaction of the first modifying reagent may occurs within a first region of the surface and reaction of the second modifying reagent may occur within a second region of the surface abutting the first region. For example, the surfaces within the channel of a microfluidic device may be selectively modified with a first surface modification and the surfaces within the sequestration pen, which abut the surfaces within the channel, may be selectively modified with a second, different surface modification.

In various embodiments, the reaction of the first modifying reagent may occurs within a plurality of first regions separated from each other on the at least one surface, and the reaction of the second modifying reaction may occur at a second region surrounding the plurality of first regions separated from each other.

In various embodiments, modification of one or more surfaces of a microfluidic device to introduce a combination of a first surface modification and a second surface modification may be performed after the microfluidic device has been assembled. For one nonlimiting example, the first and second surface modification may be introduced by chemical vapor deposition after assembly of the microfluidic device. In another nonlimiting example, a functionalized surface having a first surface modification having a first reactive moiety and a second surface modification having a second, orthogonal reactive moiety may be introduced. Differential conversion to two different surface modifying ligands having two different surface contact moieties can follow.

In various embodiments, at least one of the combination of first and second surface modification may be performed before assembly of the microfluidic device. In some embodiments, modifying the at least one surface may be performed after assembly of the microfluidic device.

In various embodiments, a covalently functionalized surface is prepared comprising a binding agent. In some embodiments, the distribution of the plurality of binding agent (e.g., plurality of multivalent binding agent, such as a tetravalent binding agent, e.g., streptavidin functionalities, which may be covalently associated or noncovalently associated with a covalently bound biotin) on the covalently functionalized synthetic surface is from about $6\times10^2$ to about $5\times10^3$ molecules per square micron, in each region where it is attached. In some embodiments, the distribution of the plurality of binding agent (e.g., plurality of multivalent binding agent, such as a trivalent binding agent) is about $1.5\times10^3$ to about $1\times10^4$, about $1.5\times10^3$ to about $7.5\times10^3$, or about $3\times10^3$ to about $7.5\times10^3$ molecules per square micron, in each region where it is attached. In some embodiments, the distribution of the plurality of binding agent (e.g., plurality of multivalent binding agent, such as a divalent binding agent) is about $2.5\times10^3$ to about $1.5\times10^4$, about $2.5\times10^3$ to about $1\times10^4$, or about $5\times10^3$ to about $1\times10^4$ molecules per square micron, in each region where it is attached. In some embodiments, the distribution of the plurality of binding agent (e.g., plurality of monovalent binding agent) is about $5\times10^3$ to about $3\times10^4$ about $5\times10^3$ to about $2\times10^4$, or about $1\times10^4$ to about $2\times10^4$ molecules per square micron, in each region where it is attached.

In various embodiments, a covalently functionalized surface is prepared comprising a binding agent, in which the distribution of the plurality of binding agent (e.g., streptavidin functionalities, which may be covalently associated or noncovalently associated with a covalently bound biotin) on the covalently functionalized synthetic surface is from about $1\times10^4$ to about $1\times10^6$ molecules per square micron, in each region where it is attached.

In various embodiments, a combined method comprising preparing a covalently functionalized surface and then preparing an antigen-presenting synthetic surface is provided. As such, any suitable combination of steps for preparing the covalently functionalized surface and steps for preparing the antigen-presenting synthetic surface may be used.

IX. ADDITIONAL ASPECTS OF SURFACE PREPARATION AND COVALENTLY FUNCTIONALIZED SURFACES

Any method of preparing a surface described herein, including methods of preparing an antigen-presenting synthetic surface and methods of preparing a covalently functionalized surface, may further comprise one or more of the following aspects. A covalently functionalized surface may further comprise one or more of the following aspects applicable to such surfaces, such as reactive groups.

A. Azide-Alkyne Reactions

In various embodiments, covalent bonds are formed by reacting an alkyne, such as an acyclic alkyne, with an azide.

For example, a "Click" cyclization reaction may be performed, which is catalyzed by a copper (I) salt. When a copper (I) salt is used to catalyze the reaction, the reaction mixture may optionally include other reagents which can enhance the rate or extent of reaction. When an alkyne, e.g., of a surface modifying reagent or a functionalized surface is a cyclooctyne, the "Click" cyclization reaction with an azide of the corresponding functionalized surface or the surface modifying reagent may be copper-free. A "Click" cyclization reaction can thereby be used to couple a surface modifying ligand to a functionalized surface to form a covalently modified surface.

B. Copper Catalysts

Any suitable copper (I) catalyst may be used. In some embodiments, copper (I) iodide, copper (I) chloride, copper (I) bromide or another copper (I) salt. In other embodiments, a copper (II) salt may be used in combination with a reducing agent such as ascorbate to generate a copper (I) species in situ. Copper sulfate or copper acetate are nonlimiting examples of a suitable copper (II) salt. In other embodiments, a reducing agent such as ascorbate may be present in combination with a copper (I) salt to ensure sufficient copper (I) species during the course of the reaction. Copper metal may be used to provide Cu (I) species in a redox reaction also producing Cu (II) species. Coordination complexes of copper such as $[CuBr(PPh_3)_3]$, silicotungstate complexes of copper, $[Cu(CH_3CN)_4]PF_6$, or $(Eto)_3P$ CuI may be used. In yet other embodiments, silica supported copper catalyst, copper nanoclusters or copper/cuprous oxide nanoparticles may be employed as the catalyst.

C. Other Reaction Enhancers

As described above, reducing agents such as sodium ascorbate may be used to permit copper (I) species to be maintained throughout the reaction, even if oxygen is not rigorously excluded from the reaction. Other auxiliary ligands may be included in the reaction mixture, to stabilize the copper (I) species. Triazolyl containing ligands can be used, including but not limited to tris(benzyl-1H-1,2,3-triazol-4-yl)methylamine (TBTA) or 3 [tris(3-hydroxypropyltriazolylmethyl)amine (THPTA). Another class of auxiliary ligand that can be used to facilitate reaction is a sulfonated bathophenanthroline, which is water soluble, as well, and can be used when oxygen can be excluded. Other chemical couplings as are known in the art may be used to couple a surface modifying reagent to a functionalized surface.

D. Cleaning the Surface

The surface to be modified may be cleaned before modification to ensure that the nucleophilic moieties on the surface are freely available for reaction, e.g., not covered by oils or adhesives. Cleaning may be accomplished by any suitable method including treatment with solvents including alcohols or acetone, sonication, steam cleaning and the like. Alternatively, or in addition, such pre-cleaning can include cleaning (e.g., of the cover, the microfluidic circuit material, and/or the substrate in the context of components of a microfluidic device) in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner. This can advantageously provide more sites for modification on the surface, thereby providing a more closely packed modified surface layer.

E. Components of Microfluidic Devices

A surface of a material that may be used as a component of a microfluidic device may be modified before assembly thereof. Alternatively, a partially or completely constructed microfluidic device may be modified such that all surfaces that will contact biomaterials including biomolecules and/or micro-objects (which may include biological micro-objects) are modified at the same time. In some embodiments, the entire interior of a device and/or apparatus may be modified, even if there are differing materials at different surfaces within the device and/or apparatus. This discussion also applies to the methods of preparing an antigen-presenting synthetic surface described herein.

When an interior surface of a microfluidic device reacted with a surface modifying reagent, the reaction may be performed by flowing a solution of the surface modifying reagent into and through the microfluidic device.

F. Surface Modifying Reagent Solutions and Reaction Conditions

In various embodiments, the surface modifying reagent may be used in a liquid phase surface modification reaction, e.g., wherein the surface modifying reagent is provided in solution, such as an aqueous solution. Other useful solvents include aqueous dimethyl sulfoxide (DMSO), DMF, acetonitrile, or an alcohol may be used. For example, surfaces activated with tosyl groups or labeled with epoxy groups can be modified in liquid phase reactions. Reactions to couple biotin or proteins such as antibodies, MHCs, or streptavidin to a binding moiety can also be performed as liquid phase reactions.

The reaction may be performed at room temperature or at elevated temperatures. In some embodiments, the reaction is performed at a temperature in a range from about 15° C. to about 60° C.; about 15° C. to about 55° C.; about 15° C. to about 50° C.; about 20° C. to about 45° C. In some embodiments, the reaction to convert a functionalized surface of a microfluidic device to a covalently modified surface is performed at a temperature of about 15° C., 20° C., 25° C., 30° C., 35° C., 40° C., 45° C., 50° C., 55° C., or about 60° C.

Alternatively, a surface modifying reagent may be used in a vapor phase surface modification reaction. For example, silica surfaces and other surfaces comprising hydroxyl groups can be modified in a vapor phase reaction. In some embodiments, a surface (e.g., a silicon surface) is treated with plasma (e.g., using an oxygen plasma cleaner; see the Examples for exemplary treatment conditions). In some embodiments, a surface, such as a plasma treated and/or silicon surface, is reacted under vacuum with a preparing reagent, e.g., comprising a methoxysilane and an azide, such as (11-azidoundecyl)trimethoxy silane. The preparing reagent can be provided initially in liquid form in a vessel separate from the surface and can be vaporized to render it available for reaction with the surface. A water source such as a hydrated salt, e.g., magnesium sulfate heptahydrate can also be provided, e.g., in a further separate vessel. For example, foil boat(s) in the bottom of a vacuum reactor can be used as the separate vessel(s). Exemplary reaction conditions and procedures include pumping the chamber to about 750 mTorr using a vacuum pump and then sealing the chamber. The vacuum reactor can then be incubated at a higher-than ambient temperature for an appropriate length of time, e.g., by placing it within an oven heated at 110° C. for 24-48 h. Following the reaction period, the chamber can be allowed to cool and an inert gas such as argon can be introduced to the evacuated chamber. The surface can be rinsed with one or more appropriate liquids such as acetone and/or isopropanol, and then dried under a stream of inert gas such as nitrogen. Confirmation of introduction of the modified surface can be obtained using techniques such as ellipsometry and contact angle goniometry.

Additional modified surfaces, surface-modifying reagents, and related methods that can be employed in accordance with this disclosure are described in WO2017/205830, published Nov. 30, 2017, which is incorporated herein by reference for all purposes.

X. CELLS AND COMPOSITIONS

An activated T lymphocyte (e.g. a T-cell) produced by any method described herein is provided. Specifically, T-cells In various embodiments, the activated T lymphocytes can be CD45RO+. In some embodiments, the activated T lymphocytes can be CD28+. In some embodiments, the activated T lymphocytes can be CD28+CD45RO+. In some embodiments, the activated T lymphocytes can be CD197+. In some embodiments, the activated T lymphocytes can be CD127+. In some embodiments, the activated T lymphocytes can be positive for CD28, CD45RO, CD127 and CD197, at least any combination of three of the foregoing markers, or at least any combination of two of the foregoing markers. The activated T lymphocytes with any of the foregoing phenotypes can further be CD8+. In some embodiments, any of the foregoing phenotypes that is CD28+comprises a CD28high phenotype.

In various embodiments, a population of T cells comprising activated T cells produced by any method described herein is provided. The population can have any of the features described above for T cell populations.

In various embodiments, a microfluidic device is provided comprising a population of T cells provided herein. The microfluidic device can be any of the antigen-presenting microfluidic devices or other microfluidic devices (e.g., for performing an antigen-specific cytotoxicity assay) described herein.

In various embodiments, a pharmaceutical composition is provided comprising a population of T cells provided herein. The pharmaceutical composition can further comprise, e.g., saline, glucose, and/or Human Serum Albumin. The composition may be an aqueous composition and can be provided in frozen or liquid form. A pharmaceutical composition can be provided as a single dose, e.g., within a syringe, and can comprise 10 million, 100 million, 1 billion, or 10 billion cells. The number of cells administered is indication specific, patient specific (e.g., size of patient), and will also vary with the purity and phenotype of the administered cells.

XI. CYTOTOXICITY ASSAYS

A. Methods of Performing an Antigen-Specific Cytotoxicity Assay

Provided herein is a method of performing an antigen-specific cytotoxicity assay, comprising:

loading one or more target cells into a sequestration pen of a microfluidic device;

loading one or more T cells in the sequestration pen, such that the one or more T cells can contact the one or more target cells;

contacting the target cells with a detectable marker that labels apoptotic cells; and detecting whether the target cells become apoptotic.

The microfluidic device can be any device described herein. The microfluidic device included in a kit for performing an antigen-specific cytotoxicity assay need not comprise an antigen-presenting synthetic surface. The one or more T cells can be produced or activated according to any method described herein for producing or activating such cells. Any type of CD8+ T cell described herein can be used. In some embodiments, the one or more T cells express a chimeric antigen receptor (CAR). In some embodiments, the one or more T cells do not express a CAR.

The target cells can express a tumor antigen, such as any of the tumor antigens described herein. In some embodiments, the T cell is specific for the antigen expressed by the target cells. In some embodiments, the target cells are from an immortal cell line and/or are derived from a cancer such as a melanoma, breast cancer, or lung cancer.

In various embodiments, a single target cell and/or a single T cell is loaded into the sequestration pen. In some embodiments, a plurality of target cells and/or a plurality of T cells are loaded into the sequestration pen. In some embodiments, the plurality of T cells is a clonal population. In some embodiments, a single T cell and plurality of target cells are loaded into the sequestration pen.

Loading cells into the sequestration pen may be performed using gravity, e.g., by tilting the microfluidic device so that cells are pulled gravitationally into the pen. Alternatively, with a microfluidic device having a dielectrophoresis (DEP) configuration, DEP force can be used to load the cells. In some embodiments, the DEP force is activated by structured light.

Any suitable marker that labels apoptotic cells can be used. Markers that label apoptotic cells include those that label dead cells distinguishably from live cells, e.g., dyes that do not cross live cell membranes but do cross compromised dead cell membranes, and labels that are dependent on an apoptosis-associated protein or enzymatic activity (e.g., an apoptosis-associated protease) for labeling. In some embodiments, the marker comprises a nucleic acid-binding moiety. In some embodiments, the marker is a fluorogenic or cleavable marker that is activated by cleavage by a protease, such as an apoptosis-associated protease, such as a caspase, e.g., caspase-3. In some embodiments, the marker comprises a binding agent (e.g., antibody) that specifically binds to apoptotic cells and/or apoptotic bodies; the binding agent can further comprise a detectable moiety, such as a fluorophore.

The method can comprise detecting whether target cells have become apoptotic one time or periodically, e.g., two, three, or more times. The method can comprise detecting whether target cells have become apoptotic 2 or more hours after contacting the cells with the marker and/or the T cell(s).

B. Kits for Performing an Antigen-Specific Cytotoxicity Assay

Also provided herein are kits for performing an antigen-specific cytotoxicity assay. In some embodiments, the kit comprises a microfluidic device. The microfluidic device can be any of the microfluidic devices described herein. In some embodiments, the microfluidic device is as described above in the section regarding methods for performing an antigen-specific cytotoxicity assay or as set forth in any embodiments disclosed herein. The microfluidic device included in a kit for performing an antigen-specific cytotoxicity assay need not comprise an antigen-presenting synthetic surface. In some embodiments, the kit comprises a reagent for detecting apoptotic cells. In some embodiments, the reagent for detecting apoptotic cells is a detectable marker that labels apoptotic cells as described above in the section regarding methods for performing an antigen-specific cytotoxicity assay or as set forth in any embodiments disclosed herein.

XII. KITS

A. Kits for Preparing an Antigen-Presenting Synthetic Surface

A kit is also provided for preparing an antigen-presenting synthetic surface for activating a T lymphocyte (T cell), including: a. any covalently functionalized synthetic surface as described herein, which includes a plurality of noncovalently or covalently associated first coupling agents; and a first modification reagent including a plurality of major histocompatibility complex (MHC) I molecules configured to bind with a T cell receptor of the T cell, and further wherein the MHC molecules are configured to bind to one of a first subset of the plurality of noncovalently or covalently associated first coupling agents of the covalently functionalized synthetic surface. In some embodiments, the first coupling agents may be a biotin-binding agent. The biotin-binding agent may be streptavidin. In some embodiments, each of the plurality of MHC molecules may further include at least one biotin functionality. Other coupling chemistries may be used, as is known in the art, wherein other site-specific protein tags may be attached to the MHC protein, which are configured to covalently attach to recognition protein-based species attached to the bead. These coupling strategies can provide the equivalent site specific and specifically orienting attachment of the MHC molecule as provided by C-terminal biotinylating of the MHC molecule. The covalently functionalized synthetic surface may be a wafer, a bead, at least one inner surface of a microfluidic device, or a tube.

The kit may further include a reagent including a plurality of co-activating molecules, each configured to bind one of a second subset of the plurality of noncovalently or covalently associated biotin-binding agents of the covalently functionalized synthetic surface. In various embodiments, each of the plurality of co-activating molecules may include a biotin functionality. Each of the co-activating molecules may include a T cell receptor (TCR) co-activating molecule, an adjunct TCR activating molecule, or any combination thereof. In various embodiments, the reagent is provided in individual containers containing the T cell receptor (TCR) co-activating molecule and/or an adjunct TCR activating molecule. Alternatively, the reagent including the plurality of co-activating molecules may be provided in one container containing the TCR co-activating molecules and/or the adjunct TCR activating molecules of the plurality of co-activating molecular ligands in a ratio from about 100:1 to 1:100. In various embodiments the reagent including the plurality of co-activating molecules includes a mixture of TCR co-activating molecules and adjunct TCR activating molecules wherein the ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about". In various embodiments, the reagent including a plurality of co-activating molecules contains the TCR co-activating molecules and the adjunct TCR activating molecules of the plurality of co-activating molecular ligands in a ratio from about 20:1 to about 1:20.

In various embodiments, the kit for preparing an antigen presenting synthetic surface may further include a reagent including adhesion stimulatory molecules, wherein each adhesion stimulatory molecule includes a ligand for a cell adhesion receptor including an ICAM protein sequence configured to react with a third subset of the plurality of noncovalently or covalently associated biotin-binding agent functionalities of the covalently functionalized synthetic surface. In some embodiments, the adhesion stimulatory molecule may include a biotin functionality.

In various embodiments, the kit for preparing an antigen presenting synthetic surface may further include a reagent including growth stimulatory molecules, wherein each growth stimulatory molecule may include a growth factor receptor ligand. In some embodiments, the growth factor receptor ligand may include a cytokine or a fragment thereof. In various embodiments, the cytokine may include IL-21 or a fragment thereof. In various embodiments, the growth stimulatory molecule may be attached to a covalently modified bead.

In various embodiments, the kit for preparing an antigen presenting synthetic surface may further include a reagent including one or more additional growth-stimulatory molecules. In some embodiments, the one or more additional growth-stimulatory molecules include IL2 and/or IL7, or fragments thereof. In various embodiments, the growth stimulatory molecule may be attached to a covalently modified bead.

B. Kits for Activating T Lymphocytes

Also provided is a kit for activating T lymphocytes, including an antigen-presenting synthetic surface as described herein. The kit can further comprise growth stimulatory molecules, wherein each growth stimulatory molecule may include a growth factor receptor ligand. The growth stimulatory molecules can be provided as free molecules, attached to the antigen presenting synthetic surface (in the same or a different region than the primary activating molecular ligand), or attached to a different covalently modified synthetic surface. For example, the kit can further comprise a plurality of covalently modified beads comprising an adjunct stimulatory molecule. In some embodiments, the growth factor receptor ligand molecule may include a cytokine or a fragment thereof. In some embodiments, the growth factor receptor ligand may include IL-21. In other embodiments, the kit may include one or more additional (e.g., a second or second and third) growth stimulatory molecules). In some embodiments, the one or more additional growth stimulatory molecules may include IL-2 and/or IL-7, or fragments thereof. Additional growth stimulatory molecules can be provided as a free molecule, attached to the antigen presenting synthetic surface (in the same or a different region than the primary activating molecular ligand), or attached to a different covalently modified synthetic surface, such as a bead.

XIII. ADDITIONAL ASPECTS OF MICROFLUIDIC DEVICE STRUCTURE, LOADING, AND OPERATION; RELATED SYSTEMS

Microfluidic devices and uses thereof described herein may have any of the following features, and can be used in conjunction with systems described below. In various embodiments, an analysis region can comprise one or more of the microfluidic devices described in this section.

A. Methods of Loading

Loading of biological micro-objects or micro-objects such as, but not limited to, beads, can involve the use of fluid flow, gravity, a dielectrophoresis (DEP) force, electrowetting, a magnetic force, or any combination thereof as described herein. The DEP force can be generated optically, such as by an optoelectronic tweezers (OET) configuration and/or electrically, such as by activation of electrodes/electrode regions in a temporal/spatial pattern. Similarly, electrowetting force may be provided optically, such as by an opto-electro wetting (OEW) configuration and/or electrically, such as by activation of electrodes/electrode regions in a temporal spatial pattern.

B. Microfluidic Devices and Systems for Operating and Observing Such Devices

FIG. 1A illustrates an example of a microfluidic device 100 and a system 150 which can be used for maintaining, isolating, assaying or culturing biological micro-objects. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106. The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164, and not explicitly illustrated in FIG. 1A), and a tilting device (part of tilting module 166, and not explicitly illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high-pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein in the context of microfluidic devices denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein in the context of microfluidic devices denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
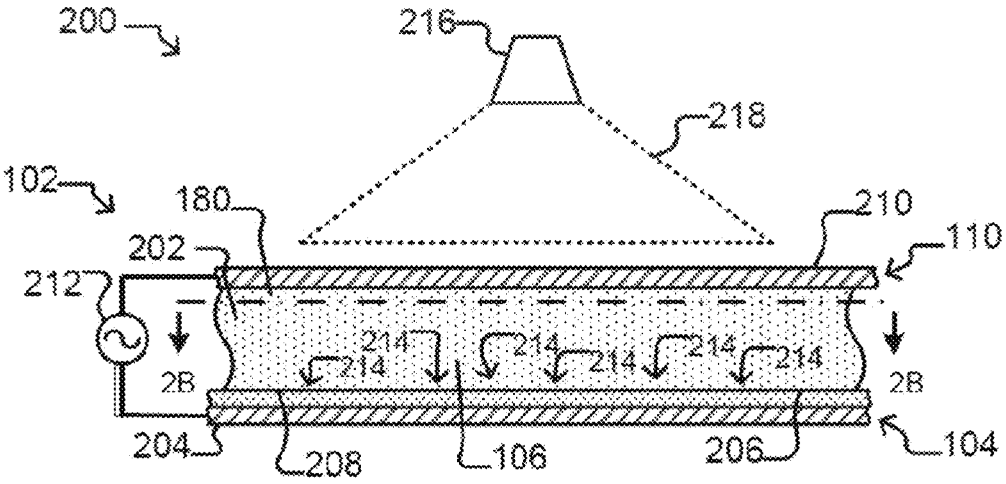
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an optoelectrowetting (OEW) configuration. Examples of suitable OET configurations are illustrated in the following U.S. patent documents, each of which is incorporated herein by reference in its entirety: U.S. Patent No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

C. Microfluidic Device Motive Configurations

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
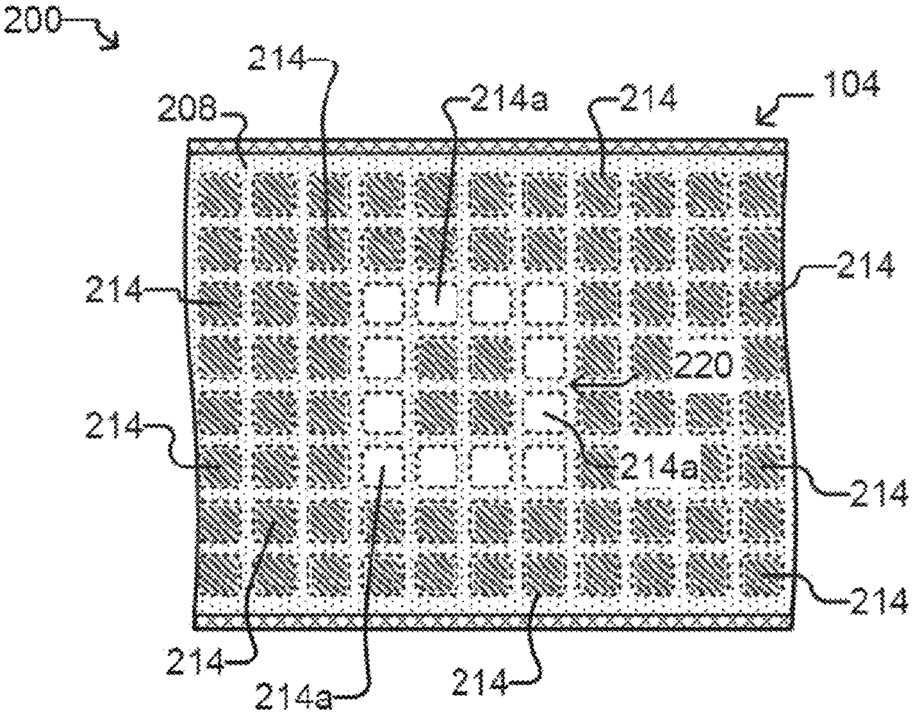

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214*a* (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214*a*, however, exhibits a reduced relative impedance through the electrode activation substrate 206 that is less than the relative impedance through the medium 180 in the region/chamber 202 at each illuminated DEP electrode region 214*a*.

With the power source 212 activated, the foregoing DEP configuration creates an electric field gradient in the fluidic medium 180 between illuminated DEP electrode regions 214*a* and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214*a* illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 Im. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Patent No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions **214*a* of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218**.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 k Ohms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 Im. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photo responsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

D. Sequestration pens

Figure 2A:
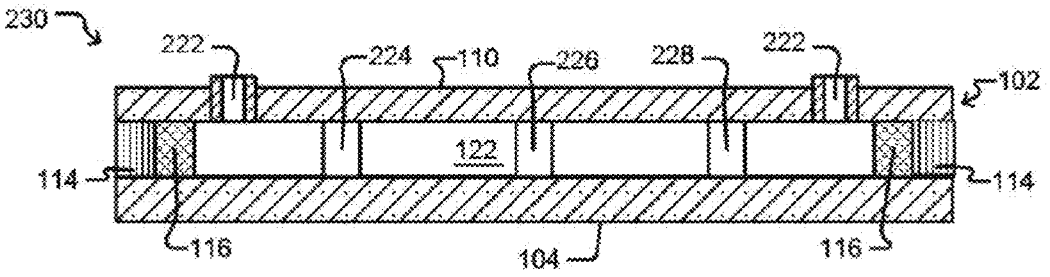
FIGS. 2A and 2B illustrate sequestration pens according to some embodiments of the disclosure.
Figure 2B:
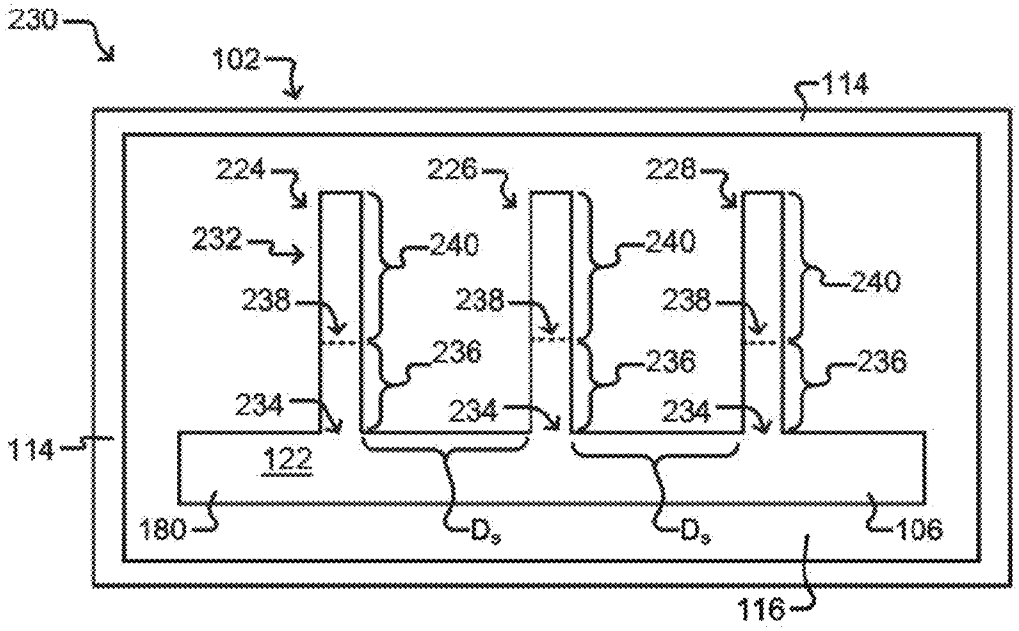
Figure 2C:
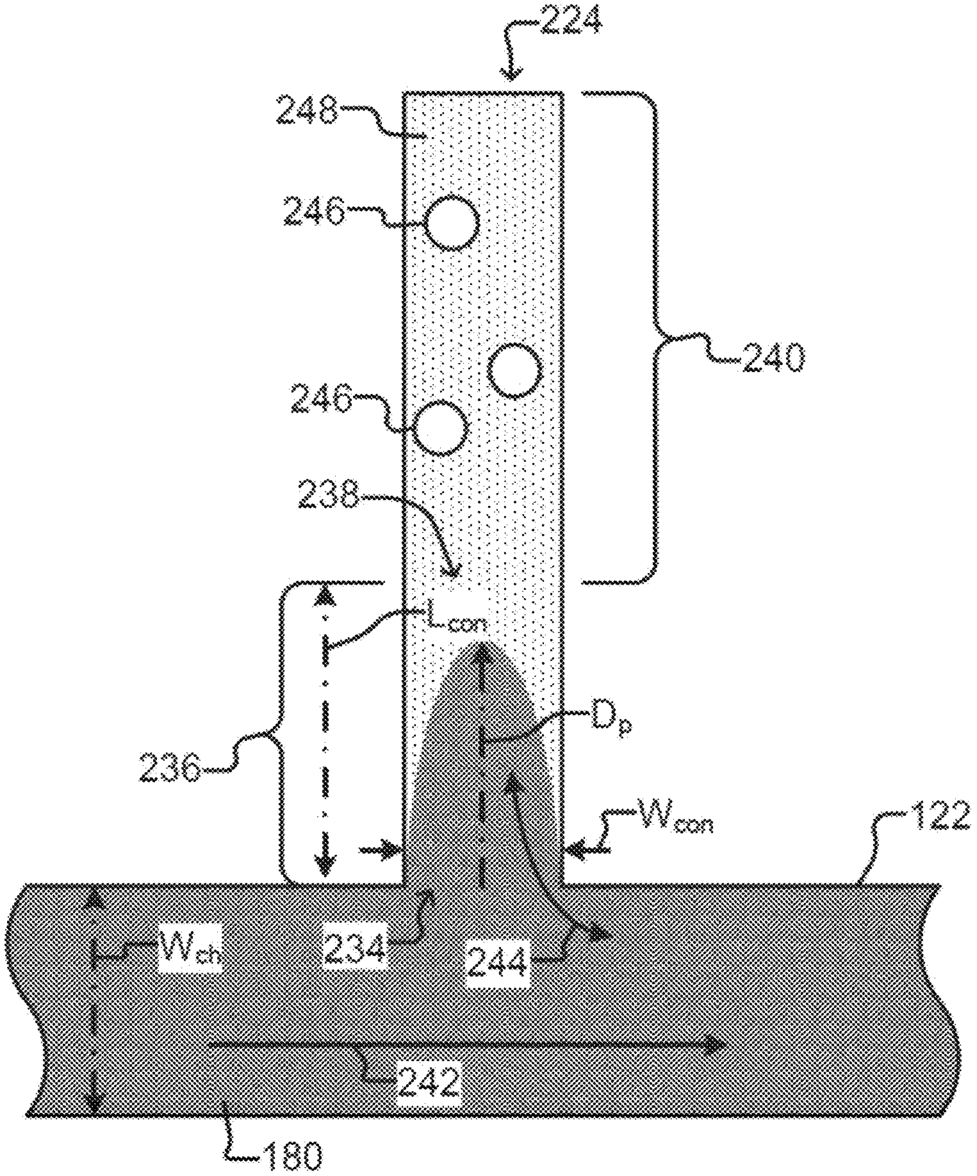
FIG. 2C illustrates a detailed sequestration pen according to some embodiments of the disclosure.

Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length Lcon of the connection region 236 of the sequestration pen 224 (i.e., from the proximal opening 234 to the distal opening 238) should be greater than the penetration depth Dp of the secondary flow 244 into the connection region 236. The penetration depth Dp of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity Vmax for the flow 242 of fluidic medium 180 in channel 122 can be identified that ensures that the penetration depth Dp of the secondary flow 244 does not exceed the length Lcon of the connection region 236. As long as the rate of the flow 242 of fluidic medium 180 in the microfluidic channel 122 does not exceed the maximum velocity Vmax, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed Vmax, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length Lcon of the connection region 236 be greater than the maximum penetration depth Dp of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth Dp of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width Wcon (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width Wcon (or cross-sectional area) of the connection region 236 at opening 234 can be substantially parallel to the flow 242 of medium 180 in the microfluidic channel 122; and/or the length Lcon of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width Wcon of the connection region 236 can be uniform from the proximal opening 234 to the distal opening 238. The width Wcon of the connection region 236 at the distal opening 238 can thus be any of the values identified herein for the width Wcon of the connection region 236 at the proximal opening 234. Alternatively, the width Wcon of the connection region 236 at the distal opening 238 can be larger than the width Wcon of the connection region 236 at the proximal opening 234.

As illustrated in FIG. 20, the width of the isolation region 240 at the distal opening 238 can be substantially the same as the width Wcon of the connection region 236 at the proximal opening 234. The width of the isolation region 240 at the distal opening 238 can thus be any of the values identified herein for the width Wcon of the connection region 236 at the proximal opening 234. Alternatively, the width of the isolation region 240 at the distal opening 238 can be larger or smaller than the width Wcon of the connection region 236 at the proximal opening 234. Moreover, the distal opening 238 may be smaller than the proximal opening 234 and the width Wcon of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
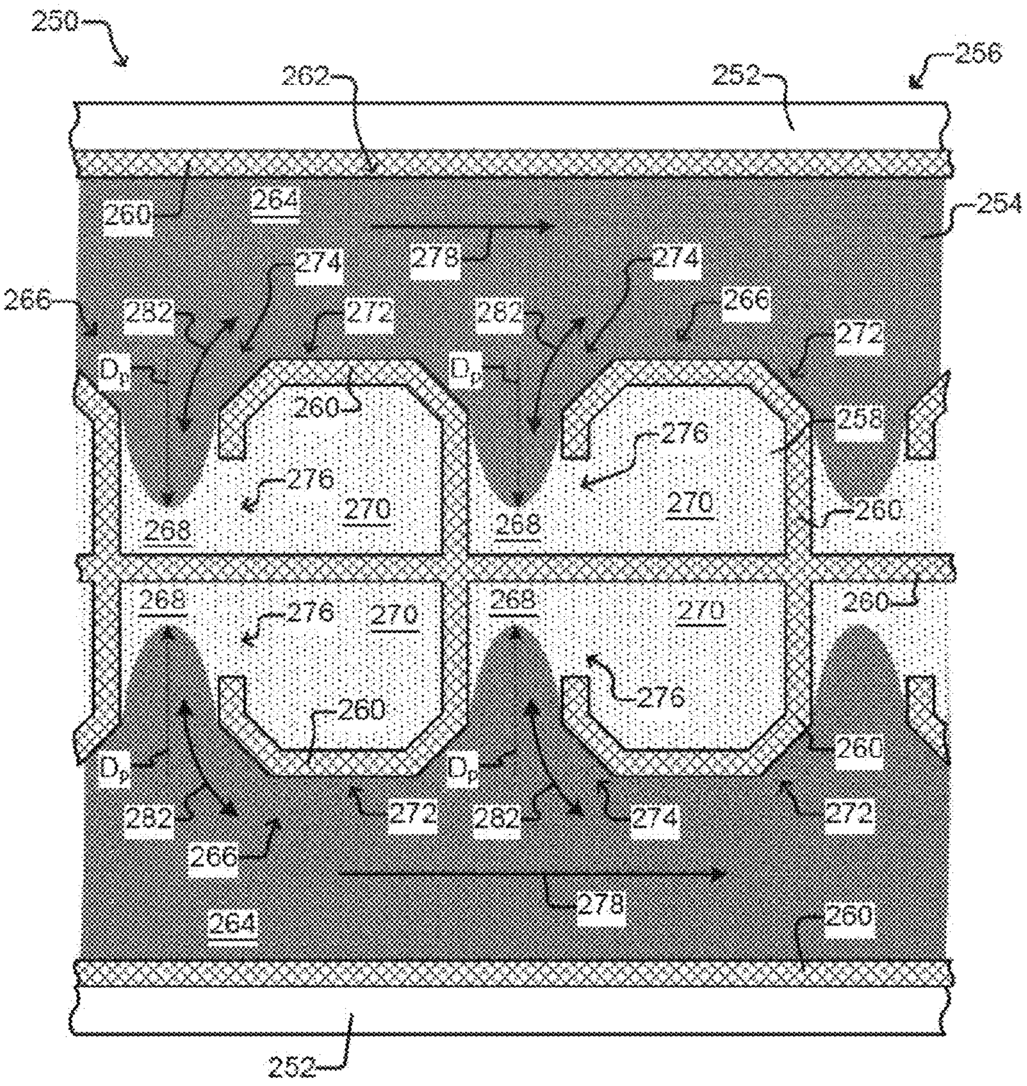
FIGS. 2D-F illustrate sequestration pens according to some other embodiments of the disclosure.
Figure 2E:
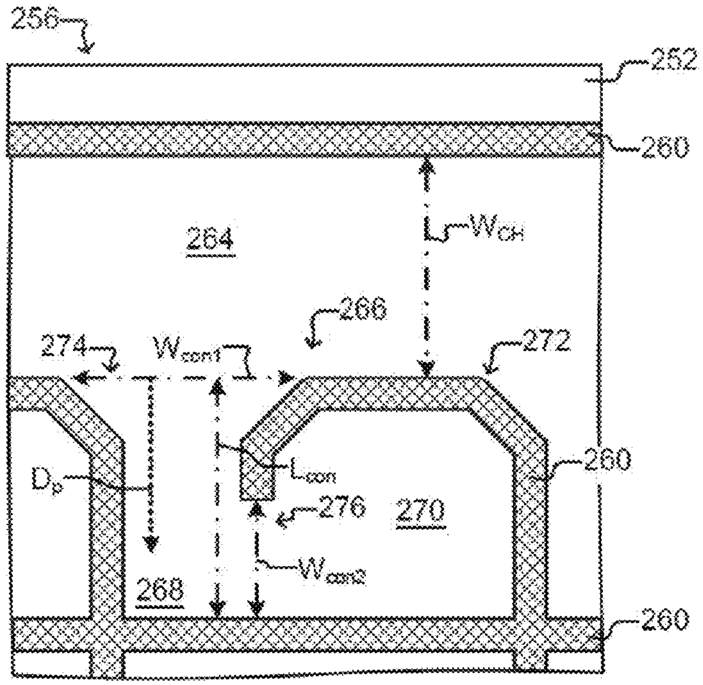
Figure 2F:
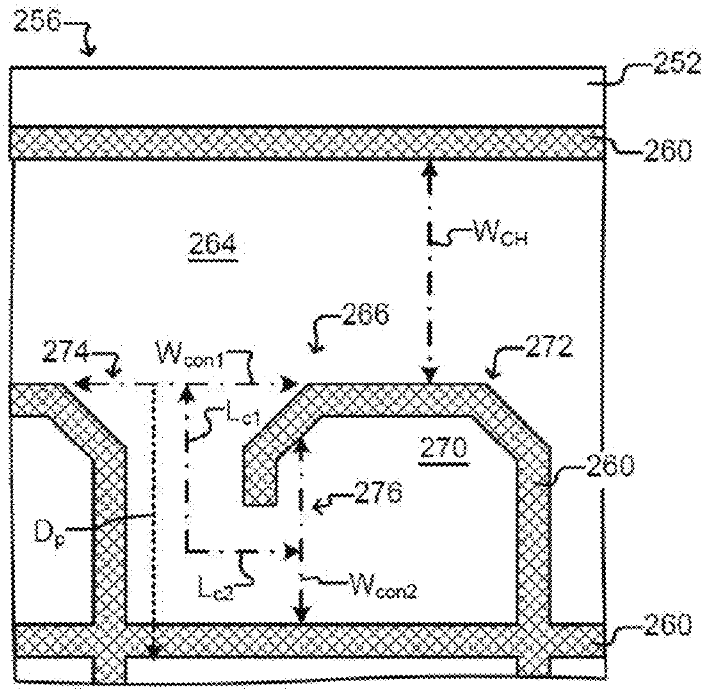

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290. Likewise, the microfluidic device 250 is another variant of the microfluidic device 100, and may also have the same or a different DEP configuration as the above-described microfluidic device 100, 200, 230, 280, 290, as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length Lcon of the connection region 268 can be greater than the maximum penetration depth Dp of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length Lcon that is less than the maximum penetration depth Dp, in which case the secondary flow 282 will extend through the connection region 268 and be redirected toward the isolation region 270. In this latter situation, the sum of lengths Lc1 and Lc2 of connection region 268 is greater than the maximum penetration depth Dp, so that secondary flow 282 will not extend into isolation region 270. Whether length Lcon of connection region 268 is greater than the penetration depth Dp, or the sum of lengths Le1 and Lo2 of connection region 268 is greater than the penetration depth Dp, a flow 278 of a first medium 254 in channel 264 that does not exceed a maximum velocity Vmax will produce a secondary flow having a penetration depth Dp, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles of: about 30° to about 90°, about 45° to about 90°, about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1\times10^6$, $2\times10^6$, $4\times10^6$, $6\times10^6$ cubic microns, or more.

In various embodiments of sequestration pens, the width $W_{ch}$ of the microfluidic channel (e.g., 122) at a proximal opening (e.g. 234) can be about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, or 100-120 microns. In some other embodiments, the width $W_{ch}$ of the microfluidic channel (e.g., 122) at a proximal opening (e.g. 234) can be about 200-800 microns, 200-700 microns, or 200-600 microns. The foregoing are examples only, and the width $W_{ch}$ of the microfluidic channel 122 can be any width within any of the endpoints listed above. Moreover, the $W_{ch}$ of the microfluidic channel 122 can be selected to be in any of these widths in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1\times10^4$–$3\times10^6$ square microns, $2\times10^4$–$2\times10^6$ square microns, $4\times10^4$–$1\times10^6$ square microns, $2\times10^4$—$5\times10^5$ square microns, $2\times10^4$–$1\times10^5$ square microns or about $2\times10^5$–$2\times10^6$ square microns.

In various embodiments of sequestration pens, the height Hch of the microfluidic channel (e.g., 122) at a proximal opening (e.g., 234) can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be a height within any of the endpoints listed above. The height $H_{ch}$ of the microfluidic channel 122 can be selected to be in any of these heights in regions of the microfluidic channel other than at a proximal opening of a sequestration pen.

In various embodiments of sequestration pens a cross-sectional area of the microfluidic channel (e.g., 122) at a proximal opening (e.g., 234) can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be any area within any of the endpoints listed above.

In various embodiments of sequestration pens, the length Lcon of the connection region (e.g., 236) can be about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length Lcon of a connection region (e.g., 236) can be in any length within any of the endpoints listed above.

In various embodiments of sequestration pens the width Wcon of a connection region (e.g., 236) at a proximal opening (e.g., 234) can be about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, or 80-100 microns. The foregoing are examples only, and the width Wcon of a connection region (e.g., 236) at a proximal opening (e.g., 234) can be different than the foregoing examples (e.g., any value within any of the endpoints listed above).

In various embodiments of sequestration pens, the width Wcon of a connection region (e.g., 236) at a proximal opening (e.g., 234) can be at least as large as the largest dimension of a micro-object (e.g., biological cell which may be a T cell, or B cell) that the sequestration pen is intended for. The foregoing are examples only, and the width Wcon of a connection region (e.g., 236) at a proximal opening (e.g., 234) can be different than the foregoing examples (e.g., a width within any of the endpoints listed above).

In various embodiments of sequestration pens, the width Wpr of a proximal opening of a connection region may be at least as large as the largest dimension of a micro-object (e.g., a biological micro-object such as a cell) that the sequestration pen is intended for. For example, the width Wpr may be about 50 microns, about 60 microns, about 100 microns, about 200 microns, about 300 microns or may be about 50-300 microns, about 50-200 microns, about 50-100 microns, about 75-150 microns, about 75-100 microns, or about 200-300 microns.

In various embodiments of sequestration pens, a ratio of the length Lcon of a connection region (e.g., 236) to a width W con of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length Lcon of a connection region 236 to a width Wcon of the connection region 236 at the proximal opening 234 can be different than the foregoing examples.

In various embodiments of microfluidic devices 100, 200, 23, 250, 280, 290, Vmax can be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, or 15 microliters/sec.

In various embodiments of microfluidic devices having sequestration pens, the volume of an isolation region (e.g., 240) of a sequestration pen can be, for example, at least $5\times10^5$, $8\times10^5$, $1\times10^6$, $2\times10^6$, $4\times10^6$, $6\times10^6$, $8\times10^6$, 1×107, 5×107, 1×108, 5×108, or 8×108 cubic microns, or more. In various embodiments of microfluidic devices having sequestration pens, the volume of a sequestration pen may be about $5\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, about 1000 to about 3500 sequestration pens, about 3000 to about 7000 sequestration pens, about 5000 to about 10,000 sequestration pens, about 9,000 to about 15,000 sequestration pens, or about 12,000 to about 20,000 sequestration pens. The sequestration pens need not all be the same size and may include a variety of configurations (e.g., different widths, different features within the sequestration pen).

Figure 2G:
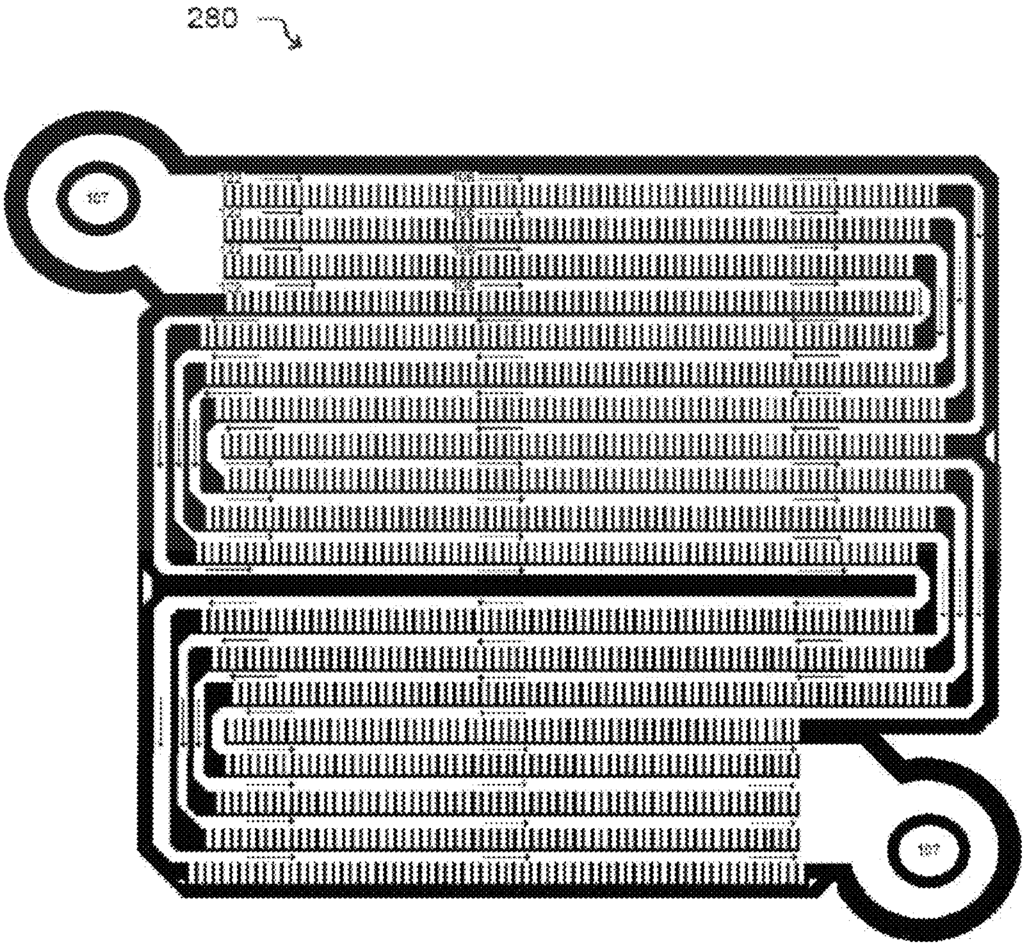
FIG. 2G illustrates a microfluidic device according to an embodiment of the disclosure.
Figure 2H:
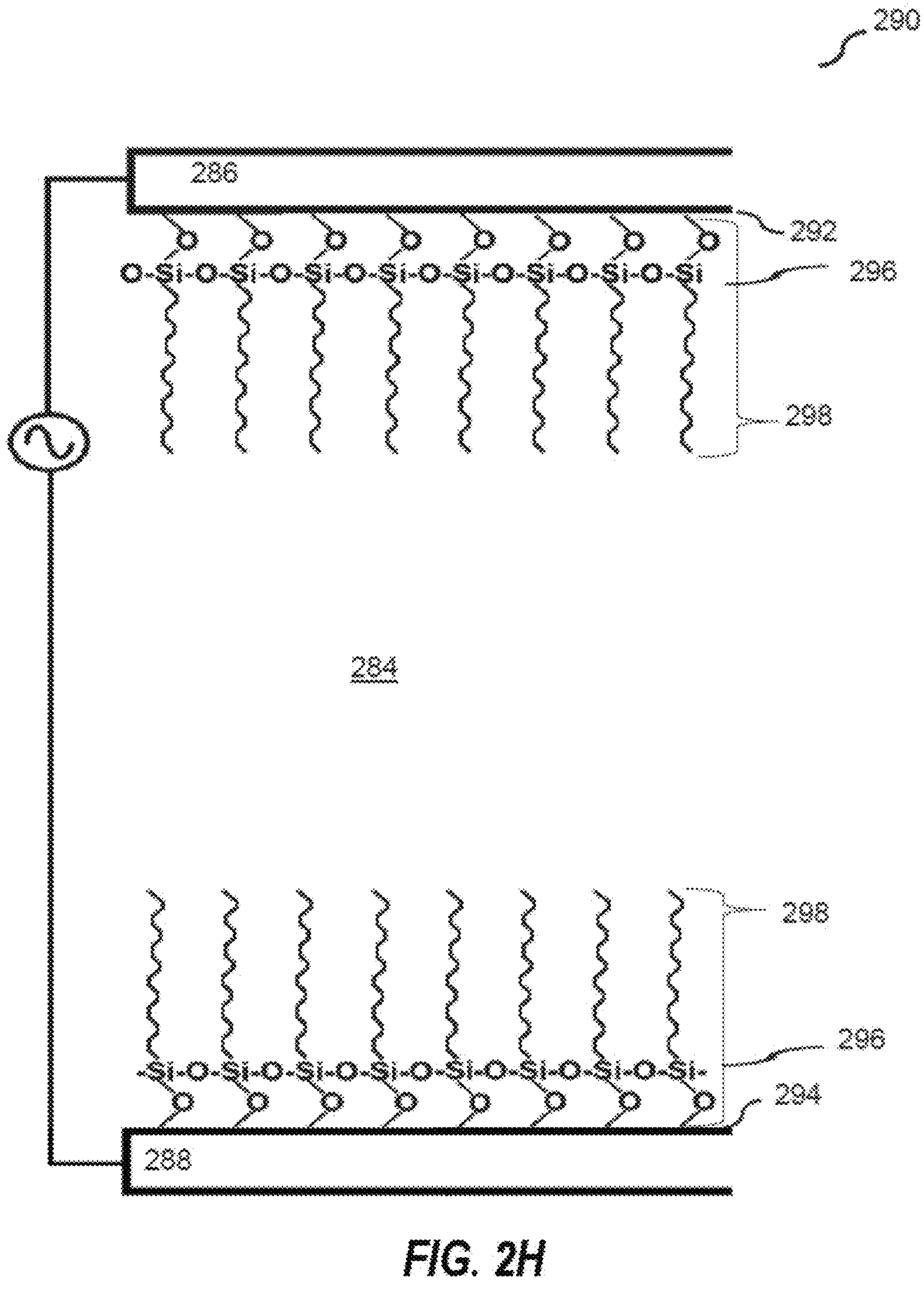
FIG. 2H illustrates a coated surface of the microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth Dp of the secondary flow 244) and non-swept regions (e.g. isolation regions 240 and portions of the connection regions 236 not within the maximum penetration depth Dp of the secondary flow 244).

Figure 3A:
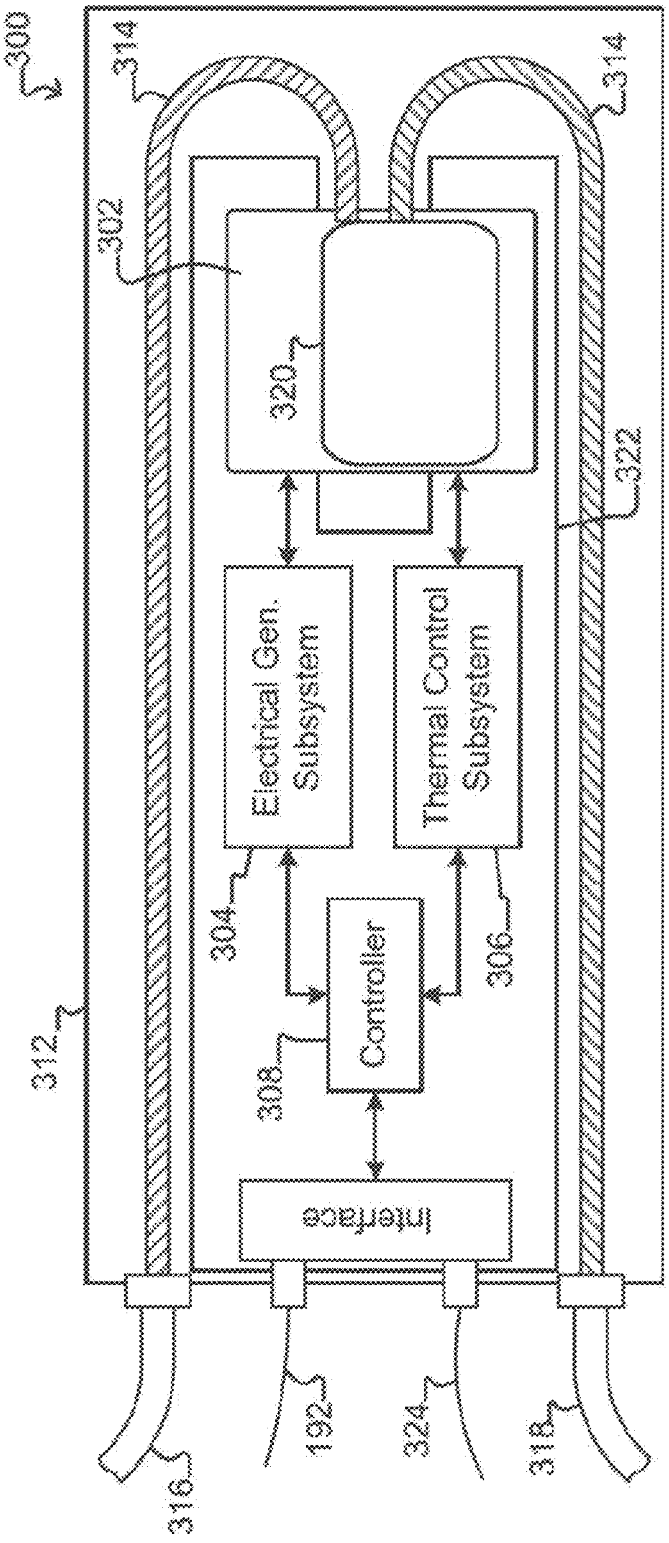
FIG. 3A illustrates a specific example of a system for use with a microfluidic device and associated control equipment according to some embodiments of the disclosure.
Figure 3B:
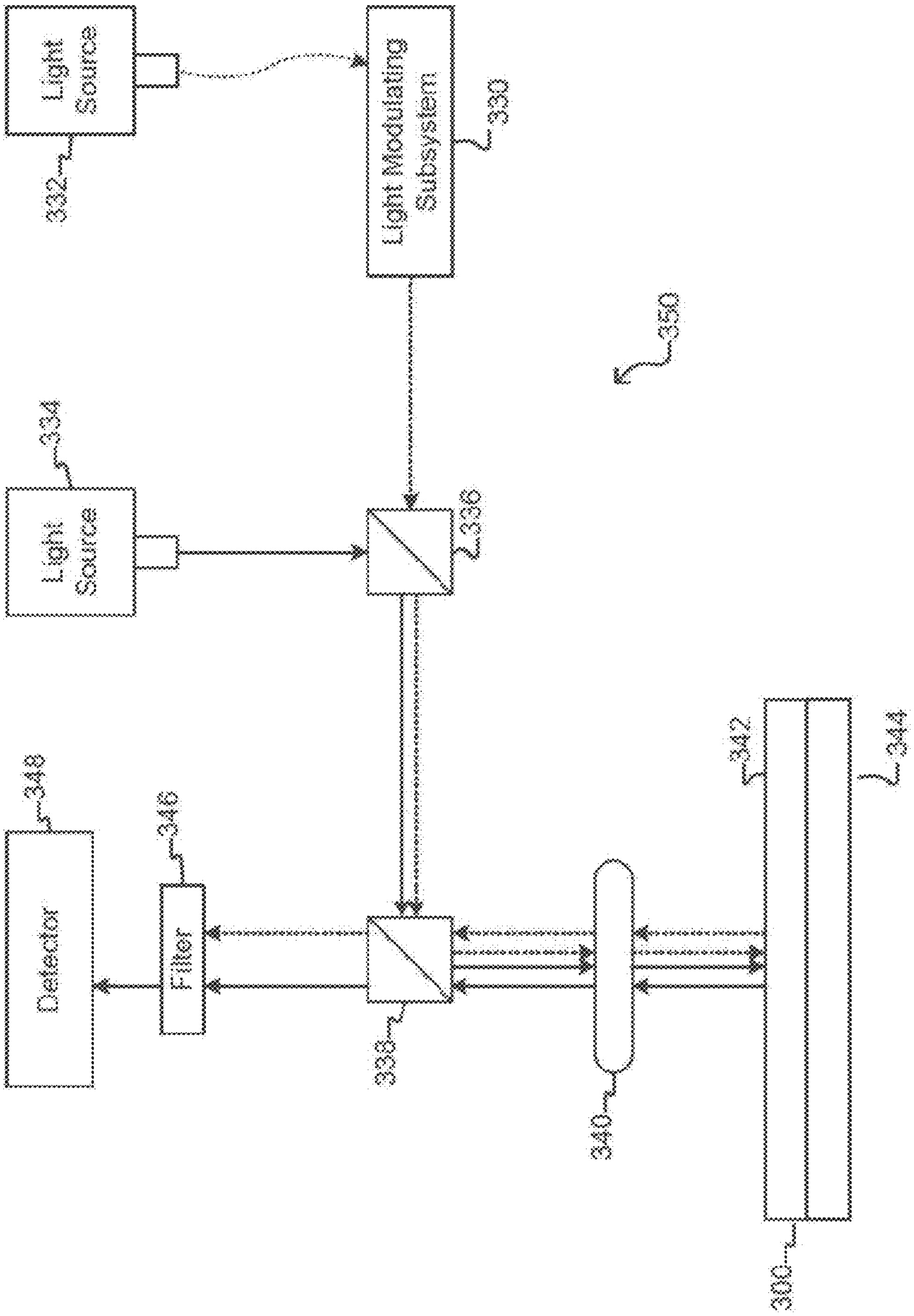
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 334 and light source 332/light modulating subsystem 330 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

E. Coating Solutions and Coating Agents

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

F. Coating Agent/Solution

Any convenient coating agent/coating solution can be used, including but not limited to: serum or serum factors, bovine serum albumin (BSA), polymers, detergents, enzymes, and any combination thereof.

G. Polymer-Based Coating Materials

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass Mw from about 2000 Da to about 20KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG Mw<100,000 Da) or alternatively polyethylene oxide (PEO, Mw>100,000). In some embodiments, a PEG may have an Mw of about 88 Da, 100 Da, 132 Da, 176 Da, 200 Da, 220 Da, 264 Da, 308 Da, 352 Da, 396 Da, 440 Da, 500 Da, 600 Da, 700 Da, 800 Da, 900 Da, 1000 Da, 1500 Da, 2000 Da, 5000 Da, 10,000 Da or 20,000 Da, or may have a Mw that falls within a range defined by any two of the foregoing values.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a concentration from about 1 mg/ml to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a concentration of about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

In addition, in embodiments in which a covalently modified surface is used in conjunction with coating agents, the anions, cations, and/or zwitterions of the covalently modified surface can form ionic bonds with the charged portions of non-covalent coating agents (e.g. proteins in solution) that are present in a fluidic medium (e.g. a coating solution) in the enclosure.

Further details of appropriate coating treatments and modifications may be found at U.S. application Ser. No. 15/135,707, filed on Apr. 22, 2016, and is incorporated by reference in its entirety.

H. Additional System Components for Maintenance of Viability of Cells within the Sequestration Pens of the Microfluidic Device In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

XIV. EXAMPLES

General Materials and Methods i. System and Microfluidic Device

An OptoSelect chip, a microfluidic (or nanofluidic) device manufactured by Berkeley Lights, Inc. and controlled by an optical instrument which was also manufactured by Berkeley Lights, Inc. The instrument included: a mounting stage for the chip coupled to a temperature controller; a pump and fluid medium conditioning component; and an optical train including a camera and a structured light source suitable for activating phototransistors within the chip. The OptoSelect™ chip included a substrate configured with OptoElectroPositioning (OEP™) technology, which provides a phototransistor-activated OET force. The chip also included a plurality of microfluidic channels, each having a plurality of NanoPen™ chambers (or sequestration pens) fluidically connected thereto. The volume of each sequestration pen was around $1\times10^6$ cubic microns.

ii. Priming Solution

Complete growth medium containing 0.1% Pluronic® F127 ((Life Technologies® Cat #P6866).

Preparation for culturing: The microfluidic device having a modified surface was loaded onto the system and purged with 100% carbon dioxide at 15 psi for 5 min. Immediately following the carbon dioxide purge, the priming solution was perfused through the microfluidic device at 5 microliters/sec for 8 min. Culture medium was then flowed through the microfluidic device at 5 microliters/sec for 5 min.

iii. Priming Regime 250 microliters of 100% carbon dioxide was flowed in at a rate of 12 microliters/sec. This was followed by 250 microliters of PBS containing 0.1% Pluronic® F27 (Life Technologies® Cat #P6866), flowed in at 12 microliters/sec. The final step of priming included 250 microliters of PBS, flowed in at 12 microliters/sec. Introduction of the culture medium follows.

iv. Perfusion regime

The perfusion method was either of the following two methods:

1. Perfuse at 0.01 microliters/sec for 2h; perfuse at 2 microliters/sec for 64 sec; and repeat.

2. Perfuse at 0.02 microliters/sec for 100 sec; stop flow 500 sec; perfuse at 2 microliters/sec for 64 sec; and repeat.

Example 1. Preparation of a Functionalized Surface of an Unpatterned Silicon Wafer A silicon wafer (780 microns thick, 1 cm by 1 cm) was treated in an oxygen plasma cleaner (Nordson Asymtek) for 5 min, using 100 W power, 240 mTorr pressure and 440 sccm oxygen flow rate. The plasma treated silicon wafer was treated in a vacuum reactor with (11-azidoundecyl) trimethoxy silane (300 microliters) in a foil boat in the bottom of the vacuum reactor in the presence of magnesium sulfate heptahydrate (0.5g, Acros Cat. #10034-99-8), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a modified surface to the wafer, where the modified surface had a structure of Formula I:

Formula I

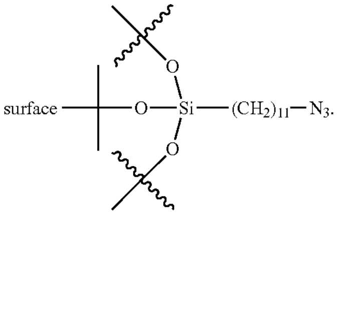

After cooling to room temperature and introducing argon to the evacuated chamber, the wafer was removed from the reactor. The wafer was rinsed with acetone, isopropanol, and dried under a stream of nitrogen. Confirmation of introduction of the modified surface was made by ellipsometry and contact angle goniometry.

Alternatively, the silicon wafer was cut to size to fit within the bottom of a flat bottomed wellplate before introducing the functionalized surface of Formula I upon it, and a plurality of the formatted silicon wafers were functionalized at the same time.

Example 2. Preparation of a Planar Unpatterned Silicon Wafer Having a Streptavidin Functionalized Surface The product silicon wafer from Example 1, having a surface of Formula I as described above, was treated with dibenzylcyclooctynyl (DBCO) Streptavidin (SAV), Nanocs, Cat. #SV1-DB-1, where there are 2-7 DBCO for each molecule of SAV) by contacting the silicon wafer with an aqueous solution containing a 2 micromolar solution of the commercially available DBCO-SAV. The reaction was allowed to proceed at room temperature for at least 1 h. The unpatterned silicon wafer having a modified surface of Formula II was then rinsed with 1×PBS.

Formula II

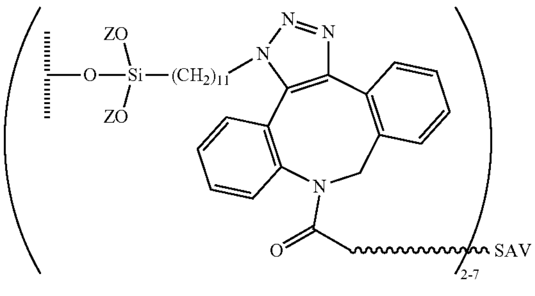

Example 3. Synthesis of DBCO-Labeled Streptavidin (SAV) Compound 1

5 mg of lyophilized SAV (ThermoFisher PN #S888) was dissolved into 1 mL of 1×PBS (Gibco) and 1 mL of 2 mM $Na_2CO_3$ (Acros) in 1×PBS. 10 mg of neat DBCO-PEG13-NHS (Compound 2, Click Chemistry Tools PN #1015-10) was dissolved into 0.4 mL of dry DMSO. 16 μL of the DBCO-PEG13-NHS solution was added to the SAV solution and mixed at 400 RPM at 25° C. for 4 h on an Eppendorf ThermoMixer. The labeled SAV (Compound 1) was purified from the DBCO-PEG13-NHS by passing the reaction mixture through Zeba size exclusion chromatography spin columns (ThermoFisher PN #89882), and used without further purification.

Compound 2

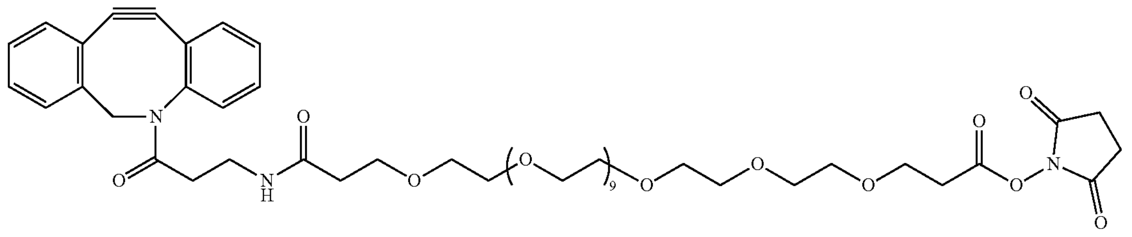

Example 4. Preparation of a Planar Unpatterned Silicon Wafer Having a Streptavidin Functionalized Surface The product silicon wafer from Example 1, having a surface of Formula I as described above, was treated with Compound 1 (DBCO linked Streptavidin (SAV), product of Example 3, having a PEG 13 linker, where there are 2-7 DBCO for each molecule of SAV) by contacting the silicon wafer with an aqueous solution containing 2 micromolar Compound 1. The reaction was allowed to proceed at room temperature for at least 1 h. The unpatterned silicon wafer having a streptavidin covalently functionalized surface including a PEG 13 linker was then rinsed with 1×PBS.

Example 5. Comparison of Functionalization of Silicon Wafers with Commercially Available DBCO Linked SAV Compared with Functionalization Using Compound 1

Comparison of the SAV modified surfaces was made by ellipsometry and contact angle goniometry after each step of introduction of reactive azide moieties (Example 1); introduction of respective SAV layers; followed by introduction of biotinylated anti-CD28, where the concentrations of reagents and reaction conditions were the same. Sample 2, using the DBCO SAV reagent having a linker including a PEG13 moiety, clearly provided a more robust functionalization of SAV than that of Sample 1, and subsequently, more robust functionalization by biotinylated anti-CD2 binding to the SAV binding sites.

| Sample | Thickness of azide layer (Angstroms) | Overall Thickness after DBCO SAV coupling (Angstroms) | Overall Thickness after anti-CD 28 binding (Angstroms) | Thickness of SAV layer introduced (Angstroms) | Thickness of anti-CD28 layer introduced (Angstroms) |
|---|---|---|---|---|---|
| Wafer 1, from Ex. 2 | 13.31 | 25.22 | 28.54 | 11.91 | 3.32 |
| Wafer 2, from Ex.4 | 13.43 | 45.08 | 62.37 | 31.65 | 17.29 |

Without being bound by theory, it was shown that a linker having a length of at least 5 PEG repeat units up to about 20 PEG repeat units (alternatively, a linker having a length from about 20 Angstroms to about 100 Angstroms) may provide superior levels of coupling to the reactive moieties on this reactive surface of the silicon wafer. This is further demonstrated by the additional thickness of the layer of anti-CD28 introduced in Sample Wafer 2, as more SAV binding sites were available.

Example 6. Preparation of Planar Patterned Surfaces, and Further Elaboration to Provide Antigen Presenting Surfaces within a Plurality of Regions Separated by a Differing Region Having No Activation Functionalization Indium tin oxide (ITO) wafers were fabricated to have a patterned plurality of regions of amorphous silicon upon the ITO. The regions were a.) 1 micron diameter round amorphous silicon regions separated by three microns from each other or b.) 2 micron square amorphous silicon regions separated by 2 microns from each other. FIGS. 6A and 6B show SEM images of portions of each type of patterned surface.

The patterned wafers were cleaned prior to functionalization by sonication for 10 minutes in acetone, rinsed with deionized water, and dried (Step 1 of FIG. 6). The patterned wafers were then treated in an oxygen plasma cleaner (Nordson Asymtek) for 5 min, using 100 W power, 240 mTorr pressure and 440 sccm oxygen flow rate.

A schematic representation of the functionalization process is shown in FIG. 6. Initial covalent modification of the ITO surface. The indium tin oxide base layer of the wafer was functionalized by reaction with 40 mM undecynyl phosphonic acid (Sikemia Catalog #SIK7110-10) in 50% N-methylpyrrolidine (NMP)/water solution (Step 2 of FIG. 6). The cleaned surface of the wafers was submerged in the solution within a vial and sealed. The vial was maintained in a 50° C. water bath overnight. The next day, the wafers were removed and washed with 50% isopropyl alcohol/water, followed by isopropyl alcohol.

A. Biotinylation of the ITO region of the patterned surface. The alkyne functionalized ITO region was further covalently modified by reaction with 1.5 mM biotin linked to an azido reactive moiety (azide-S-S-biotin, Broadpharm Catalog #BP-2877), 0.5 mM sodium ascorbate; and 1 mM Cu (II) $SO_4$/THPTA in water (Step 3 of FIG. 6). Care was taken to premix the copper ligand and sodium ascorbate prior to contact with the disulfide containing biotin reagent. The surfaces were allowed to remain in contact with the biotin reagent solution for one hour. The surfaces of the wafers were then washed with water, and dried, in preparation for the next step.

B. Covalent modification of the surfaces of the plurality of amorphous silicon regions of the patterned wafer. The patterned wafers having biotinylated surface within the ITO region of the wafer was treated in a vacuum reactor with (11-azidoundecyl)trimethoxy silane (Compound 3, 300 microliters) in a foil boat in the bottom of the vacuum reactor in the presence of magnesium sulfate heptahydrate (0.5 g, Acros Cat. #10034-99-8), as a water reactant source in a separate foil boat in the bottom of the vacuum reactor (Step 4 of FIG. 6). The chamber was then pumped to 750 mTorr using a vacuum pump and then sealed. The vacuum reactor was placed within an oven heated at 110° C. overnight. This introduced a modified surface to the plurality of amorphous silicon regions on the wafer, where the modified surface had a structure of Formula I:

Formula I

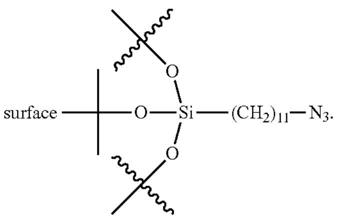

After cooling to room temperature and introducing argon to the evacuated chamber, the wafer was removed from the reactor. The wafer was rinsed with acetone, isopropanol, and dried under a stream of nitrogen. Metrology showed that the biotinylated ITO region of the patterned wafer did not have substantial amounts of contamination of the functionalizing ligands of Formula I; 10% or less contaminant was found.

C. Covalent modification of the biotin-modified ITO region of the patterned wafer to provide supportive moieties. The patterned wafers having a plurality of undecyl azido modified amorphous silicon regions separated by a biotin modified ITO region was reacted with a solution of streptavidin (SAV, 3.84 micromolar) in PBS containing 0.02% sodium azide and allowed to incubate for 30 min (Step 5 of FIG. 6). The wafer was then washed with PBS and dried.

The streptavidin modified surface of the ITO region of the patterned wafers is then modified by reaction with a 200 micromolar solution of biotin-RGD (Anaspec Catalog #AS-62347) in PBS containing 0.02% sodium azide, thereby providing adhesive moieties for general improvement in viability of the T lymphocytes when cultured upon these surfaces (Step 6 of FIG. 6). After incubating for 45 min, the wafers are rinsed with PBS and then dried.

Further generalization. The streptavidin modified surface of the ITO region of the patterned wafers may alternatively be modified by reaction with a 200 micromolar solution of biotin-PEG-5K (Jenkem Catalog #M-BIOTIN-5000) to provide hydrophilic moieties within this non-activating region of the patterned surface. Further the streptavidin surface may be modified by a mixture of the adhesive and hydrophilic moieties by reacting the streptavidin surface with a mixture of 200 micromolar stock solutions of the biotinylated moieties, in any ratio, e.g., 1:1: 1:10; 10:1 or any ration therebetween.

D. Providing a secondary functionalized surface to the plurality of azido functionalized amorphous silicon regions of the patterned wafers. A solution of DBCO-SAV (Nanocs Catalog #SV1-DB-1, 2 micromolar) in PBS containing 0.02% sodium azide was contacted with the patterned wafer having a plurality of azido-functionalized amorphous silicon regions separated by a region of ITO having supportive moieties (e.g., adhesive motifs such as RGD, or hydrophilic moieties such as PEG-5K) covalently attached thereupon, for an incubation period of 30 min, providing a plurality of amorphous regions having a streptavidin functionalized surface separated by the region of supportively modified ITO surface (Step 7 of FIG. 6). The patterned wafers were maintained in PBS/0.02% sodium azide until final introduction of the antigen activating ligands.

E. Functionalization of streptavidin modified surfaces of the amorphous silicon regions of the patterned wafer (Step 8 of FIG. 6). Stepwise functionalization is performed similarly as in Example 12, first exposing the patterned surfaces to biotinylated Monomer MHC (HLA-A* 02:01 MART-1 (MBL International Corp., Catalog No. MR01008, ELAGIGILTV) in solution, and incubation for 45 minutes. After rinsing the patterned wafer having a plurality of MHC modified amorphous silicon regions with Wash Buffer, the patterned wafer is then contacted with a solution of biotinylated anti-CD28 (Miltenyi Biotec, Catalog #130-100-144) and incubated for 30-45 minutes to provide a plurality of pMHC/anti-CD28 regions separated by a supportively modified ITO region of the patterned wafer.

Figure 8A:
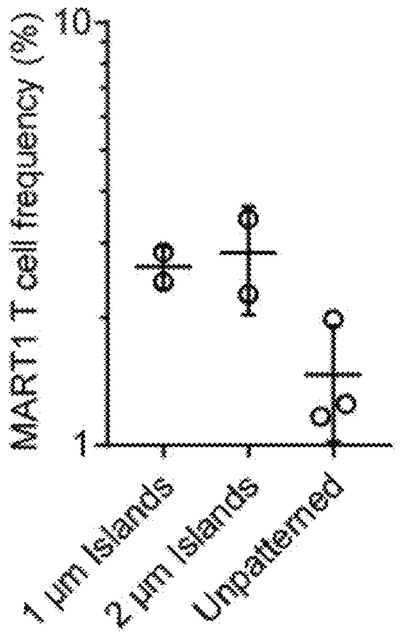
FIGS. 8A-8D are graphical representations of various characterization parameters for activation of T lymphocytes at 7 days of culturing, according to some embodiments of the disclosure.
Figure 8B:
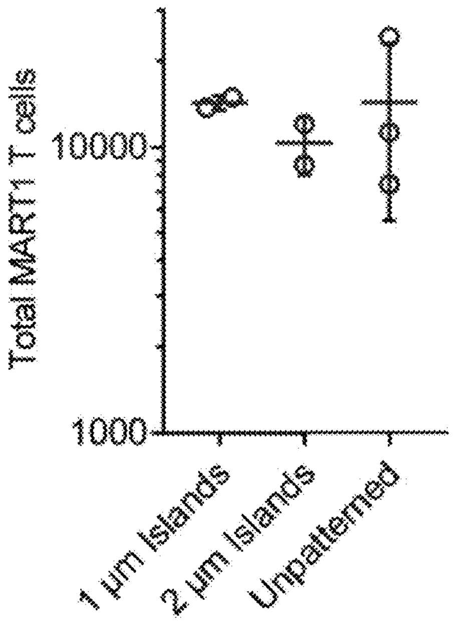
Figure 8C:
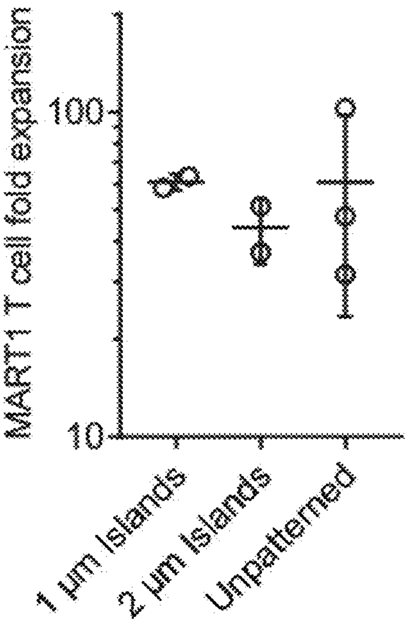
Figure 8D:
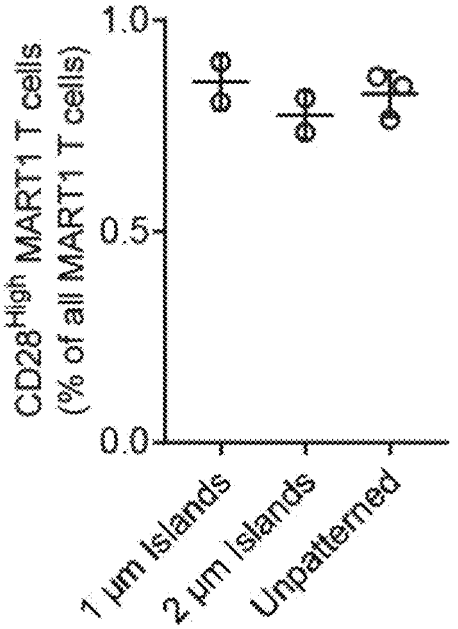
Figure 9:
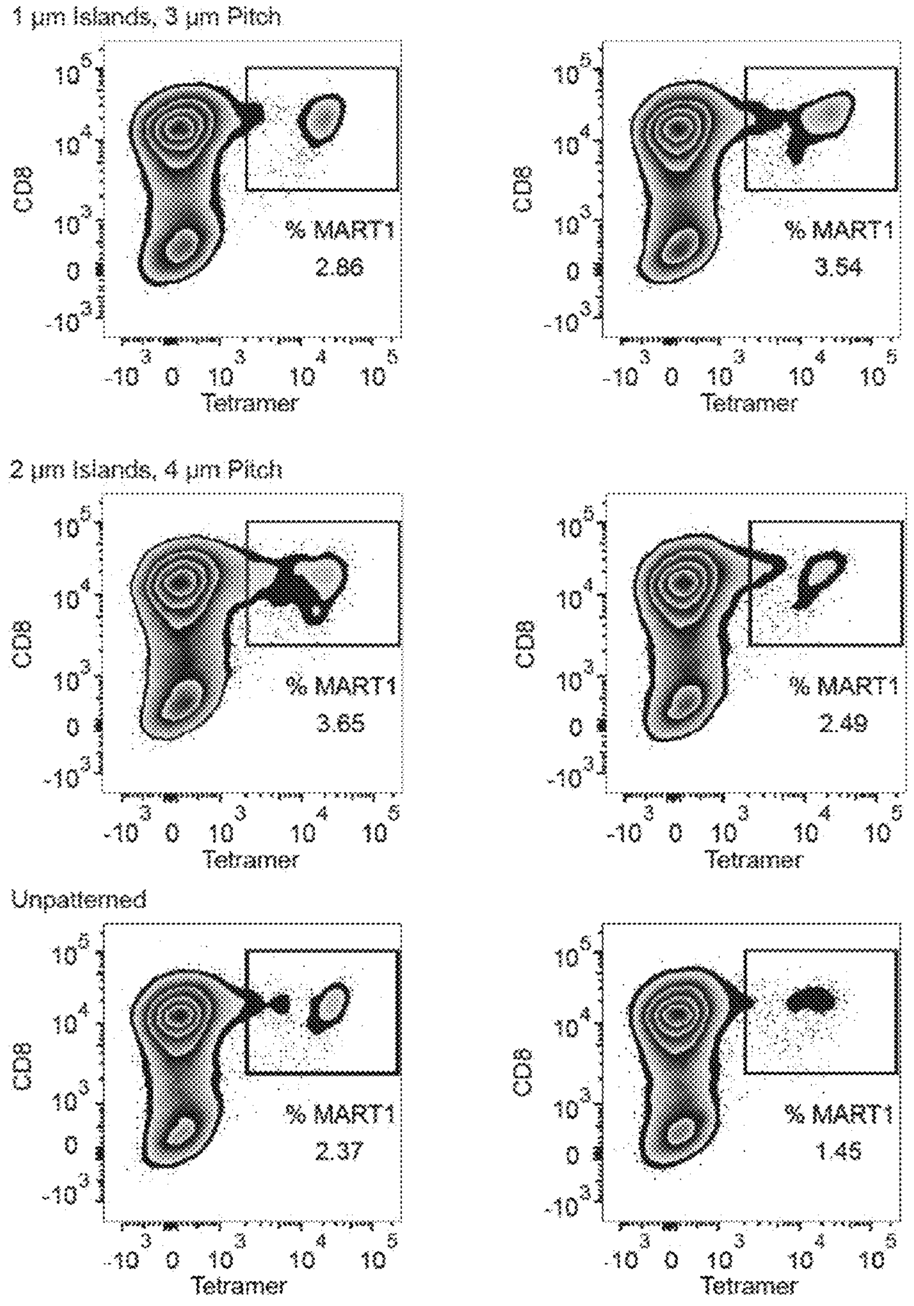
FIG. 9 is a graphical representation of the distribution of characteristics for activated T lymphocytes according to some embodiments of the disclosure.

Example 7. Activation of CD8+T Lymphocytes Using a Patterned Surface Containing a Plurality of Regions Having pMHC And Anti-CD28 Connected Thereto, Separated by a Region Having Supportive Moieties Connected Thereto Compared to an Unpatterned Surface The product patterned wafer of Example 6 was sized for placement within the bottom of a well of a 48-well plate. Two different patterned surfaces were used, the first having circular regions having a diameter of 1 micron, such as shown in FIG. 7A and the second having square regions of 2 microns each side as shown in FIG. 7B. A planar third surface, unpatterned, having a random distribution of the same level of MHC peptide modification and anti-CD28 was used in a third well of a third 48 well plate. Only one level of anti-CD28 antibody loading to the planar surfaces was used. Naïve T-lymphocytes, obtained as described in Example 12 (below) were disposed within the wells of the well plates and in contact with the patterned or unpatterned wafer. The stimulation protocol and culturing protocol were each performed as in Example 12 for days 1-7. Flow cytometry analysis showed activation of the naïve T lymphocytes. The flow cytometry results as shown in FIGS. 8A-8D show that each of the three kinds of surfaces can activate T lymphocytes. Graphical characterization shown in FIGS. 8A-D for these three conditions of activation show that phenotypic specificity is obtained. FIG. 8A shows the percentage of antigen specific (MART1) T cells found in the product cell populations for each of the 1 micron activating island patterns, 2 micron activating island patterns, and unpatterned wafer surface. FIG. 8B shows the total number of MART 1 antigen specific T cells found in each of the resultant cell populations for each surface type. FIG. 8C shows the fold expansion of MART 1 antigen specific T cells for each of the surface type. FIG. 8D shows the percentage of CD28high expressing antigen specific T cells within the antigen specific T cell population for each surface type. The patterned surfaces demonstrate more reproducible and controllable amounts of expansion, phenotype and actual numbers of cells. The smaller 1 micron regions may more effectively mimic the natural preferred arrangement of presented antigen, MHC molecule and anti-CD 28. See FIG. 9.

After the first period of stimulation is complete, the resultant T cells are restimulated for Days 7-14, and optionally for Days 14-21 within the same well of the well plate, adding the cytokine additions as above. Alternatively, on Day 7 and/or Day 14, the resultant T lymphocytes may be moved to a new well having a fresh patterned wafer, and the protocol of Example 12 continued. At the end of the desired repetitions of stimulation, a portion of the cells may be stained and examined by flow cytometry to determine the extent of activation. It is expected that the patterned surface wafers stimulate T cell activation as readily as bead-based activation or activation by antigen presenting Dendritic cells.

Example 8. Preparation of a Microfluidic Device Having Modified Interior Surfaces of Formula I A microfluidic device (Berkeley Lights, Inc.) as described in the general experimental section above, having a first silicon electrode activation substrate and a second ITO substrate on the opposite wall, and photopatterned silicone microfluidic circuit material separating the two substrates, was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with 3-azidoundecyl) trimethoxy silane (300 microliters) in a foil boat in the bottom of the vacuum reactor in the presence of magnesium sulfate heptahydrate (0.5 g, Acros), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a modified surface to the microfluidic device, where the modified surface had a structure of Formula I:

Formula I

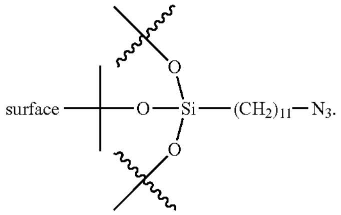

After cooling to room temperature and introducing argon to the evacuated chamber, the microfluidic device was removed from the reactor. The microfluidic device having the functionalized surface was rinsed with at least 250 microliters of deionized water, and was ready for further use.

Example 9. Introduction of a T-Cell Activating Surface within a Microfluidic Device A. The internal surfaces of an OptoSelect microfluidic device were covalently modified to include azido moieties as in Example 8 (Formula I). To functionalize the surface with streptavidin, the OptoSelect microfluidic device is first flushed repeatedly with 100% carbon dioxide, and then loaded with DBCO-streptavidin solution having a concentration from about 0.5 to about 2 micromolar, as produced in Example 4. After incubation for 15-30 minutes, during which the DBCO and azide groups coupled, the OptoSelect microfluidic device is washed repeatedly with 1×PBS to flush unbound DBCO-modified streptavidin.

This streptavidin surface is then further modified with biotinylated pMHC, and a selection of biotinylated anti CD28, biotinylated anti CD2 or any combination thereof. These molecules are suspended in PBS with 2% Bovine Serum Albumin at concentrations of about 1-10 micrograms/mL, in a ratio of pMHC molecules to antiCD28/antiCD2 from about 2:1 to about 1:2. This solution is perfused through the OptoSelect microfluidic device having streptavidin functionalized surfaces, facilitating conjugation to the surface. After one hour of incubation, the OptoSelect microfluidic device is flushed with PBS or media prior to loading cells.

B. Alternatively, biomolecules of interest are conjugated via biotin modification of the biomolecules to streptavidin prior to reaction with the azido-modified surfaces of the OptoSelect microfluidic device. DBCO-streptavidin and biotinylated biomolecule are prepared separately in PBS solution at concentrations in the range of 0.5-2 micromolar, then mixed at any desired ratio, as described below. After allowing the biotinylated biomolecules to conjugate to the streptavidin for at least 15 minutes, this complex is used to modify the surface of an azido-modified OptoSelect microfluidic device as described above.

Cells may be imported into the microfluidic device having at least one antigen-presenting inner surface and activated during periods of culturing similarly as described for activation of T cells with antigen-presenting beads of Example 19.

Example 10. Covalent Modification and Functionalization of Silica Beads

10A. Silica beads having covalent PEG 3 disulfide biotin linked to streptavidin. Spherical silica beads (2.5 micron, G biosciences Catalog #786-915, having a substantially simple spherical volume, e.g. the surface area of the bead is within the range predicted by the relationship 4TTr2+/−no more than 10%) were dispersed in isopropanol, and then dried. The dried beads were treated in an oxygen plasma cleaner (Nordson Asymtek) for 5 min, using 100 W power, 240 mTorr pressure and 440 sccm oxygen flow rate. The cleaned beads were treated in a vacuum reactor with (11-azidoundecyl)trimethoxy silane (300 microliters) in a foil boat in the bottom of the vacuum reactor in the presence of magnesium sulfate heptahydrate (0.5 g, Acros Cat. #10034-99-8), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a covalently modified surface to the beads, where the modified surface had an azide functionalized structure of Formula I:

Formula I

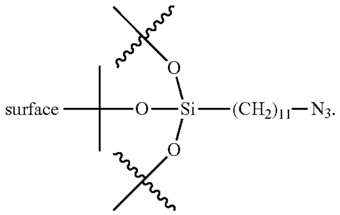

After cooling to room temperature and introducing argon to the evacuated chamber, the covalently modified beads were removed from the reactor. The beads having a covalently modified surface functionalized with azide reactive moieties were rinsed with acetone, isopropanol, and dried under a stream of nitrogen. The covalently modified azide functionalized beads were dispersed at a concentration of 1 mg/20 microliters in a 5.7 mM DMSO solution of dibenzylcyclooctynyl (DBCO)S-S biotin modified-PEG3 (Broadpharm, Cat. #BP-22453) then incubated at 90° C./2000 RPM in a thermomixer for 18 hours. The biotin modified beads were washed three times each in excess DMSO, then rinsed with PBS. The biotin modified beads in PBS were dispersed in PBS solution containing approximately 30 micromoles/700 microliter concentration streptavidin. The reaction mixture was shaken at 30° C./2000 RPM in a thermomixer for 30 minutes. At the completion of the reaction period, the covalently modified beads presenting streptavidin were washed three times in excess PBS. FTIR analysis determined that SAV was added to the surface (Data not shown). The disulfide containing linker may be particularly useful if cleavage from the surface may be desirable. The disulfide linker is susceptible to cleavage with dithiothreitol at concentrations that were found to be compatible with T lymphocyte viability (Data not shown).

10B. Silica beads having covalent PEG4 biotin linked to streptavidin diluted with PEG5-carboxylic acid surface-blocking molecular ligands. Beads having a covalently modified surface functionalized with azide reactive moieties of Formula 1, prepared as above in Example 10A, were rinsed with acetone, isopropanol, and dried under a stream of nitrogen. The covalently modified azide functionalized beads were dispersed at a concentration of 1 mg/10 microliters in a DMSO solution of 0.6 mM dibenzylcyclooctynyl (DBCO)-modified-PEG4-biotin (Broadpharm, Cat. #BP-22295), 5.4 mM dibenzylcyclooctynyl (DBCO)-modified-PEG5-carboxylic acid (Broadpharm, Cat. #BP-22449), and 100 mM sodium iodide then incubated at 30° C./1,000 RPM in a thermomixer for 18 hours. The biotin modified beads were washed three times each in excess DMSO, then rinsed with PBS. The biotin modified beads in PBS were dispersed in PBS solution containing approximately 10 nanomoles/1 milliliter concentration streptavidin. The reaction mixture was shaken at 30° C./1000 RPM in a thermomixer for 30 minutes. At the completion of the reaction period, the covalently modified beads presenting streptavidin were washed three times in excess PBS. FTIR analysis determined that SAV was added to the surface (Data not shown).

Example 11. Preparation of an antigen presenting surface of a polymeric bead

Streptavidin functionalized (covalently coupled) convoluted spherical polymeric beads (e.g., the actual surface area of the bead is greater than the relationship surface area=4TTr2+/−no more than 10%, DynaBeads™ (ThermoFisher Catalog #11205D, bead stock at 6.67e8/mL)) were delivered (15 microliters; 1e7 beads) to a 1.5 mL microcentrifuge tube with 1 mL of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 ml of the Wash Buffer was repeated, and a further 200 microliters of Wash Buffer was added with subsequent pulse centrifugation. Supernatant Wash Buffer was removed.

Wash Buffer (600 microliters) containing 1.5 micrograms biotinylated Monomer MHC (HLA-A* 02:01 MART-1 (MBL International Corp., Catalog No. MR01008, ELAGIGILTV) was dispensed into the microcentrifuge tube, and the beads were resuspended by pipetting up and down. The monomer was allowed to bind for 30 min at 4° C. After 15 minutes, the mixture was pipetted up and down again. The tube was pulse centrifuged and the supernatant liquid removed, and the tube was placed within the magnetic rack to remove more supernatant without removing beads.

A solution of biotinylated anti-CD28 (Miltenyi Biotec, Catalog #130-100-144, 22.5 microliters) in 600 microliters Wash Buffer was added to the microcentrifuge tube. The beads were resuspended by pipetting up and down. The beads were incubated at 4° C. for 30 min, resuspending after 15 min with another up and down pipetting. At the end of the incubation period, the tube was briefly pulse centrifuged. After placing back into the magnetic rack, and allowing separation for 1 min, the Buffer solution was aspirated away from the functionalized beads. The MHC monomer/anti-CD28 antigen presenting beads were resuspended in 100 microliters Buffer Wash, stored at 4° C., and used without further manipulation. The 1e7 2.80 micron diameter functionalized DynaBeads have a nominal (ideal predicted surface area of a sphere) surface area of about 24e6 square microns available for contact with T lymphocyte cells. However, the convolutions of this class of polymeric bead which are not necessarily accessible by T lymphocyte cells, are also functionalized in this method. Total ligand count may not reflect what is available to contact and activate T lymphocyte cells.

The MHC monomer/anti-CD28 antigen presenting beads were characterized by staining with Alexa Fluor 488-conjugated Rabbit anti Mouse IgG (H+L) Cross-adsorbed secondary antibody (Invitrogen Catalog #A-11059) and APC-conjugated anti-HLA-$A_2$ antibody (Biolegend Catalog #343307), and characterized by flow cytometry.

Example 12. Activation of CD8+T lymphocytes by antigen presenting beads compared to activation CD8+T lymphocytes by dendritic cells Cells: CD8+T lymphocytes were enriched in a medium including RPMI plus 10% fetal bovine serum (FBS) from commercially available PBMCs following manufacturer's directions for EasySep™ Human CD8 Positive Selection Kit II, commercially available kit from StemCell Technologies Canada Inc. (Catalog #17953), by negative selection.

Dendritic cells: were generated from autologous PBMCs. Autologous PBMCs (10-50 e6) were thawed into 10 ml of pre-warmed RPMI media including 10% FBS. Cells were pelleted by centrifuging for 5 mins at 400 xg. Cells were resuspended in RPMI and counted.

The cells were enriched for monocytes using negative bead isolation (EasySep™ Human Monocyte Isolation Kit, StemCell Technologies, Catalog #19359), according to manufacturer's instructions. The resulting monocytes were counted, providing about a 5% yield, and then plated at 1.5-3 e6 cells per 3 mL per well in AIM-V® Medium (ThermoFisher Catalog #12055091) containing 17 ng/ml IL-4 and 53 ng/ml Human Granulocyte Macrophage Colony-Stimulating Fact (GM-CSF, ThermoFisher Catalog #PHC2013). The cells were incubated for a total of 6 days at 37° C. At Day 2 and Day 4, 100 microliters of feeding media (AIM-V® Medium plus IL-4 (167 U/mL) and GM-CSF (540 ng/mL)) was added to each well, and incubation was continued.

On Day 6, 0.5 mL of a maturation cocktail was added to each well. The maturation cocktail included 10 ng/ml TNF-alpha; 2 ng/ml IL-1B; 1000 U/mL IL-6, 1000 ng/ml PGE2; 167 U/mL IL-4 and 267 U/mL GM-CSF in AIM-V® Medium. The cells were incubated for a further 24 h at 37° C. Mature DCs were then collected from the maturation medium, counted, and prepared for further use. The DCs were characterized by staining for CD3 (BD Catalog #344828), DC-SIGN (CD209, Biolegend Catalog #330104), CD14 (Biolegend Catalog #325608), CD86 (BD Catalog #560359), Fc Block (BioLegend Catalog #422302), and viability (BD Catalog #565388); suspended in FACS buffer; and examined by FACS flow cytometry.

Dendritic cells presenting antigen were prepared by plating at a concentration of 2e6/mL in 1% HSA, and pulsing with antigen (MART1 peptide, Anaspec, custom synthesis, 40 micrograms/mL) and beta2-microglobulin (Sigma Aldrich Catalog #M4890, 3 micrograms/mL), and then culturing with agitation for 4 h. The pulsed DCs were irradiated in a Faxitron CellRad® x-ray cell irradiator for 30 min before use, with a target dose of 50 greys.

Culture medium and diluent for reagent additions: Advanced RPMI (ThermoFisher Catalog #12633020, 500 mL); 1× GlutaMAX (ThermoFisher Catalog #35050079, 5 mL); 10% Human AB serum (zen-bio, Catalog #HSER-ABP 100 mL, 50 mL); and 50 nM beta-mercaptoethanol (ThermoFisher Catalog #31350010, 50 nm stock, 0.5 mL, final conc 50 micromolar).

Experimental Setup: For each activating species, a single 96-well tissue-culture treated plate (VWR Catalog #10062-902) was used (wellplate 1 (DCs); wellplate 2 (Antigen presenting beads). CD8+T lymphocytes (2e5) (80-90% pure) were added to each individual well.

Pulsed DCs were added at 5e3 for each well in wellplate 1, yield a 1:40 ratio of DCs: CD8+T lymphocytes.

Antigen presenting surface polymeric beads (2e5), prepared as in Example 11, presenting pMHC including MART1 and anti-CD28 antibody, were added to each of the wells in wellplate 2. pMHC was loaded at 1.5 micrograms/1e7 beads. Anti-CD 28 antibody was loaded on the beads at three different levels: 0.25 micrograms/1e7 beads; 0.75 micrograms/1e7 beads; and 2.25 micrograms/1e7 beads.

Each wellplate was cultured at 37° C. On day 0, IL-21 (150 ng/milliliter) in CTL media, was added to each well of wellplates 1 and 2, providing a final concentration in each well of 30 ng/ml. On day 2, IL21 was added to each well of the wellplates, to a final concentration of 30 ng/mL. Culturing was continued to day 7.

Figure 10:
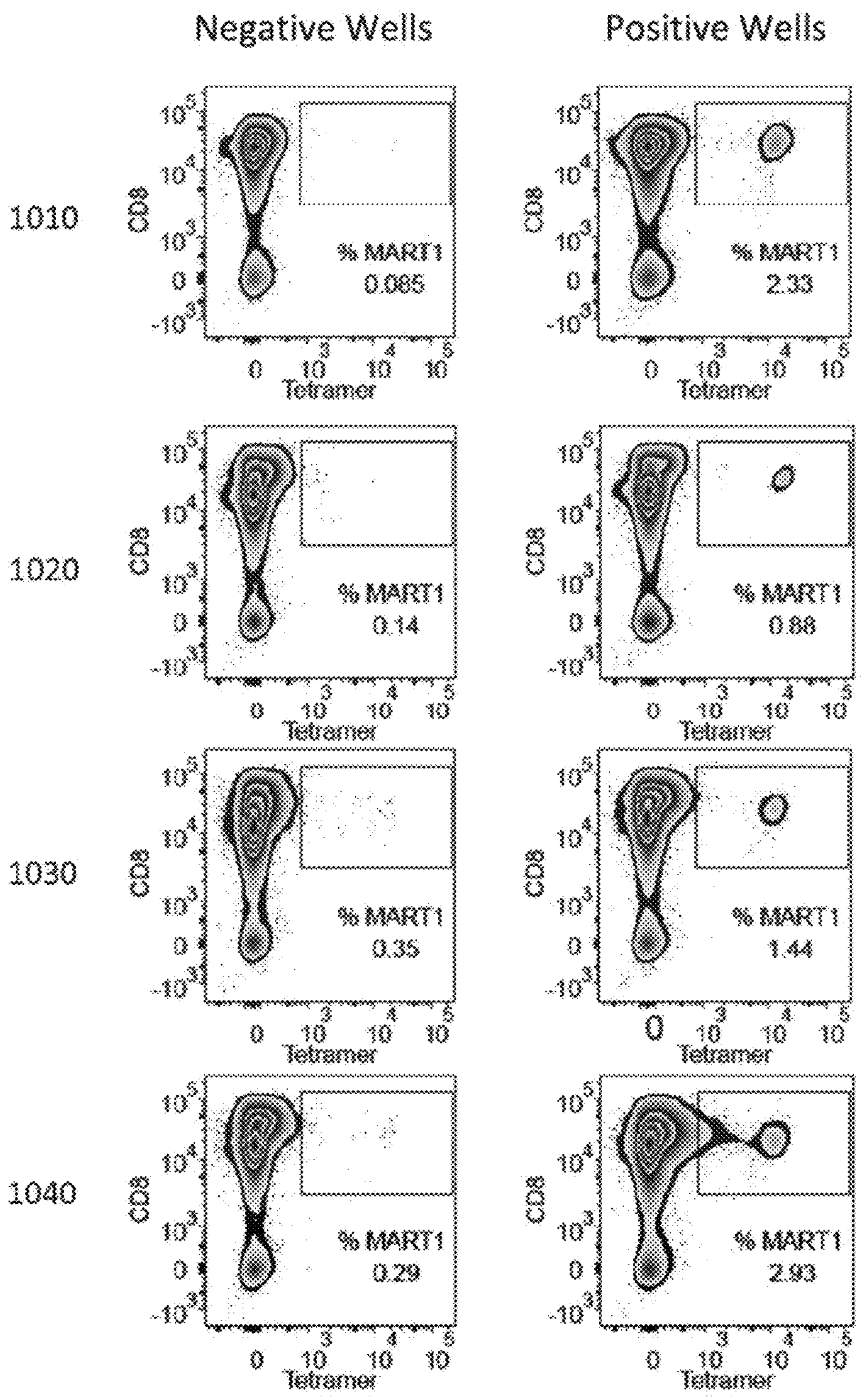
FIG. 10 is a graphical representation of the distribution of activated T lymphocytes after a first period of stimulation and culturing, comparing the use of antigen-presenting bead activation to dendritic cell activation, according to one embodiment of the disclosure.

Day 7. A subset of wells from each wellplate was individually stained for MHC tetramer (Tetramer PE, MBL Catalog #T02000, 1microliter/well), CD4 (Biolegend Catalog #300530, 0.5 microliters/well); CD8 (Biolegend Catalog #301048, 0.5 microliters/well); CD28 (Biolegend Catalog #302906, 0.31 microliters/well); CD45RO (Biolegend Catalog #304210, 0.63 microliters/well); CCR7 (CD197, Biolegend Catalog #353208, 0.5 microliters/well); and viability (BD Catalog #565388, 0.125 microliters/well). Each well was resuspended with 150 microliters FACS buffer and 10 microliters of Countbright™ beads (ThermoFisher Catalog #C36950). FACS analysis was performed on a FACSCelesta™ flow cytometer (BD Biosciences). FIG. 10 shows the zebra plots for the flow cytometry analyses for CD8/MART1 phenotypes. For each row of zebra plots, 1010, 1020, 1030, and 1040, the left hand plot is a representative negative well, and the right hand plot is a representative positive well. Row 1010 are wells from the DC stimulated well plate. Rows 1020, 1030, and 1040 show results from the antigen-presenting bead stimulated well plate. Row 1020 shows the results for 0.25 micrograms/1e7 beads of anti-CD28 antibody loading and 1.5 micrograms//1e7 beads of pMHC. Row 1030 shows the results for 0.75 micrograms/1e7 beads anti CD28 antibody loading and 1.5 micrograms/1e7 beads of pMHC. Row 1040 shows the results for 2.25 micrograms/1e7 beads anti CD28 antibody loading and 1.5 micrograms/1e7 beads of pMHC. It can be seen that the antigen presenting beads initiate activation in a dose/responsive manner when varying the levels of anti-CD28 antibody, and that the MHC peptides loaded with MART1 are sufficient in combination with the anti-CD28 loading to activate T lymphocytes similarly to that of DCs.

Day 7. Restimulation. A second aliquot of pulsed DCs or antigen presenting beads, respectively, was delivered to each occupied well in wellplate 1 and wellplate 2. IL21 was added to each well of the wellplate to a final concentration of 30 ng/mL. Culturing was continued.

Day 8. Addition of 50 microliters of IL-2 (50 IU/mL) and IL-7 (25 ng/ml) was made to each well in wellplate 1 and wellplate 2 to provide a final concentration of 10 IU/mL and 5 ng/ml respectively. Culturing was continued.

Day 9. Addition of 50 microliters of IL-21 (150 ng/ml) was made to each occupied well of wellplate 1 and wellplate 2 to a final concentration of 30 ng/ml. Culturing was continued.

Figure 11:
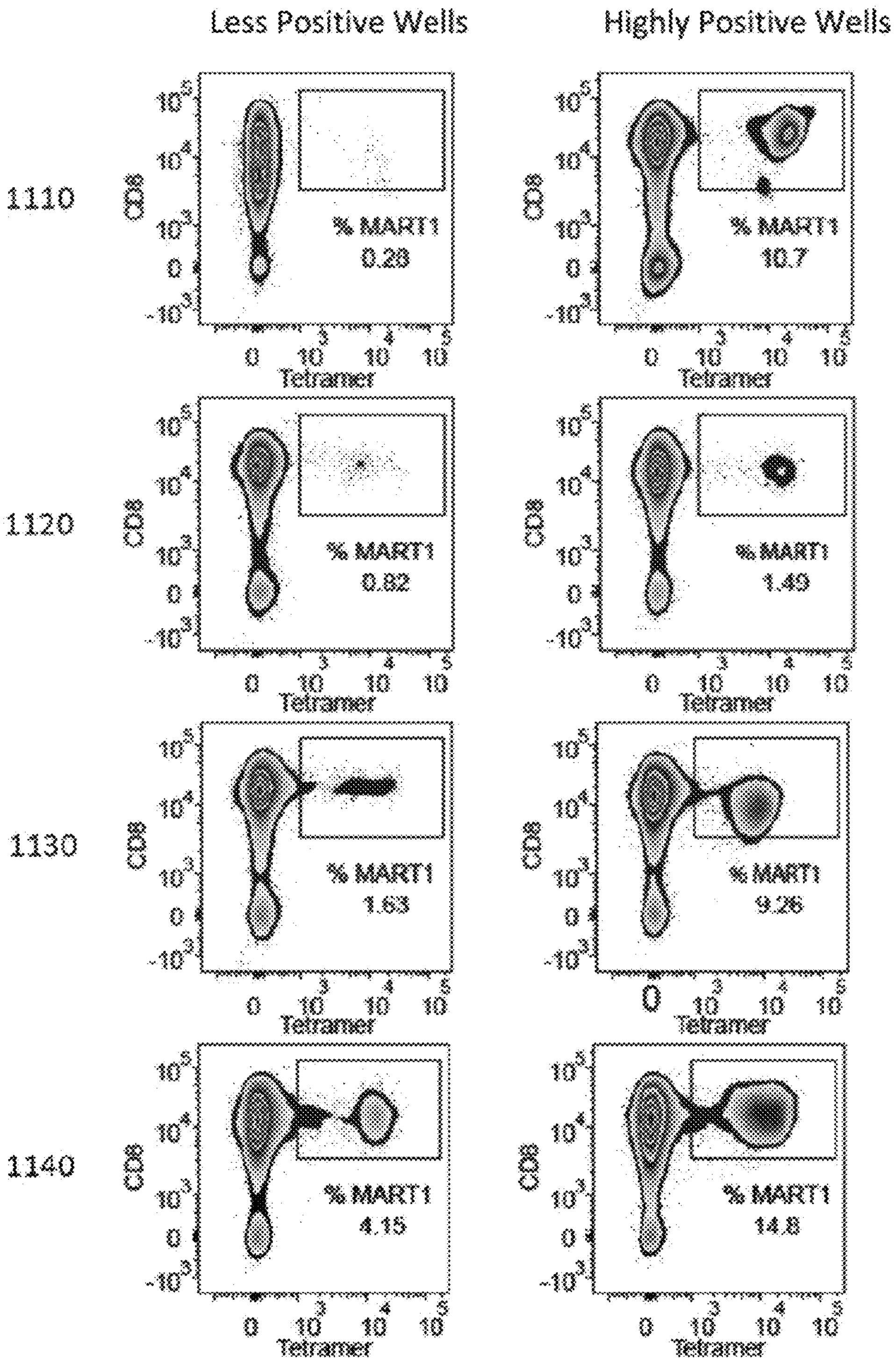
FIG. 11 is a graphical representation of the distribution of activated T lymphocytes after a second period of stimulation and culturing, comparing the use of antigen-presenting bead activation to dendritic cell activation, according to one embodiment of the disclosure.

Day 14. A second subset of wells from each wellplate was individually stained and FACS sorted as described for the analysis on Day 7. The flow cytometry results are shown in FIG. 11. For each row 1110, 1120, 1130, 1140 has a representative Less Positive Well (left hand graph of each row) and a Highly Positive Well (right hand graph of each row). Row 1110 shows the amount of activation resulting from DC activation. Rows 1120, 1130, and 1140 represent results for the increasing amounts of anti-CD 28 as discussed for the 7 day results. Row 1120 shows the results for 0.25 micrograms/1e7 beads of anti-CD28 antibody loading and 1.5 micrograms/1e7 beads of pMHC. Row 1130 shows the results for 0.75 micrograms/1e7 beads anti CD28 antibody loading and 1.5 micrograms/1e7 beads of pMHC. Row 1140 shows the results for 2.25 micrograms/1e7 beads anti CD28 antibody loading and 1.5 micrograms/1e7 beads of pMHC. It is notable that for antigen-presenting beads having increasing amounts of costimulatory ligands, there are no wells having no antigen specific T cells. Particularly at the 0.75 microgram and 2.25 microgram CD28 antibody loading levels (Rows 1130 and 1140), there are more significant numbers of antigen specific T cells than for the DC pulsed wells (Row 1110).

Figure 12:
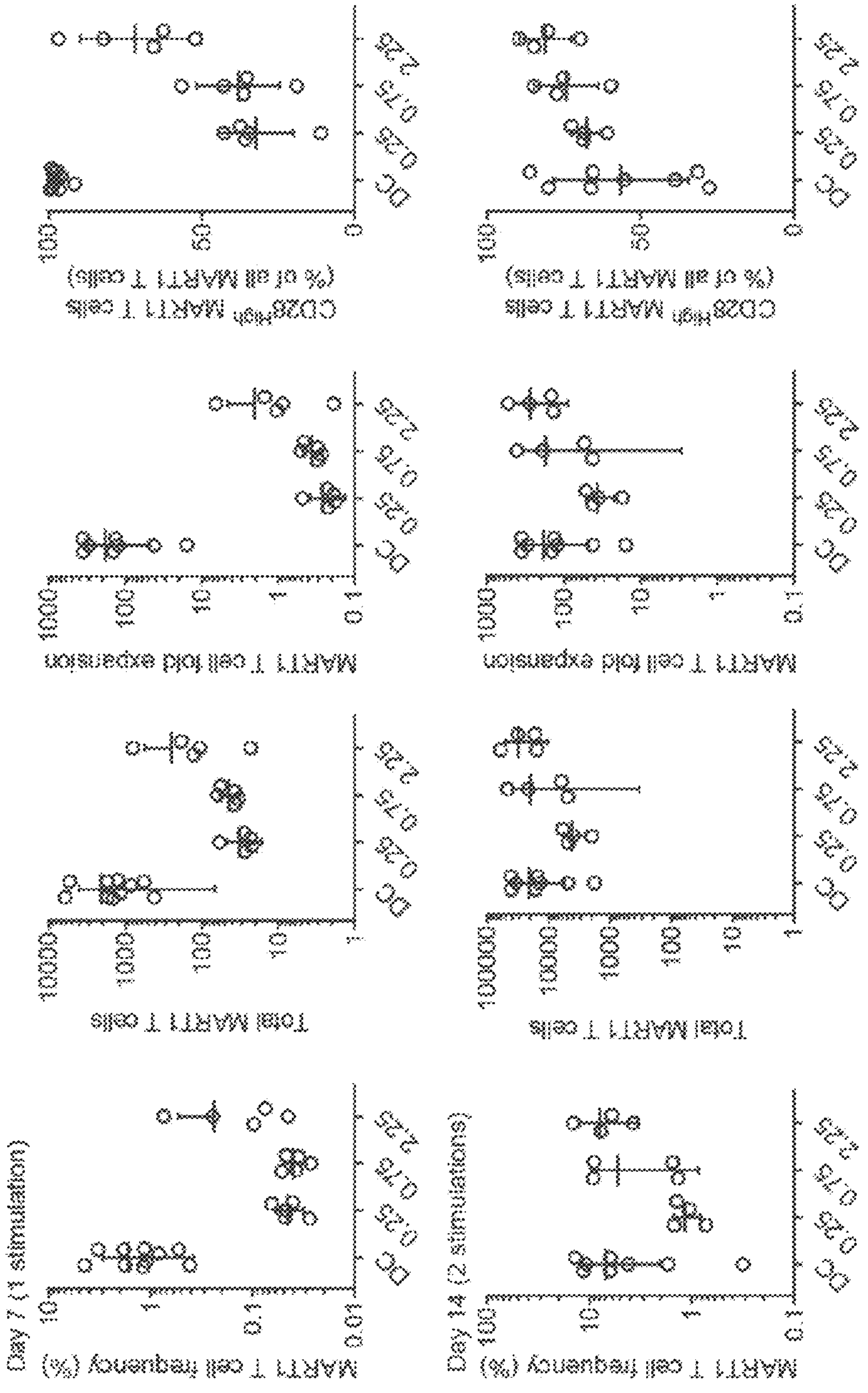
FIG. 12 is a graphical representation of various characterization parameters for activation of T lymphocytes at 7 and 14 days, compared to dendritic cell activation.

FIG. 12 shows tabularized results from these experiments. Row 1210 shows graphical representations of T cell activation characterization at Day 7. Row 1220 shows graphical representation of T cell activation characterization at Day 14. From left to right in each row, the y axis represents percentage of antigen specific T cells; total number of antigen specific T cells; antigen specific T cell fold expansion; and % of CD28 highly expressing cells within the antigen-specific T cell population. The x-axis for each graph shows the data set of each of DC, 0.25 microgram CD28 loaded beads, 0.75 microgram CD28 beads, and 2.25 microgram CD28 loaded beads. The antigen presenting bead stimulated activation appears to be initially slower than DC stimulation but production reached the same level by the end of the second culturing period. The phenotypic results show a good specificity of activation using the antigen presenting beads. FIG. 12 shows equivalent levels of MART 1 activated T lymphocytes in the antigen presenting bead initiated examples compared to the DC stimulated examples. However, using dendritic cells as activating species, there are wells that have no activated T lymphocytes after 14 days. Therefore, antigen-presenting bead activation provides more controllable and reproducible activation than dendritic cells.

Third period of culturing. In another experiment, where antigen presenting surfaces on beads were used as described in the immediately preceding paragraphs, but where comparison was not made with DCs, a third period of stimulation and culturing was performed. Day 14 to Day 21. Restimulation and feeding was performed as above for Day 7-Day 14, during continuation of culture conditions until Day 21. On Day 21, a last subset of wells from each wellplate was individually stained and FACS sorted as described for the analysis on Day 7. Additional activation was observed for the extended third stimulation sequence (Data not shown).

Example 13. Preparation of covalently functionalized glass beads

Silica beads (2.5 micron, G biosciences Catalog #786-915, having a substantially simple spherical surface, e.g. the surface area of the bead is within the range predicted by the relationship 4TTr2+/−no more than 10%) were dispersed in isopropanol, and then dried. The dried beads were treated in an oxygen plasma cleaner (Nordson Asymtek) for 5 min, using 100 W power, 240 mTorr pressure and 440 sccm oxygen flow rate. The cleaned beads were treated in a vacuum reactor with (11-azidoundecyl)trimethoxy silane (300 microliters) in a foil boat in the bottom of the vacuum reactor in the presence of magnesium sulfate heptahydrate (0.5 g, Acros Cat. #10034-99-8), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a covalently linked surface presenting reactive azide moieties to the beads, where the modified surface has a structure of Formula I.

After cooling to room temperature and introducing argon to the evacuated chamber, the intermediate reactive azide presenting beads were removed from the reactor and were rinsed with acetone, isopropanol, and dried under a stream of nitrogen. The azide presenting reactive beads (50 mg) were dispersed in 500 microliters DMSO with vigorous vortexing/brief sonication. The beads were pelleted, and 450 microliters of the DMSO were aspirated away from the beads. The pellet, in the remaining 50 microliters DMSO was vortexed vigorously to disperse. DBCO-SAV (52 microliters of 10 micromolar concentration, Compound 1) as synthesized in Example 3, having a PEG13 linker, was added. The beads were dispersed by tip mixing, followed by vortexing. 398 microliters of PBS with 0.02% sodium azide solution was added, followed by additional vortexing. The reaction mixture was incubated overnight on a thermomixer at 30° C., 1000 RPM.

After 16 hrs, 10 microliters of 83.7 mM DBCO-PEG5-acid were added to each sample and they were incubated an additional 30 minutes at 30° C./1,000 RPM. The beads were washed 3X in PBS/azide, then suspended in 500 microliters of the same.

These covalently functionalized beads are modified to introduce primary activating molecules and co-activating molecules as described below in Example 18.

Example 14. Preparation of Covalently Functionalized Polystyrene Bead

Divinylbenzene-crosslinked polystyrene beads (14-20 micron, Cospheric Catalog #786-915) were dispersed in isopropanol, and then dried in a glass petri dish. The dried beads were treated in an oxygen plasma cleaner (Nordson Asymtek) for 40 seconds, using 100 W power, 240 mTorr pressure and 440 sccm oxygen flow rate. The cleaned beads were treated in a vacuum oven with (11-azidoundecyl) trimethoxy silane (Compound 5, 900 microliters) in a foil boat on the shelf of the oven in the presence of magnesium sulfate heptahydrate (1 g, Acros Cat. #10034-99-8), as a water reactant source in a separate foil boat on the same shelf of the oven. The oven was then pumped to 250 mTorr using a vacuum pump and then sealed. The oven was heated at 110° C. for 18-24 h. This introduced a covalently modified surface to the beads, where the modified surface had a structure of Formula I:

Formula I

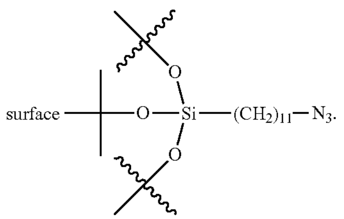

After pump-purging the oven three times, the covalently modified beads were removed from the oven and cooled. The covalently modified azide functionalized beads were dispersed at a concentration 15 mg/50 microliters in DMSO. To this, a 450 microliter solution of DBCO-labeled streptavidin (SAV) (Compound 1) at a concentration of 9.9 micromolar were added. The solution was then incubated at 30° C./1000 RPM in a thermomixer for 18 hours. The SAV modified beads were washed three times in PBS. FTIR analysis determined that SAV was added to the surface as shown in FIG. 13.

Figure 13:
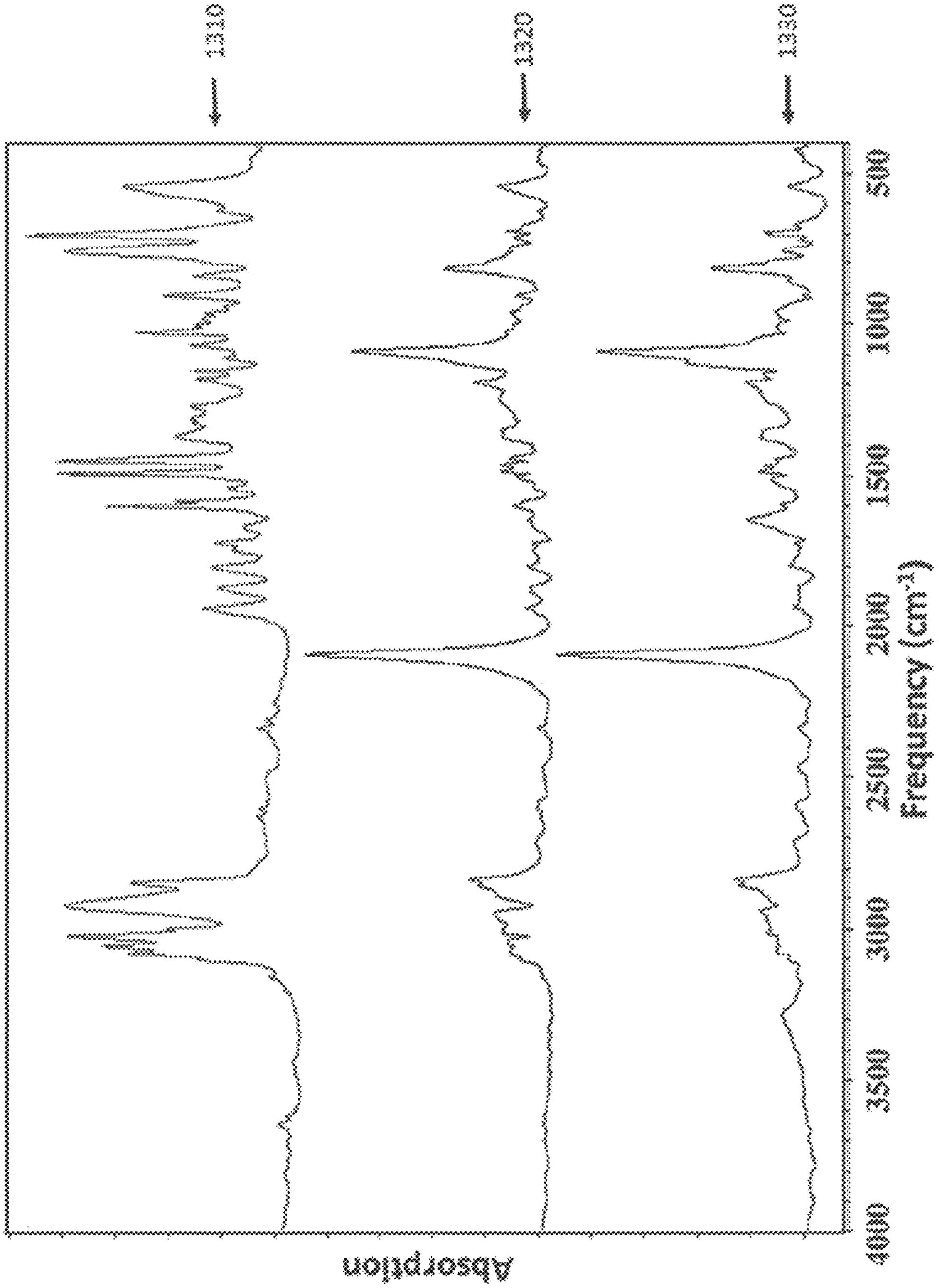
FIG. 13 is a graphical representation of Fourier Transform Infrared spectra of a covalently functionalized polystyrene bead at selected steps of the functionalization.

FIG. 13 shows superimposed FTIR traces of the functionalized bead as the covalently functionalized surface is built up. Trace 1310 showed the original unfunctionalized surface of the polystyrene bead. Trace 1320 showed the FTIR of the surface after introduction of the azide functionalized surface (having a structure of Formula I). Trace 1330 showed the FTIR of the surface after introduction of covalently linked PEG13-streptavidin surface to the polystyrene bead. Traces 1320 and 1330 showed introduction of FTIR absorption bands consistent with the introduction of each set of chemical species in the stepwise synthesis.

Example 15. Preparation of an antigen presenting surface of a bead with anti-CD28 and anti-CD2

Streptavidin functionalized (covalently coupled) DynaBeads™ (ThermoFisher Catalog #11205D), bead stock at 6.67e8/mL, convoluted (as described above) polymeric beads) were delivered (15 microliters; 1e7 beads) to 1.5 ml microcentrifuges tube with 1 ml of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 mL of the Wash Buffer was repeated, and a further 200 microliters of Wash Buffer was added with subsequent pulse centrifugation. Supernatant Wash Buffer was removed.

Wash Buffer (600 microliters) containing 0.5 micrograms biotinylated Monomer MHC (HLA-A* 02:01 MART-1

(MBL International Corp., Catalog No. MR01008, ELA-GIGILTV) was dispensed into the microcentrifuge tubes, and the beads were resuspended by pipetting up and down. The monomer was allowed to bind for 30 min at 4° C. After 15 minutes, the mixtures were pipetted up and down again. The tubes were pulse-centrifuged and the supernatant liquid removed, and the tubes were placed within the magnetic rack to remove more supernatant without removing beads.

Solutions of biotinylated anti-CD28 (Biolegend, Catalog #302904) and biotinylated anti-CD2 (Biolegend, Catalog #300204) in 600 microliters Wash Buffer were added to the microcentrifuge tubes. Solutions contained a total of 3 micrograms of antibody. The solutions contained: 3 micrograms of anti-CD28 and 0 micrograms of anti-CD2, 2.25 micrograms of anti-CD28 and 0.75 micrograms of anti-CD2, 1.5 micrograms of anti-CD28 and 1.5 micrograms of anti-CD2, 0.75 micrograms of anti-CD28 and 2.25 micrograms of anti-CD2, or 0 micrograms of anti-CD28 and 3 micrograms of anti-CD2. The beads were resuspended by pipetting up and down. The beads were incubated at 4° C. for 30 min, then resuspended after 15 min with another up and down pipetting. At the end of the incubation period, the tube was briefly pulse centrifuged. After placing back into the magnetic rack, and allowing separation for 1 min, the Buffer solution was aspirated away from the functionalized beads. The MHC monomer/anti CD28 antigen presenting beads were resuspended in 100 microliters Buffer Wash, stored at 4° C., and used without further manipulation. The 1e7 2.80 micron diameter functionalized DynaBeads have a nominal surface area of about 24e6 square microns available for contact with T lymphocyte cells, but as described above, these convoluted spherical beads have a practical surface area of more than 10% above that of the nominal surface area.

Example 16. Preparation of Covalently Functionalized Polymeric Beads. Preparation of an Intermediate Reactive Synthetic Surface In the first step of the manufacturing process, M-450 Epoxy-functionalized paramagnetic convoluted polymeric beads (DynaBeads™, ThermoFisher Cat. #14011 (convoluted having the same meaning as above) were reacted with Tetrabutylammonium Azide to prepare polymeric beads presenting azide reactive moieties capable of reacting with functionalizing reagents having Click chemistry compatible reactive groups.

Example 17. Preparation of a covalently functionalized synthetic surface of a bead The azide-prepared convoluted beads from Example 16 were then reacted with dibenzocyclooctynyl (DBCO)-coupled Streptavidin to attach Streptavidin covalently to the polymeric beads. The DBCO-Streptavidin reagent was generated by reacting Streptavidin with amine-reactive DBCO-polyethylene glycol (PEG) 13-NHS Ester, providing more than one attachment site per Streptavidin unit.

Further reaction with surface-blocking molecules. The resulting covalently functionalized polymeric beads presenting streptavidin functionalities from Example 17 may subsequently be treated with DBCO functionalized surface-blocking molecules to react with any remaining azide reactive moieties on the polymeric bead. In some instances, the DBCO functionalized surface-blocking molecule may include a PEG molecule. In some instances, the DBCO PEG molecule may be a DBCO PEG5-carboxylic acid. Streptavidin functionalized polymeric beads including additional PEG or PEG-carboxylic acid surface-blocking molecules provide superior physical behavior, demonstrating improved dispersal in aqueous environment. Additionally, the surface-blocking of remaining azide moieties prevents other unrelated/undesired components present in this or following preparation steps or activation steps from also covalently binding to the polymerio bead. Finally, introduction of the surface-blocking molecular ligands can prevent surface molecules present on the T lymphocytes from contacting reactive azide functionalities.

Further generalization. It may be desirable to modify the azide functionalized surface of Example 16 with a mixture of DBCO containing ligand molecules. For example, DBCO-polyethylene glycol (PEG) 13-streptavidin (Compound 1, prepared as in Example 3) may be mixed with DBCO-PEG5-COOH (surface-blocking molecules) in various ratios, and then placed in contact with the azide functionalized beads. In some instances, the ratio of DBCO-streptavidin molecules to DBCO-PEG5-COOH may be about 1:9; about 1:6, about 1:4 or about 1:3. Without wishing to be bound by theory, surface-blocking molecular ligands prevent excessive loading of streptavidin molecules to the surface of the bead, and further provide enhanced physico-chemical behavior by providing additional hydrophilicity. The surface-blocking molecules are not limited to PEG5-COOH but may be any suitable surface-blocking molecule described herein.

Example 18. Preparation of Covalently Modified Antigen Presenting Bead. Conjugation of Peptide-HLAs and Monoclonal Antibody Co-Activating Molecules Materials: A. Antigen bearing major histocompatibility complex (MHC) I molecule. Biotinylated peptide-Human Leukocyte Antigen complexes (pMHC), were commercially available from MBL, Immunitrack or Biolegend. The biotinylated peptide-HLA complex included an antigenic peptide non-covalently bound to the peptide-binding groove of a Class I HLA molecule, which was produced and folded into the HLA complex at the manufacturer. The biotinylated peptide-HLA complex was also non-covalently bound to Beta2-Microglobulin. This complex was covalently biotinylated at the side chain amine of a lysine residue introduced by the BirA enzyme at a recognized location on the C-terminal peptide sequence of the HLA, also performed by the manufacturer.

B. Co-activating molecules. Biotinylated antibodies were used for costimulation and were produced from the supernatants of murine hybridoma cultures. The antibodies were conjugated to biotin through multiple amine functionalities of the side chains of lysines, randomly available at the surfaces of the antibodies. The biotinylated antibodies were commercially available (Biolegend, Miltenyi, or Thermo Fisher).

Biotinylated anti-CD28 useful in these experiments were produced from clone CD28.2, 15e8, or 9.3.

Biotinylated anti-CD2 useful in these experiments were produced from clone LT2 or RPA-2.10. Other clones may also be used in construction of covalently modified antigen presenting synthetic surfaces such as these polymeric beads.

Conjugation of the primary activating and co-activating molecules to a covalently functionalized surface of a bead. The MHC molecule (containing the antigenic molecule) and the co-activating molecules were conjugated to beads produced in a two-step process. In various experiments, the ratio of the co-activating molecules—in this case, biotinylated anti-CD28 and biotinylated anti-CD2-may be varied in a range from about 100:1 to about 1:100; or from about 20:1 to about 1:20. In other experiments, the ratio of the co-activating molecules was from about 3:1 to about 1:3 or about 1:1. See FIGS. 14A-D.

pMHC loading. Streptavidin functionalized (covalently coupled) DynaBeads™ (ThermoFisher Catalog #11205D), bead stock at 6.67e8/mL, convoluted (as described above) polymeric beads) were washed with Wash Buffer (Dulbecco's Phosphate-Buffered Saline without Calcium or Magnesium; 0.1% Bovine Serum Albumin; 2 mM Ethylenediaminetetraacetic Acid). Wash buffer was pipetted into a tube, to which the Streptavidin beads were added. Typically, ~1e7 beads were pipetted into 1 mL of Wash Buffer. The beads were collected against the wall of the tube using a magnet (e.g., DYNAL DynaMag-2, ThermoFisher Cat. #12-321-D). After the beads migrated to the wall of the tube, the Wash Buffer was removed via aspiration, avoiding the wall to which the beads were held. This wash process was repeated twice more. After the third wash, the beads were resuspended at 1.67e7 beads/mL in Wash Buffer.

The beads were then mixed with pMHC. The pMHC was added to the beads in Wash Buffer at a final concentration of 0.83 micrograms of pMHC/mL. The beads and pMHC were thoroughly mixed by vortexing, then incubated at 4° C. for 15 minutes. The beads were again vortexed, then incubated at 4° C. for an additional 15 minutes.

Co-activating molecule loading. The pMHC-functionalized beads were again captured via magnet, and the pMHC reagent mixture removed by aspiration. The beads were then brought to 1.67e7/mL in Wash Buffer. Biotinylated Anti-CD28 and biotinylated anti-CD2 (if used) were then added to the beads at a final concentration of 5 micrograms/ml of total antibody. If both anti-CD28 and anti-CD2 were used, then each antibody was added at 2.5 micrograms/mL.

The beads and pMHC were thoroughly mixed by vortexing, then incubated at 4° C. for 15 minutes. The beads are again vortexed, then incubated at 4° C. for an additional 15 minutes.

After modification by the biotinylated antibodies, the beads were captured via magnet, and the antibody mixture was removed by aspiration. The beads were resuspended in Wash Buffer at a final density of 1e8 beads/mL. The beads were used directly, without further washing.

Characterization. To assess the degree of loading and homogeneity of the resulting antigen-presenting beads, the beads were stained with antibodies that bind the pMHC and co-activating CD28/CD2 (if present) antibodies on the beads. The resulting amount of staining antibody was then quantified by flow cytometry. The number of pMHC and costimulatory antibodies on the beads was then determined using a molecular quantification kit (Quantum Simply Cellular, Bangs Labs) according to the manufacturer's instructions.

To analyze the beads, 2e5 beads were added to each of two microcentrifuge tubes with 1 mL of Wash Buffer. The pMHC quantification, and costimulation antibody quantification were performed in separate tubes. In each separate experiment, the beads were collected against the wall of the tube using a magnet, and the Wash Buffer removed. The beads were resuspended in the respective tubes in 0.1 mL of Wash Buffer, and each tube was briefly vortexed to separate the beads from the wall of the tube. To detect pMHC, 0.5 microliters of anti-HLA-A conjugated to APC (Clone BB7.2, Biolegend) was added to the first tube. The first tube was again vortexed briefly to mix the beads and detection antibody. To detect the costimulation antibodies, 0.5 microliters of anti-mouse IgG conjugated to APC was added to the second tube. Depending on the costimulation antibody clones used, different anti-mouse antibodies were used, e.g., RMG1-1 (Biolegend) is used to detect CD28.2 (anti-CD28) and RPA-2.10 (anti-CD2). The detection antibodies were incubated with the beads for 30 minutes in the dark at room temperature for each tube.

For each tube, the beads were then captured against the wall of the tube via magnet, and the staining solution was removed by aspiration. 1 mL of Wash Buffer was added to each tube, then aspirated to remove any residual staining antibody. The beads in each tube were resuspended in 0.2 mL of Wash Buffer and then the beads from each tube was transferred to a 5 mL Polystyrene tube, keeping the two sets of beads separate.

To quantify the loading of the different species, the beads were analyzed on a flow cytometer (FACS Aria or FACS Celesta, BD Biosciences). First, a sample of unstained product antigen-bearing beads is collected. A gate is drawn around the singlet and doublet beads. Doublet beads are discriminated from singlet beads based on their higher forward and side scatter amplitudes. Typically, approximately 10,000 bead events were recorded. The beads stained for pMHC and costimulation antibodies are then analyzed in separate experiments. Again, approximately 10,000 bead events were collected for each sample, and the APC median fluorescence intensity (MFI) and coefficient of variation of the APC MFI (100* [Standard Deviation of the MFI]/[MFI]) of the singlet bead events was recorded.

To determine the number of pMHC and costimulation antibodies per bead, a molecular quantification kit is used. The kit (Quantum Simply Cellular (Bangs Laboratories) included a set of beads with specified antibody binding capacities (determined by the manufacturer). These beads are used to capture the detection antibody. Briefly, the quantification beads are incubated with saturating amounts of the detection binding, then washed thoroughly to remove excess antibody. The beads with different binding capacities are mixed, along with negative control beads and resuspended in Wash Buffer. The mixed beads are then analyzed by Flow Cytometry. The APC MFI of each bead with specified binding capacity is recorded, and a linear fit of the MFI vs binding capacity is generated. The MFI of the aAPCs is then used to determine the number of detection antibodies bound per aAPC. This number is equal to the number of (pMHC or costimulation) antibodies on the bead. The following table shows results for:

A. Antigen-presenting convoluted polymeric beads produced in Examples 16-17 and functionalized above in this experiment.

B. Antigen-presenting substantially spherical silica beads as produced in Example 10B

| Condition | Labeling | Ligands/ Bead | Ligands/ sq um | Target antibodies (ug)/mg beads |
|---|---|---|---|---|
| A. Polymeric bead | HLA | 487209 | 19781 | 8.1 |
| A. Polymeric bead | Costim | 426992 | 17336 | 7.1 |
| B. 4 micron monodisperse silica (10B) | HLA | 604471 | 12026 | 2.35 |

-continued

| Condition | Labeling | Ligands/ Bead | Ligands/ sq um | Target antibodies (ug)/mg beads |
|---|---|---|---|---|
| B. 4 micron monodisperse silica (10B) | Costim | 760489 | 15129 | 2.96 |

Example 19. Stimulation by Antigen-Presenting Beads

Input cell populations. To increase the number of antigen-specific, CD8+ T cells plated per well, CD8+ T cells were first isolated from Peripheral Blood Mononuclear Cells using commercially available reagents. The cells can be isolated using negative selection, e.g., EasySep™ Human CD8+T Cell Isolation Kit (StemCell Technologies) or by positive selection, e.g., CliniMACS CD8 Reagent (Miltenyi Biotec). The CD8+ T cells were isolated according to the manufacturers recommended protocol. Alternatively, different subsets of T cells can be isolated, e.g., Naïve CD8+ T cells only, or a less-stringent purification can be performed, e.g., depletion of Monocytes by CliniMACS CD14 Reagent (Miltenyi Biotec). Alternatively, if T cells specific for a Class II-restricted antigen are desired, CD4+ T cells can be isolated by corresponding methods.

First T cell stimulation period. The enriched CD8+ T cells were resuspended at 1e6/mL in media with IL-21 at 30 nanograms/mL (R&D Systems). The media used for T cells was Advanced RPMI 1640 Medium (Thermo Fisher) supplemented with 10% Human AB Serum (Corning Cell-Gro) plus GlutaMax (Thermo Fisher) and 50 micromolar Beta-MercaptoEthanol (Thermo Fisher) or ImmunoCult™-XF T Cell Expansion Medium (StemCell Technologies).

Antigen-presenting beads were prepared as described in Example 18, where the convoluted polymeric beads were loaded at a final concentration of 0.83 micrograms of pMHC/mL. The resulting lot of beads was split into five portions, loading the costimulating ligands in the following proportions:

- Set 1: CD28 at 3.00 micrograms/mL and CD2 at zero concentration.
- Set 2: CD28 at 2.25 micrograms/mL and CD2 at 0.75 micrograms/mL.
- Set 3: CD28 at 1.50 micrograms/mL and CD2 at 2.25 micrograms/mL.
- Set 4: CD28 at 0.75 micrograms/mL and CD2 at 2.25 micrograms/mL.
- Set 5: CD28 at 0.00 micrograms/mL and CD2 at 3.00 micrograms/mL.

To the T cells in media, an aliquot of each set of antigen-presenting beads were added to separate wells to a final concentration of 1 antigen-presenting bead per cell. The cells and antigen-presenting beads were mixed and seeded into tissue culture-treated, round-bottom, 96-well microplates. 0.2 mL (2e5 cells) was added to each well of the plate, which was then placed in a standard 5% $CO_2$, 37° C. incubator. Typically, 48-96 wells were used per plate. Two days later, IL-21 was diluted to 150 nanograms/mL in media. 50 microliters of IL-21 diluted in media was added to each well, and the plate was returned to the incubator.

After culturing the cells for an additional 5 days (seven days total), the cells were analyzed for antigen-specific T cell expansion. Alternatively, the cells were-stimulated in a second stimulation period as described in the following paragraphs to continue expanding antigen specific T cells.

Second T cell stimulation period. From each well of the above well plate at the conclusion of the first stimulation period, 50 microliters of media were removed, being careful not to disturb the cell pellet at the bottom of the well. IL-21 was diluted to 150 ng/ml in fresh media, and the antigen-presenting beads as produced above were added to the IL-21/media mixture at a final density of 4e6 antigen-presenting beads/mL. 50 microliters of this IL-21/antigen-presenting bead/media mixture was added to each well, resulting in an additional 2e5 antigen-presenting beads being added to each well. Optionally, the wellplate can be centrifuged for 5 minutes at 400 xg to pellet the antigen-presenting beads onto the cells. The wellplate was returned to the incubator.

The next day (8 days from start of stimulation experiments), the wellplate was removed from the incubator, and 50 microliters of media was removed from each well. IL-2 (R&D Systems) was diluted into fresh media to 50 Units/mL. To this, media containing IL-2, IL-7 (R&D Systems) was added to a final concentration of 25 ng/ml. 50 microliters of this IL-2/IL-7/media mixture was added to each well, and the wellplate was returned to the incubator.

The following day (9 days from start of stimulation experiments), the wellplate was removed from the incubator, and 50 microliters of media was again removed from each well. IL-21 was diluted into fresh media to 150 nanograms/mL. 50 microliters of this IL-21/media mixture was added to each well, and the wellplate was returned to the incubator.

After culturing the cells for an additional 5 days (14 days from the start of stimulation experiments), the cells were typically analyzed for antigen-specific T cell expansion. However, the cells can be re-stimulated with more antigen-presenting beads for another period of culturing as above to continue expanding antigen specific T cells.

Analysis of antigen-specific T cell stimulation and expansion. Once the desired number of T cell stimulations were performed, the cells were analyzed for expansion of T cells specific for the pMHC complex used to prepare the antigen-presenting beads. Antigen-specific T cells are detected using Phycoerythrin (PE) conjugated Streptavidin, which is bound to 4 pMHC complexes. These complexes are referred to as tetramers. Typically, a tetramer manufactured with the same peptide used in the pMHC of the antigen-presenting beads was used to detect the antigen-specific T cells.

To detect and characterize the antigen-specific T cells, a mixture of PE-tetramer (MBL, Intl) and antibodies specific for various cell surface markers with various fluorophores, e.g., FITC-conjugated anti-CD28, PerCP-Cy5.5-conjugated anti-CD8, was prepared in FACS Buffer (Dulbecco's Phosphate-Buffered Saline without Calcium or Magnesium; 2% Fetal Bovine Serum; 5 mM Ethylenediaminetetraacetic Acid, 10 mM HEPES). The amount of antibody used was determined by titration against standard cell samples. The surface markers typically used for characterization used are: CD4, CD8, CD28, CD45RO, CD127 and CD197. Additionally, a Live/Dead cell discrimination dye, e.g., Zombie Near-IR (Biolegend) and Fc Receptor blocking reagent, e.g., Human TruStain FcX™ (Biolegend) were added to distinguish live cells and prevent non-specific antibody staining of any Fc-Receptor expressing cells in the culture, respectively.

Typically, the wells were mixed using a multi-channel micro-pipettor, and 50 microliters of cells from each well were transferred to a fresh, non-treated, round-bottom, 96-well microplate. The cells were washed by addition of 0.2 mL of FACS buffer to each well. Cells were centrifuged at 400×g for 5 minutes at room temperature, and the wash removed. To each well, 25 microliters of the Tetramer, Antibody, Live/Dead, Fc blocking reagent mixture was added. The cells were stained for 30 minutes under foil at room temperature. The cells were then washed again, and finally resuspended in FACS Buffer with CountBright Absolute Counting Beads (Thermo Fisher). The cells were then analyzed by Flow Cytometry (FACS Aria or FACS Celesta, BD Biosciences). The frequency of antigen-specific T cells was determined by gating first on Single/Live cells, then gating on $CD8^+$/$Tetramer^+$ cells. Appropriate gating conditions were determined from control stains, such as a negative control Tetramer with no known specificity (MBL, Intl) or antibody isotype controls. Within the antigen-specific T cell population, the frequency of CD45RO+/$CD28^{High}$ cells was determined, as well as the number of cells expressing CD127. Activated T cells, which express CD45RO, that continue to express high levels of CD28 and CD127 have been shown to include memory precursor effector cells. Memory precursor cells have been shown to be less differentiated and have higher replicative potential than activated T cells that do not express these markers.

Figure 14B:
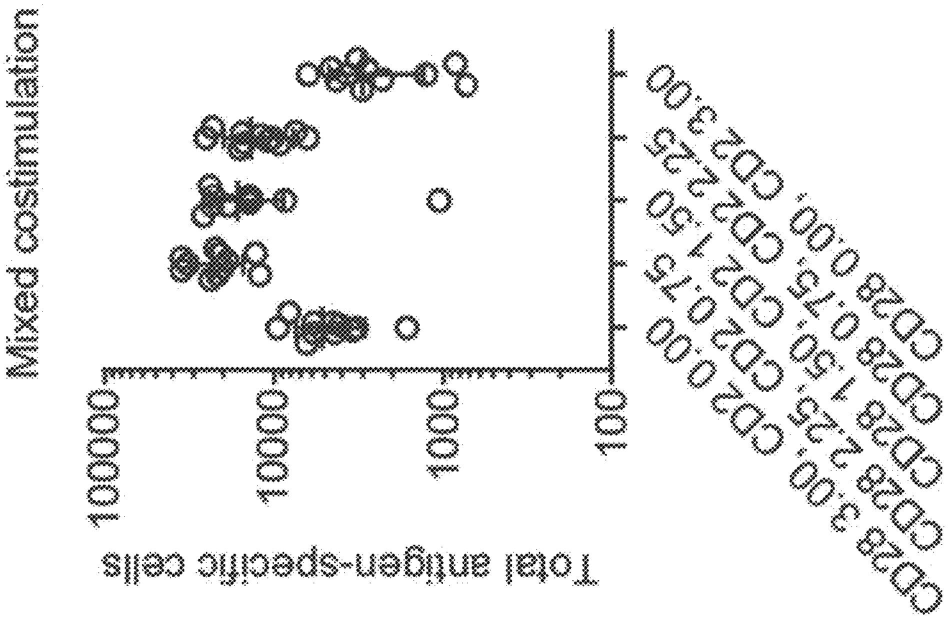
FIGS. 14A-14D are graphical representations of various characterization parameters for activation of T cells, according to an embodiment of the disclosure.
Figure 14A:
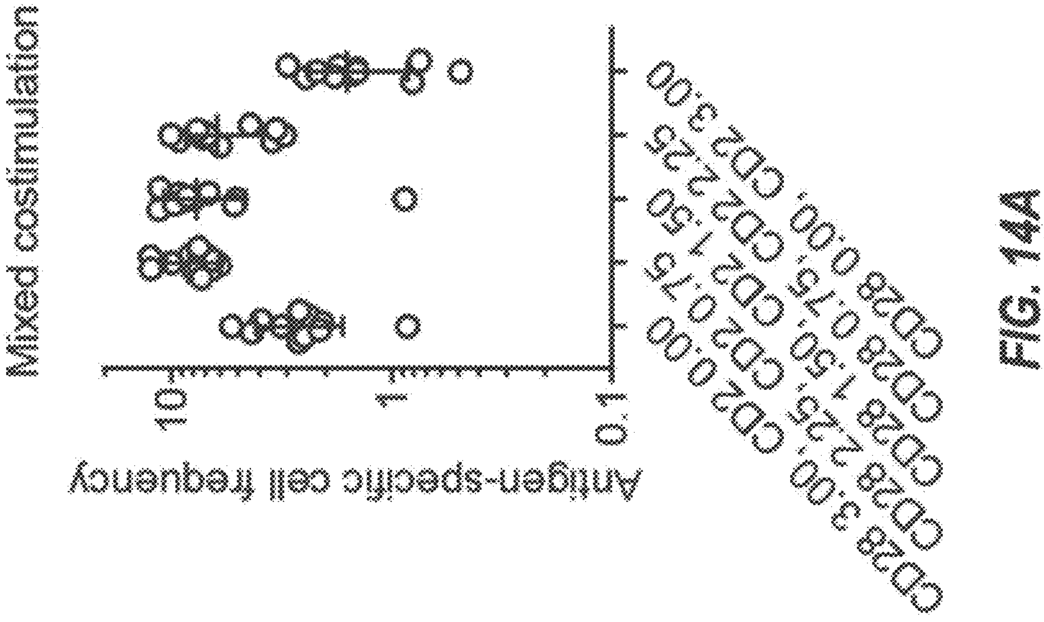

FIG. 14A: The frequency of MART1-specific T cells (percent of live cells) 7 days after stimulation with antigen-presenting beads prepared with the indicated amount (in micrograms) of anti-CD28 and/or anti-CD2. Each point represents a well of a 96-well microplate. Data is pooled from two independent experiments.

FIG. 14B: The total number of MART1-specific T cells 7 days after stimulation with antigen-presenting beads prepared with the indicated amount (in micrograms) of anti-CD28 and/or anti-CD2. Each point represents a well of a 96-well microplate. Data is pooled from two independent experiments.

Figure 14C:
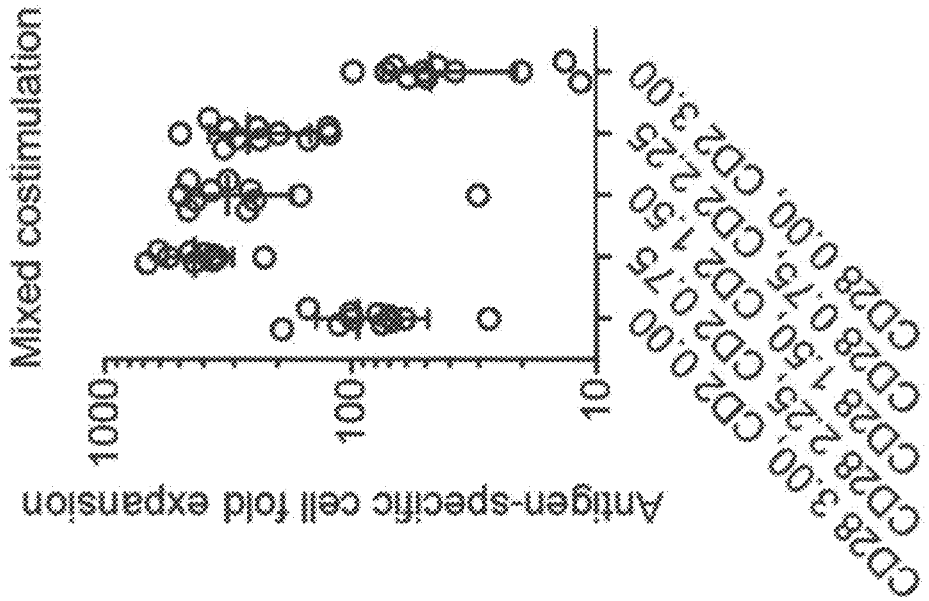

FIG. 14C: The fold expansion of MART1-specific T cells 7 days after stimulation with aAPCs prepared with the indicated amount (in micrograms) of anti-CD28 and/or anti-CD2. Each dot represents a well of a 96-well microplate. Data was pooled from two independent experiments. Fold expansion is calculated by dividing the frequency of MART1 T cells in each well at day 7 by the frequency of MART1 T cells in the sample at day 0.

Figure 14D:
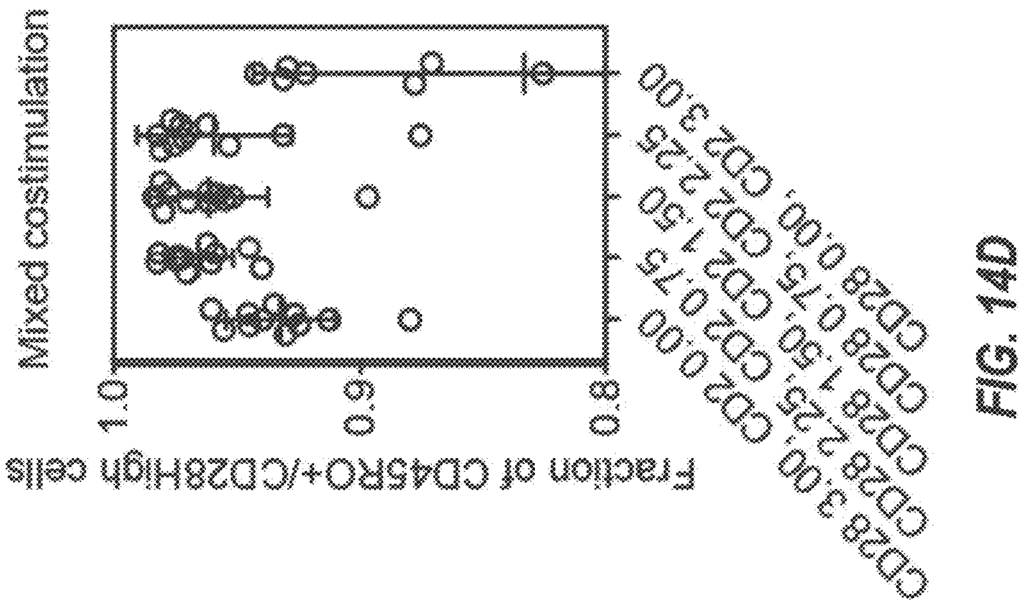

FIG. 14D: The fraction of MART1-specific T cells that were positive for CD45RO and expressing high levels of CD28 7 days after stimulation with aAPCs prepared with the indicated amount (in micrograms) of anti-CD28 and/or anti-CD2. Each dot represents a well of a 96-well microplate. Data was pooled from two independent experiments. Fold expansion is calculated by dividing the frequency of MART1 T cells in each well at day 7 by the frequency of MART1 T cells in the sample at day 0.

It was observed that production of antigen specific T cells was possible with a wide range of proportions of the costimulatory ligands anti-CD28 and anti-CD2. Production was possible using only one of the two costimulatory ligands. However, a combination of anti-CD28 and anti-CD2, including at ratios of anti-CD28: anti-CD2 from about 3:1 to about 1:3, provided increased measurements of each of the above characteristics.

Figures 15A, 15B, 15C, 15D, 15E:
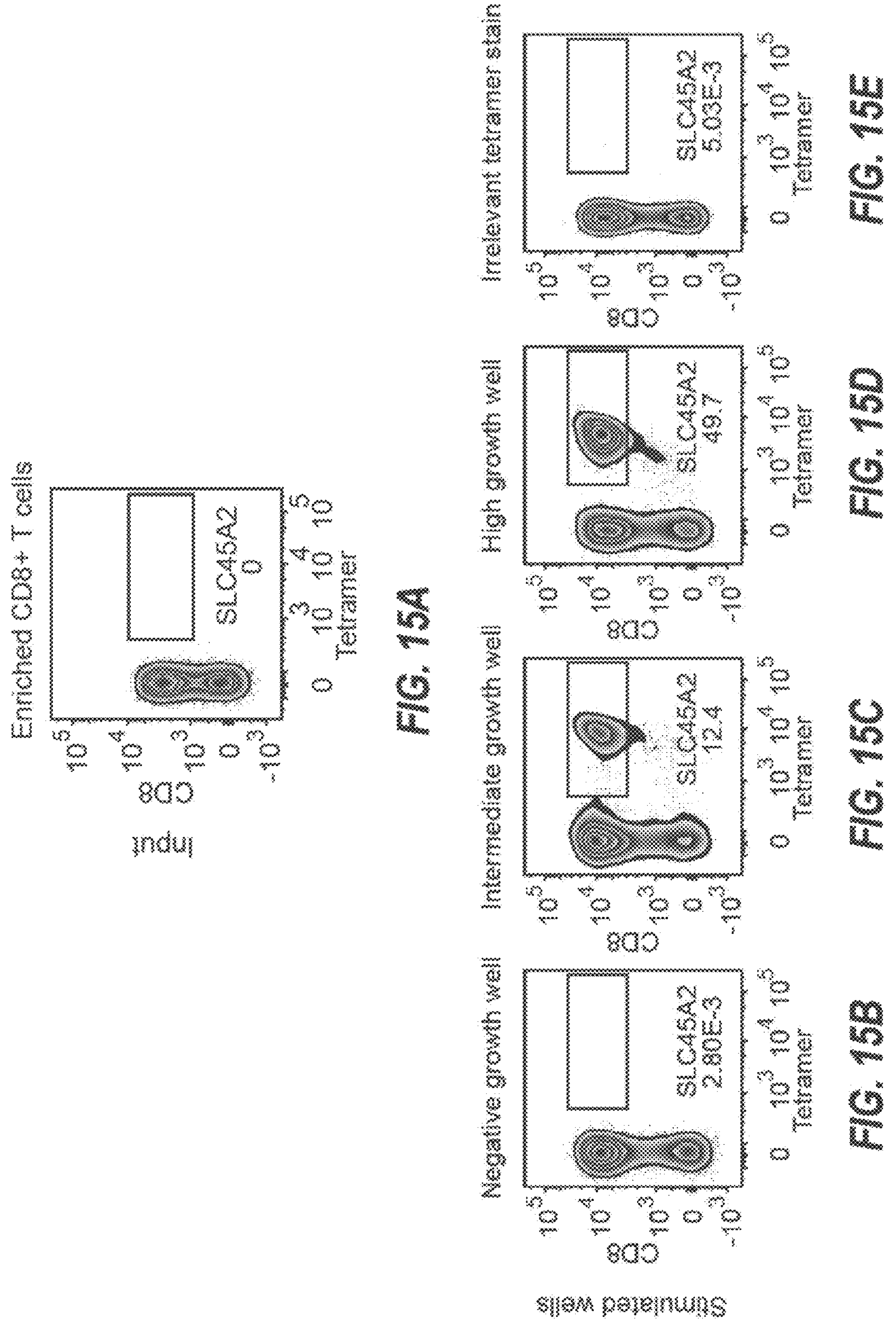
FIGS. 15A-15E are graphical representations of cell product characterization according to an embodiment of the disclosure.

FIGS. 15A-15E: For T cells stimulated as described above, using the SLC45A2 antigen in the antigen-presenting beads produced as described above, exemplary Flow Cytometry graphs are shown. FIG. 15A showed the results of T cells, prior to stimulation ("Input"). Representative stimulated wells are shown in the lower panels: Negative growth well (FIG. 15B); intermediate growth well (FIG. 15C); High growth well (FIG. 15D); and Irrelevant Tetramer staining (FIG. 15E).

Figure 16:
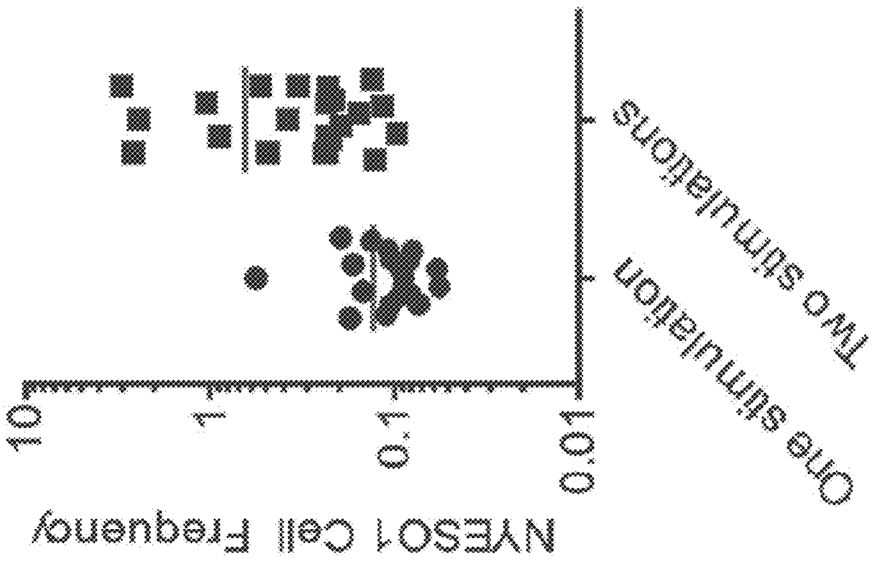
FIG. 16 is a graphical representation of cell product characterization according to an embodiment of the disclosure.

FIG. 16: For T cells stimulated as described above, using the NYESO1 antigen, the frequency of T cells positive for CD45RO and expressing high levels of CD28 are shown respectively after a single period of stimulation (7 days, left column) and after two periods of stimulation as described above (14 days, right column). Increased frequency of antigen specific activated T cells were observed.

Figure 17:
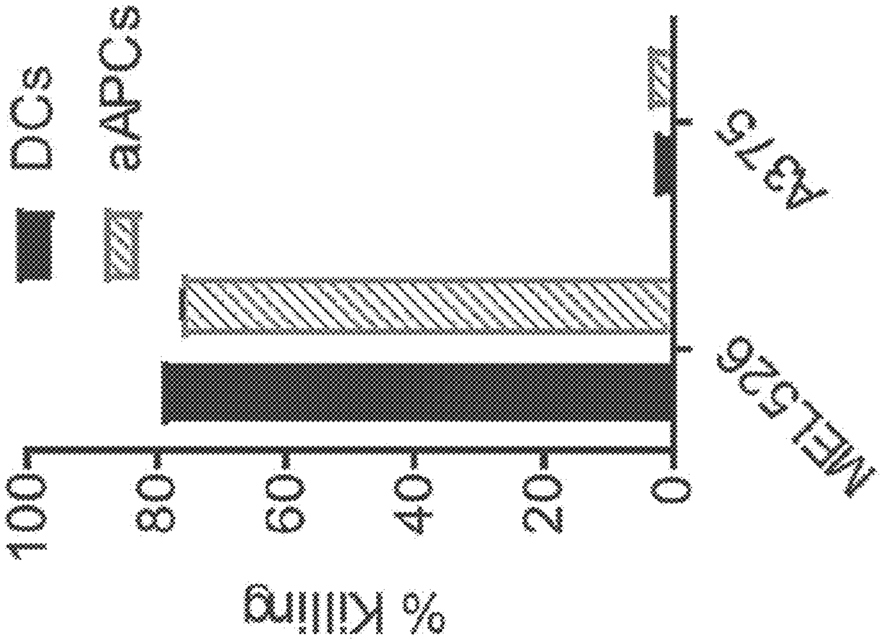
FIG. 17 is a graphical representation of cytotoxicity experiments according to one embodiment of the disclosure.

Cytotoxicity: Killing of target tumor cells and non-target tumor cells by SLC45A2-specific T cells expanded using Dendritic cells pulsed with SLC45A2 antigen (DCs, Black bars) or antigen-presenting beads (presenting SLC45A2 antigen) produced as described above (gray hatched bars). See FIG. 17. Killing was measured by activation of Caspase-3 in target cells. MEL526 tumor cells express SLC45A2 and were killed by T cells expanded using both DCs and the antigen-presenting beads. A375 cells do not express SLC45A2 and were not killed by T cells expanded using DCs or the antigen-presenting beads. The antigen-presenting beads performed as well as the Dendritic cells.

Figure 18C:
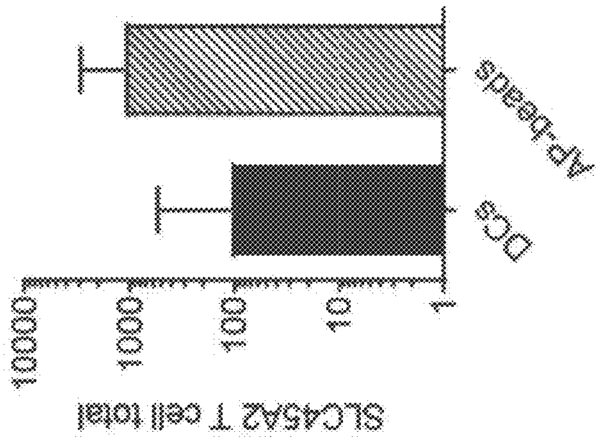
FIGS. 18A-18C are graphical representations of cell product characterization according to an embodiment of the disclosure.
Figure 18B:
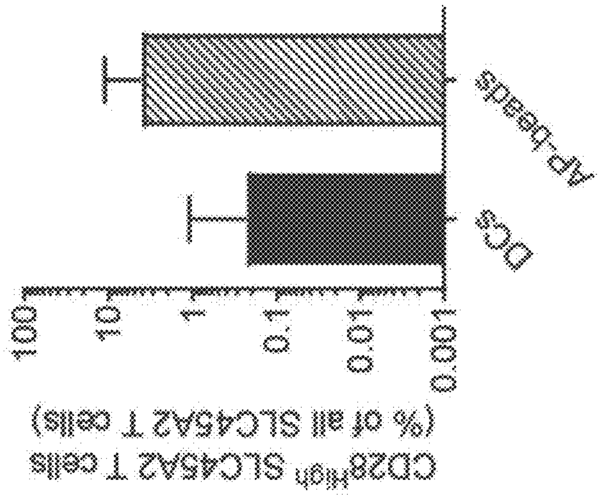
Figure 18A:
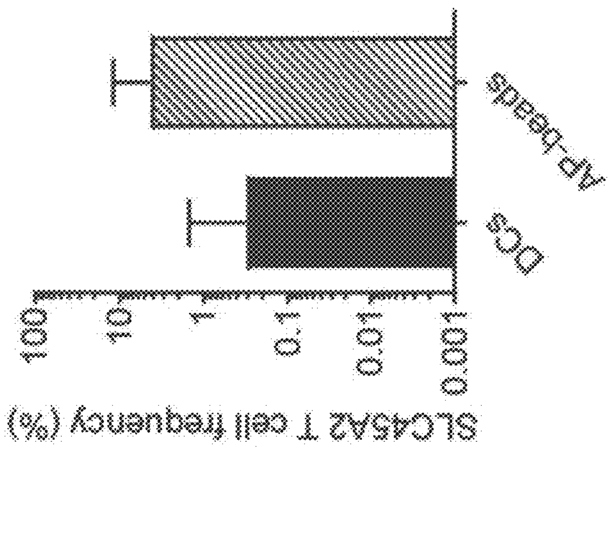

FIGS. 18A-18C show the comparison between the cell product of the dendritic cell stimulation and the antigen-presenting bead stimulated cell product. FIG. 18A showed that the percentage of Antigen Specific (AS) activated T cells is higher in the antigen-presenting bead stimulation experiment. FIG. 18B showed that the cell product of the antigen-presenting bead stimulation experiment has higher percentages of the desired CD45RO positive/highly CD28 positive phenotype, compared to that of the dendritic cell stimulated cell product. FIG. 18C showed that the actual numbers of antigen-specific T cells is higher in the cell product produced by the antigen-presenting bead stimulation experiment. Overall, antigen-presenting bead stimulation provides a more desirable cell product, and is a more controllable and cost effective method of activating T cells than the use of dendritic cell activation.

Example 20. Preparation of an Antigen-Presenting Bead Having Protein Fragment Co-Activating Ligands 20A. Preparation of an antigen presenting surface of a bead with lysine-biotinylated CD80 and CD58.

Streptavidin functionalized (covalently coupled, convoluted (as described above) polymeric) DynaBeads™ (ThermoFisher Catalog #11205D, bead stock at 6.67e8/mL) were delivered (15 microliters; 1e7 beads) to 1.5 mL microcentrifuges tube with 1 mL of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 mL of the Wash Buffer was repeated, and a further 200 microliters of Wash Buffer was added with subsequent pulse centrifugation. Supernatant Wash Buffer was removed.

Wash Buffer (600 microliters) containing 0.5 micrograms biotinylated Monomer MHC (HLA-A* 02:01 SLC45A2 (Biolegend, Custom Product, SLYSYFQKV) was dispensed into the microcentrifuge tubes, and the beads were resuspended by pipetting up and down. The monomer was allowed to bind for 30 min at 4° C. After 15 minutes, the mixtures were pipetted up and down again. The tubes were pulse centrifuged and the supernatant liquid removed, and the tubes were placed within the magnetic rack to remove more supernatant without removing beads.

A solution of biotinylated recombinant CD80 protein (R&D Systems, Custom Product) and biotinylated recombinant CD58 (R&D Systems, Custom Product) in 600 microliters Wash Buffer was added to the microcentrifuge tubes. The CD80 was prepared as an N-terminal fusion to a human IgG1 Fc domain and biotinylated on random Lysine residues by the manufacturer. The CD58 was biotinylated in the same manner. The solution contained a total of 4.5 micrograms of CD80 and 1.5 micrograms of CD58. The beads were resuspended by pipetting up and down. The beads were incubated at 4C for 30 min, resuspending after 15 min with another up and down pipetting. At the end of the incubation period, the tube was briefly pulse centrifuged. After placing back into the magnetic rack, and allowing separation for 1 min, the Buffer solution was aspirated away from the functionalized beads. The MHC monomer/CD80/CD58 antigen presenting beads were resuspended in 100 microliters Wash Buffer, stored at 4° C., and used without further manipulation. The 1e7 2.80 micron diameter functionalized DynaBeads have a nominal surface area of about 24e6 square microns available for contact with T lymphocyte cells, which, as described herein, does not reflect the total surface occupied by pMHC and costimulatory molecular ligands.

20B. Preparation of an antigen presenting surface of a bead with BirA biotinylated CD80 and CD58.

Streptavidin functionalized (covalently coupled, convoluted (as described above) polymeric) DynaBeads™ (ThermoFisher Catalog #11205D, bead stock at 6.67e8/mL) were delivered (15 microliters; 1e7 beads) to 1.5 mL microcentrifuges tube with 1 mL of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 mL of the Wash Buffer was repeated, and a further 200 microliters of Wash Buffer was added with subsequent pulse centrifugation. Supernatant Wash Buffer was removed.

Wash Buffer (600 microliters) containing 0.5 micrograms biotinylated Monomer MHC (HLA-A* 02:01 MART1 (Biolegend, Custom Product, ELAGIGILTV) was dispensed into the microcentrifuge tubes, and the beads were resuspended by pipetting up and down. The monomer was allowed to bind for 30 min at 4° C. After 15 minutes, the mixtures were pipetted up and down again. The tubes were pulse centrifuged and the supernatant liquid removed, and the tubes were placed within the magnetic rack to remove more supernatant without removing beads.

A solution of biotinylated recombinant CD80 protein (BPS Biosciences, Catalog Number 71114) and biotinylated recombinant CD58 (BPS Biosciences, Catalog Number 71269) in 600 microliters Wash Buffer was added to the microcentrifuge tubes. The recombinant proteins were prepared as N-terminal fusions to a human IgG1 Fc domain, with a final C-terminal BirA biotinylation site, and biotinylated by the manufacturer. The solution contained a total of 1.5 micrograms of recombinant CD80 and 1.5 micrograms of recombinant CD58 proteins. The beads were resuspended by pipetting up and down. The beads were incubated at 4° C. for 30 min, then resuspended after 15 min with another up and down pipetting. At the end of the incubation period, the tube was briefly pulse centrifuged. After placing back into the magnetic rack, and allowing separation for 1 min, the Buffer solution was aspirated away from the functionalized beads. The MHC monomer/CD80/CD58 antigen presenting beads were resuspended in 100 microliters Wash Buffer, stored at 4° C., and used without further manipulation. The 1e7 2.80 micron diameter functionalized DynaBeads have a nominal surface area of about 24e6 square microns available for contact with T lymphocyte cells, which, as described herein, does not reflect the total surface occupied by pMHC and costimulatory molecular ligands.

Example 21. Activation of CD8+ T Lymphocytes by Antigen Presenting Beads with Antibody Costimulation Compared to Recombinant Protein Costimulation Cells: CD8+ T lymphocytes were enriched in a medium including RPMI plus 10% fetal bovine serum (FBS) from commercially available PBMCs following manufacturer's directions for EasySep™ Human CD8+ T Cell Isolation Kit, commercially available kit from StemCell Technologies Canada Inc. (Catalog #17953), by negative selection.

Culture medium and diluent for reagent additions: Advanced RPMI (ThermoFisher Catalog #12633020, 500 mL); 1× GlutaMAX (ThermoFisher Catalog #35050079, 5 mL); 10% Human AB serum (zen-bio, Catalog #HSER-ABP 100 mL, 50 mL); and 50 nM beta-mercaptoethanol (ThermoFisher Catalog #31350010, 50 nm stock, 0.5 mL, final conc 50 micromolar).

Experimental Setup: For each activating species, a single 96-well tissue-culture treated plate (VWR Catalog #10062-902) was used:

Wellplate 1. Antigen presenting beads with antibody costimulation).

Wellplate 2. Antigen presenting beads with random biotinylated recombinant protein co-activation.

Wellplate 3. Antigen presenting beads with BirA biotinylated recombinant protein co-activation.

CD8+ T lymphocytes (2e5) (80-90% pure) were added to each individual well.

Antigen presenting surface beads (2e5), prepared by a similar preparation as described in Example 15, presenting pMHC including MART1, anti-CD28 antibody and anti-CD2 antibody, were added to each of the wells in wellplate 1. pMHC was loaded at 0.5 micrograms/1e7 beads. Anti-CD28 antibody was loaded at 1.5 micrograms/1e7 beads. Anti-CD2 antibody was loaded at 1.5 micrograms/1e7 beads.

Antigen presenting surface beads (2e5), prepared as in Example 20A, presenting pMHC including MART1, recombinant CD80 and recombinant CD58, were added to each of the wells in wellplate 2. pMHC was loaded at 0.5 micrograms/1e7 beads. Recombinant CD80 was loaded at 4.5 micrograms/1e7 beads. Recombinant CD58 was loaded at 1.5 micrograms/1e7 beads.

Antigen presenting surface beads (2e5), prepared as in Example 20B, presenting pMHC including MART1, BirA biotinylated recombinant CD80 and recombinant CD58, were added to each of the wells in wellplate 3. pMHC was loaded at 0.5 micrograms/1e7 beads. Recombinant CD80 was loaded at 1.5 micrograms/1e7 beads. Recombinant CD58 was loaded at 1.5 micrograms/1e7 beads.

Each wellplate was cultured at 37° C. On day 0, IL-21 (150 ng/milliliter) in CTL media, was added to each well of wellplates 1 and 2, providing a final concentration in each well of 30 ng/ml. On day 2, IL21 was added to each well of the wellplates, to a final concentration of 30 ng/ml. Culturing was continued to day 7.

Day 7. Restimulation. A second aliquot of antigen presenting beads with antibody costimulation or recombinant protein costimulation was delivered to each occupied well in wellplate 1, wellplate 2 and wellplate 3, respectively. IL21 was added to each well of the wellplate to a final concentration of 30 ng/ml. Culturing was continued.

Day 8. Addition of 50 microliters of IL-2 (50 IU/mL) and IL-7 (25 ng/ml) was made to each well in each wellplate to provide a final concentration of 10 IU/mL and 5 ng/ml respectively. Culturing was continued.

Day 9. Addition of 50 microliters of IL-21 (150 ng/ml) was made to each occupied well of each well plate to a final concentration of 30 ng/mL. Culturing was continued.

Day 14. The wells from each wellplate were individually stained for MHC tetramer (Tetramer PE, MBL Catalog #T02000, 1 microliter/well), CD4 (Biolegend Catalog #300530, 0.5 microliters/well); CD8 (Biolegend Catalog #301048, 0.5 microliters/well); CD28 (Biolegend Catalog #302906, 0.31 microliters/well); CD45RO (Biolegend Catalog #304210, 0.63 microliters/well); CCR7 (CD197, Biolegend Catalog #353208, 0.5 microliters/well); and viability (BD Catalog #565388, 0.125 microliters/well). Resuspend each well with 150 microliters FACS buffer and 10 microliters of Countbright™ beads (ThermoFisher Catalog #C36950). FACS analysis was performed on a FACSCelesta™ flow cytometer (BD Biosciences).

Figure 19A:
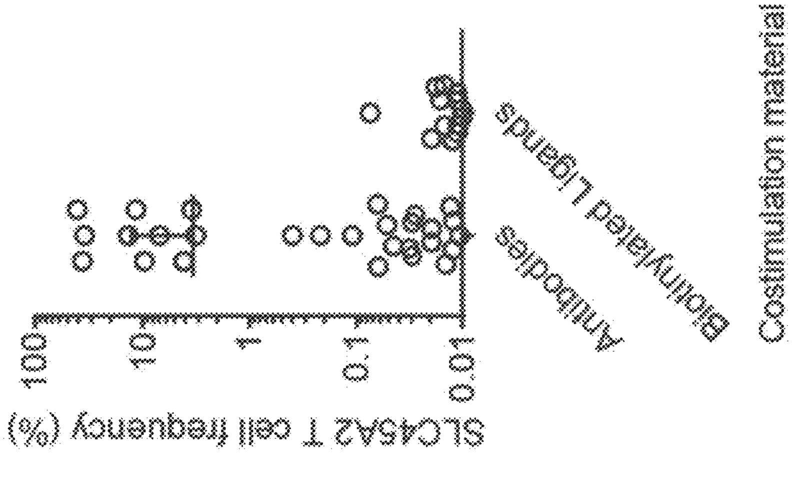
FIGS. 19A-19F are graphical representations of the characterization of activation using an antigen-presenting surface according to some embodiments of the disclosure.
Figure 19B:
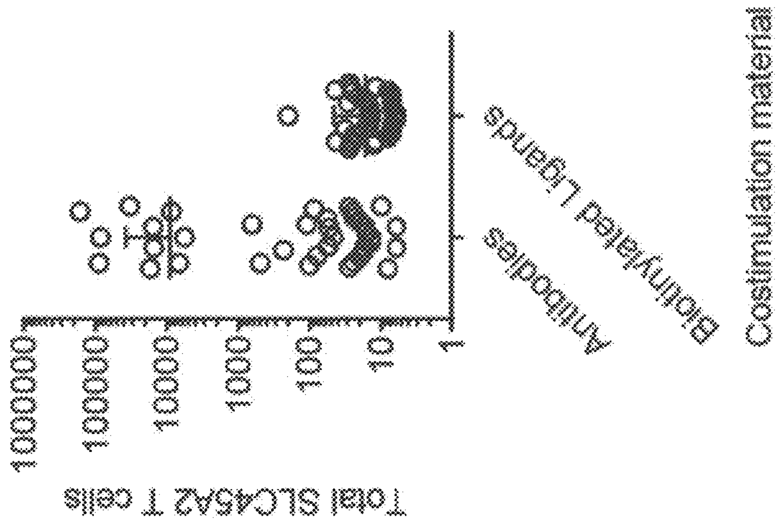
Figure 19C:
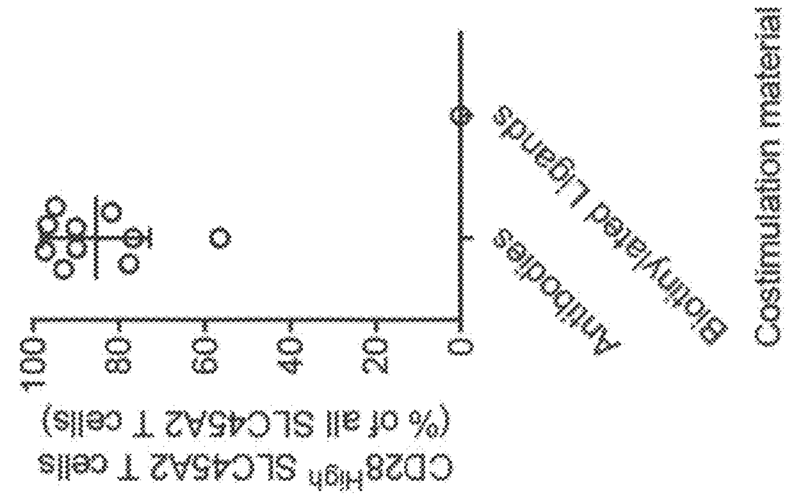

FIG. 19A shows the frequency of MART1-specific T cells (% of all live cells) in each well expanded using Antigen presenting beads with Antibodies or randomly biotinylated recombinant protein ligands. FIG. 19B shows the number of MART1-specific T cells in each well expanded using Antigen presenting beads with Antibodies or randomly biotinylated recombinant protein ligands. FIG. 19C shows the frequency of MART1 T cells that express high levels of CD28, an indicator of a memory precursor phenotype comparing antibody stimulation or randomly biotinylated recombinant protein ligands.

Figure 19F:
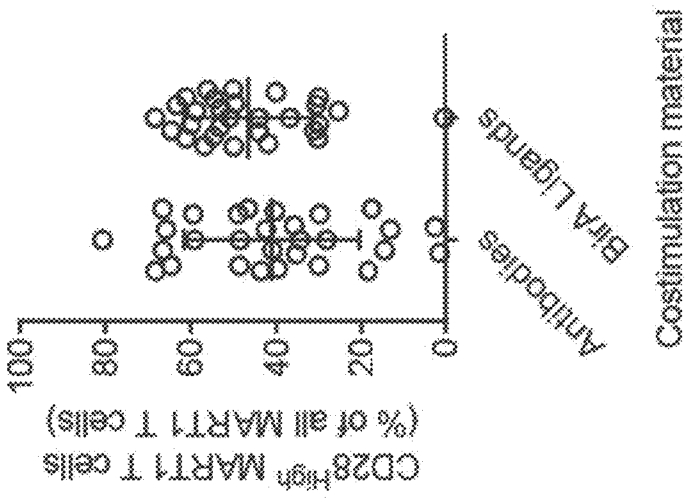
Figure 19E:
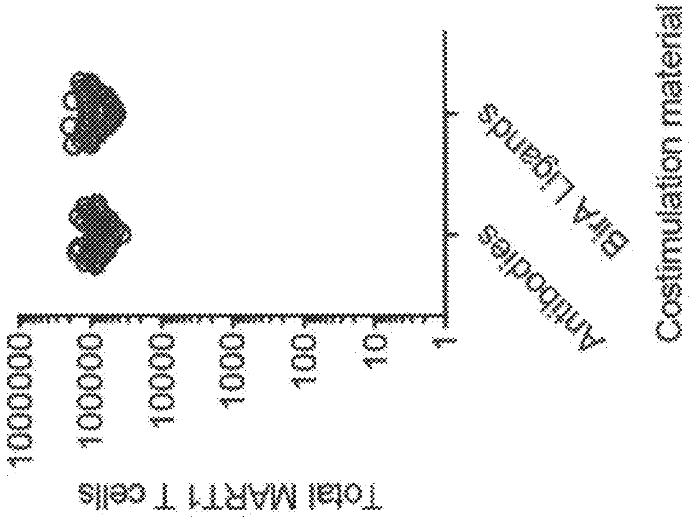
Figure 19D:
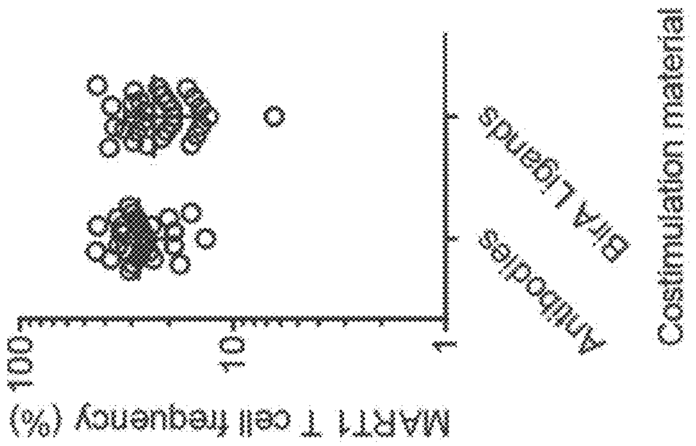

FIG. 19D shows the frequency of MART1-specific T cells (% of all live cells) in each well expanded using Antigen presenting beads with Antibodies or recombinant protein BirA ligands. FIG. 19E shows the number of MART1-specific T cells in each well expanded using Antigen presenting beads with Antibodies or recombinant protein BirA ligands. FIG. 19F shows the frequency of MART1 T cells that express high levels of CD28, an indicator of a memory precursor phenotype. It can be seen that the antigen presenting beads with recombinant protein ligands biotinylated by BirA effectively expand antigen-specific $CD8^+$ T cells and that many of the expanded cells take on a memory precursor phenotype. In contrast, use of randomly biotinylated protein ligands did not lead to significant populations of antigen specific T cells and also did not provide cells with a memory precursor phenotype.

Example 22. Comparison Between Loading of and Activation with Convoluted Polymeric Beads Vs. Substantially Spherical Silica Beads

Example 22A. Comparison of Activating Species Loading onto Polymer and Silica Antigen Presenting Beads Amounts of pMHC and costimulation antibodies that could be deposited onto Polymer and Silica beads was measured. Streptavidin functionalized (covalently coupled) DynaBeads™ (ThermoFisher Catalog #11205D, bead stock at 6.67e8/mL) were delivered (15 microliters; 1e7 beads) to 1.5 mL microcentrifuges tube with 1 mL of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 mL of the Wash Buffer was repeated, and a further 200 microliters of Wash Buffer was added with subsequent pulse centrifugation. Supernatant Wash Buffer was removed.

Biotin functionalized (covalently coupled) smooth silica beads were first coated with Streptavidin by storage in 100 micromolar Streptavidin. Approximately 5e6 beads were washed by dilution into 1 milliliter of Wash Buffer in a microcentrifuge tube, followed by centrifugation at 1,000×g for 1 minute. The supernatant was carefully removed by aspiration, and the wash process repeated twice more. Supernatant Wash Buffer was removed.

To prepare antigen presenting beads, Wash Buffer (600 microliters) containing 0.5 micrograms biotinylated Monomer MHC (HLA-A* 02:01 SLC45A2 (Biolegend, Custom Product, SLYSYFQKV) was dispensed into the tubes with the DynaBeads and Silica beads, and the beads were resuspended by pipetting up and down. The monomer was allowed to bind for 30 min at 4° C. After 15 minutes, the mixtures were pipetted up and down again. The tubes were centrifuged at 1,000×g for one minute, and the supernatant liquid removed.

Wash Buffer (600 microliters) with 1.5 micrograms of biotinylated anti-CD28 and 1.5 micrograms of biotinylated anti-CD2 was used to resuspend each bead sample, and the beads were resuspended by pipetting up and down. The antibodies were allowed to bind for 30 min at 4C. After 15 minutes, the mixtures were pipetted up and down again. The tubes were centrifuged at 1,000×g for one minute, and the supernatant liquid removed. Finally, the beads were resuspended in 100 microliters of Wash Buffer.

Two samples of approximately 2e5 Polymer antigen presenting beads or 1e5 Silica antigen presenting beads were washed with Wash Buffer (1 milliliter). The bead samples were resuspended in 100 microliters of Wash Buffer and stained by addition of 1 microliter of APC-conjugated anti-HLA-A (Biolegend, Catalog Number 343308) or 1 microliter of APC-conjugated monoclonal anti-Mouse-IgG1 (Biolegend, Catalog Number 406610). The beads were mixed with the antibody and allowed to stain for 30 minutes in the dark. After staining, beads were washed, resuspended in Wash Buffer (200 microliters) and transferred to tubes for analysis by Flow Cytometry.

A set of Quantum Simply Cellular fluorescence quantitation beads (Bangs Labs, Catalog Number 815) was then prepared to determine the number of anti-HLA-A antibodies and anti-Mouse IgG1 antibodies bound to each antigen presenting bead sample. The quantitation beads have antibody binding capacities determined by the manufacturer. A drop of each bead with pre-determined binding capacity was placed in microcentrifuge tubes with 50 microliters of Wash Buffer. To the tubes, 5 microliters of APC-conjugated anti-HLA-A or APC-conjugated anti-Mouse IgG1 was added and mixed by vortexing. The beads were stained for 30 minutes in the dark, washed using the same method as above. The beads with different binding capacities were then pooled into one sample and transferred to a single tube. A drop of blank beads (no antibody binding capacity) was added and the beads were analyzed by Flow Cytometry.

The quantitation beads were analyzed by Flow Cytometry (BD FACSCelesta, Becton Dickinson and Company) by recording 5,000 events. The quantitation beads were identified by Forward Scatter and Side Scatter, and the median intensity in the APC channel of each bead recorded. This data was recorded in a proprietary Excel spreadsheet provided by the manufacturer (Bangs) that calculates a standard curve of APC intensity versus antibody binding capacity. After verifying that the calibration was linear, the antigen presenting bead samples were analyzed. The beads were identified by Forward and Side Scatter, and the median intensity in the APC channel recorded on the spreadsheet. The spreadsheet calculates the number of APC anti-HLA-A antibodies or APC anti-Mouse IgG1 on each antigen presenting bead. Assuming that 1 anti-HLA-A antibody binds to one pMHC on the antigen presenting bead, this value represents the number of pMHC molecules on each bead. Similarly, the number of costimulation antibodies can be determined.

Figure 20A:
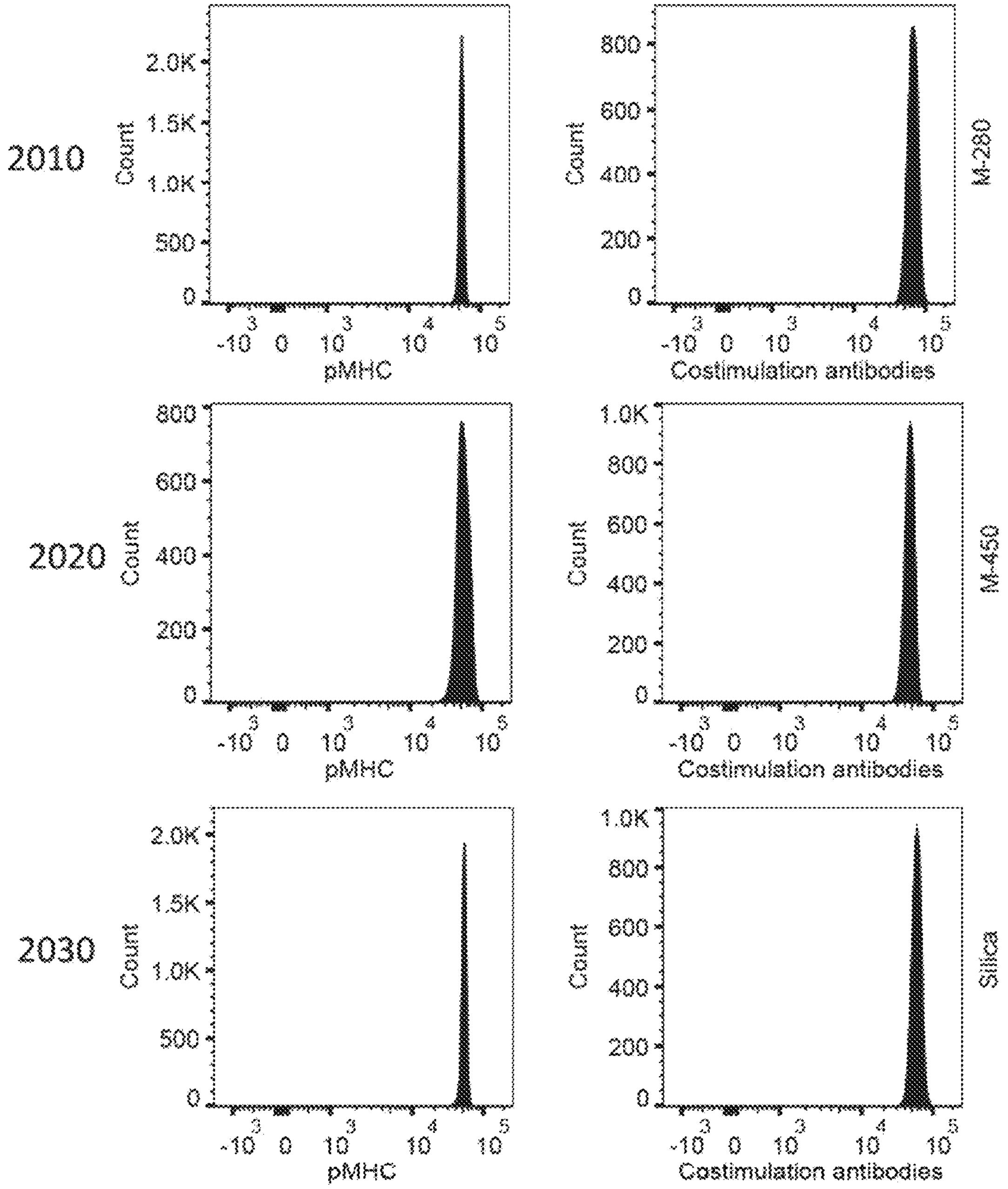

From the nominal surface area of each antigen presenting bead, the density (number of molecules/square micron of bead surface) of each species can be determined. The total number of pMHC on the Silica microspheres was determined to be approximately 800,000 pMHC/antigen presenting bead. The total number of costimulation antibodies was determined to be about 850,000 antibodies/bead. As there is no way to distinguish the anti-CD28 and anti-CD2 clones used to prepare the antigen presenting beads (they are the same isotype), it is assumed that the ratio of the two antibodies is 1:1. Due to the regularity of the Silica bead surfaces, the surface area can be reasonably modeled from a sphere. For a 4.08 micron diameter microsphere, this corresponds to a surface area of about 52.3 square microns. From this, it can be estimated that about 15,000 pMHC and 15,000 costimulation antibodies per square micron of bead surface are presented by the Silica antigen presenting beads as shown in Table 1. The distribution across each bead population for each ligand class is shown in FIG. 20A, where each row 2010, 2020, and 2030 shows the distribution of pMHC in the left hand graph, and the distribution of costimulation antibodies in the right hand graph for each type of bead. Row 2010 shows distribution of the ligands for 2.8 micron diameter convoluted polymer beads (Dynal). Row 2020 shows distribution of ligands for 4.5 micron diameter convoluted polymer beads (Dynal). Row 2030 shows distribution of ligands for a 2.5 micron diameter substantially spherical silica bead as produced in Example 10B. Tightly controlled populations of beads were produced, with the substantially spherical silica beads having even more tightly controlled distribution of ligands over the entire population, and slightly higher median distribution. Thus, the use of substantially spherical silica beads can lead to more reproducible and controllable production of these activating species. Additionally, since all of the ligands are accessible to T lymphocytes, unlike the convoluted polymer bead ligand distribution, more efficient use is made of precious biological ligands such as antibodies.

TABLE 1

Ligand quantification and density for convoluted polymer beads and substantially spherical silica beads.

| Bead | pMHC/ bead | pMHC Density (molecules/ sq micron) | Costimulation antibodies/ bead | Costimulation Antibody Density (molecules/ sq micron) |
|---|---|---|---|---|
| M-280 Polymer | 487,209 | 19,781 | 426,992 | 17,336 |
| Silica | 807,180 | 14,847 | 845,388 | 15,550 |

For Polymer beads, the convoluted surface makes the relationship between bead diameter and surface area less straightforward. From the quantitation, it was determined that Polymer antigen presenting beads based on M-280 DynaBeads had about 480,000 pMHC molecules and 425,000 costimulation antibodies on their surface. For a sphere of radius 1.4 microns (equal to the nominal radius of M-280 DynaBeads, this corresponds to about 20,000 pMHC and 17,000 costimulation antibodies per square micron, as shown in Table 1. However, due to the convoluted surface of the Polymer beads, the actual surface area is likely larger, and thus the actual density lower. From FIGS. 20E, 20F and 20G, though, it can be seen that these beads can be used as antigen presenting bead substrates to expand large numbers of antigen-specific T cells, where the expansion was performed in a similar manner as in Example 22B. In addition, from FIG. 20H, these antigen presenting beads generated large numbers of antigen-specific T cells with high expression of CD28, indicative of a memory precursor phenotype.

Antigen presenting beads were prepared in the same manner using M-450 Epoxy DynaBeads modified with Streptavidin. From flow cytometry, antigen presenting beads prepared from M-450 beads had approximately the same number of pMHC and costimulation antibody molecules as antigen presenting beads prepared with M-280 DynaBeads. As the M-450 DynaBeads are larger than the M-280 beads, this implies that the density of the activating species on the M-450 antigen presenting beads was about 2-3 times lower than on M-280 antigen presenting beads. However, as can be seen from FIG. 20F, M-450 antigen presenting beads generated positive wells (in which SLC45A2-specific T cells expanded to represent 0.5% or more of the live cells in the well) when used to expand SLC45A2 T cells. From FIGS. 20G and 20H, it can be seen that these wells generated SLC45A2 T cells at high frequencies, and the number of SLC45A2 T cells was comparable to the number obtained from M-280 antigen presenting beads. In addition, from FIG. 201, the fraction of SLC45A2 T cells expressing high levels of CD28 was comparable when using M-280 or M-450 antigen presenting beads to expand SLC45A2 T cells.

Example 22B. Expansion of Antigen-Specific T Cells with Polymer Vs Silica Beads

Expansion of Antigen-Specific T cells using Silica antigen presenting beads was tested and compared to convoluted polymeric beads (polystyrene).

Streptavidin functionalized (covalently coupled, convoluted) DynaBeads™ (ThermoFisher Catalog #11205D, bead stock at 6.67e8/mL) were delivered (15 microliters; 1e7 beads) to 1.5 mL microcentrifuges tube with 1 mL of Wash Buffer (DPBS (No Magnesium+2, No Calcium+2, 244 mL); EDTA (1 ml, final concentration 2 mM); and BSA (5 ml of 5%, final concentration 0.1%), and separated using a magnetic DynaBead rack. The wash/separation with 1 mL of the Wash Buffer was repeated, and a further 200 microliters of Wash Buffer was added with subsequent pulse centrifugation. Supernatant Wash Buffer was removed.

Biotin functionalized (covalently coupled) smooth silica beads, prepared as in Example 10B, were first coated with Streptavidin by storage in 100 micromolar Streptavidin. Approximately 5e6 beads were washed by dilution into 1 milliliter of Wash Buffer in a microcentrifuge tube, followed by centrifugation at 1,000×g for 1 minute. The supernatant was carefully removed by aspiration, and the wash process repeated twice more. Supernatant Wash Buffer was removed.

To prepare antigen presenting beads, Wash Buffer (600 microliters) containing 0.5 micrograms biotinylated Monomer MHC (HLA-A* 02:01 SLC45A2 (Biolegend, Custom Product, SLYSYFQKV) was dispensed into the tubes with the DynaBeads and Silica beads, and the beads were resuspended by pipetting up and down. The monomer was allowed to bind for 30 min at 4° C. After 15 minutes, the mixtures were pipetted up and down again. The tubes were centrifuged at 1,000×g for one minute, and the supernatant liquid removed.

Wash Buffer (600 microliters) with 1.5 micrograms of biotinylated anti-CD28 and 1.5 micrograms of biotinylated anti-CD2 was used to resuspend each bead sample, and the beads were resuspended by pipetting up and down. The antibodies were allowed to bind for 30 min at 4° C. After 15 minutes, the mixtures were pipetted up and down again. The tubes were centrifuged at 1,000×g for one minute, and the supernatant liquid removed. Finally, the beads were resuspended in 100 microliters of Wash Buffer.

Cells: CD8+ T lymphocytes were enriched in a medium including RPMI plus 10% fetal bovine serum (FBS) from commercially available PBMCs following manufacturer's directions for EasySep™ Human CD8+ T Cell Isolation Kit, commercially available kit from StemCell Technologies Canada Inc. (Catalog #17953), by negative selection.

Culture medium and diluent for reagent additions: Advanced RPMI (ThermoFisher Catalog #12633020, 500 mL); 1× GlutaMAX (ThermoFisher Catalog #35050079, 5 mL); 10% Human AB serum (zen-bio, Catalog #HSER-ABP 100 mL, 50 mL); and 50 nM beta-mercaptoethanol (ThermoFisher Catalog #31350010, 50 nm stock, 0.5 mL, final conc 50 micromolar).

Experimental Setup: For each type of antigen presenting bead (Silica or Polymer, as prepared above in this example), a single 96 tissue-culture treated wellplate (VWR Catalog #10062-902) was used. Silica antigen presenting beads were mixed with CD8+ T lymphocytes at ~1:2 beads: cell. CD8+ T lymphocytes (2e5) (80-90% pure) were added to each well with approximately 1e5 antigen presenting beads (wellplate 1). Polymer antigen presenting beads were mixed with CD8+ T lymphocytes at ~1:1 beads: cell. CD8+ T lymphocytes (2e5) (80-90% pure) were added to each well with approximately 2e5 antigen presenting beads (wellplate 2).

Each wellplate was cultured at 37° C. On day 0, IL-21 (150 ng/milliliter) in CTL media, was added to each well of wellplates 1 and 2, providing a final concentration in each well of 30 ng/ml. On day 2, IL21 was added to each well of the wellplates, to a final concentration of 30 ng/ml. Culturing was continued to day 7.

Day 7. Restimulation. A second aliquot of antigen presenting beads was added to the corresponding wells in wellplate 1 and wellplate 2. For the Silica beads, approximately 1e5 beads (Silica beads as prepared above in this example) were added. For the Polymer beads, approximately 2e5 beads (convoluted polymer beads as prepared above in this example) were added. IL21 was added to each well of the wellplate to a final concentration of 30 ng/ml. Culturing was continued.

Day 8. Addition of 50 microliters of IL-2 (50 IU/mL) and IL-7 (25 ng/ml) was made to each well in wellplate 1 and wellplate 2 to provide a final concentration of 10 IU/mL and 5 ng/ml respectively. Culturing was continued.

Day 9. Addition of 50 microliters of IL-21 (150 ng/ml) was made to each occupied well of wellplate 1 and wellplate 2 to a final concentration of 30 ng/ml. Culturing was continued.

Day 14. The wells from each wellplate were individually stained for MHC tetramer (Tetramer PE, MBL Catalog #T02000, 1 microliter/well), CD4 (Biolegend Catalog #300530, 0.5 microliters/well); CD8 (Biolegend Catalog #301048, 0.5 microliters/well); CD28 (Biolegend Catalog #302906, 0.31 microliters/well); CD45RO (Biolegend Catalog #304210, 0.63 microliters/well); CCR7 (CD197, Biolegend Catalog #353208, 0.5 microliters/well); and viability (BD Catalog #565388, 0.125 microliters/well). Each well was resuspended with 150 microliters FACS buffer and 10 microliters of Countbright™ beads (ThermoFisher Catalog #C36950). FACS analysis was performed on a FACSCelesta™ flow cytometer (BD Biosciences).

Figures 20B, 20C, 20D, 20E:
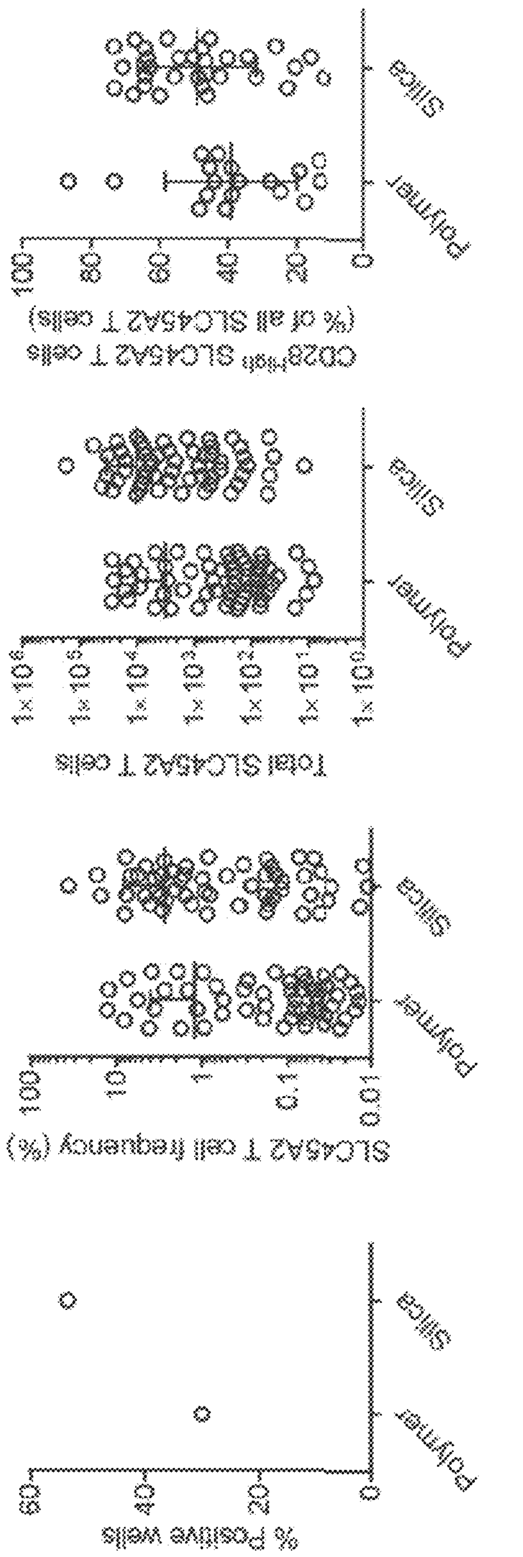
Figures 20F, 20G, 20H, 20I:
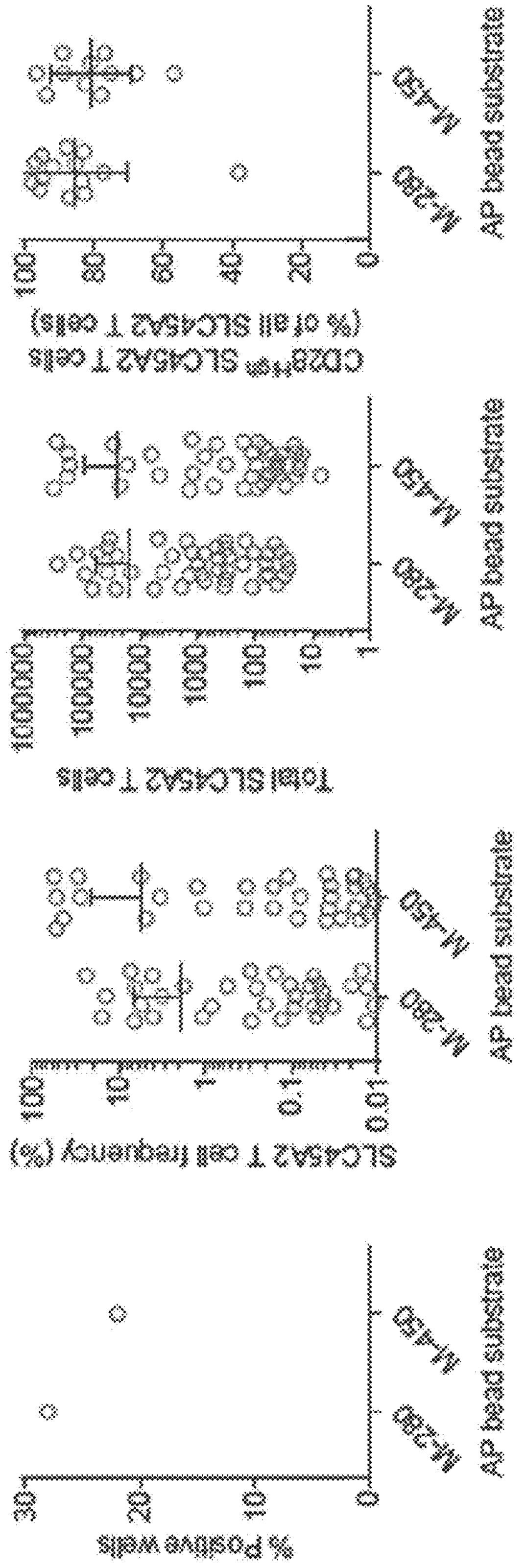

FIG. 20B shows the percentage of positive wells (in which SLC45A2-specific T cells expanded to represent 0.5% or more of the live cells in the well) after expansion using the Polymer or Silica antigen presenting beads. FIG. 20C shows SLC45A2 T cell frequency (% of live cells in each well) after expansion with the Polymer or Silica antigen presenting beads. FIG. 20D shows the total number of SLC454A2 T cells in each of the wells. FIG. 20E shows the percentage of SLC45A2 T cells in the wells that expressed high levels of CD28, indicating the potential for differentiation into a memory T cell. From these plots, it can be seen that the Silica antigen presenting beads generate positive wells, and that the Silica antigen presenting beads expand SLC45A2 T cells as well or better than Polymer antigen presenting beads. In addition, the Silica antigen presenting beads produce cells with high expression of CD28, indicating that they support formation of memory precursor T cells, a desired phenotype for the cellular product.

For Polymer beads, the convoluted surface makes the relationship between bead diameter and surface area less straightforward. From the quantitation, it was determined that Polymer antigen presenting beads based on M-280 DynaBeads had about 480,000 pMHC molecules and 425,000 costimulation antibodies on their surface. For a sphere of radius 1.4 microns (equal to the nominal radius of M-280 DynaBeads, this corresponds to about 20,000 pMHC and 17,000 costimulation antibodies per square micron. However, due to the convoluted surface of the Polymer beads, the actual surface area is likely larger, and thus the actual density lower. However, from FIGS. 20F, 20G and 20H, it can be seen that these beads can be used as antigen presenting bead substrates to expand large numbers of antigen-specific T cells. In addition, from FIG. 201, these antigen presenting beads generate large numbers of antigen-specific T cells with high expression of CD28, indicative of a memory precursor phenotype.

Example 23. Preparation of antigen presenting beads with defined ligand densities

Example 23A.1. Preparation of streptavidin presenting beads. Three-fold serial dilutions of pMHC (HLA-A* 02:01

SLC45A2 (Biolegend, Custom Product, SLYSYFQKV) in Wash Buffer were prepared. 20 microliters of Wash Buffer was added to a microcentrifuge tube for each serial dilution to be performed. Into the first serial dilution tube, 10 microliters of the pMHC were added. The diluted pMHC was mixed by vortexing. 10 ul of the diluted pMHC mixture was then used to prepare the subsequent serial dilution for a total of seven dilutions.

To determine the relationship between concentration of pMHC in solution and the density (molecules/unit area) deposited on the beads, Biotin functionalized (covalently coupled) smooth (e.g., substantially spherical as described above) 4 micron monodisperse silica beads (Cat. #SiO2MS- 1.8 4.08 μm-1 g, Cospheric), prepared as in Example 10B, were first coated with Streptavidin by storage in 100 micromolar Streptavidin. Approximately 1e7 beads were washed by dilution into 1 milliliter of Wash Buffer in a microcentrifuge tube, followed by centrifugation at 1,000×g for 1 minute. The supernatant was carefully removed by aspiration, and the wash process repeated twice more. After washing, approximately 1e6 beads were delivered into eight microcentrifuge tubes, centrifuged again, and the supernatant carefully removed.

Example 23A.2. Preparation of Beads Having a Range of MHC Concentration

Wash Buffer (120 microliters) containing 4.5 micrograms biotinylated Monomer MHC (HLA-A* 02:01 SLC45A2 (Biolegend, Custom Product, SLYSYFQKV) was dispensed into one of the microcentrifuge tubes, and the beads were resuspended by pipetting up and down. The undiluted pMHC and serial dilutions of pMHC were further diluted into Wash Buffer (120 microliters) and used to resuspend beads, resulting in beads suspended in solutions with 4.5, 1.5, 0.5, 0.167, 0.056, 0.019, 0.006, or 0.002 micrograms of pMHC monomer per 5e6 beads. The monomer was allowed to bind for 30 min at 4° C. After 15 minutes, the mixtures were pipetted up and down again. The tubes were centrifuged, the supernatant liquid removed, and the beads resuspended at approximately 5e7/milliliter.

Approximately 1e5 beads prepared with each concentration of pMHC were washed with Wash Buffer (1 milliliter). The bead samples were resuspended in 100 microliters of Wash Buffer and stained by addition of 1 microliter of APC-conjugated anti-HLA-A (Biolegend, Catalog Number 343308). The beads were mixed with the antibody and allowed to stain for 30 minutes in the dark. After staining, beads were washed, resuspended in Wash Buffer (200 microliters) and transferred to tubes for analysis by Flow Cytometry.

A set of Quantum Simply Cellular fluorescence quantitation beads (Bangs Labs, Catalog Number 815) was then prepared to determine the number of anti-HLA-A antibodies bound to each antigen presenting bead sample. The quantitation beads have antibody binding capacities determined by the manufacturer. A drop of each bead with pre-determined binding capacity was placed in a microcentrifuge tube with 50 microliters of Wash Buffer. To the tube, 5 microliters of APC-conjugated anti-HLA-A was added and mixed by vortexing. The beads were stained for 30 minutes in the dark, washed using the same method as above. The beads with different binding capacities were then pooled into one sample and transferred to a single tube. A drop of blank beads (no antibody binding capacity) was added and the beads were analyzed by Flow Cytometry.

Figure 21A:
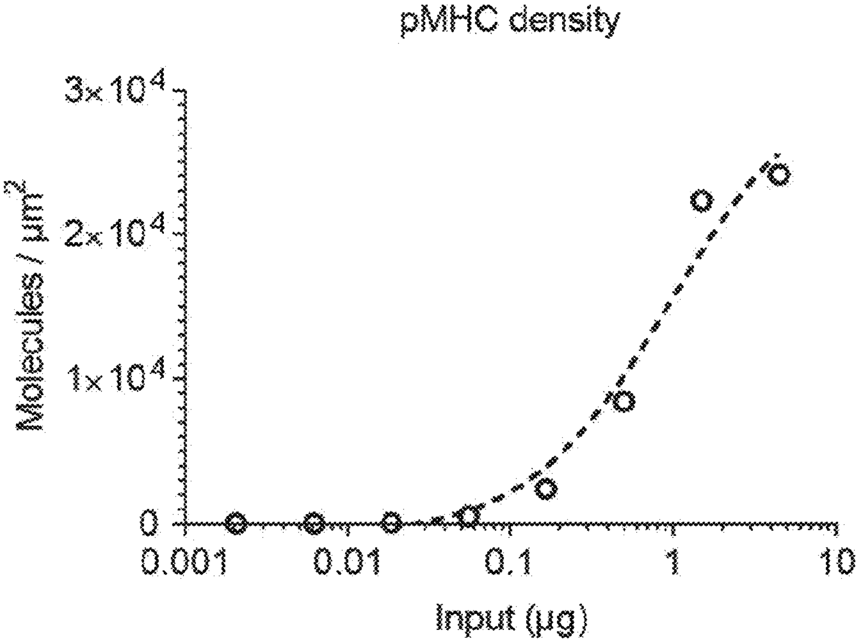
FIGS. 21A-21F are graphical representations of characterization of activation using antigen-presenting surfaces according to some embodiments of the disclosure.

The quantitation beads were analyzed by Flow Cytometry (BD FACSCelesta, Becton Dickinson and Company) by recording 5,000 events. The quantitation beads were identified by Forward Scatter and Side Scatter, and the median intensity in the APC channel of each bead recorded. Quantitation was calculated as described in Example 22A, using the proprietary methodology provided by the quantitation bead manufacturer. From the antigen presenting bead standard, it is then possible to determine the concentration of pMHC in solution with beads that generates antigen presenting beads with a targeted density of pMHC, e.g., beads with approximately 10,000, 1,000, or 100 pMHC molecules per square micron, as seen in FIG. 21A.

Example 23A.3. Costimulation Molecule Concentration Variation

Three-fold serial dilutions of biotinylated anti-CD28 and anti-CD2 in Wash Buffer were prepared. 20 microliters of anti-CD28 was mixed with 20 microliters of anti-CD2 in a microcentrifuge tube. Wash Buffer (20 microliters) was then added to a microcentrifuge tube for each serial dilution. The anti-CD28/anti-CD2 mixture (10 microliters) was then added to the first serial dilution tube. The solution was mixed using a vortexer, and 10 ul of the diluted anti-CD28/anti-CD2 mixture was then used to prepare the subsequent serial dilution for a total of seven dilutions.

To quantify the relationship between costimulation antibody in solution and the density (molecules/unit area) deposited on the beads, approximately 1e7 substantially spherical 4 micron silica beads, prepared as in Example 23A. 1, having streptavidin binding moieties, were first washed by dilution into 1 milliliter of Wash Buffer in a microcentrifuge tube, followed by centrifugation at 1,000×g for 1 minute. The supernatant was carefully removed by aspiration, and the wash process repeated twice more. After washing, approximately 1e6 beads were delivered into eight microcentrifuge tubes, centrifuged again, and the supernatant carefully removed.

The beads were first functionalized with 1.0 micrograms of pMHC in Wash Buffer (1,200 microliters). After washing, the beads were resuspended in Wash Buffer (1,000 microliters). Into eight microcentrifuge tubes, 100 microliters of pMHC functionalized beads was dispended. The beads were centrifuged, and the supernatant carefully removed.

The undiluted mixed anti-CD28 and anti-CD2 and serial dilutions of anti-CD28/anti-CD2 were further diluted into Wash Buffer (120 microliters) and used to resuspend the beads, resulting in beads suspended in solutions with 4.5, 1.5, 0.5, 0.167, 0.056, 0.019, 0.006, or 0.002 micrograms of mixed costimulation antibodies monomer per 5e6 beads. The monomer was allowed to bind for 30 min at 4° C. After 15 minutes, the mixtures were pipetted up and down again. The tubes were centrifuged, the supernatant liquid removed, and the beads resuspended at approximately 5e7/milliliter.

Approximately 1e5 beads prepared with each concentration of costimulation antibodies was washed with Wash Buffer (1 milliliter). The bead samples were resuspended in 100 microliters of Wash Buffer and stained by addition of 1 microliter of APC-conjugated monoclonal anti-Mouse-IgG1 (Biolegend, Catalog Number 406610). The beads were mixed with the antibody and allowed to stain for 30 minutes in the dark. After staining, beads were washed, resuspended in Wash Buffer (200 microliters) and transferred to tubes for analysis by Flow Cytometry.

A set of Quantum Simply Cellular fluorescence quantitation beads (Bangs Labs, Catalog Number 815) was then prepared to determine the number of APC anti-Mouse IgG1 antibodies bound to each antigen presenting bead sample. A drop of each bead with pre-determined binding capacity was placed in a microcentrifuge tube with 50 microliters of Wash Buffer. To the tube, 5 microliters of APC-conjugated anti-Mouse IgG1 was added and mixed by vortexing. The beads were stained for 30 minutes in the dark, washed using the same method as above. The beads with different binding capacities were then pooled into one sample and transferred to a single tube. A drop of blank beads (no antibody binding capacity) was added and the beads were analyzed by Flow Cytometry.

Figure 21B:
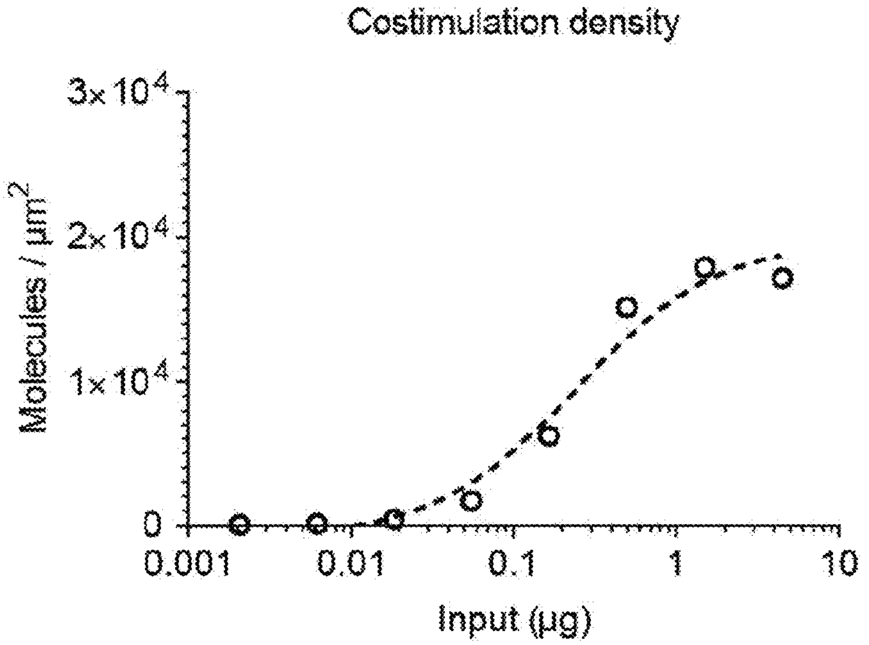

The quantitation beads were analyzed by Flow Cytometry (BD FACSCelesta, Becton Dickinson and Company) by recording 5,000 events. The quantitation beads were identified by Forward Scatter and Side Scatter, and the median intensity in the APC channel of each bead recorded. Quantitation was performed as described in Example 22A, using proprietary methods provided by the quantitation bead manufacturer. This quantitation method calculates the number of APC anti-Mouse IgG1 antibodies on each antigen presenting bead. Assuming that 1 anti-Mouse IgG1 antibody binds to one costimulation antibody on the antigen presenting bead, this value represents the number of costimulation antibodies on each bead. From the antigen presenting bead standards, it is then possible to determine the concentration of costimulation antibodies in solution with beads that generates antigen presenting beads with a targeted density of costimulation antibodies, e.g., beads with approximately 10,000, 1,000, or 100 costimulation molecules per square micron, as seen in FIG. 21B.

Example 23B. Expansion of antigen-specific T cells with antigen presenting beads with different ligand densities. Using the plots of pMHC and costimulation antibody concentration versus density on the resulting antigen presenting beads (FIG. 21A), it was determined what concentration of each pMHC should be used to prepare antigen presenting beads with ~10,000, ~1,000 or ~100 pMHC per square micron of bead surface. This process was repeated to determine the concentration of anti-CD28 and anti-CD2 to be used to prepare antigen presenting beads with ~10,000, ~1,000 or ~100 costimulation antibodies per square micron of bead surface.

Example 23B.1. Biotin functionalized (covalently coupled) smooth silica beads, prepared as in Example 23.A.1 were first coated with Streptavidin by storage in 100 micromolar Streptavidin. Approximately 5e7 beads were washed by dilution into 1 milliliter of Wash Buffer in a microcentrifuge tube, followed by centrifugation at 1,000×g for 1 minute. The supernatant was carefully removed by aspiration, and the wash process repeated twice more. After washing, approximately 5e6 beads were delivered into three microcentrifuge tubes, centrifuged again, and the supernatant carefully removed.

Example 23B.2. To prepare antigen presenting beads with titrated pMHC, Wash Buffer (600 microliters) containing 0.5, 0.056, or 0.006 micrograms biotinylated Monomer MHC (HLA-A* 02:01 MART-1 (MBL International Corp., Catalog No. MR01008, ELAGIGILTV) was dispensed into three microcentrifuge tubes, and the beads were resuspended by pipetting up and down. The monomer was allowed to bind for 30 min at 4° C. After 15 minutes, the mixtures were pipetted up and down again. The tubes were centrifuged at 1,000×g for one minute, and the supernatant liquid removed.

Wash Buffer (600 microliters) with 1.0 microgram of mixed biotinylated anti-CD28 and biotinylated anti-CD2 was used to resuspend each bead sample, and the beads were resuspended by pipetting up and down. The antibodies were allowed to bind for 30 min at 4° C. After 15 minutes, the mixtures were pipetted up and down again. The tubes were centrifuged at 1,000×g for one minute, and the supernatant liquid removed. Finally, the beads were resuspended in 100 microliters of Wash Buffer. The loading of the beads with the desired order of magnitude of pMHC and antibodies was verified by Flow Cytometry analysis and comparison to quantitation beads.

Wash Buffer (600 microliters) with 1.0 micrograms of anti-CD28 and anti-CD2 was used to resuspend each bead sample, and the beads were resuspended by pipetting up and down. The monomer was allowed to bind for 30 min at 4° C. After 15 minutes, the mixtures were pipetted up and down again. The tubes were centrifuged at 1,000×g for one minute, and the supernatant liquid removed. Finally, the beads were resuspended in 100 microliters of Wash Buffer. The loading of the beads with the desired order of magnitude of pMHC was verified by Flow Cytometry analysis and comparison to quantitation beads.

Example 23B.3. To prepare antigen presenting beads with titrated costimulation antibodies, Wash Buffer (1,200 microliters) containing 1.5 micrograms biotinylated Monomer MHC (HLA-A* 02:01 MART-1 (MBL International Corp., Catalog No. MR01008, ELAGIGILTV) was dispensed into a microcentrifuge tube containing 1.5e7 washed beads from Example 23.B.1, and the beads were resuspended by pipetting up and down. The monomer was allowed to bind for 30 min at 4° C. After 15 minutes, the mixtures were pipetted up and down again. The tubes were centrifuged at 1,000×g for one minute, and the supernatant liquid removed.

The beads were then resuspended in Wash Buffer (900 microliters), and 300 microliters of the beads transferred to 3 microcentrifuge tubes.

Wash Buffer (300 microliters) with 1.0 microgram of mixed anti-CD28 and anti-CD2, 0.111 micrograms of mixed antiCD28 and anti-CD2, or 0.012 micrograms of mixed anti-CD28 and anti-CD2 was mixed into the three bead samples, and the beads were thoroughly mixed by pipetting up and down. The antibodies were allowed to bind for 30 min at 4° C. After 15 minutes, the mixtures were pipetted up and down again. The tubes were centrifuged at 1,000×g for one minute, and the supernatant liquid removed. Finally, the beads were resuspended in 100 microliters of Wash Buffer. The loading of the beads with the desired order of magnitude of costimulation antibodies was verified by Flow Cytometry analysis and comparison to quantitation beads.

Example 23B.4. Stimulation. Cells: CD8+ T lymphocytes were enriched in a medium including RPMI plus 10% fetal bovine serum (FBS) from commercially available PBMCs following manufacturer's directions for EasySep™ Human CD8+ T Cell Isolation Kit, commercially available kit from StemCell Technologies Canada Inc. (Catalog #17953), by negative selection.

Culture medium and diluent for reagent additions: Advanced RPMI (ThermoFisher Catalog #12633020, 500 mL); 1× GlutaMAX (ThermoFisher Catalog #35050079, 5 mL); 10% Human AB serum (zen-bio, Catalog #HSER-ABP 100 mL, 50 mL); and 50 nM beta-mercaptoethanol (ThermoFisher Catalog #31350010, 50 nm stock, 0.5 mL, final conc 50 micromolar).

Experimental Setup: For each activation species titration (pMHC or costimulation antibodies), a single 96 tissue-culture treated wellplate (VWR Catalog #10062-902) was used. Antigen presenting beads with ~10,000, ~1,000 or ~100 pMHC per square micron of bead surface and with ~10,000 costimulation antibodies per square micron of bead surface (from Example 23.B.2) were mixed with CD8+ T lymphocytes at ~1:2 beads: cell. CD8+ T lymphocytes (2e5) (80-90% pure) were added to each well with approximately 1e5 antigen presenting beads (wellplate 1). Antigen presenting beads with ~10,000 pMHC per square micron of bead surface and with ~10,000, ~1,000 or ~100 costimulation antibodies per square micron of bead surface (from Example 23.B.3) were mixed with CD8+ T lymphocytes at ~1:2 beads: cell. CD8+ T lymphocytes (2e5) (80-90% pure) were added to each well with approximately 1e5 antigen presenting beads (wellplate 2).

Each wellplate was cultured at 37° C. On day 0, IL-21 (150 ng/milliliter) in CTL media, was added to each well of wellplates 1 and 2, providing a final concentration in each well of 30 ng/ml. On day 2, IL21 was added to each well of the wellplates, to a final concentration of 30 ng/ml. Culturing was continued to day 7.

Day 7. Restimulation. A second aliquot of antigen presenting beads with the targets density of pMHC or costimulation antibody was added to the corresponding wells in wellplate 1 and wellplate 2. IL21 was added to each well of the wellplate to a final concentration of 30 ng/ml. Culturing was continued.

Day 8. Addition of 50 microliters of IL-2 (50 IU/mL) and IL-7 (25 ng/ml) was made to each well in wellplate 1 and wellplate 2 to provide a final concentration of 10 IU/mL and 5 ng/ml respectively. Culturing was continued.

Day 9. Addition of 50 microliters of IL-21 (150 ng/mL) was made to each occupied well of wellplate 1 and wellplate 2 to a final concentration of 30 ng/ml. Culturing was continued.

Figure 21C:
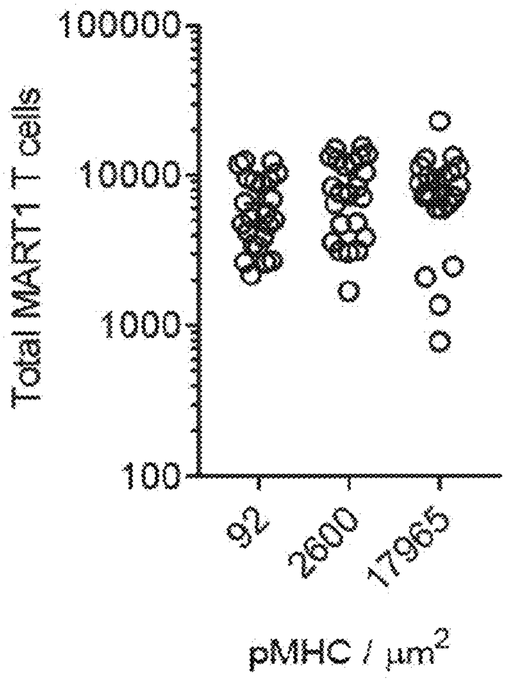
Figure 21D:
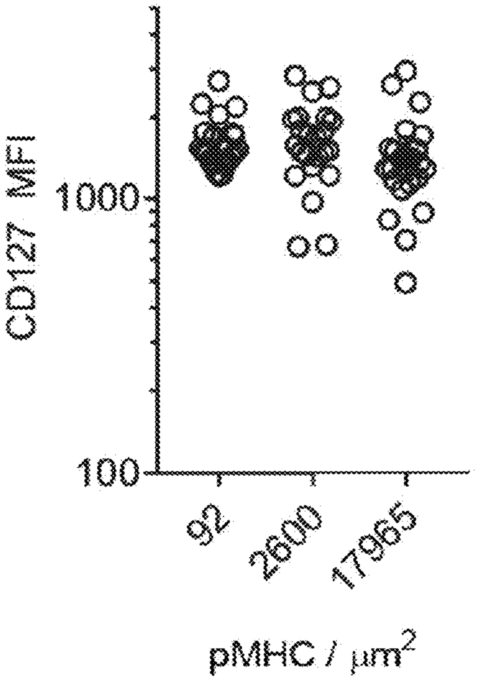

Day 14. The wells from each wellplate were individually stained for MHC tetramer (Tetramer PE, MBL Catalog #T02000, 1 microliter/well), CD4 (Biolegend Catalog #300530, 0.5 microliters/well); CD8 (Biolegend Catalog #301048, 0.5 microliters/well); CD28 (Biolegend Catalog #302906, 0.31 microliters/well); CD45RO (Biolegend Catalog #304210, 0.63 microliters/well); CCR7 (CD197, Biolegend Catalog #353208, 0.5 microliters/well); and viability (BD Catalog #565388, 0.125 microliters/well). Each well was resuspended with 150 microliters FACS buffer and 10 microliters of Countbright™ beads (ThermoFisher Catalog #C36950). FACS analysis was performed on a FACSCelesta™ flow cytometer (BD Biosciences). FIG. 21C shows the number of MART1-specific T cells in each well expanded using antigen presenting beads with various densities of pMHC/square micron. FIG. 21D shows the expression level of CD127, a marker of memory precursor T cells, on the MART1-specific T cells from FIG. 21C. From these plots, it can be seen that the number of MART1-specific T cells and the expression of CD127 on these cells is insensitive to pMHC density when the density is ~100 pMHC/square micron or higher.

Figure 21E:
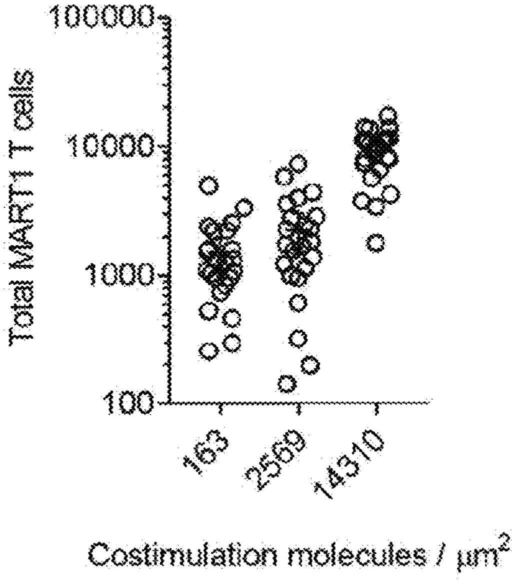
Figure 21F:
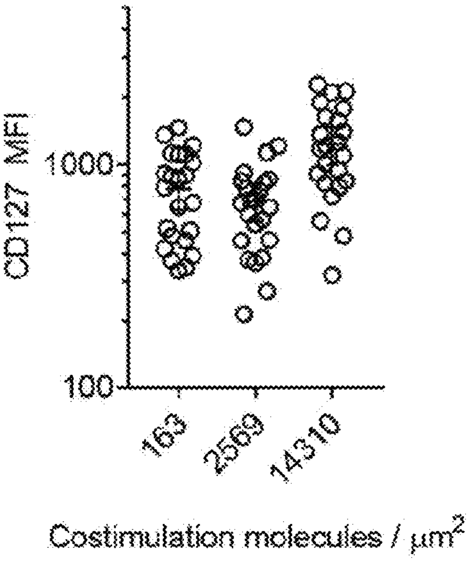

FIG. 21E shows the number of MART1-specific T cells in each well expanded using antigen presenting beads with various densities of costimulation antibodies/square micron. FIG. 21F shows the expression level of CD127, a marker of memory precursor T cells, on the MART1-specific T cells from FIG. 21E. From these plots, it can be seen that the number of MART1-specific T cells and the expression of CD127 on these cells is sensitive to costimulation antibody density. Beads prepared with ~10,000 costimulation antibodies per square micron, which nearly saturated the biotin binding sites of the bead (see FIG. 21B), generated the highest number of antigen-specific T cells, and those cells expressed the highest levels of CD127. As the number of costimulatory ligands was decreased to the lower end of the loading regime, primary stimulation by the pMHC was not as effectively co-stimulated, and the phenotype of the cell product is affected.

Example 24. Performance of an Antigen-Specific Cytotoxicity Assay within a Microfluidic Device Experimental Design: Tumor cell lines obtained from melanoma cells, including Mel 526 cells and A375 cells, were tested in an on-chip T cell killing assay. Each cell line was grown up in vitro according to standard procedures, then labeled with CellTrace™ Far Red dye (Cat. #C34572, ThermoFisher Scientific), which provides stable intracellular labelling. Each population of labeled tumor cells were flowed into an individual microfluidic chip (Berkeley Lights, Inc.) in T cell media (Adv. RPMI+10% Human AB serum (Cat. #35-060-CI, Corning)+Gln+50 μM 2-mercaptoethanol (BME, Cat. #31350-010, Gibco, ThermoFisher Scientific) supplemented with 10 uM fluorogenic Caspase-3 substrate (DEVD, Green) (Nucview® 488, Cat. #10403, Biotium). Groups of labeled tumor cells (~2-10) were loaded into each of a plurality of sequestration pens on each of the two microfluidic chips (one for Mel 526 cells, and one for A375 cells) by tilting the microfluidic chip and allowing gravity to pull the tumor cells into the sequestration pens, providing a final concentration of the Caspase-3 substrate at 5 uM at Time=0 for the assay for each microfluidic chip. The Caspase-3 substrate provides no fluorescent signal until cleaved, so at Time=0, there was no fluorescent signal due to this reagent. T cells expanded against the SLC45A2 antigen, according to an endogenous T cell (ETC) protocol as described above, were flowed into each of the two microfluidic chips and gravity loaded on top of the tumor cells of each respective chip. Typically, after loading the tumor cells and T cells, each sequestration pen contained 0-5 tumor cells per T cell. As shown in the brightfield image (BF) for each time point and for each microfluidic chip containing SLC45A2-specific T cells and Mel526 tumor cells (FIG. 22A) and SLC45A2-specific T cells and A375 cells (FIG. 22B), respectively, populations of the cells are present. T cell media (Adv. RPMI+10% Human AB serum+Gln+50 uM BME) supplemented with 5 uM Caspase-3 substrate (Green) (Nucview 488 from Biotium) was perfused through the microfluidic channels on each microfluidic chip and images of the sequestration pens were taken every 30 minutes (starting from the end of the T cell loading) for a period of 7 hours. The CellTrace Far Red label and cleaved, now fluorescent Caspase-3 label were visualized using different fluorescent cubes (Cy5, FITC respectively).

The Mel526 melanoma cell line expresses the SLC45A2 tumor-associated antigen and was expected to be targeted and killed by the SLC45A2-specific T cells. The A375 melanoma cell line does not express the SLC45A2 tumor-associated antigen and was not expected to be targeted or killed by the SLC45A2-specific T cells, and thus was used as a negative control for T cell cytotoxicity.

Figure 22A:
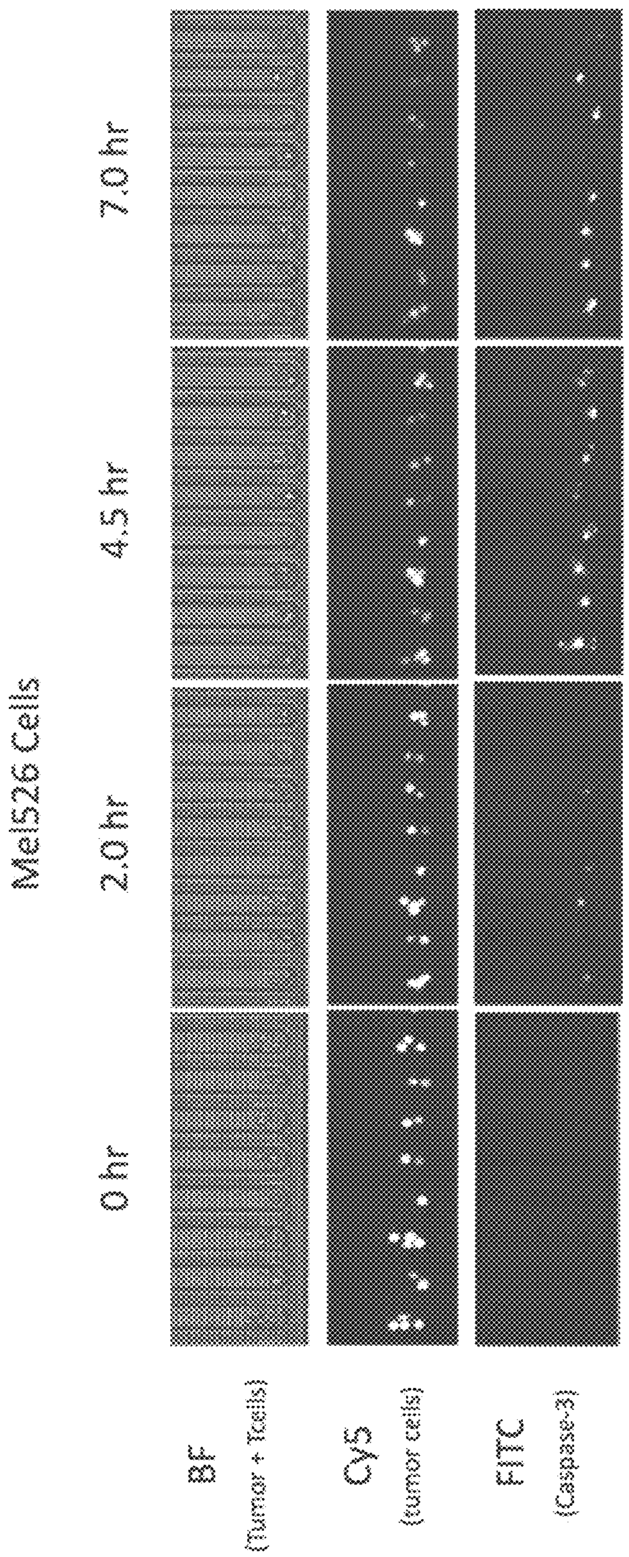
FIGS. 22A-22B are images of target cells taken at selected time points after being contacted with T lymphocytes and a Caspase 3 substrate in an antigen specific cytotoxicity assay according to some embodiments of the disclosure.
Figure 22B:
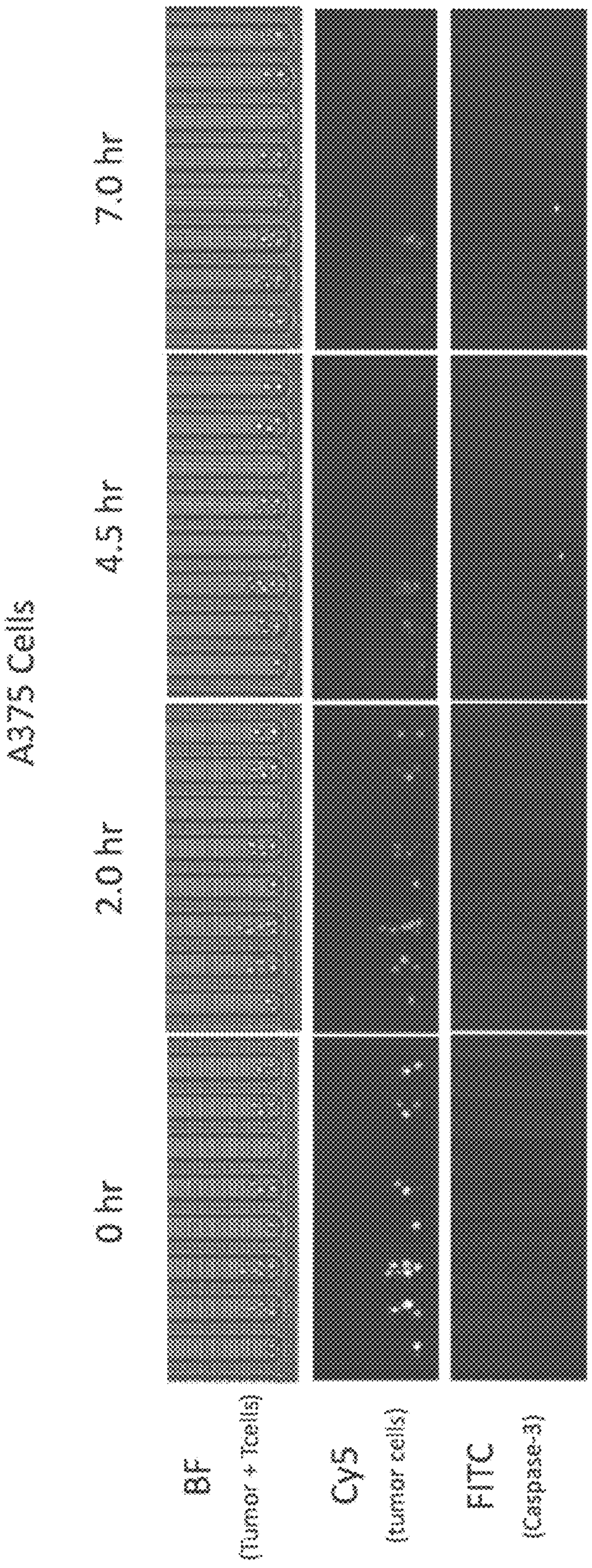
Figure 22C:
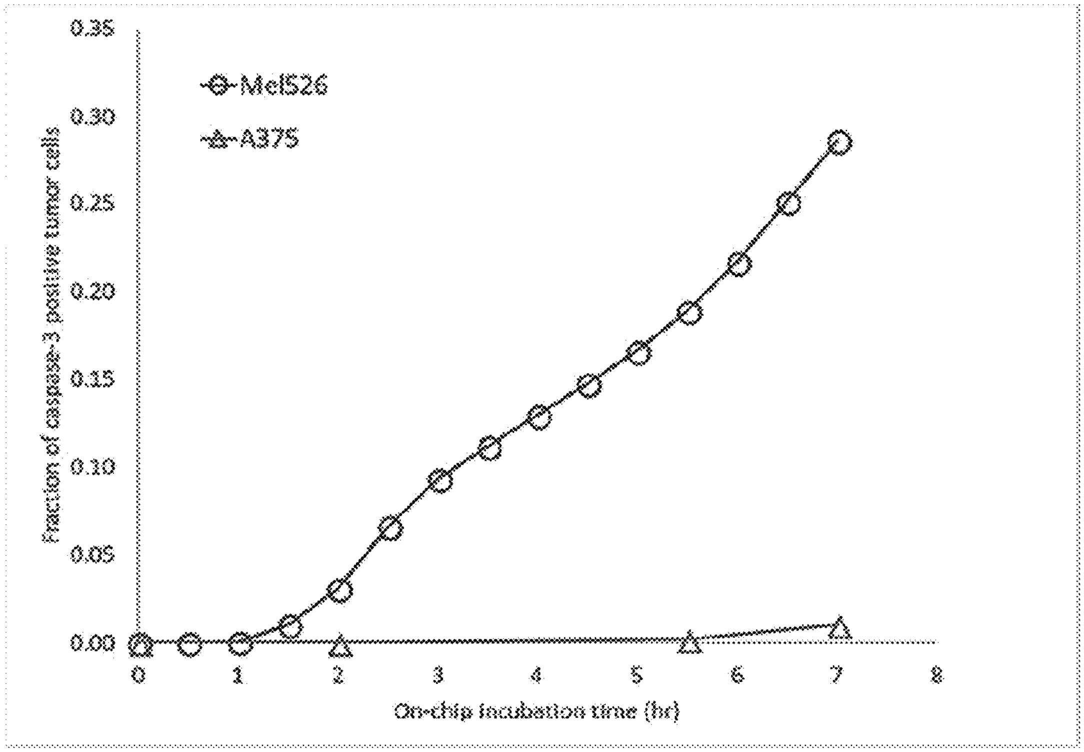
FIG. 22C is a graphical representation of the course of an antigen specific cytotoxicity assay according to some embodiments of the disclosure.

Results: Mel526 tumor cells (FIG. 22A) and A375 tumor cells (FIG. 22B) exhibited the CellTrace Far Red signal (Cy5 fluorescent cube) but no signal associated with cleavage of the Caspase-3 substrate (Green fluorescent signal, FITC fluorescent cube) at the 1 hour time point. As time progresses, the green fluorescent signal associated with cleavage of the Caspase-3 substrate increased in the Mel526 tumor cells (FIG. 22A, up to 7 hr. time points shown) but not in the A375 tumor cells (FIG. 22B, up to 7 hrs. time point shown). The results indicate that the Mel526 tumor cells were efficiently killed by the SLC45A2-specific T cells, with 6 of 8 sequestration pens that contain Mel526 tumor cells in FIG. 22A showing high levels of Caspase-3 substrate cleavage. FIG. 22C showed quantification of the extent of antigen-specific Mel526 tumor cell killing vs the extent of cell killing of A375 non-targeted cells over the course of the experiment. A very low amount of SLC45A2-specific T cell (fractional) killing was observed for A375 non-targeted cells, whereas the targeted antigen-specific cell killing of the Mel 526 tumor cells by the SLC45A2-specific T cells approached a 0.25 fractional killing over the same 7 hr. time period. The exposure times for each of the fluorescent images was the same for each microfluidic chip and for each time point. The decrease seen over time of the Cy5 signal from the Cell Trace Far Red stain is often observed for any set of cells; observation of such decrease for each cell type was not unexpected.

Example 25. Rapid Expansion of Antigen-Specific T Lymphocytes after Bead Stimulation and Characterization of Cellular Product Typically after completion of antigen specific T lymphocyte activation as described in the preceding experiments, the antigen specific enriched T cells were sorted by FACS on an FACSAria Fusion System (Becton Dickinson, San Jose, CA) after staining 30 min RT in FACS buffer (1XDPBS w/o $Ca2^{+}Mg2^{+}$ (Cat. #4190250, ThermoFisher), 5 mM EDTA (Cat. #AM9260G, ThermoFisher), 10 mM HEPES (Cat. #15630080, ThermoFisher), 2% FBS) with anti-CD8-PerCPCy5.5 (Clone RPA-T8, 301032, Biolegend, San Diego, CA), Tetramer-PE (MBL International, Woburn, MA) specific to the antigen, and Zombie NIR (Cat. #423106, Biolegend, San Diego, CA) to exclude dead cells. Desired cells were purity sorted by gating: size, singles, live, CD8 positive, and Tetramer positive into CTL media (Advanced RPMI (Cat. #12633020, ThermoFisher), 1× Glutamax (Cat. #35050079, ThermoFisher), 10% Human Serum (Cat. #MT35060Cl, ThermoFisher), 50UM b-Mercaptoethanol (Cat. #31350010, ThermoFisher) with 2 mM HEPES.

The sorted antigen-specific T cells were then expanded in at least one round of Rapid Expansion Protocol (REP), as described in Riddell, U.S. Pat. No. 5,827,642. Lymphoblastoid Cell Line cells (LCL, the LCL cell line was a gift from Cassian Yee, M.D. Anderson Cancer Center) were irradiated with 100 Gy and PBMC from 3 donors were irradiated with 50 Gy using an X-ray irradiator. Irradiated cells were washed in RPMI containing 10% FBS and mixed in a ratio of 1:5 (LCL: PBMC). These irradiated cells were added to either FACS-sorted T cells (for a first cycle of REP), or to the product of a first cycle of REP in 200 to 500-fold excess. Cultures were set up in T cell media (Advanced RPMI, 10% Human AB Serum, GlutaMax, 50 UM b-mercaptoethanol) supplemented with 50 U/mL IL-2 (Cat. #202-IL, R&D Systems) and 30 ng/ml anti-CD3 antibody (Cat. #16-0037-85, ThermoFisher). Cells were fed with fresh IL-2 on days 2, 5 and 10, and expanded according to their growth rates.

Figure 23A:
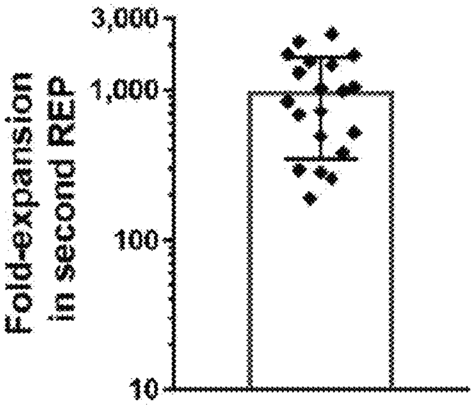
FIGS. 23A-23E are graphical representations of the characterization of the cellular product obtained using an antigen-presenting surface according to some embodiments of the FIG. 24 is a depiction of the goals of the cartridges, systems and methods according to some embodiments of the disclosure.

Expansion is typically 1,000-fold during a first REP cycle. Expansion during REP1 varied highly (316-7,800-fold, data not shown). Inaccurate quantification of low input cell numbers may have contributed to this variability. Shown here in FIG. 23A is fold-expansion obtained from a second REP protocol following the first cycle (n=20 experiments, 11 donors, 12 STIMs). Expansion ranged from about 200 up to about 2000 fold. However, there was no clear correlation between extent of expansion in REP1 and REP2 for a particular cell population in these experiments.

Figure 23B:
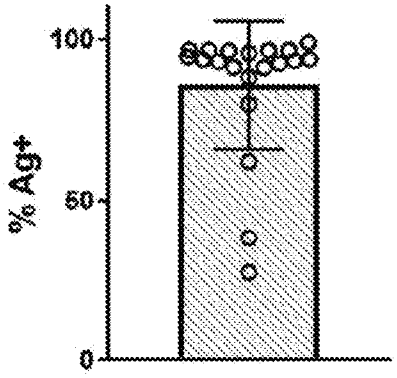

In FIG. 23B, the percentages of antigen-specific T cells in the REP populations are shown for the 20 experiments of the REP protocol. What was observed was that high percentages of antigen-specific T cells (% Ag+), typically ~90%, were maintained during at least two REP cycles. In contrast, Low % Ag+after REP1 led to low % Ag+after REP2.

Figure 23C:
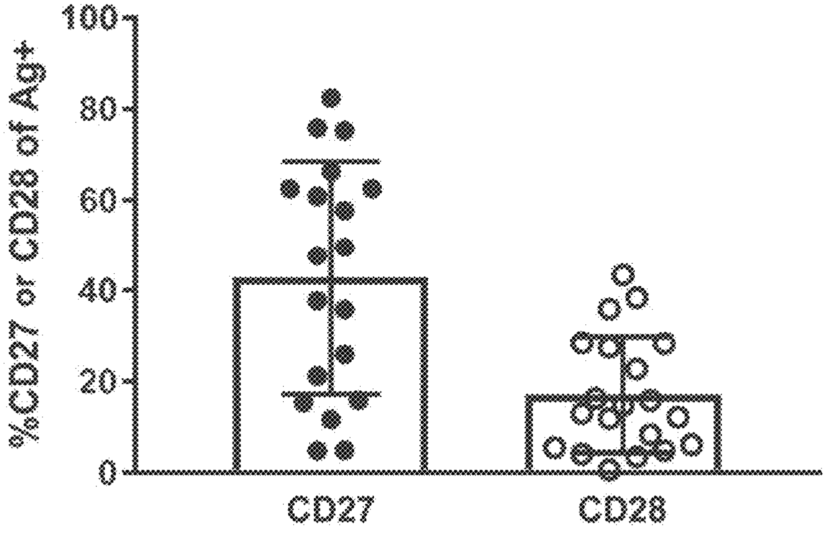
Figure 23D:
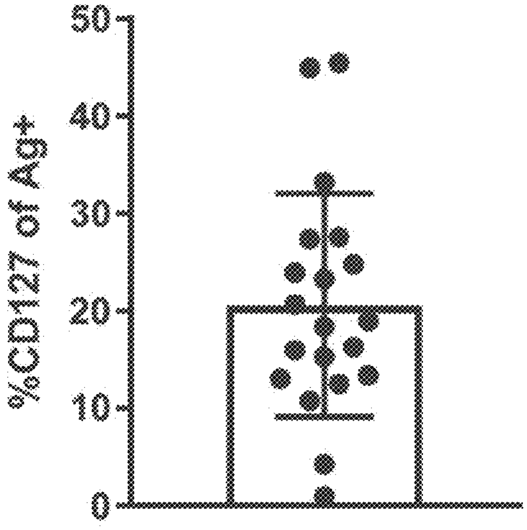

In FIG. 23C, the percentages of antigen-specific T cells also expressing co-stimulatory receptors CD27 and CD28, after the completion of REP2, are shown. In FIG. 23D, the percentages of antigen-specific T cells also expressing CD127, a marker for a central memory phenotype which can presage persistence in vivo, after the completion of REP2 is shown. While the distribution of expression of any of the markers was not tightly clustered, and some of the individual experiments showed low (e.g., a few percent) of cells that express the desired markers, the cellular products obtained in each of these experiments demonstrated sufficiently positive phenotype across all categories to render them candidates for in-vivo introduction. Some of the depressed values seen, such as expression of CD28, may be due to the extensive stimulation using CD28 ligands used during the activation cycles, leading to depressed expression of these surface markers.

Figure 23E:
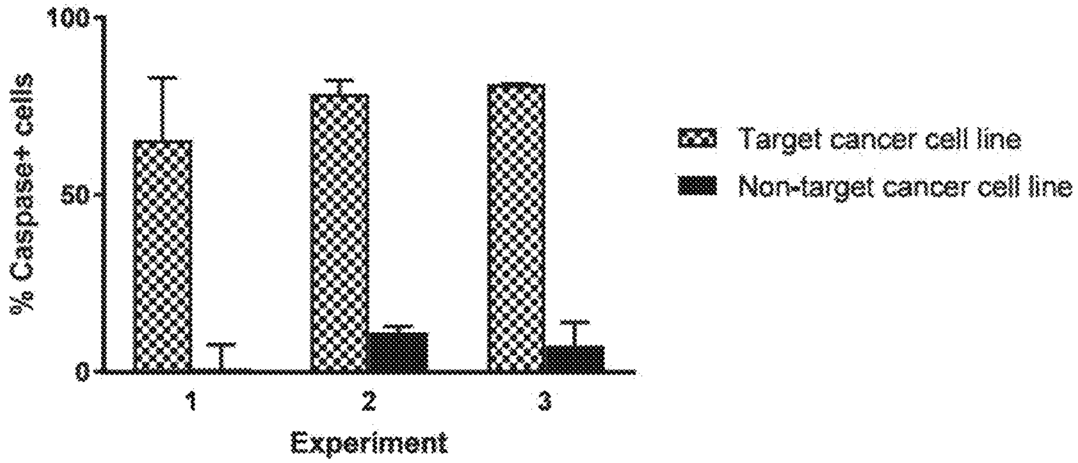
Figure 24:
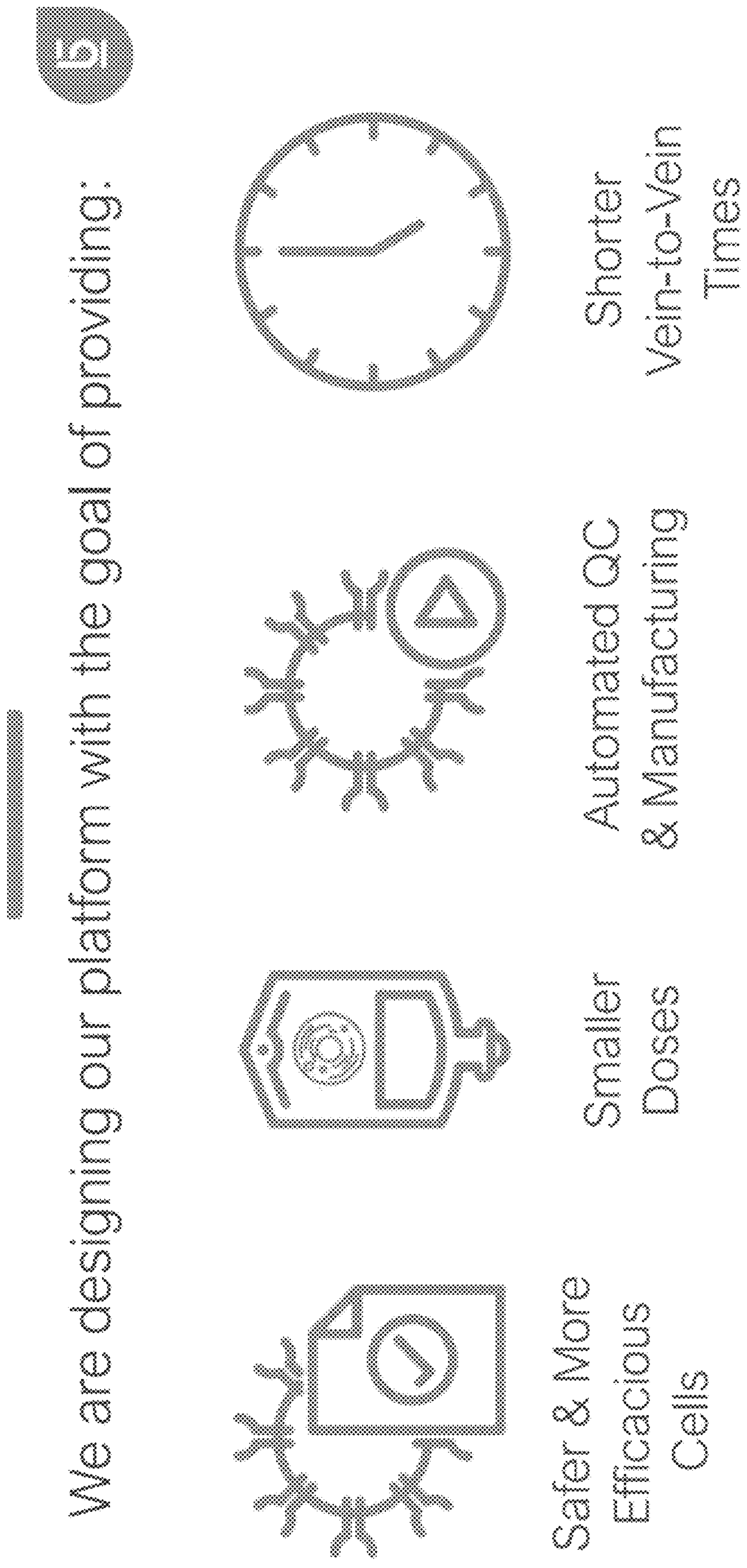
Figure 25A:
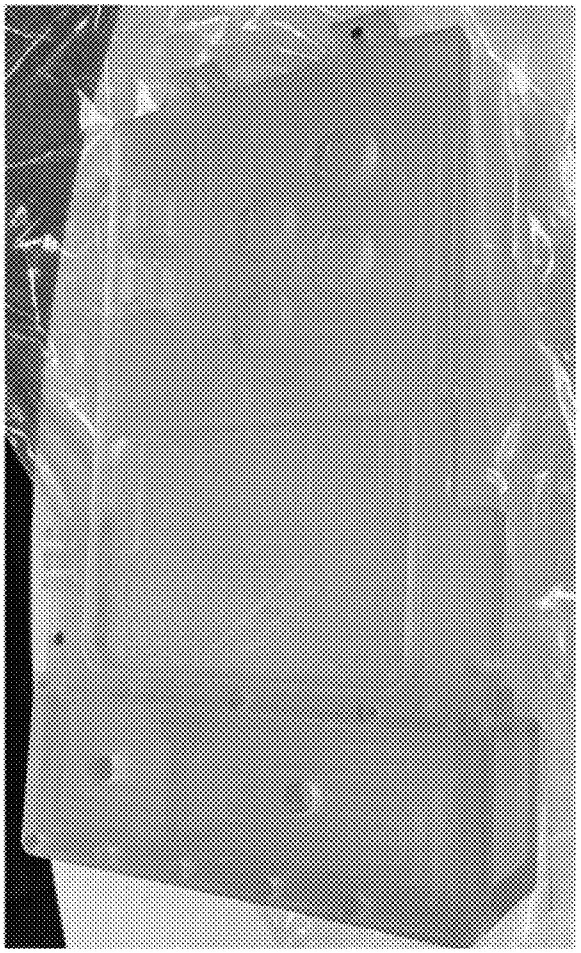
FIGS. 25A-25B are images of an exemplary cartridge and first chamber of the cartridge according to some embodiments of the disclosure.
Figure 25B:
Figure 26:
FIG. 26 is a depiction of various benefits that can be provided by the cartridges according to some embodiments of the disclosure.
Figure 27:
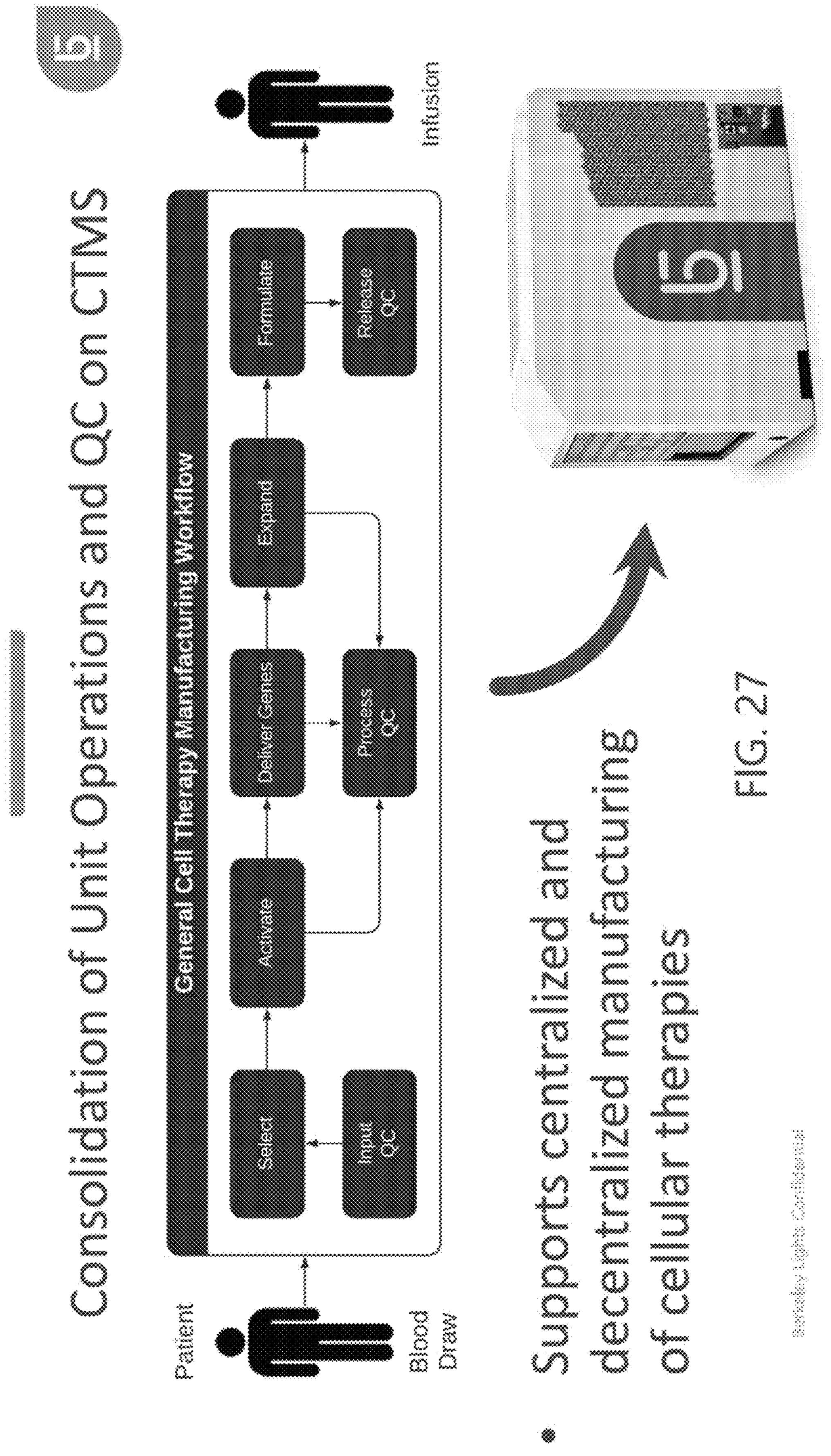
FIG. 27 is a depiction of workflow steps than be can performed by the systems according to some embodiments of the disclosure.

In FIG. 23E, the results of antigen-specific cytotoxicity assay for each of three individual cellular populations, after two rounds of REP, are shown. The assay was performed as described in Example 24, using Mel526 cells as the Target cancer cell line and A375 cells as the non-targeted cell line, wherein the antigen specific T cells were SLC45A2-specific T cells. In each experiment, more than 50% of the targeted Mel526 cells exhibited Caspase 3 triggered fluorescent signal, while none to a few percent of the A375 non-targeted cells exhibited apoptotic behavior as signaled by the fluorogenic cleavage product of the Caspase-3 substrate. Therefore, the activated T cells still exhibited antigen-specific cell killing behavior after all of the rounds of activation and expansion.

Therefore, the processes of activation via antigen presentation on a synthetic surface as described herein can provide well controlled, reproducible and characterizable cellular products suitable for use in immunotherapy. The antigen-presenting surfaces described herein provide lower cost of manufacture for these individualized therapies compared to currently available experimental processes.

XV. RECITATION OF SOME EMBODIMENTS OF THE DISCLOSURE

1. An antigen-presenting surface for activating a T lymphocyte (T cell), including:
   - a plurality of primary activating molecular ligands, wherein each primary activating molecular ligand includes a major histocompatibility complex (MHC) Class I molecule configured to bind to a T cell receptor (TCR) of the T cell; and a plurality of co-activating molecular ligands each including a TCR co-activating molecule or an adjunct TCR activating molecule, wherein each of the plurality of primary activating molecular ligands and the plurality of co-activating molecular ligands is specifically bound to the antigen presenting surface.

2. The antigen-presenting surface of embodiment 1, wherein the plurality of co-activating molecular ligands comprises TCR co-activating molecules and adjunct TCR activating molecules.

3. The antigen-presenting surface of embodiment 1 or 2, wherein a ratio of the TCR co-activating molecules to the adjunct TCR activating molecules of the plurality of co-activating molecular ligands is about 100:1 to about 1:100.

4. The antigen-presenting surface of embodiment 1 or 2, wherein a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about."

5. The antigen-presenting surface of embodiment 1 or 2, wherein the ratio of the TCR co-activating molecules to the adjunct TCR activating molecule is about 10:1 to about 1:20.

6. The antigen-presenting surface of embodiment 1 or 2, wherein a ratio of the TCR co-activating molecules to the adjunct TCR activating molecules of the plurality of co-activating molecular ligands is about 10:1 to about 1:10.

7. The antigen-presenting surface of any one of the preceding embodiments, wherein the plurality of primary activating molecular ligands is disposed upon at least a portion of the antigen-presenting surface at a density from about $4\times10^2$ to about $3\times10^4$ molecules per square micron, in each portion or sub-region where it is attached.

8. The antigen-presenting surface of embodiment 7, wherein the plurality of primary activating molecular ligands is disposed upon at least a portion of the antigen-presenting surface at a density from about $4\times10^2$ to about $2\times10^3$ molecules per square micron.

9. The antigen-presenting surface of embodiment 7, wherein the plurality of primary activating molecular ligands is disposed upon at least a portion of the antigen-presenting surface at a density from about $2\times10^3$ to about $5\times10^3$ molecules per square micron.

10. The antigen-presenting surface of embodiment 7, wherein the plurality of primary activating molecular ligands is disposed upon at least a portion of a surface of the antigen-presenting surface at a density from about $5\times10^3$ to about $2\times10^4$ molecules per square micron, about $1\times10^4$ to about $2\times10^4$ molecules per square micron, or about $1.25\times10^4$ to about $1.75\times10^4$ molecules per square micron.

11. The antigen-presenting surface of any one of embodiments 7-10, wherein the plurality of primary activating molecular ligands is disposed upon substantially all of the antigen-presenting surface at the stated density.

12. The antigen-presenting surface of any one of embodiments 1-11, further including a plurality of surface-blocking molecular ligands.

13. The antigen-presenting surface of any one of embodiments 1-12, wherein the adjunct TCR activating molecule is configured to provide adhesion stimulation.

14. The antigen-presenting surface of any one of embodiments 1-13, wherein the plurality of co-activating molecular ligands is disposed upon at least a portion the antigen-presenting surface at a density from about $5\times10^2$ to about $2\times10^4$ molecules per square micron or about $5\times10^2$ to about $1.5\times10^4$ molecules per square micron.

15. The antigen-presenting surface of any one of embodiments 1 to 14, wherein the plurality of co-activating molecular ligands is disposed upon at least a portion of the antigen-presenting surface at a density from about $5\times10^3$ to about $2\times10^4$ molecules per square micron, about $5\times10^3$ to about $1.5\times10^4$ molecules per square micron, about $1\times10^4$ to about $2\times10^4$ molecules per square micron, about $1\times10^4$ to about $1.5\times10^4$ molecules per square micron, about $1.25\times10^4$ to about $1.75\times10^4$ molecules per square micron, or about $1.25\times10^4$ to about $1.5\times10^4$ molecules per square micron.

16. The antigen-presenting surface of any one of embodiments 1-14, wherein the plurality of co-activating molecular ligands is disposed upon at least a portion of the antigen-presenting surface at a density from about $2\times10^3$ to about $5\times10^3$ molecules per square micron.

17. The antigen-presenting surface of any one of embodiments 1-14, wherein the plurality of co-activating molecular ligands is disposed upon at least a portion of a surface of the antigen-presenting surface at a density from about $5\times10^2$ to about $2\times10^3$ molecules per square micron.

18. The antigen-presenting surface of any one of embodiments 14-17, wherein the plurality of co-activating molecular ligands is disposed upon substantially all of the antigen-presenting surface at the stated density.

19. The antigen-presenting surface of any one of embodiments 1-18, wherein a ratio of the primary activating molecular ligands to the co-activating molecular ligands present on the antigen-presenting surface is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

20. The antigen-presenting surface of any one of embodiments 1-19, wherein the antigen-presenting surface includes glass, metal, ceramic, and/or a metal oxide or any combination thereof.

21. The antigen-presenting surface of any one of embodiments 1-20, wherein the antigen-presenting surface includes a polymeric surface.

22. The antigen-presenting surface of embodiment 20 or 21, wherein the surface includes a magnetic material.

23. The antigen-presenting surface of any one of embodiments 1 to 22, wherein each of the plurality of primary activating molecular ligands is noncovalently bound to a binding moiety, and further wherein the binding moiety is covalently bound to the antigen-presenting surface.

24. The antigen-presenting surface of embodiment 23, wherein each of the plurality of primary activating molecular ligands comprises a biotin and is noncovalently bound to a biotin-binding agent, and further wherein the biotin-binding agent is covalently bound to the antigen-presenting surface.

25. The antigen-presenting surface of any one of embodiments 1 to 22, wherein each of the plurality of primary activating molecular ligands is noncovalently bound to a binding moiety, and further wherein the binding moiety is noncovalently bound to the antigen-presenting surface.

26. The antigen-presenting surface of embodiment 25, wherein each of the plurality of primary activating molecular ligands comprises a biotin moiety, the binding moiety comprises a biotin-binding agent, and the biotin-binding agent is noncovalently bound to a second biotin moiety covalently attached to the antigen-presenting surface.

27. The antigen-presenting surface of 24 or 26, wherein the biotin-binding agent is streptavidin.

28. The antigen-presenting surface of any one of embodiments 1 to 27, wherein the MHC molecule includes an MHC protein sequence and a beta microglobulin.

29. The antigen-presenting surface of any one of embodiments 1 to 28, wherein the MHC molecule further includes a tumor specific antigen.

30. The antigen-presenting surface of embodiment 29, wherein the tumor specific antigen is non-covalently associated with the MHC molecule.

31. The antigen-presenting surface of embodiment 29 or 30, wherein the antigen is SLC45A2, TCL1, VCX3A, MART1 or NYESO1.

32. The antigen-presenting surface of any one of embodiments 1-31, wherein the TCR co-activating molecule includes a protein.

33. The antigen-presenting surface of embodiment 32, wherein the TCR co-activating protein molecule includes a CD-28 binding protein or a fragment thereof which retains binding ability with CD28.

34. The antigen-presenting surface of embodiment 32 or 33, wherein the TCR co-activating molecule further comprises a site-specific C-terminal biotin moiety.

35. The antigen-presenting surface of embodiment 33 or 34, wherein the CD28 binding protein includes a CD80 molecule or a fragment thereof, wherein the fragment retains binding ability to CD28.

36. The antigen-presenting surface of any one of embodiments 32-35 wherein the TCR co-activating molecule includes an anti-CD28 antibody or fragment thereof, wherein the fragment retains binding activity with CD28.

37. The antigen-presenting surface of any one of embodiments 1-36, wherein the adjunct TCR activating molecular ligand includes a CD2 binding protein or a fragment thereof, wherein the fragment retains binding ability with CD2.

38. The antigen-presenting surface of embodiment 37, wherein the CD2 binding protein further comprises a site-specific C-terminal biotin moiety.

39. The antigen-presenting surface of embodiment 37 or 38, wherein the adjunct TCR activating molecular ligand includes a CD58 molecule or fragment thereof, wherein the fragment retains binding activity with CD2.

40. The antigen-presenting surface of any one of embodiments 1-39, wherein the adjunct TCR activating molecule includes an anti-CD2 antibody or a fragment thereof, wherein the fragment retains binding activity with CD2.

41. The antigen-presenting surface of any one of embodiments 1-40, wherein each of the plurality of co-activating molecular ligands is non-covalently attached to a streptavidin wherein the streptavidin is non-covalently attached to a streptavidin binding molecule, further wherein the streptavidin binding molecule is covalently attached via a linker to the antigen-presenting surface, optionally wherein the streptavidin binding molecule comprises biotin.

42. The antigen-presenting surface of any one of embodiments 1-40, wherein each of the plurality of co-activating molecular ligands is covalently connected to the surface via a linker.

43. The antigen-presenting surface of embodiment 41 or 42, wherein the linker links the streptavidin binding molecule and/or co-activating molecular ligands to the surface through a series of about 15, 20, 25, 30, 35, 40, 45, 50, 55, 60, 65, 70, 75, 80, 85, 95, 100, 200 bond lengths, or any number of bond lengths therebetween bonds.

44. The antigen-presenting surface of any one of embodiments 1-40, wherein each of the plurality of co-activating molecular ligands is non-covalently attached to a streptavidin moiety; and the streptavidin moiety is covalently attached to the antigen-presenting surface.

45. The antigen-presenting surface of embodiment 42, wherein the streptavidin moiety is linked by a linker to the surface through a series of about 15, 20, 25, 30, 35, 40, 45, 50, 55, 60, 65, 70, 75, 80, 85, 95, 100, 200 bond lengths, or any number of bond lengths therebetween.

46. The antigen-presenting surface of any one of embodiments 5-45, wherein:

(i) each of the plurality of surface-blocking molecular ligands includes a hydrophilic moiety, an amphiphilic moiety, a zwitterionic moiety, and/or a negatively charged moiety;

(ii) each of the plurality of surface-blocking molecular ligands includes a linker and a terminal surface-blocking group, optionally wherein the linkers of the plurality of surface-blocking molecular ligands are of the same length or are of different lengths; or (iii) each of the plurality of surface-blocking molecular ligands includes a linker and a terminal surface-blocking group, wherein the terminal surface-blocking group comprises a hydrophilic moiety, amphiphilic moiety, zwitterionic moiety, and/or negatively charged moiety, optionally wherein the linkers of the plurality of surface-blocking molecular ligands are of the same length or are of different lengths.

47. The antigen-presenting surface of embodiment 46, wherein:

(i) the plurality of surface-blocking molecular ligands all have the same terminal surface-blocking group; or (ii) the plurality of surface-blocking molecular ligands have a mixture of terminal surface-blocking groups; optionally wherein each of the plurality of surface-blocking molecular ligands includes a polyethylene glycol (PEG) moiety, a carboxylic acid moiety, or a combination thereof, further optionally wherein the PEG moiety of each of the surface-blocking molecular ligands has a backbone linear chain length of about 10 atoms to about 100 atoms.

48. The antigen-presenting surface of any one of embodiments 5-47, wherein:

(i) each of the plurality of surface-blocking molecular ligands is covalently connected to the antigen-presenting surface; and/or (ii) the plurality of the surface-blocking molecular ligands and may include 2, 3, or 4 different surface-blocking groups and/or 2, 3, 4, or more different lengths of linkers, chosen in any combination.

49. The antigen-presenting surface of any one of embodiments 1-48, further including a plurality of adhesion stimulatory molecular ligands, optionally wherein each adhesive molecular ligand includes a ligand for a cell adhesion receptor comprising an ICAM protein sequence.

50. The antigen-presenting surface of embodiment 49, wherein the adhesion stimulatory molecular ligand is covalently connected to the antigen-presenting surface via a linker.

51. The antigen-presenting surface of embodiment 50, wherein the adhesion stimulatory molecular ligand is non-covalently attached to a streptavidin moiety, wherein the streptavidin moiety is covalently attached via a linker to the antigen-presenting surface.

52. The antigen-presenting surface of embodiment 50, wherein the adhesion stimulatory molecular ligand is non-covalently attached to a streptavidin, wherein the streptavidin is noncovalently attached to a biotin and the biotin is covalently attached via a linker to the antigen-presenting surface.

53. The antigen-presenting surface of any one of embodiments 1-52, wherein the ratio of the TCR co-activating molecules to the adjunct TCR activating molecules of the plurality of co-activating molecular ligands is from about 3:1 to about 1:3.

54. The antigen-presenting surface of any one of embodiments 1-53, wherein the ratio of the TCR co-activating molecules to the adjunct TCR activating molecules of the plurality of co-activating molecular ligands is about 1:2 to about 2:1.

55. The antigen-presenting surface of any one of embodiments 1-54, wherein the ratio of the TCR co-activating molecules to the adjunct TCR activating molecules of the plurality of co-activating molecular ligands is about 1:1.

56. The antigen-presenting surface of any one of embodiments 1-55, further including a plurality of growth-stimulatory molecular ligands, wherein each of the growth-stimulatory molecular ligands includes a growth factor receptor ligand.

57. The antigen-presenting surface of embodiment 56, wherein the growth factor receptor ligand includes a cytokine or fragment thereof, wherein the fragment retains receptor binding ability, optionally wherein the cytokine comprises IL-21.

58. The antigen-presenting surface of any one of the embodiments 1-57, which is an antigen-presenting surface of a bead.

59. The antigen-presenting surface of embodiment 58, wherein the bead has a surface area within 10% of the surface area of a sphere having an equal volume or diameter.

60. The antigen-presenting surface of embodiment 58, wherein the bead has a surface area exceeding by more than 10% the surface area of a sphere having an equal volume or diameter.

61. The antigen-presenting surface of any one of the embodiments 1-57, which is an antigen-presenting surface of a microfluidic device, wafer, or tube.

62. The antigen-presenting surface of embodiment 61, further including a first portion and a second portion, wherein the distribution of the plurality of primary activating molecular ligands and the distribution of the plurality of co-activating molecular ligands are located in the first portion of the antigen-presenting surface, and the second portion is configured to substantially exclude the primary activating molecular ligands.

63. The antigen-presenting surface of embodiment 62, wherein at least one plurality of surface-blocking molecular ligands is located in the second portion of the at least one inner surface of the antigen-presenting surface.

64. The antigen-presenting surface of 62 or 63, wherein the first portion of the antigen-presenting surface further includes a plurality of first regions, each first region including at least a subset of the plurality of the primary activating molecular ligands, wherein each of the plurality of first regions is separated from another of the plurality of first region by the second portion configured to substantially exclude primary activating molecular ligands.

65. The antigen-presenting surface of embodiment 64, wherein each of the plurality of first regions including the at least a subset of the plurality of the primary activating molecular ligands further includes a subset of the plurality of the co-activating molecular ligands.

66. The antigen-presenting surface of embodiment 64 or 65, wherein each of the plurality of first regions including at least the subset of the plurality of the primary activating molecular ligands has an area of about 0.10 square microns to about 4.0 square microns.

67. The antigen-presenting surface of any one of embodiments 64-66, wherein the area of each of the plurality of first regions including at least the subset of the plurality of the primary activating molecular ligands is about 4.0 square microns to about 0.8 square microns.

68. The antigen-presenting surface of any one of embodiments 64-67, wherein each of the plurality of first regions further includes at least a subset of a plurality of adhesion stimulatory molecular ligands, and optionally wherein each of the adhesion stimulatory molecular ligands includes a ligand for a cell adhesion receptor comprising an ICAM protein sequence.

69. The antigen-presenting surface of any one of embodiments 63-68, wherein the second portion configured to substantially exclude the primary activating molecular ligands is also configured to substantially exclude co-activating molecular ligands.

70. The antigen-presenting surface of any one of embodiments 62-69, wherein the second portion configured to substantially exclude the primary activating molecular ligands is further configured to include a plurality of growth stimulatory molecular ligands, wherein each of the growth stimulatory molecular ligands includes a growth factor receptor ligand.

71. The antigen-presenting surface of any one of embodiments 62-70, wherein the second portion configured to substantially exclude the primary activating molecular ligands includes a plurality of adhesion stimulatory molecular ligands, wherein each of the adhesion stimulatory molecular ligands includes a ligand for a cell adhesion receptor including an ICAM protein sequence.

72. The antigen-presenting surface of any one of embodiments 61-71, which is an antigen-presenting surface of a wafer.

73. The antigen-presenting surface of any one of embodiments 61-71, which is an antigen-presenting surface of a tube.

74. The antigen-presenting surface of any one of embodiments 61-71, which is an antigen-presenting surface of a microfluidic device.

75. The antigen-presenting microfluidic device of embodiment 74, wherein each of the plurality of first regions including at least a subset of the plurality of primary activating molecular ligands is disposed at least one surface within a chamber of the antigen-presenting microfluidic device.

76. The antigen-presenting microfluidic device of embodiment 75, wherein the chamber is a sequestration pen.

77. The antigen-presenting microfluidic device of embodiments 74-76, wherein the microfluidic device further comprises a flow region for containing a flow of a first fluidic medium; and the sequestration pen comprises an isolation region for containing a second fluidic medium, the isolation region having a single opening, wherein the isolation region of the sequestration pen is an unswept region of the microfluidic device; and a connection region fluidically connecting the isolation region to the flow region; optionally wherein the microfluidic device comprises a microfluidic channel comprising at least a portion of the flow region.

78. The antigen-presenting microfluidic device of embodiment 77, wherein the microfluidic device comprises a microfluidic channel comprising at least a portion of the flow region, and the connection region comprises a proximal opening into the microfluidic channel having a width $W_{con}$ ranging from about 20 microns to about 100 microns and a distal opening into the isolation region, and wherein a length $L_{con}$ of the connection region from the proximal opening to the distal opening is as least 1.0 times a width $W_{con}$ of the proximal opening of the connection region.

79. The antigen-presenting microfluidic device of embodiment 78, wherein the length $L_{con}$ of the connection region from the proximal opening to the distal opening is at least 1.5 times the width $W_{con}$ of the proximal opening of the connection region.

80. The antigen-presenting microfluidic device of embodiment 78, wherein the length $L_{con}$ of the connection region from the proximal opening to the distal opening is at least 2.0 times the width $W_{con}$ of the proximal opening of the connection region.

81. The antigen-presenting microfluidic device of any one of embodiments 78-80, wherein the width $W_{con}$ of the proximal opening of the connection region ranges from about 20 microns to about 60 microns.

82. The antigen-presenting microfluidic device of any one of embodiments 78-81, wherein the length $L_{con}$ of the connection region from the proximal opening to the distal opening is between about 20 microns and about 500 microns.

83. The antigen-presenting microfluidic device of any one of embodiments 78-82, wherein a width of the microfluidic channel at the proximal opening of the connection region is between about 50 microns and about 500 microns.

84. The antigen-presenting microfluidic device of any one of embodiments 78-83, wherein a height of the microfluidic channel at the proximal opening of the connection region is between 20 microns and 100 microns.

85. The antigen-presenting microfluidic device of any one of embodiments 77-84, wherein the volume of the isolation region ranges from about $2\times10^4$ to about $2\times10^6$ cubic microns.

86. The antigen-presenting microfluidic device of any one of embodiments 77-85, wherein the proximal opening of the connection region is parallel to a direction of the flow of the first medium in the flow region.

87. The antigen-presenting microfluidic device of any one of embodiments 77-86, wherein the microfluidic device comprises an enclosure comprising a base, a microfluidic circuit structure disposed on the base, and a cover which collectively define a microfluidic circuit, and the microfluidic circuit comprises the flow region, the microfluidic channel, and the sequestration pen.

88. The antigen-presenting microfluidic device of any one of embodiments 77-87, wherein the microfluidic circuit further comprises one or more inlets through which the first medium can be input into the flow region and one or more outlets through which the first medium can be removed from the flow region.

89. The antigen-presenting microfluidic device of embodiment 87, wherein the cover is an integral part of the microfluidic circuit structure.

90. The antigen-presenting microfluidic device of embodiment 87 or 88, wherein barriers defining the microfluidic sequestration pen extend from a surface of the base of the microfluidic device to a surface of the cover of the microfluidic device.

91. The antigen-presenting microfluidic device of any one of embodiments 87-90, wherein the cover and the base are part of a dielectrophoresis (DEP) mechanism for selectively inducing DEP forces on a micro-object.

92. The antigen-presenting microfluidic device of any one of embodiments 87-91, wherein the microfluidic device further comprises a first electrode, an electrode activation substrate, and a second electrode, wherein the first electrode is part of a first wall of the enclosure and the electrode activation substrate and the second electrode is part of a second wall of the enclosure, wherein the electrode activation substrate comprises a photoconductive material, semiconductor integrated circuits, or phototransistors.

93. The antigen-presenting microfluidic device of embodiment 92, wherein the first wall of the microfluidic device is the cover, and wherein the second wall of the microfluidic device is the base.

94. The antigen-presenting microfluidic device of embodiment 92 or 93, wherein the electrode activation substrate comprises phototransistors.

95. The antigen-presenting microfluidic device of any one of embodiments 87-94, wherein the cover and/or the base is transparent to light.

96. The antigen-presenting microfluidic device of any one of embodiments 61-95, wherein the second portion is disposed at at least one surface of a microfluidic channel of the antigen-presenting microfluidic device.

97. A covalently functionalized synthetic surface including at least one plurality of biotin-binding agent or biotin functionalities and at least one plurality of surface-blocking molecular ligands, wherein each of the biotin-binding agent or biotin functionalities and each of the plurality of surface-blocking molecular ligands are covalently attached to the covalently functionalized synthetic surface.

98. The covalently functionalized synthetic surface of embodiment 97, wherein the surface includes the plurality of biotin functionalities.

99. The covalently functionalized synthetic surface of embodiment 98, wherein the surface further includes a plurality of biotin-binding agent functionalities noncovalently attached to the surface through the biotin functionalities.

100. The covalently functionalized synthetic surface of any one of embodiments 97-99, wherein each of the plurality of biotin functionalities is attached to the covalently functionalized surface via a linker.

101. The covalently functionalized synthetic surface of any one of embodiments 97-100, wherein the biotin-binding agent is streptavidin.

102. The covalently functionalized synthetic surface of embodiment 97 or 101, wherein each of the plurality of biotin or biotin-binding agent functionalities is attached to the covalently functionalized surface via a linker.

103. The covalently functionalized synthetic surface of embodiment 102, wherein the linker linking the biotin or biotin-binding agent functionality has a length of about 20 Angstroms to about 100 Angstroms.

104. The covalently functionalized synthetic surface of embodiment 102 or 103, wherein the linker links the biotin-binding agent functionality to the surface through a series of about 15, 20, 25, 30, 35, 40, 45, 50, 55, 60, 65, 70, 75, 80, 85, 95, 100, 200 bond lengths, or any number of bond lengths therebetween . . .

105. The covalently functionalized synthetic surface of embodiment 102 or 103, wherein the linker links the biotin to the surface through a series of about 15, 20, 25, 30, 35, 40, 45, 50, 55, 60, 65, 70, 75, 80, 85, 95, 100, 200 bond lengths, or any number of bond lengths therebetween.

106. The covalently functionalized synthetic surface of any one of embodiments$10^2$-105, wherein the linker of each biotin or biotin-binding agent functionality includes a polyethylene glycol (PEG) moiety.

107. The covalently functionalized synthetic surface of embodiment 106, wherein the PEG linker includes a $(PEG)_{13}$ repeating sequence, optionally wherein the surface includes the plurality of biotin-binding agent functionalities.

108. The covalently functionalized synthetic surface of embodiment 106, wherein the PEG linker includes a $(PEG)_4$ repeating sequence, optionally wherein the surface includes the plurality of biotin functionalities.

109. The covalently functionalized synthetic surface of any one of embodiments 97-108, wherein:

(i) each of the plurality of surface-blocking molecular ligands includes a hydrophilic moiety, an amphiphilic moiety, a zwitterionic moiety, and/or a negatively charged moiety;

(ii) each of the plurality of surface-blocking molecular ligands includes a linker and a terminal surface-blocking group, optionally wherein the linkers of the plurality of surface-blocking molecular ligands are of the same length or are of different lengths; or (iii) each of the plurality of surface-blocking molecular ligands includes a linker and a terminal surface-blocking group, wherein the terminal surface-blocking group comprises a hydrophilic moiety, amphiphilic moiety, zwitterionic moiety, and/or negatively charged moiety, optionally wherein the linkers of the plurality of surface-blocking molecular ligands are of the same length or are of different lengths;

(iv) each of the plurality of surface-blocking molecular ligands is covalently connected to the antigen-presenting surface; and/or (v) the plurality of the surface-blocking molecular ligands and may include 2, 3, or 4 different surface-blocking groups and/or 2, 3, 4, or more different lengths of linkers, chosen in any combination.

110. The covalently functionalized synthetic surface of embodiment 109, wherein:

(i) the plurality of surface-blocking molecular ligands all have the same terminal surface-blocking group; or (ii) the plurality of surface-blocking molecular ligands have a mixture of terminal surface-blocking groups; optionally wherein each of the plurality of surface-blocking molecular ligands includes a polyethylene glycol (PEG) moiety, a carboxylic acid moiety, or a combination thereof.

111. The covalently functionalized synthetic surface of embodiment 108, wherein the PEG moiety of each of the surface-blocking molecular ligands has a backbone linear chain length of about 10 atoms to about 100 atoms.

112. The covalently functionalized synthetic surface of any one of embodiments 97-111, wherein the at least one plurality of streptavidin moieties is disposed upon the covalently functionalized synthetic surface in a density from about $4\times10^2$ to about $3\times10^4$ molecules per square micron, in each portion or sub-region where it is attached.

113. The covalently functionalized synthetic surface of any one of embodiments 97-111, wherein the at least one plurality of streptavidin moieties is disposed upon the covalently functionalized synthetic surface in a density from about $5\times10^3$ to about $3\times10^4$ molecules per square micron, in each portion or sub-region where it is attached.

114. The covalently functionalized synthetic surface of any one of embodiments 97-111, wherein the at least one plurality of streptavidin moieties is disposed upon the covalently functionalized synthetic surface from about $6\times10^2$ to about $5\times10^3$ molecules per square micron, about $5\times10^3$ to about $2\times10^4$ molecules per square micron, about $1\times10^4$ to about $2\times10^4$ molecules per square micron, or about $1.25\times10^4$ to about $1.75\times10^4$ molecules per square micron, in each portion or sub-region where it is attached.

115. The covalently functionalized synthetic surface of any one of embodiments 97-114, wherein the surface includes glass, polymer, metal, ceramic, and/or a metal oxide.

116. The covalently functionalized synthetic surface of any one of embodiments 97-115, wherein the covalently functionalized synthetic surface is a covalently functionalized wafer, a covalently functionalized inner surface of a tube, or a covalently functionalized inner surface of a microfluidic device.

117. The covalently functionalized synthetic surface of embodiment 116, wherein the tube is a glass or polymer tube.

118. The covalently functionalized synthetic surface of any one of embodiments 97 to 115, wherein the covalently functionalized synthetic surface is a covalently functionalized bead.

119. The covalently functionalized synthetic surface of embodiment 118, wherein the covalently functionalized bead includes a magnetic material.

120. The covalently functionalized synthetic surface of embodiment 118 or 119, wherein the bead has a surface area within 10% of the surface area of a sphere of an equal volume or diameter.

121. The covalently functionalized synthetic surface of any one of embodiments 118-120, wherein the at least one plurality of streptavidin or biotin moieties is disposed upon substantially all of the covalently functionalized synthetic surface.

122. The covalently functionalized synthetic surface of any one of embodiments 97-117, further including a first portion and a second portion, wherein the distribution of the at least one plurality of streptavidin or biotin functionalities is located in the first portion of the covalently modified synthetic surface, and the distribution of the at least one plurality of the surface-blocking molecular ligands is located in the second portion.

123. The covalently functionalized synthetic surface of embodiment 122, wherein a second plurality of surface-blocking molecular ligands is disposed in the first portion of the covalently functionalized synthetic surface.

124. The covalently functionalized synthetic surface of embodiment 123, wherein the second plurality of surface-blocking molecular ligands limits the density of functionalizing moieties of an antigen-presenting synthetic surface formed from the covalently functionalized synthetic surface.

125. The covalently functionalized synthetic surface of embodiment 123 or 125, wherein the first portion of the covalently functionalized synthetic surface further includes a plurality of first regions, each first region including at least a subset of the plurality of the streptavidin or biotin functionalities, wherein each of the plurality of first regions is separated from another of the plurality of first regions by the second region configured to substantially exclude the streptavidin or biotin functionalities.

126. The covalently functionalized synthetic surface of embodiment 125, wherein each of the plurality of first regions including at least the subset of the plurality of the streptavidin or biotin functionalities has an area of about 0.10 square microns to about 4.0 square microns.

127. The covalently functionalized synthetic surface of embodiment 125 or 126, wherein the area of each of the plurality of first regions including at least the subset of the plurality of the primary activating molecular ligands is about 4.0 square microns to about 0.8 square microns.

128. The covalently functionalized synthetic surface of any one of embodiments 97-116 or 122-127, wherein the covalently functionalized synthetic surface is at least one inner surface of a microfluidic device.

129. The covalently functionalized synthetic surface of embodiment 128, wherein each of the plurality of first regions including at least a subset of the plurality of biotin-binding agent or biotin functionalities includes at least one surface within a chamber of the microfluidic device.

130. The covalently functionalized synthetic surface of embodiment 129, wherein the chamber is a sequestration pen.

131.A kit for preparing an antigen-presenting synthetic surface for activating a T lymphocyte (T cell), including:

a. the covalently functionalized synthetic surface of any one of embodiments 95-128, which includes a plurality of noncovalently or covalently associated first coupling agents; and b. a first modification reagent including a plurality of major histocompatibility complex (MHC) I molecules configured to bind with a T cell receptor of the T cell, and further wherein the MHC molecules are configured to bind to one of a first subset of the plurality of noncovalently or covalently associated first coupling agents of the covalently functionalized synthetic surface;

optionally wherein the first coupling agents are biotin-binding agents.

132. The kit of embodiment 131, wherein each of the plurality of MHC molecules further includes at least one biotin functionality.

133. The kit of embodiment 131 or 132, further including a reagent including a plurality of co-activating molecules, each configured to bind one of a second subset of the plurality of noncovalently or covalently associated first coupling agents of the covalently functionalized synthetic surface.

134. The kit of embodiment 133, wherein each of the plurality of co-activating molecules includes a biotin functionality.

135. The kit of embodiment 134, wherein each of the plurality of co-activating molecules further comprises a site-specific C-terminal biotin moiety.

136. The kit of any one of embodiments 133-135, wherein each of the co-activating molecules includes a T cell receptor (TCR) co-activating molecule, an adjunct TCR activating molecule, or any combination thereof.

137. The kit of embodiment 136, wherein the plurality of co-activating molecular ligands comprises TCR co-activating molecules and adjunct TCR activating molecules.

138. The kit of embodiment 136 or 137, wherein a container containing the reagent including a plurality of co-activating molecules contains the TCR co-activating molecules and/or the adjunct TCR activating molecules of the plurality of co-activating molecular ligands in a ratio from about 100:1 to about 1:100 or in a ratio of about 3:1 to about 1:3.

139. The kit of any one of embodiments 136-138, wherein a container containing the reagent including a plurality of co-activating molecules contains the TCR co-activating molecules and the adjunct TCR activating molecules of the plurality of co-activating molecular ligands in a ratio from about 10:1 to about 1:10 or from about 10:1 to about 1:20.

140. The kit of any one of embodiments 136-139, wherein the ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about".

141. The kit of any one of embodiments 136-140, wherein a container containing the reagent including a plurality of co-activating molecules contains the TCR co-activating molecules and the adjunct TCR activating molecules of the plurality of co-activating molecular ligands in a ratio from about 20:1 to about 1:20.

142. The kit of embodiment 136, wherein the reagent including a plurality of co-activating molecules is contained in two containers, wherein the first container contains T cell receptor (TCR) co-activating molecules, and the second container contains adjunct TCR activating molecules.

143. The kit of any one of embodiments 136-142, wherein the TCR co-activating molecule is a CD28 binding protein or a fragment thereof which retains binding ability with CD28.

144. The kit of any one of embodiments 136-143, wherein the adjunct TCR co-activating molecule is a CD2 binding protein or a fragment thereof.

145. The kit of any one of embodiments 131-144, further including a reagent including adhesion stimulatory molecules, wherein each adhesion stimulatory molecule includes a ligand for a cell adhesion receptor including an ICAM protein sequence configured to react with a third subset of the plurality of noncovalently or covalently associated first coupling agent functionalities of the covalently functionalized synthetic surface.

146. The kit of embodiment 145, wherein the adhesion stimulatory molecule includes a biotin functionality.

147. The kit of any one of embodiments 131-146, further including a reagent including growth stimulatory molecules, wherein each growth stimulatory molecule includes a includes a growth factor receptor ligand.

148. The kit of embodiment 147, wherein the growth factor receptor ligand includes a cytokine or a fragment thereof.

149. The kit of embodiment 148, wherein the cytokine includes IL-21 or a fragment thereof.

150. The kit of any one of embodiments 147-149, further including one or more additional growth-stimulatory molecules.

151. The kit of embodiment 150, wherein the one or more additional growth-stimulatory molecules include IL2 and/or IL7, or fragments thereof.

152. The kit of any one of embodiments 148-151, wherein the growth stimulatory molecule is attached to a covalently modified bead.

153. The kit of any one of embodiments 131-152, wherein the first coupling agent is streptavidin.

154.A method of preparing a covalently functionalized surface including a plurality of biotin-binding agent or biotin functionalities and at least a first plurality of surface-blocking molecular ligands, wherein the method includes: reacting at least a first subset of reactive moieties of an intermediate reactive synthetic surface with a plurality of linking reagents, each linking reagent including biotin-binding agent or biotin; and reacting at least a second subset of reactive moieties of the intermediate reactive synthetic surface with a plurality of surface-blocking molecules, thereby providing the covalently functionalized synthetic surface including at the least one plurality of biotin-binding agent or biotin functionalities and at the least first plurality of surface-blocking molecular ligands.

155. The method of embodiment 154, wherein the linking reagents comprise biotin and the method further comprises noncovalently associating a biotin-binding agent with the biotin functionalities.

156. The method of embodiment 154 or 155, wherein the reactive moieties of at least first region of the intermediate reactive synthetic surface include azide moieties.

157. The method of any one of embodiments 154-156, wherein the reacting of the surface-blocking molecules is performed after the reacting of the linking reagents including biotin-binding agent or biotin functionalities.

158. The method of any one of embodiments 154-156, wherein the reacting of the surface-blocking molecules is performed at the same time as the reacting of the plurality of linking reagents.

159. The method of any one of embodiments 154-158, wherein the plurality of biotin-binding agent or biotin functionalities and the at least first plurality of surface-blocking molecular ligands are disposed in at least a first region of the covalently functionalized synthetic surface.

160. The method of embodiment 159, wherein the covalently functionalized synthetic surface includes a second region wherein the plurality of biotin-binding agent or biotin functionalities is excluded.

161. The method of embodiment 160, wherein the at least first plurality of surface-blocking molecular ligands are disposed in the second region of the covalently functionalized synthetic surface.

162. The method of embodiment 161, wherein the reacting of the reagent including surface-blocking molecules in the second region of the intermediate reactive synthetic surface is performed before the reacting of the linking reagents including biotin-binding agent or biotin functionalities in the at least first region of the intermediate reactive synthetic surface.

163. The method of embodiment 162, further including reacting a second plurality of surface-blocking molecules with a second subset of reactive moieties in the at least first region of the intermediate reactive synthetic surface.

164. The method of any one of embodiments 159-163, wherein the reacting of the plurality of biotin-binding agent or biotin functionalities and the reacting of the at least first plurality of surface-blocking molecules is performed at a plurality of sub-regions of the at least first region of the covalently prepared synthetic surface including reactive moieties.

165. The method of any one of embodiments 154-164, further including preparing the intermediate reactive synthetic surface, including: reacting at least a first surface preparing reagent including azide reactive moieties with surface-exposed moieties disposed at at least a first region of a reactive synthetic surface.

166. The method of embodiment 165, further including reacting a second portion of surface-exposed moieties disposed in a second region of the reactive synthetic surface with a plurality of surface-blocking molecules.

167. The method of embodiment 165 or 166, wherein the surface-exposed moieties of the at least first region of the reactive synthetic surface and the surface-exposed moieties of the second region of the reactive synthetic surface are not the same surface-exposed moieties.

168. The method of embodiment 166 or 167, wherein the second portion of the reactive synthetic surface includes surface exposed moieties configured to substantially not react with the pluralities of the primary activating and co-activating molecules.

169. The method of any one of embodiments 166-168, wherein the reacting the surface-exposed moieties of the second portion of the reactive synthetic surface with the plurality of surface-blocking molecules is performed before reacting the surface exposed moieties of the first portion of synthetic surface with the at least first surface preparing reagent to provide a covalently prepared surface at the first portion of the surface.

170. The method of any one of embodiments 165-169, wherein the surface-exposed moieties are nucleophilic moieties.

171. The method of any one of embodiments 165-170, wherein the surface-exposed moieties are displaceable moieties.

172. The method of any one of embodiments 154-171, wherein the distribution of the plurality of biotin-binding agent or biotin functionalities on the covalently functionalized synthetic surface is from about $6\times10^2$ to about $5\times10^3$ molecules per square micron, in each region where it is attached.

173. The method of any one of embodiments 154-171, wherein the distribution of the plurality of biotin-binding agent or biotin functionalities on the covalently functionalized synthetic surface is from about $5\times10^3$ molecules to about $1\times10^4$ molecules per square micron, in each region where it is attached.

174. The method of any one of embodiments 154-171, wherein the distribution of the plurality of biotin-binding agent or biotin functionalities on the covalently functionalized synthetic surface is from about $5\times10^3$ to about $3\times10^4$ molecules per square micron, about $5\times10^3$ to about $2\times10^4$ molecules per square micron, about $1\times10^4$ to about $3\times10^4$ molecules per square micron, about $1\times10^4$ to about $2\times10^4$ molecules per square micron, or about $1.25\times10^4$ to about $1.75\times10^4$ molecules per square micron, in each region where it is attached.

175. The method of any one of embodiments 154-174, wherein the surface is metal, glass, ceramic, polymer, or a metal oxide.

176. The method of any one of embodiments 154-175, wherein the surface is a surface of a bead, a surface of a wafer of any configuration, an inner surface of a tube, or at least one inner surface of a microfluidic device.

177. The method of embodiment 176, wherein the bead has a surface area within 10% of the surface area of a sphere of an equal volume or diameter.

178. The method of embodiment 176, wherein the tube is a glass or polymer tube.

179. The method of any one of embodiments 154 or 156-178, wherein the linking reagents include the biotin-binding agent.

180. The method of any one of embodiments 154-179, further comprising preparing an antigen-presenting surface for activating a T lymphocyte (T cell), including:

reacting a plurality of primary activating molecules, each including a major histocompatibility complex (MHC) Class I molecule configured to bind to a T cell receptor (TCR) of the T cell, with a first plurality of binding moieties disposed on a covalently functionalized surface, wherein each of the first plurality of binding moieties is configured for binding the primary activating molecule; and reacting a plurality of co-activating molecules, each including: a TCR co-activating molecule; or an adjunct TCR activating molecule, with a second plurality of binding moieties of the covalently functionalized surface configured for binding the co-activating molecule, thereby providing a plurality of specifically bound primary activating molecular ligands and a plurality of specifically bound co-activating molecular ligands on the antigen-presenting surface.

181. A method of preparing an antigen-presenting surface for activating a T lymphocyte (T cell), including: reacting a plurality of primary activating molecules, each including a major histocompatibility complex (MHC) Class I molecule configured to bind to a T cell receptor (TCR) of the T cell, with a first plurality of binding moieties disposed on a covalently functionalized surface, wherein each of the first plurality of binding moieties is configured for binding the primary activating molecule; and reacting a plurality of co-activating molecules, each including: a TCR co-activating molecule; or an adjunct TCR activating molecule, with a second plurality of binding moieties of the covalently functionalized surface configured for binding the co-activating molecule, thereby providing a plurality of specifically bound primary activating molecular ligands and a plurality of specifically bound co-activating molecular ligands on the antigen-presenting surface.

182. The method of embodiment 181, wherein the plurality of co-activating molecular ligands comprises TCR co-activating molecules and adjunct TCR activating molecules.

183. The method of embodiment 181 or 182, wherein a ratio of the TCR co-activating molecules to the adjunct TCR activating molecules of the plurality of co-activating molecular ligands is about 100:1 to about 1:100.

184. The method of any one of embodiments 181-183, wherein a ratio of the TCR co-activating molecules to the adjunct TCR activating molecules of the plurality of co-activating molecular ligands is about 10:1 to about 1:10.

185. The method of any one of embodiments 181-184, wherein a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about".

186. The method of any one of embodiments 181-185, wherein the ratio of the TCR co-activating molecules to the adjunct TCR activating molecules is about 20:1 to about 1:20 or about 3:1 to about 1:3.

187. The method of any one of embodiments 181-186, further including reacting a plurality of surface-blocking molecules with a third plurality of binding moieties of the covalently functionalized surface, wherein each of the binding moieties of the third plurality is configured for binding the surface-blocking molecule.

188. The method of any one of embodiments 181-187, wherein the MHC molecule includes a protein sequence and a beta microglobulin.

189. The method of any one of embodiments 181-188 wherein each of the plurality of primary activating molecules including an MHC molecule further includes a tumor specific antigen.

190. The method of embodiment 189, wherein the tumor specific antigen is SLC45A2, TCL1, VCX3A, MART1 or NYESO1.

191. The method of any one of embodiments 181-190, further including reacting a plurality of adhesion stimulatory molecular ligands, wherein each adhesion stimulatory molecular ligand includes a ligand for a cell adhesion receptor including an ICAM protein sequence, with a fourth plurality of binding moieties of the covalently functionalized surface, wherein each of the binding moieties of the fourth plurality is configured for binding with the cell adhesion receptor ligand molecule.

192. The method of any one of embodiments 181-191, wherein each of the first plurality of binding moieties of the covalently functionalized surface includes a biotin-binding agent or a biotin moiety.

193. The method of any one of embodiments 181-192, wherein the first plurality of binding moieties and the second plurality of binding moieties include the same binding moiety.

194. The method of any one of embodiments 181-193, wherein the second plurality of binding moieties and the third plurality of binding moieties configured to bind the surface-blocking molecules include the same binding moiety.

195. The method of any one of embodiments 181-194, further including producing the covalently functionalized surface including the first plurality of binding moieties by reacting at least a first subset of reactive moieties of an intermediate reactive surface with a first linking reagent each including a binding moiety.

196. The method of embodiment 195, wherein the binding moiety is a biotin-binding agent.

197. The method of any one of embodiments 193-196, wherein the second plurality of binding moieties is a second sub-set of the at least first plurality of binding moieties.

198. The method of any one of embodiments 195-197, wherein the second plurality of binding moieties of the covalently functionalized synthetic surface is a second sub-set of reactive moieties of the intermediate reactive surface.

199. The method of any one of embodiments 187-198, wherein the third plurality of binding moieties configured to bind the surface-blocking molecules is a third sub-set of the at least first plurality of binding moieties.

200. The method of any one of embodiments 195-198, wherein the third plurality of binding moieties configured to bind the surface-blocking molecules is a further subset of the reactive moieties of the intermediate reactive bead.

201. The method of any one of embodiments 181-200, wherein the covalently functionalized surface includes metal, glass, ceramic, polymer, a metal oxide, or any combination thereof.

202. The method of any one of embodiments 181-201, wherein the MHC molecule includes an MHC protein sequence and a beta microglobulin.

203. The method of embodiment 202, wherein the MHC molecule is connected to the covalently modified surface via a C-terminal connection of the MHC protein sequence.

204. The method of any one of embodiments 181-203, wherein the MHC molecule further includes an antigen specific peptide sequence.

205. The method of any one of embodiments 181-204, wherein the density of the plurality of primary activating molecular ligands on the antigen-presenting surface is from about $4\times10^2$ to about $2\times10^3$ molecules per square micron, in each portion or sub-region where it is attached.

206. The method of any one of embodiments 181-204, wherein the density of the plurality of primary activating molecular ligands on the antigen-presenting surface is from about $2\times10^3$ to about $5\times10^3$ molecules per square micron, in each portion or sub-region where it is attached.

207. The method of any one of embodiments 181-204, wherein the density of the plurality of primary activating molecular ligands on the antigen-presenting surface is from about $5\times10^3$ to about $3\times10^4$ molecules per square micron, about $5\times10^3$ to about $2\times10^4$ molecules per square micron, about $1\times10^4$ to about $2\times10^4$ molecules per square micron, or about $1.25\times10^4$ to about $1.75\times10^4$ molecules per square micron, in each portion or sub-region where it is attached.

208. The method of any one of embodiments 181-207, wherein the TCR co-activating molecule includes a CD28 binding protein or a fragment thereof.

209. The method of embodiment 209, wherein the CD28 binding protein or the fragment thereof further comprises a site-specific C-terminal biotin moiety.

210. The method of any one of embodiments 181-209, wherein the TCR co-activating molecule includes a CD80 molecule or a fragment thereof, wherein the fragment retains binding activity to CD28.

211. The method of any one of embodiments 181-209, wherein the TCR co-activating molecule includes an anti-CD28 antibody or a fragment thereof.

212. The method of any one of embodiments 181-211, wherein the adjunct TCR activating molecule includes a CD2 binding protein.

213. The method of embodiment 212, wherein the CD2 binding protein or the fragment thereof further comprises a site-specific C-terminal biotin moiety.

214. The method of any one of embodiments 181-213, wherein the adjunct TCR activating molecule includes a CD58 molecule or a fragment thereof, wherein the fragment retains binding activity with CD2.

215. The method of a one of embodiments 181-214, wherein the adjunct TCR activating molecule includes an anti-CD2 antibody or a fragment thereof.

216. The method of any one of embodiments 181-215, wherein a ratio of the primary activating molecular ligands to the co-activating molecular ligands on the antigen-presenting surface is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

217. The method of any one of embodiments 181-216, wherein a ratio of the primary activating molecular ligands to the co-activating molecular ligands on the antigen-presenting surface is about 1:1.

218. The method of any one of embodiments 181-217, wherein the method produces an antigen-presenting surface according to any one of embodiments 1-96.

219. The method of any one of embodiments 181-218, wherein the covalently functionalized surface is a surface of a bead.

220. The method of any one of embodiments 181-218, wherein the antigen-presenting surface is an antigen-presenting bead.

221. The method of any one of embodiments 219-220, wherein the bead has a surface area within 10% of the surface area of a sphere of an equal volume or diameter.

222. The method of any one of embodiments 219-221, wherein the bead comprises glass.

223. The method of any one of embodiments 219-222, wherein the bead comprises a polymer.

224. The method of any one of embodiments 219-223, wherein the bead comprises a magnetic material.

225. The method of any one of embodiments 181-224, wherein a ratio of the TCR co-activating molecules to the adjunct TCR activating molecules of the plurality of co-activating molecular ligands is about 3:1 to about 1:3.

226. The method of any one of embodiments 181-225, wherein the plurality of primary activating molecular ligands is disposed upon the surface of the antigen-presenting bead at a density from about $4\times10^2$ to about $3\times10^4$ molecules per square micron.

227. The method of any one of embodiments 181-226, wherein the distribution of the plurality of primary activating molecular ligands on the antigen-presenting bead is from about $4\times10^2$ to about $2\times10^3$ molecules per square micron.

228. The method of any one of embodiments 181-226, wherein the plurality of primary activating molecular ligands is disposed upon at least a portion of a surface of the antigen-presenting bead at a density from about $2\times10^3$ to about $3\times10^4$ molecules per square micron.

229. The method of any one of embodiments 181-226, wherein the plurality of primary activating molecular ligands is disposed upon at least a portion of a surface of the antigen-presenting bead at a density from about $5\times10^3$ to about $2\times10^4$ molecules per square micron, about $1\times10^4$ to about $2\times10^4$ molecules per square micron, or about $1.25\times10^4$ to about $1.75\times10^4$ molecules per square micron.

230. The method of any one of embodiments 219-229, wherein the distribution of the plurality of co-activating molecular ligands is from about $2\times10^2$ to about $1\times10^3$ molecules per square micron on the antigen-presenting bead.

231. The method of any one of embodiments 219-230, wherein the distribution of the plurality of co-activating molecular ligands on the antigen-presenting bead is from about $1\times10^3$ to about $2\times10^4$ molecules per square micron, about $5\times10^3$ to about $2\times10^4$ molecules per square micron, about $5\times10^3$ to about $1.5\times10^4$ molecules per square micron, about $1\times10^4$ to about $2\times10^4$ molecules per square micron, about $1\times10^4$ to about $1.5\times10^4$ molecules per square micron, about $1.25\times10^4$ to about $1.75\times10^4$ molecules per square micron, or about $1.25\times10^4$ to about $1.5\times10^4$ molecules per square micron.

232. The method of any one of embodiments 181-218 or 225-231, wherein the covalently functionalized surface is an inner surface of a microfluidic device.

233. The method of any one of embodiments 181-218 or 225-229 or 232, wherein the antigen-presenting surface is an antigen-presenting inner surface of a microfluidic device.

234. The method of embodiment 233, wherein the microfluidic device comprising the antigen-presenting inner surface is the microfluidic device of any one of embodiments 61-96.

235. The method of any one of embodiments 181-218 or 224-229, wherein the covalently functionalized surface is a surface of a wafer.

236. The method of any one of embodiments 181-218 or 224-229 or 235, wherein the antigen-presenting surface is an antigen-presenting wafer.

237. The method of any one of embodiments 181-218 or 224-2231, wherein the covalently functionalized surface is an inner surface of a tube.

238. The method of any one of embodiments 181-218 or 224-229 or 237, wherein the antigen-presenting surface is an antigen-presenting inner surface of a tube.

239. The method of any one of embodiments 237 or 238, wherein the tube is (i) a glass tube or (ii) a polymer tube.

240. The method of any one of embodiments 181-239, wherein the plurality of primary activating molecules is reacted with the first plurality of binding moieties before the plurality of co-activating molecules is reacted with the second plurality of binding moieties.

241. The method of any one of embodiments 154-240, further including producing the intermediate reactive surface, including: reacting at least a first plurality of surface-exposed moieties disposed at at least a first portion of a synthetic reactive surface with a plurality of intermediate preparation molecules including reactive moieties, thereby producing the intermediate reactive surface including a plurality of reactive moieties.

242. The method of embodiment 241, wherein producing the intermediate reactive surface further includes reacting at least a second plurality of surface-exposed moieties disposed at the at least first portion of the synthetic reactive surface with a plurality of surface-blocking molecules.

243. The method of embodiment 241 or 242, further including reacting a second plurality of surface-exposed moieties disposed in a second portion of the synthetic reactive surface with a plurality of surface-blocking molecules, thereby providing a plurality of surface-blocking molecular ligands at the second portion of the intermediate reactive surface.

244. The method of embodiment 243, wherein each surface-blocking molecular ligand is configured to exclude the primary activating molecular ligands including an MHC molecule.

245. The method of any one of embodiments 241-244, wherein the surface-exposed moieties are nucleophilic moieties.

246. The method of any one of embodiments 241-244, wherein the surface-exposed moieties are displaceable moieties.

247. The method of any one of embodiments 241-246, wherein the surface-exposed moieties of the at least first portion of the synthetic reactive surface and the surface-exposed moieties of the second portion of the synthetic reactive surface are not the same surface-exposed moieties.

248. The method of any one of embodiments 241-247, wherein the reacting the plurality of primary activating molecules and the reacting the plurality of co-activating molecules is performed at a plurality of sub-regions of the at least first portion of the covalently functionalized surface wherein each sub-region includes the respective first binding moieties, and second binding moieties.

249. The method of embodiment 248, further including reacting a plurality of surface-blocking molecules at the plurality of sub-regions of the at least first portion of the covalently functionalized surface including binding moieties.

250. The method of embodiment 249, wherein the reacting the plurality of surface-blocking molecules at the plurality of sub-regions of the at least first portion of the covalently functionalized surface is performed before the reacting of the plurality of primary activating molecules and the reacting the plurality of co-activating molecules is performed at the plurality of sub-regions.

251. The method of embodiment 248, wherein the reacting of the plurality of surface-blocking molecules at the plurality of sub-regions of the at least first portion of the covalently functionalized surface is performed after the reacting of the plurality of primary activating molecules and the reacting the plurality of co-activating molecules is performed at the plurality of sub-regions.

252. The method of any one of embodiments 241-250, wherein each of the plurality of first sub-regions of the covalently functionalized surface is separated from another of the plurality of first sub-regions by a second portion of the covalently functionalized surface.

253. The method of embodiment 252, further including reacting a plurality of surface-blocking molecules with respective pluralities of binding moieties located at the second portion of the covalently functionalized surface.

254. The method of embodiment 252, wherein the second portion of the intermediate reactive surface includes surface exposed moieties configured to substantially not react with the pluralities of the primary activating and co-activating molecules.

255. The method of embodiment 253 or 254, wherein the reacting the surface-exposed moieties of the second portion of the synthetic reactive surface with the plurality of surface-blocking molecules is performed before reacting the surface exposed moieties of the first portion of synthetic reactive surface with one or more surface preparing reagents, thereby providing the intermediate reactive surface.

256. The method of any one of embodiments 181-255, wherein reacting the plurality of co-activating molecules is performed after the reacting of the first plurality of molecules including the MHC molecules.

257. The method of any one of embodiments 227-256, wherein the MHC molecule is connected to the antigen-presenting surface via a C-terminal connection of the MHC protein sequence.

258. The method of any one of embodiments 181-257, wherein the distribution of the plurality of primary activating molecular ligands on the antigen-presenting surface is from about $4\times10^2$ to about $2\times10^3$ molecules per square micron in each portion or sub-region of the antigen-presenting surface where the co-activating molecular ligands are present.

259. The method of any one of embodiments 181-258, wherein the distribution of the plurality of primary activating molecular ligands on the antigen-presenting surface is from about $2\times10^3$ to about $5\times10^3$ molecules per square micron in each portion or sub-region of the antigen-presenting surface where the co-activating molecular ligands are present.

260. The method of any one of embodiments 181-258, wherein the distribution of the plurality of primary activating molecular ligands on the antigen-presenting wafer is from about $5\times10^3$ to about $3\times10^4$ molecules per square micron, about $5\times10^3$ to about $2\times10^4$ molecules per square micron, about $1\times10^4$ to about $2\times10^4$ molecules per square micron, or about $1.25\times10^4$ to about $1.75\times10^4$ molecules per square micron, in each portion or sub-region of the antigen-presenting surface where the co-activating molecular ligands are present.

261. The method of any one of embodiments 181-260, wherein the distribution of the plurality of co-activating molecular ligands is from about $2\times10^2$ to about $1\times10^3$ molecules per square micron on the antigen-presenting surface in each portion or sub-region of the antigen-presenting surface where the co-activating molecular ligands are present.

262. The method of any one of embodiments 181-260, wherein the distribution of the plurality of co-activating molecular ligands is from about $1\times10^3$ to about $5\times10^3$ molecules per square micron on the antigen-presenting surface in each portion or sub-region of the antigen-presenting surface where the co-activating molecular ligands are present.

263. The method of any one of embodiments 181-260, wherein the distribution of the plurality of co-activating molecular ligands on the antigen-presenting surface is from about $5\times10^3$ to about $2\times10^4$ molecules per square micron, about $5\times10^3$ to about $1.5\times10^4$ molecules per square micron, about $1\times10^4$ to about $2\times10^4$ molecules per square micron, about $1\times10^4$ to about $1.5\times10^4$ molecules per square micron, about $1.25\times10^4$ to about $1.75\times10^4$ molecules per square micron, or about $1.25\times10^4$ to about $1.5\times10^4$ molecules per square micron in each portion or sub-region of the antigen-presenting surface where the co-activating molecular ligands are present.

264. The method of any one of embodiments 154-263, wherein the biotin-binding agent is streptavidin.

265.A method of activating T lymphocytes (T cells) including: contacting a plurality of T cells with an antigen-presenting synthetic surface including: a plurality of primary activating molecular ligands, each including a major histocompatibility (MHC) Class I molecule configured to bind to a T cell receptor of the T cell; and a plurality of co-activating molecular ligands each including a T cell receptor (TCR) co-activating molecule or an adjunct TCR activating molecule; and culturing the plurality of T cells in contact with the antigen-presenting synthetic surface, thereby converting at least a portion of the plurality of T cells to activated T cells.

266.A method of activating T lymphocytes (T cells) including: contacting a plurality of T cells with the antigen-presenting synthetic surface of any one of embodiments 1-96; and culturing the plurality of T cells in contact with the antigen-presenting synthetic surface, thereby converting at least a portion of the plurality of T cells to activated T cells.

267. The method of embodiment 265 or 266, wherein the T cells include CD8+ T cells.

268. The method of any one of embodiments 265-267, wherein the plurality of co-activating molecular ligands comprises TCR co-activating molecules and adjunct TCR activating molecules.

269. The method of any one of embodiments 265-268, wherein a ratio of the TCR co-activating molecules to the adjunct TCR activating molecules of the plurality of co-activating molecular ligands is about 100:1 to about 1:100.

270. The method of any one of embodiments 265-269, wherein a ratio of the TCR co-activating molecules to the adjunct TCR activating molecules of the plurality of co-activating molecular ligands is 100:1 to 90:1, 90:1 to 80:1, 80:1 to 70:1, 70:1 to 60:1, 60:1 to 50:1, 50:1 to 40:1, 40:1 to 30:1, 30:1 to 20:1, 20:1 to 10:1, 10:1 to 1:1, 3:1 to 1:3; 1:1 to 1:10, 1:10 to 1:20, 1:20 to 1:30, 1:30 to 1:40, 1:40 to 1:50, 1:50 to 1:60, 1:60 to 1:70, 1:70 to 1:80, 1:80 to 1:90, or 1:90 to 1:100, wherein each of the foregoing values is modified by "about".

271. The method of any one of embodiments 265-270, wherein the ratio of the TCR co-activating molecules to the adjunct TCR activating molecules of the plurality of co-activating molecular ligands is from about 20:1 to about 1:20 or about 3:1 to about 1:3.

272. The method of any one of embodiments 265-271, wherein the plurality of MHC molecules each include an MHC protein sequence and a beta microglobulin.

273. The method of embodiment 272, wherein the protein sequence of the MHC molecule is connected to the antigen-presenting synthetic surface via a C-terminal connection of the protein sequence.

274. The method of any one of embodiments 265-273, wherein the MHC molecule includes a biotin moiety and is attached to the antigen-presenting synthetic surface via a noncovalent interaction with biotin-binding agent.

275. The method of embodiment 274, wherein the biotin-binding agent s itself covalently bonded to the antigen-presenting synthetic surface.

276. The method of embodiment 275, wherein the biotin-binding agent s bonded to the surface through a series of about 15, 20, 25, 30, 35, 40, 45, 50, 55, 60, 65, 70, 75, 80, 85, 95, 100, 200 bond lengths, or any number of bond lengths therebetween.

277. The method of embodiment 274, wherein the biotin-binding agent is noncovalently associated with the antigen-presenting synthetic surface.

278. The method of embodiment 274, wherein the biotin-binding agent is noncovalently associated with a biotin, and the biotin is covalently bonded to the antigen-presenting synthetic surface.

279. The method of embodiment 278, wherein the biotin is linked by a linker to the surface through a series of 2 about 15, 20, 25, 30, 35, 40, 45, 50, 55, 60, 65, 70, 75, 80, 85, 95, 100, 200 bond lengths, or any number of bond lengths therebetween . . .

280. The method of any one of embodiments 274-279, wherein the biotin-binding agent is streptavidin.

281. The method of any one of embodiments 265-280, wherein the MHC molecule further includes an antigen molecule.

282. The method of embodiment 281, wherein the antigen molecule is SLC45A2, TCL1, VCX3A, MART1 or NYESO1. 283. The method of any one of embodiments 265-282, wherein each of the plurality of co-activating molecule ligands is connected to the antigen-presenting synthetic surface.

284. The method of any one of embodiments 265-283, wherein the T cell receptor (TCR) co-activating molecule includes a CD28 binding protein or a fragment thereof which retains binding ability to CD28.

285. The method of embodiment 284, wherein the CD28 binding protein or the fragment thereof further comprises a site-specific C-terminal biotin moiety.

286. The method of any one of embodiments 265-285, wherein the T cell receptor (TCR) co-activating molecule includes a CD80 molecule or a fragment thereof, wherein the fragment retains binding activity to CD28.

287. The method of any one of embodiments 265-286, wherein the T cell receptor (TCR) co-activating molecule includes an anti-CD28 antibody or a fragment thereof.

288. The method of any one of embodiments 265-287, wherein the adjunct TCR activating molecule includes a CD2 binding protein.

289. The method of embodiment 288, wherein the CD2 binding protein or the fragment thereof further comprises a site-specific C-terminal biotin moiety.

290. The method of any one of embodiments 265-289, wherein the adjunct TCR activating molecule includes a CD58 molecule or fragment thereof, wherein the fragment retains binding activity with CD2.

291. The method of any one of embodiments 265-290, wherein the adjunct TCR activating molecule includes an anti-CD2 antibody or a fragment thereof.

292. The method of any one of embodiments 265-291, wherein the plurality of primary activating molecular ligands is present on at least one region of the antigen-presenting surface at a density from about $4\times10^2$ to about $2\times10^3$ molecules per square micron, in each portion or sub-region where it is attached.

293. The method of any one of embodiments 265-292, wherein the plurality of co-activating molecular ligands is disposed upon at least a portion of the antigen-presenting surface at a density from about $2\times10^2$ to about $1\times10^3$ molecules per square micron on the antigen-presenting synthetic surface, in each portion or sub-region where it is attached.

294. The method of any one of embodiments 265-292, wherein the plurality of primary activating molecular ligands is disposed upon at least a portion of a surface of the antigen-presenting synthetic surface at a density from about $5\times10^3$ to about $3\times10^4$ molecules per square micron, in each portion or sub-region where it is attached.

295. The method of any one of embodiments 265-292 or 294, wherein the plurality of co-activating molecular ligands is disposed upon at least a portion of the antigen-presenting synthetic surface at a density from about $5\times10^3$ to about $2\times10^4$ molecules per square micron or about $5\times10^2$ to about $1.5\times10^4$ molecules per square micron, in each portion or sub-region where it is attached.

296. The method of any one of embodiments 265-295, wherein the plurality of primary activating molecular ligands is present on at least one region of the antigen-presenting surface at a density from about $5\times10^3$ to about $2\times10^4$, about $2\times10^3$ to about $5\times10^3$, about $1\times10^4$ to about $2\times10^4$, or about $1.25\times10^4$ to about $1.75\times10^4$ molecules per square micron, in each portion or sub-region where it is attached.

297. The method of any one of embodiments 265-296, wherein the plurality of co-activating molecular ligands is disposed upon at least a portion of the antigen-presenting surface at a density from about $5\times10^3$ to about $2\times10^4$ molecules per square micron, about $5\times10^3$ to about $1.5\times10^4$ molecules per square micron, about $1\times10^4$ to about $2\times10^4$ per square micron, about $1\times10^4$ to about $1.5\times10^4$ per square micron, about $1.25\times10^4$ to about $1.75\times10^4$, or about $1.25\times10^4$ to about $1.5\times10^4$ per square micron, in each portion or sub-region where it is attached.

298. The method of any one of embodiments 265-297, wherein a ratio of the primary activating molecular ligands to the co-activating molecular ligands on the covalently modified surface is about 1:10 to about 2:1, about 1:5 to about 2:1, about 1:2 to about 2:1, about 1:10 to about 1:1, about 1:5 to about 1:1, about 1:1 to about 2:1, or about 1:2 to about 1:1.

299. The method of any one of embodiments 265-298, wherein a ratio of the TCR co-activating molecules to the adjunct TCR activating molecules of the plurality of co-activating molecular ligands is about 3:1 to about 1:3.

300. The method of any one of embodiments265-299, wherein a ratio of the TCR co-activating molecules to the adjunct TCR activating molecules of the plurality of co-activating molecular ligands is about 2:1 to about 1:2.

301. The method of any one of embodiments 265-300, wherein a ratio of the TCR co-activating molecules to the adjunct TCR activating molecules of the plurality of co-activating molecular ligands is about 1:1.

302. The method of any one of embodiments 265-301, further including contacting the plurality of T cells with a plurality of adhesion-stimulating molecular ligands including an ICAM molecule, wherein each of the plurality of adhesion-stimulating molecular ligands is attached to the antigen-presenting synthetic surface.

303. The method of embodiment 302, wherein the plurality of adhesion-stimulating molecular ligands is covalently attached to the antigen-presenting synthetic surface.

304. The method of any one of embodiments 265-303, wherein the antigen-presenting synthetic surface further includes a plurality of surface-blocking molecular ligands.

305. The method of embodiment 304, wherein the plurality of surface-blocking molecular ligands limits the density of the primary activating molecular ligands and/or the density of the co-activating molecular ligands.

306. The method of embodiment 304 or 305, wherein the plurality of surface-blocking molecular ligands substantially excludes the plurality of primary activating molecular ligands from a selected region of the covalently modified synthetic surface.

307. The method of embodiment 306, wherein the selected region of the antigen-presenting synthetic surface configured to substantially exclude the plurality of primary activating molecular ligands includes a microfluidic channel of a microfluidic device.

308. The method of embodiment 306, wherein the plurality of the primary activating molecular ligands is disposed in a plurality of sub-regions of a first portion of the antigen-presenting synthetic surface and the plurality of surface-blocking molecular ligands are disposed in a second region, and further wherein each of the plurality of sub-regions of the first portion of the antigen-presenting synthetic surface is separated from the others of the plurality of sub-regions of the first portion by the second region of the antigen-presenting synthetic surface.

309. The method of embodiment 308, wherein the plurality of sub-regions of the first portion of the antigen-presenting synthetic surface further includes a second plurality of surface-blocking molecular ligands.

310. The method of embodiments 308 or 309, wherein the plurality of co-activating molecular ligands is disposed in the plurality of sub-regions of the first portion of the antigen-presenting synthetic surface.

311. The method of any one of embodiments 265-310, further including contacting the plurality of T cells with a plurality of growth stimulatory molecular ligands.

312. The method of embodiment 311, wherein each of the growth stimulatory molecular ligands includes a growth factor receptor ligand.

313. The method of embodiment 312, wherein the growth factor receptor ligand includes IL-21 or a fragment thereof.

314. The method of any one of embodiments 265-313, wherein the contacting with the plurality of growth stimulatory molecular ligands is performed after a first period of culturing of at least one day.

315. The method of any one of embodiments 311-314, wherein the growth factor receptor ligand is connected to the antigen-presenting synthetic surface.

316. The method of any one of embodiments 311-315, wherein the plurality of growth factor receptor ligands is connected to an antigen-presenting synthetic surface that is a different surface than the antigen-presenting synthetic surface including the plurality of primary activating molecular ligands.

317. The method of any one of embodiments 265-316, wherein the antigen-presenting synthetic surface is the product of any one of embodiments 181-264.

318. The method of any one of embodiments 265 to 317, wherein the culturing in contact with the antigen-presenting synthetic surface is performed for a period from about four days to about seven days.

319. The method of any one of embodiments 265 to 318, wherein when the antigen-presenting synthetic surface is a bead, the ratio of antigen-presenting beads to cells is about 1:1.

320. The method of any one of embodiments 265 to 319, wherein when the antigen-presenting synthetic surface is a bead, the ratio of antigen-presenting beads to cells is about 1:1 at the beginning of the culturing.

321. The method of any one of embodiments 265 to 320, further including: completing a first period of activation in contact with the antigen-presenting synthetic surface, wherein the antigen-presenting synthetic surface is a first antigen-presenting synthetic surface; contacting the plurality of activated T cells with a second antigen-presenting synthetic surface including a plurality of primary activating molecular ligands, each including a MHC molecule, and a plurality of co-activating molecular ligands each including a T cell receptor (TCR) co-activating molecule or an adjunct TCR activating molecule; and, culturing the plurality of activated T cells in contact with the second antigen-presenting synthetic surface for a second period of culturing, thereby providing an expanded plurality of activated T cells.

322. The method of embodiment 321, wherein the second antigen-presenting synthetic surface is the antigen-presenting bead, antigen-presenting wafer or antigen-presenting microfluidic device of any one of embodiments 1-96 or is the product of any one of embodiments 181-264.

323. The method of embodiment 321 or 322, wherein when the first antigen-presenting synthetic surface includes a first plurality of antigen-presenting beads, then the contacting the plurality of activated T cells with the second antigen-presenting synthetic surface includes introducing a second plurality of antigen-presenting beads to the plurality of activated T cells.

324. The method of embodiment 323, further including adding the second plurality of antigen-presenting beads in a 1:1 ratio to the plurality of activated T cells.

325. The method of embodiment 323 or 324, wherein when the first antigen-presenting synthetic surface includes the antigen-presenting wafer or the antigen-presenting microfluidic device, then the contacting the plurality of activated T cells with the second antigen-presenting synthetic surface includes introducing a plurality of antigen-presenting beads to the plurality of activated T cells.

326. The method of any one of embodiments 321-325, further including adding a second plurality of growth stimulatory molecular ligands s during the second culturing period.

327. The method of embodiment 326, wherein the second plurality of growth stimulatory molecular ligands is connected to a surface of a bead that is a different bead from the antigen-presenting bead.

328. The method of any one of embodiments 321-327, wherein a plurality of IL-2 molecules and a plurality of IL-7 molecules are added to contact the activated T cells for a remainder of the second culturing period.

329. The method of any one of embodiments 321-328, wherein the culturing in contact with the second antigen-presenting synthetic surface is performed for a period from about four days to about seven days.

330. The method of any one of embodiments 321-329, further including: completing the second period of activation in contact with the second antigen-presenting synthetic surface; contacting the expanded plurality of activated T cells with a third antigen-presenting synthetic surface including a plurality of primary activating molecular ligands, and a plurality of co-activating molecular ligands each including a T cell receptor (TCR) co-activating molecule or an adjunct TCR activating molecule; and, culturing the expanded plurality of activated T cells in contact with the third antigen-presenting synthetic surface for a third period of culturing, thereby providing a plurality of highly activated T cells.

331. The method of embodiment 330, wherein the third antigen-presenting synthetic surface is the antigen-presenting bead, the antigen-presenting wafer or the antigen-presenting microfluidic device of any one of embodiments 1-96 or is the product of any one of embodiments 181-264.

332. The method of embodiment 330 or 331, further including adding a third plurality of growth stimulatory molecular ligands during the third culturing period.

333. The method of embodiment 332, wherein the third plurality of growth stimulatory molecular ligands is connected to a surface of a bead that is a different bead from the third antigen-presenting bead.

334. The method of any one of embodiments 330-333, wherein a plurality of IL-2 molecules and a plurality of IL-7 molecules are added to contact the activated T cells for a remainder of the third culturing period.

335. The method of any one of embodiments 330-334, wherein the culturing in contact with the third antigen-presenting synthetic surface is performed for a period from about four days to about seven days.

336. The method of any one of embodiments 265-335, wherein the activated T cell is CD45RO+.

337. The method of any one of embodiments 265-336, wherein the activated T cell is CD28 positive.

338. A kit for activating T lymphocytes (T cells), including: an antigen-presenting synthetic surface of any one of embodiments 1-96.

339. The kit of embodiment 338, wherein the antigen-presenting synthetic surface is an antigen-presenting bead, an antigen-presenting wafer, an antigen-presenting tube, or an antigen-presenting microfluidic device.

340. The kit of embodiment 338 or 339, further including a plurality of covalently modified beads including a plurality of growth-stimulatory molecular ligands, wherein each of the growth-stimulatory molecular ligands includes a growth factor receptor ligand.

341. The kit of embodiment 340, wherein the growth factor receptor ligand includes a cytokine or a fragment thereof.

342. The kit of embodiment 341, wherein the cytokine includes IL-21 or a fragment thereof.

343. The kit of any one of embodiments 340-342, further including one or more additional growth-stimulatory molecules.

344. The kit of embodiment 343, wherein the additional growth-stimulatory molecule(s) includes IL2 and/or IL7, or fragments thereof.

345. The kit of embodiment 344, wherein the second or more growth stimulatory molecule is attached to a covalently modified bead.

346.A method of performing an antigen-specific cytotoxicity assay, comprising:

loading one or more target cells into a sequestration pen of a microfluidic device;

loading one or more T cells in the sequestration pen, such that the one or more T cells can contact the one or more target cells;

contacting the target cells with a detectable marker that labels apoptotic cells; and detecting whether the target cells become apoptotic.

347. The method of embodiment 346, wherein the microfluidic device further comprises a microfluidic channel, and wherein the sequestration pen comprises an opening which opens to the microfluidic channel such that the sequestration pen is fluidically connected to the microfluidic channel.

348. The method of embodiment 346, wherein the microfluidic device further comprises a flow region for containing a flow of a first fluidic medium; and the sequestration pen comprises an isolation region for containing a second fluidic medium, the isolation region having a single opening, wherein the isolation region of the sequestration pen is an unswept region of the microfluidic device; and a connection region fluidically connecting the isolation region to the flow region; optionally wherein the flow region is a microfluidic channel.

349. The method of any one of embodiments 346 to 348, wherein a plurality of target cells are loaded into the sequestration pen.

350. The method of any one of embodiments 346 to 348, wherein a single target cell is loaded into the sequestration pen.

351. The method of any one of embodiments 346 to 350, wherein a single T cell is loaded into the sequestration pen.

352. The method of any one of embodiments 346 to 350, wherein a plurality of T cells are loaded into the sequestration pen.

353. The method of any one of embodiments 346 to 352, wherein loading the target cell(s) and/or T cell(s) into the sequestration pen comprises:

flowing the target cell(s) and/or T cell(s) into the microfluidic channel; and tilting the microfluidic device such that gravity is able to pull the target cell(s) and/or T cell(s) into the sequestration pen.

354. The method of any one of embodiments 346 to 353, wherein the microfluidic device comprises a DEP configuration and DEP force is used to load the target cell(s) and/or T cell(s) into the sequestration pen.

355. The method of embodiment 354, wherein the DEP force is activated by structured light.

356. The method of any one of embodiments 346 to 355, wherein the detectable marker is provided in a solution that is flowed through the microfluidic channel, whereupon the detectable marker can diffuse from the microfluidic channel into the sequestration pen and contact the target cells.

357. The method of any one of embodiments 346 to 356, wherein the detectable marker is an enzymatic substrate.

358. The method of any one of embodiments 346 to 357, wherein the detectable marker is a Caspase 3 substrate.

359. The method of any one of embodiments 346 to 356, wherein the detectable marker is a labeled antibody that specifically binds to apoptotic cells and/or apoptotic bodies.

360. The method of any one of embodiments 346 to 359, wherein detecting whether the target cells become apoptotic is performed periodically.

361. The method of any one of embodiments 346 to 360, wherein detecting whether the target cells become apoptotic is performed 2 or more hours after contacting the target cell(s) with the detectable marker.

362. The method of any one of embodiments 346 to 361, wherein the target cell(s) are cancer cells.

363. The method of any one of embodiments 346 to 362, wherein the target cell(s) are cells from a cell line that express a cancer-associated or cancer-specific antigen.

364. The method of any one of embodiments 346 to 363, wherein the target cell(s) express an antigen associated with melanoma, breast cancer, or lung cancer.

365. The method of any one of embodiments 346 to 364, wherein the T cells express a chimeric antigen receptor (CAR).

366. The method of any one of embodiments 346 to 365, wherein the T cells do not express a chimeric antigen receptor.

367. A kit for performing an antigen-specific cytotoxicity assay, comprising:

a microfluidic device; and a reagent for detecting apoptotic cells.

368. The kit of embodiment 367, wherein the microfluidic device is an antigen-presenting microfluidic device of any one of embodiments 61-96.

369. The kit of embodiment 367 or 368, wherein the reagent for detecting apoptotic cells is a enzymatic substrate.

370. The kit of embodiment 369, wherein the enzymatic substrate is a Caspase 3 substrate.

371. The kit of embodiment 367 or 368 wherein the reagent for detecting apoptotic cells is a labeled antibody that specifically binds to apoptotic cells and/or apoptotic bodies.

372. The surface, kit, or method of any one of the preceding embodiments, wherein the surface is an inner surface of a microfluidic device and at least part of the inner surface is in a sequestration pen of the microfluidic device.

373. The surface, kit, or method of embodiment 372, or the kit or method of any one of embodiments 346-371 wherein the microfluidic device further comprises a flow region for containing a flow of a first fluidic medium; and the sequestration pen comprises an isolation region for containing a second fluidic medium, the isolation region having a single opening, wherein the isolation region of the sequestration pen is an unswept region of the microfluidic device; and a connection region fluidically connecting the isolation region to the flow region; optionally wherein the microfluidic device comprises a microfluidic channel comprising at least a portion of the flow region.

374. The surface, kit, or method of embodiment 373, wherein the microfluidic device comprises a microfluidic channel comprising at least a portion of the flow region, and the connection region comprises a proximal opening into the microfluidic channel having a width $W_{con}$ ranging from about 20 microns to about 100 microns and a distal opening into the isolation region, and wherein a length $L_{con}$ of the connection region from the proximal opening to the distal opening is as least 1.0 times a width $W_{con}$ of the proximal opening of the connection region.

375. The surface, kit, or method of embodiment 373, wherein the length $L_{con}$ of the connection region from the proximal opening to the distal opening is at least 1.5 times the width $W_{con}$ of the proximal opening of the connection region.

376. The surface, kit, or method of embodiment 373, wherein the length $L_{con}$ of the connection region from the proximal opening to the distal opening is at least 2.0 times the width $W_{con}$ of the proximal opening of the connection region.

377. The surface, kit, or method of any one of embodiments 373-376, wherein the width $W_{con}$ of the proximal opening of the connection region ranges from about 20 microns to about 60 microns.

378. The surface, kit, or method of any one of embodiments 373-376, wherein the length $L_{con}$ of the connection region from the proximal opening to the distal opening is between about 20 microns and about 500 microns.

379. The surface, kit, or method of any one of embodiments 373--378, wherein a width of the microfluidic channel at the proximal opening of the connection region is between about 50 microns and about 500 microns.

380. The surface, kit, or method of any one of embodiments 373-379, wherein a height of the microfluidic channel at the proximal opening of the connection region is between 20 microns and 100 microns.

381. The surface, kit, or method of any one of embodiments 373-380, wherein the volume of the isolation region ranges from about $2\times10^4$ to about $2\times10^6$ cubic microns.

382. The surface, kit, or method of any one of embodiments 373-381, wherein the proximal opening of the connection region is parallel to a direction of the flow of the first medium in the flow region.

383. The surface, kit, or method of any one of embodiments 363-382, wherein the microfluidic device comprises an enclosure comprising a base, a microfluidic circuit structure disposed on the base, and a cover which collectively define a microfluidic circuit, and the microfluidic circuit comprises the flow region, the microfluidic channel, and the sequestration pen.

384. The surface, kit, or method of embodiment 383, wherein the microfluidic circuit further comprises one or more inlets through which the first medium can be input into the flow region and one or more outlets through which the first medium can be removed from the flow region.

385. The surface, kit, or method of embodiment 383 or 384, wherein the cover is an integral part of the microfluidic circuit structure.

386. The surface, kit, or method of any one of embodiments 383-385, wherein barriers defining the microfluidic sequestration pen extend from a surface of the base of the microfluidic device to a surface of the cover of the microfluidic device.

387. The surface, kit, or method of any one of embodiments 383-386, wherein the cover and the base are part of a dielectrophoresis (DEP) mechanism for selectively inducing DEP forces on a micro-object.

388. The surface, kit, or method of any one of embodiments 383-387, wherein the microfluidic device further comprises a first electrode, an electrode activation substrate, and a second electrode, wherein the first electrode is part of a first wall of the enclosure and the electrode activation substrate and the second electrode is part of a second wall of the enclosure, wherein the electrode activation substrate comprises a photoconductive material, semiconductor integrated circuits, or phototransistors.

389. The surface, kit, or method of embodiment 388, wherein the first wall of the microfluidic device is the cover, and wherein the second wall of the microfluidic device is the base.

390. The surface, kit, or method of embodiment 388 or 389, wherein the electrode activation substrate comprises phototransistors.

391. The surface, kit, or method of any one of embodiments 383-390, wherein the cover and/or the base is transparent to light.

392. One or more activated T cells produced by the method of any one of embodiments 265 to 337.

393.A population of T cells comprising activated T cells produced by the method of any one of embodiments 265-337, 394. The cell or population of embodiment 392 or 393, wherein the activated T cells are CD45RO+.

395. The cell or population of any one of embodiments 392-394, wherein the activated T cells are CD28+.

396. The cell, population, or method of any one of embodiments 265-337 or 392-395, wherein the activated T cells are CD28high.

397. The cell, population, or method of any one of embodiments 265-337 or 392-396, wherein the activated T cells are CD127+.

398. The cell, population, or method of any one of embodiments 265-337 or 392-397, wherein the activated T cells are CD197+.

399. The cell, population, or method of any one of embodiments 265-337 or 392-398, wherein the activated T cells are CD8+.

400.A microfluidic device comprising the cell or population of any one of embodiments 392-399.

401. The microfluidic device of any one of embodiments61-96, comprising the cell or population of any one of embodiments 392-399.

402. A pharmaceutical composition comprising the cell or population of any one of embodiments 392-399.

403. The method of any one of embodiments 257-327, 362-381. or 382-389, wherein the method produces a population of T cells, wherein at least 1%, 1.5%, 2%, 3%, 4%, 5%, 6%, 7%, 8%, 9%, or 10% of the population of T cells are antigen-specific T cells, wherein each of the foregoing values are modified by "about.".

404. The method of embodiment 403, wherein 1%-2%, 2%-3%, 3%-4%, 4%-5%, 5%-6%, 6%-7%, 7%-8%, 8%-9%, 9%-10%, 10%-11%, or 11%-12% of the T cells are antigen-specific T cells wherein each of the foregoing values are modified by "about.".

405. The method of embodiment 403 or 404, wherein at least 65%, 70%, 75%, 80%, 85%, 86%, 87%, 88%, 89%, 90%, 91%, 92%, 93%, 94%, 95%, 96%, 97%, or 98% of the antigen-specific T cells are CD45RO+/CD28$^{High}$ cells, wherein each of the foregoing values are modified by "about."

406.A method of treating a subject in need of treating a cancer; including: obtaining a plurality of T lymphocytes (T cells) from the subject; contacting the plurality of T cells with an antigen-presenting synthetic surface including a plurality of major histocompatibility complex (MHC) I molecules configured to bind to a T cell receptor of each of the plurality of T cells, wherein the MHC molecules include an antigen specific for the cancer of the subject and wherein the antigen-presenting synthetic surface is the antigen-presenting synthetic surface of any one of embodiments 1-96 or produced according to a method of any one of embodiments 181-264; producing a plurality of activated T cells, wherein the activation is configured to be specific against the cancer of the subject; separating the plurality of specific activated T cells from unactivated cells; and, introducing the plurality of antigen-specific activated T cells into the subject.

407. The method of embodiment 406, wherein the T cells are activated using the method of any one of embodiments 365-337.

408. The method of embodiment 406 or 407, further including enriching the sample including T lymphocytes before contacting the T lymphocytes with the covalently modified synthetic surface.

409. The method of any one of embodiments 406-408, wherein the separating the plurality of antigen-specific activated T cells further includes detecting a plurality of surface biomarkers of the antigen-specific activated T cells.

410. The method of embodiment 409, wherein the plurality of surface biomarkers comprises CD45RO+.

411. The method of embodiment 409 or 410, wherein the plurality of surface biomarkers comprises CD28+.

412. The method of any one of embodiments 409-411, wherein plurality of surface biomarker comprises CD28$^{high}$.

413. The method of any one of embodiments 409-412, wherein plurality of surface biomarkers comprises CD8.

414. The method of any one of embodiments 409-413, wherein plurality of surface biomarkers comprises CD127.

415. The method of any one of embodiments 409-414, wherein plurality of surface biomarkers comprises CD197.

416. The method of any one of embodiments 406-415, further including rapidly expanding the antigen-specific activated T cells to provide an expanded population of antigen-specific activated T cells.

417. The method of embodiment 416, wherein the rapid expansion is performed after separating the specific activated T cells from the unactivated T cells.

418. The method of any one of embodiments 406-417, wherein the method of treating the subject delays or stops progression of the cancer in the subject.

What is claimed:

1. A cartridge for manufacturing a population of cells, comprising:

- a sealed enclosure with an inlet port and an outlet port, comprising:
- a first fluidic network connected to the outlet port;
- a first reagent reservoir connected to the first fluidic network;

a first cell analysis region connected to the first fluidic network; and a chamber for culturing cells, wherein the chamber comprises:

a first input opening for introduction of fluid into the chamber;

a first output opening for removal of fluid from the chamber; and a second output opening for removal of fluid from the chamber;

wherein:

the chamber is connected to each of the outlet port, the first reagent reservoir, and the first cell analysis region via the first fluidic network;

the first and second output openings are positioned at different vertical elevations within the chamber; and an internal surface of a base of the chamber comprises a plurality of concave features defined thereon.

2. The cartridge of claim 1, wherein the first output opening of the chamber is located in the base of the chamber, wherein the second output opening of the chamber is located above the base, and wherein the second output opening is located at or above a position in the chamber that corresponds to at least 15% of a vertical height of the chamber.

3. The cartridge of claim 1, wherein the first fluidic network comprises a plurality of valves and a plurality of channels.

4. The cartridge of claim 3, wherein a single valve in the plurality of valves of the first fluidic network is connected to, and thereby regulates flow through, the first output opening and/or the second output opening of the chamber, and wherein the single valve of the first fluidic network is directed connected to, and thereby regulates flow through, both the first output opening and the second output opening of the chamber.

5. The cartridge of claim 1 further comprising: a second fluidic network, and wherein the second fluidic network comprises a plurality of valves and a plurality of channels.

6. The cartridge of claim 5, wherein the second fluidic network is connected to the inlet port or the first input opening of the chamber.

7. The cartridge of claim 5, further comprising: a first reservoir for cell culture medium, and wherein the first reservoir is connected to the second fluidic network.

8. The cartridge of claim 7, wherein the first reservoir for cell culture medium is connected to the chamber via the first input opening of the chamber.

9. The cartridge of claim 1, further comprising: a second reservoir for collecting waste material, and wherein the second reservoir is connected to the first fluidic network.

10. The cartridge of claim 9, wherein the second reservoir for collecting waste material is connected to the chamber via at least one outlet opening of the first outlet opening, and the second outlet opening, or a third outlet opening of the chamber.

11. The cartridge of claim 9, wherein the second reservoir for collecting waste material comprises a second compartment located within the cartridge.

12. The cartridge of claim 1, wherein each concave feature of the plurality of concave features on the internal surface of the base of the chamber has a volume of about 500 nanoliters to about 20 microliters.

13. The cartridge of claim 1, wherein each concave feature of the plurality of concave features on the internal surface of the base of the first chamber defines a hemispherical cavity.

14. The cartridge of claim 1, wherein each concave feature of the plurality of concave features on the internal surface of the base of the chamber defines an elongated cavity and wherein a long axis of each elongated cavity is substantially parallel to a long access of every other elongated cavity of the plurality of concave features.

15. The cartridge of claim 14, wherein each elongated cavity includes a deepest point, wherein the long axis of each elongated cavity includes a first end and a second end, wherein an angle defined by the internal surface of the base of the chamber and a line segment connecting the first end of the long axis with the deepest point of the elongated cavity is between 45° and 90°, and wherein an angle defined by the internal surface of the base of the chamber and a line segment connecting the second end of the long axis with the deepest point of the elongated cavity is less than 45°.

16. The cartridge of claim 1, wherein each concave feature of the plurality of concave features on the internal surface of the base of the first chamber comprises a surface for activating a T lymphocyte (T cell).

17. The cartridge of claim 16, wherein the surface for activating a T cell comprises an antigen-presenting surface.

18. The cartridge of claim 16, wherein the surface for activating a T cell covers a portion of a surface of each concave feature.

19. The cartridge of claim 18, wherein the surface for activating a T cell comprises a first region that is a T cell activating region and a second region that is covalently modified with surface blocking ligands.

20. The cartridge of claim 19, wherein the first region of each concave feature comprises an area of between 0.5 $mm^2$ and 1.0 $mm^2$.

21. The cartridge of claim 1, wherein the concave features of the internal surface of the base of the first chamber comprises 100s to 1000s of concave features.

22. The cartridge of claim 1, wherein the chamber further comprises a moveable lid for controlling an inner volume of the chamber.

23. The cartridge of claim 22, wherein the moveable lid of the chamber has a maximally expanded position during which the chamber comprises a volume between 10 cubic centimeters ($cm^3$) and 150 $cm^3$.

24. The cartridge of claim 22, wherein the moveable lid of the chamber has a minimally expanded position during which the chamber comprises a volume less than 2 $cm^3$.

25. The cartridge of claim 1, wherein the first reagent reservoir is configured to store a cytokine.

26. The cartridge of claim 1 further comprising a second reagent reservoir connected to the first fluidic network.

27. The cartridge of claim 26, wherein the second reagent reservoir is configured to store a cytokine, a reagent for transfecting/transforming cells, or a cell staining reagent.

28. The cartridge of claim 1, wherein the first cell analysis region is configured for counting cells and/or detecting cells having a desirable and/or undesirable phenotype.

29. The cartridge of claim 1, wherein the chamber is a first chamber and the cartridge further comprises a second chamber for culturing cells, wherein the second chamber comprises:

a first output opening for removal of fluid from the second chamber, and an internal surface of a base of the second chamber comprises a second plurality of concave features.

30. The cartridge of claim 29, wherein each concave feature of the second plurality of concave features on the internal surface of the base of the second chamber lacks an antigen-presenting surface for activating a T cell.

31. The cartridge of claim 29, wherein the second chamber further comprises a second output opening for removal of fluid from the second chamber, and, wherein the first and second output openings of the second chamber are positioned at different vertical elevations within the second chamber.

32. The cartridge of claim 4, wherein the single valve is connected to the first output opening and/or the second output opening of the chamber via an intervening channel.

33. The cartridge of claim 14, wherein the elongated cavity is in the shape of a bisected tear-drop.

34. The cartridge of claim 25, wherein the cytokine is one or more of IL2, IL7 and IL15.

35. The cartridge of claim 27, wherein the cytokine is one or more of IL2, IL7 and IL15.

36. The cartridge of claim 27, wherein the reagent for transfecting/transforming cells is a nucleic acid reagent, or a nucleic acid reagent paired with a chemical transfection reagent.

37. The cartridge of claim 27, wherein the cell staining reagent is a fluorescently labeled compound or an antibody used to assess a cellular phenotype.

* * * * *